US007465544B2

(12) United States Patent
Rajski et al.

(10) Patent No.: US 7,465,544 B2
(45) Date of Patent: Dec. 16, 2008

(54) SYNTHETIC COFACTOR ANALOGS OF S-ADENOSYLMETHIONINE AS LIGATABLE PROBES OF BIOLOGICAL METHYLATION AND METHODS FOR THEIR USE

(75) Inventors: Scott R. Rajski, Madison, WI (US); Lindsay R. Comstock, Madison, WI (US); Rachel L. Weller, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 10 days.

(21) Appl. No.: 11/330,370

(22) Filed: Jan. 11, 2006

(65) Prior Publication Data

US 2007/0161007 A1 Jul. 12, 2007

(51) Int. Cl.
*C12Q 1/68* (2006.01)
*C07H 21/00* (2006.01)
*C07H 19/16* (2006.01)
*C07H 19/20* (2006.01)

(52) U.S. Cl. .................. 435/6; 536/25.32; 536/27.3; 536/23.1

(58) Field of Classification Search .................. 435/6; 536/23.1, 27.3
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 6,617,434 B1 | 9/2003 | Duffy |
| 6,875,750 B1 | 4/2005 | Pignot |
| 2002/0016003 A1 | 2/2002 | Saxon |
| 2003/0082609 A1 | 5/2003 | Olek et al. |
| 2003/0199084 A1 | 10/2003 | Saxon |
| 2005/0148032 A1 | 7/2005 | Saxon |
| 2005/0158731 A1 | 7/2005 | Plass |

FOREIGN PATENT DOCUMENTS

WO WO0006587 2/2000

OTHER PUBLICATIONS

Allerson, C. R. et al., J. Am. Chem. Soc. (1997) 119:7423-7433.
Cardillo, G. et al., Tetrahedron: Asymmetry (1996) 7:755-762.
Cimato, et al. J. Cell. Bio. 138 (1997) 1089-1103.
Comstock, J.R., Rajski, S. R., Tetrahedron (2002) 58:6019-6026.
Comstock, L. R., J. Org. Chem. (Feb. 20, 2004) 69(4): 1425-1428.
Comstock, L.R., Rajski, S.R., Nucleic Acids Res. (2005) 33:1644-1652.
Erdem, G. et al., J. BioscL (1994) 19: 9-17.
Fei, L., Austin, D. L., Org. Lett. (2001) 3:2273-2276.
Gano, K.W. et al., Tetrahedron Lett. (2001) 42:2249-2251.
Garcia, J. et al., Tetrahedron Lett. (1984) 25:4841-4844.
Herd, M., Kocks, C., Infection and Immunity (2001) 69:3972-3979.
Kanan, M. W. et al., Nature (2004) 431: 545-549.
Kolb, M. et al., J. Med. Chem. (1982) 25(5) 550-556.
Lee J. W. et al., Tetrahedron Lett. (2001) 42:2719-2711.
Lindstrom U. M., Somfai, P., Synthesis (1998) 109-117.
Link, A. J., Tirrell, D. A., J. Am. Chem. Soc. (2003) 125: 11164-11165.
Liu, F., Austin, D. J., J. Org. Chem. (2001) 66:8643-8645.
Martelli, A. et al., Tetrahedron (2002) 58:4291.
Menes-Arzate, M. et al., J. Org. Chem. (2004) 69:4001-4004.
Petersen, S. G., Rajski, S. R., J. Org. Chem. (2005) 70:5833-5839.
Pljevaljcic, G. et al., ChemBioChem. (2004) 5:265-269.
Rapoport, H., J. Org. Chem. (1993) 58:2369-2376.
Restituyo, J. A. et al., Org. Lett. (2003) 5:4357-4360.
Sakaitani, M., Ohfune, Y., J. Org Chem. (1990) 55:870-876.
Saxon, E., Bertozzi, C. R., Science (2000) 287:2007-2010.
Siegfried, Z. et al., Nat. Genet. (1999) 22:203-206.
Speers, A. E. et al., J. Am. Chem. Soc. (2003) 125:4686-4687.
Tanner et al., Tetrahedron (1998) 54:14213-14232.
Toyota, M. et al., J. Org. Chem (2000) 65:7110-7113.
Tse, W. C., Boger, D. L., Chem. Biol. (2004) 11:1607-1617.
Weller, R. L., Rajski, S. R., Organic Letters (2005) 7:2141-2144.
Zaloom, J. et al., J. Org Chem. (1985) 50:2601-2603.
Zhang, C., J. Am Chem. Soc. (2006) 128:2760-2761.
Comstock, L. R. and Rajski, S. R., J. Am Chem. Soc. (2005) 127:14136-4137.
Bjelakovic, G. et al., Competitive Inhibitors of Enzymes and Their Therapeutic Application, FACTA Universitas (2002) 9(3): 201-206.
Jeltsch et al., On the Substrate Specificity of DNA Methltransferases, *J. Biochem.*, (1999) 274:19538-19544.
Kolb, M. et al., Synthesis of 5'-[3-Aminooxypropyl)amino]-5'-deoxyadenosine, *J. Leibigs Ann. Chem.* (1985) pp. 1036-1040.
Pignot, M. et al., Coupling of a Nucleoside with DNA by a Methyltransferase, *Angew. Chem. Int. Ed.* (1998) 37:2888-2891.

(Continued)

*Primary Examiner*—L. E. Crane
(74) *Attorney, Agent, or Firm*—Joseph T. Leone, Esq.; DeWitt Ross & Stevens S.C.

(57) ABSTRACT

The present invention discloses compounds and methods used to specifically target substrates of methylation by S-adenosyl-L-methionine (SAM)-dependent methyltransferases. The substrates can be peptides, single stranded nucleic acids or double stranded nucleic acids, including RNA, DNA and PNA or phospholipids. The compounds disclosed are SAM analogs that are ligated to a methylation site by the methyltransferase. Also disclosed, are reacting groups that are ligatable to the cofactor analogs and can also be used as detectable labels. The reacting group can be used to cleave the substrate providing a methylation footprint. The invention can be used clinically to determine methylation state of a gene or gene promoter such as those involved in imprinting and transcription. In some preferred embodiments, the invention includes a kit, which can include one or more suitable SAM analogs and may include one or more detectable labels. In other preferred embodiments, the invention includes a pharmaceutical composition.

17 Claims, 21 Drawing Sheets

OTHER PUBLICATIONS

Urata, H. et al., Racemic synthesis of cabocyclic purine nucleoside analogues with restricted glycosyl conformation, *J. Chem. Soc.* (1999 Perkin Trans) 1:1833.

Van Der Wenden, E. M. et al., 5'-Substitutes Adenosine Analogs as a New High-Affinity Partial Agonists for the Adenosine A, Receptor, *J. Med. Chem.* (1998) 41:102-108.

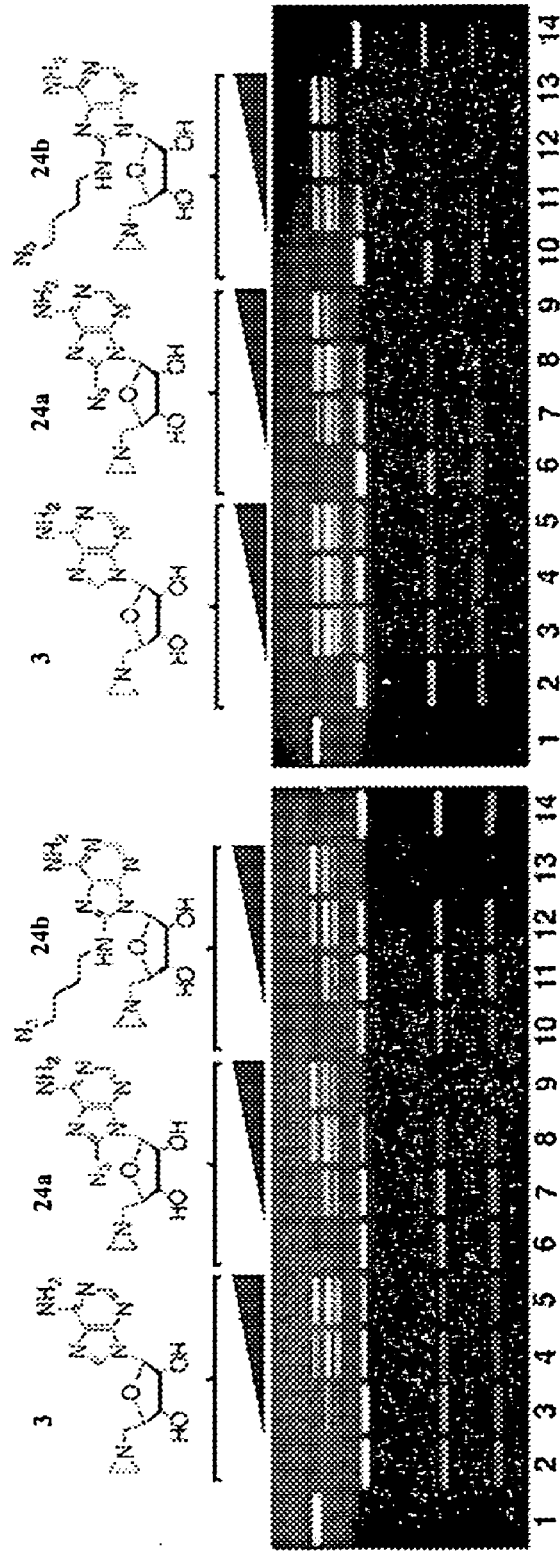

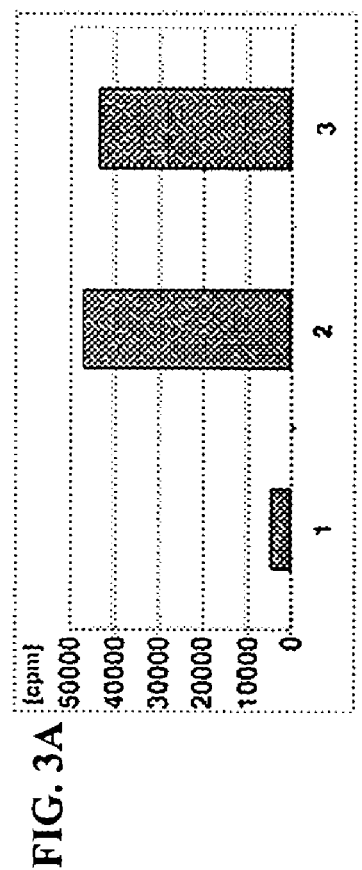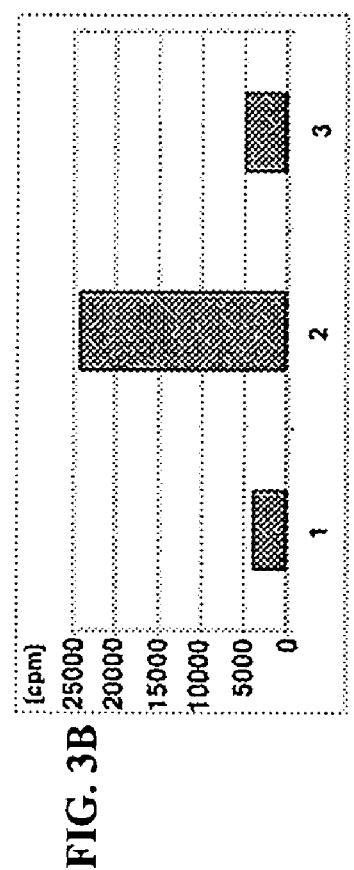

ϖ = alkylated DNA
β = native DNA

SYNTHETIC COFACTOR ANALOGS OF S-ADENOSYLMETHIONINE AS LIGATABLE PROBES OF BIOLOGICAL METHYLATION AND METHODS FOR THEIR USE

FEDERAL FUNDING

This invention was made with United States government support awarded by the following agencies: NIH ES09090. The United States has certain rights in this invention.

FIELD OF THE INVENTION

This invention is generally directed to analogs of S-Adenosyl-L-methionine, ligatable probes thereof and methods for their use.

BACKGROUND OF THE INVENTION

DNA methylation is found in most eukaryotic organisms. While the role of differential methylation is still being investigated it is understood that methylation is an important regulatory event in the cell. Methylation is a dynamic process as enzymes are present in cells to methylate as well as demethylate nucleic acids and proteins. Differential methylation of proteins and genes affects activity of proteins and expression of genes. In mammals, gene methylation has been found to be important in X-chromosome inactivation, control of imprinted genes, suppression of testis specific genes and cell type specific expression.

Aberrations in the normal methylated state of genes are correlated to a growing list of diseases or disorders. Diseases associated with aberrant methylation include adult T-cell leukemia, diabetes, various cancers and developmental disorders identified with genetic imprinting, such as Prader-Willi and Angleman's syndrome. In some cases, normally methylated oncogenes become unmethylated allowing their transcription. In other cases, tumor suppressor genes, such as BRCA and RASSF1A, which are normally unmethylated, become methylated resulting in non-suppression of oncogenes. In addition, numerous physiological changes associated with normal aging are now thought to be the effect of changes in the methylation status of genes. In particular, it is thought that the methylation state of CpG islands, those CG-rich areas of genes that are generally found within the promoter region of the gene, are important regulators of gene expression. The methylated state of CpG islands range from fully methylated to hemimethylated to unmethylated. While it is known that methylation plays an important role in gene expression, the mechanisms behind this effect are not fully understood with some genes silenced by methylation while others are expressed.

The methylation state of DNA, RNA and proteins in cells affects cellular signaling through regulation of gene expression and subcellular localization and activation of proteins. DNA methylation is essential for the normal development and functioning of organisms. Aberrant DNA methylation has been linked to developmental diseases and cancer and alterations in DNA and protein methylation and/or acetylation have been documented in studies of age-related neurodegenerative disorders including Alzheimer's disease, Parkinson's disease and Huntington's disease. The most important cofactor in substrate methylation, S-adenosyl-L-methionine (SAM), is administered as a pharmaceutical, under the tradenames Gumbaral and Samyr, either orally or by intramuscular or intraperitoneal injection in Europe and sold over-the-counter, in the United States where it is administered orally to treat disorders such as depression, Parkinson's disease, Alzheimer's disease, dementia, fibromyalgia and schizophrenia.

Protein methylation is a posttranslational modification that regulates biochemical pathways. In these modifications, methyl groups are added to carboxyl groups or side chain nitrogens present in arginine and lysine residues of proteins. Protein methylation plays a role in signal transduction, growth, protein sorting, regulatory mechanisms and the remodeling of chromatin via methylation of histone moieties. Protein methylation is thought to have a role in chemotaxis, insulin secretion and photoreceptor signal transduction. Carboxy methylated proteins include the Ras and Rho families of G-proteins and the protein phosphatase catalytic subunit 2A. N-methylated proteins include cytoskeleton proteins actin and myosin and nuclear proteins; nucleolin, fibrillarin, histones, heterogenous nuclear RNPs and metabolic proteins such as, calmodulin and FGF-2.

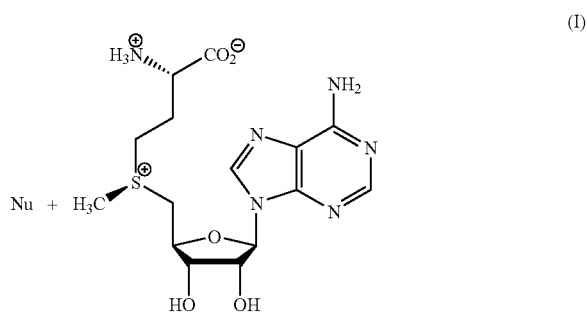

(I)

S-adenosyl-L-methionine (SAM), formula I, dependent methylation of nucleic acids and proteins plays a crucial role in DNA methylation and the regulation of gene transcription. Some researchers view SAM as the universal methyl donor for both proteins and nucleic acids (Cimato et al., JCB138: 1997 1089-1103). The maintenance DNA methyltransferase (DNMT1) utilizes SAM to methylate cytosine at the replication fork to insure fidelity of methylation patterns in normal cells. Flaws in the activity and expression levels of the eukaryotic DNA methyltransferase (MTase) DNMT1 have been integrally linked to oncogenic potential. Thus, non-methylating agents capable of undergoing DNMT1-dependent transfer to DNA might represent an attractive new chemotherapeutic strategy. DNMT1 transfer of non-methyl entities to the methylation sites on DNA may alter transcriptional repression mechanisms controlled through methylation. Such an approach is significantly different from those exemplified by simple inhibition of MTases with SAM analogs. Substances capable of undergoing transfer to nucleic acids in an MTase-dependent way also holds tremendous promise as biochemical tools by which to dissect and understand biological methylation. For instance, posttranslational protein methylation plays a large role in transcription regulation and constitutes an important facet of proteomics. The absence of functionality, however, renders the methyl group difficult to identify and isolate from complex biological mixtures. Thus, substances that take part in SAM-dependent MTase pathways are important proteomic and genomic tools in addition to DNA modifying agents.

Currently, methods used to label polynucleotides for genomic studies rely on the use of DNA polymerases and ligases to incorporate labeled deoxynucleoside triphosphate (dNTPs) bases into the polynucleotide during de novo synthesis. For example, classical sequencing of DNA requires the incorporation of $^{32}$P labeled bases by DNA polymerase into the growing DNA strand. More recently, it has become possible to label DNA with fluorophore conjugated dNTPs. Labeling of DNA by these methods is not limited to incorporation of the labeled fragments into the growing DNA molecule by DNA polymerase I but can also be accomplished by end labeling of DNA fragments resulting from a restriction digest. While these methods of labeling polynucleotides using DNA polymerases have revolutionized the ability to sequence and synthesize DNA and RNA, they are limited by the ability of the polymerase to label the DNA in sequential order as the conjugate base is ligated in position with its partner on the template strand.

Present techniques used to determine the methylation state of DNA require complex multi-step procedures. For example, published U.S. patent application 2003/0082609, hereby incorporated by reference in its entirety, describes a method of determining methylation state by chemically pretreating a genomic DNA digest with bisulfite followed by alkaline hydrolysis to convert non-methylated cytosine bases to uracil. The presence of the methylated cytosine is inferred only if it (not a transformed uracil) subsequently hybridizes to a second probe. U.S. Pat. No. 6,617,434, hereby incorporated by reference in its entirety, describes a method of detecting differential methylation at CpG sequences by cutting test and control DNA with a restriction enzyme that will not cut methylated DNA and comparing the two digests. In this instance, the methylated state is inferred by the reduced ability of the enzyme to cut the DNA. Similarly, published U.S. Patent Application 2005/0158731, hereby incorporated by reference in its entirety, describes methods to determine the methylation state of DNA by using a series of restriction enzymes that are alternately methylase sensitive and labeling the ends of the cleaved fragments with $^{32}$P followed by gel separation and restriction.

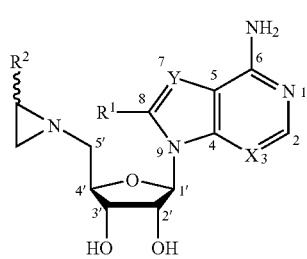

II

Recently, a 5'-aziridine adenylate cofactor analog as a substitute for SAM was described having the formula II. II can be used in the M.TaqI catalyzed alkylation of adenine within the TaqI recognition sequence d(TCGA). Generally, restriction-modification systems consist of two enzymes, a methylase and a restriction enzyme, each having the same recognition sequences herein denoted by 'M' for methylase and 'R' for restriction enzyme. In this M.TaqI catalyzed reaction, instead of generating the N$^6$-methyladenine, substrate adenylation is accomplished via ring opening of the aziridine to yield substrate conjugation to the modified cofactor analog. This chemistry is tolerant of cofactor C8 modification and has been successfully used to fluorescently tag short oligonucleotides and large plasmid substrates in an M.TaqI-dependent fashion. The aziridine nucleoside also undergoes M.HhaI-dependent DNA attachment within the M.HhaI recognition sequence d(GCGC) (Pignot, M et al. (1998) *Angew. Chem. Int. Ed.*, 37, 2888-2891; Pljevaljcic, G. et al., (2004) *ChemBioChem*, 5, 265-269 and U.S. Pat. No. 6,875,750 and published PCT Patent Application WO 00/06587, each hereby incorporated by reference in their entirety).

The 5' aziridine cofactor analog II, provides a method of attaching a detectable molecule to a methyltransferase substrate using methyltransferase reactions. Thus, physiologically relevant substrates and their sites of methylation can be identified directly, without resorting to a multi-step, indirect process as has been previously necessary. However, one problem to the use of II as a method of methylation detection is that the presence of the modified cofactor analog requires previous linkage to a detectable label such as a fluorophore, as previously described in U.S. Pat. No. 6,875,750. Pre-labeling limits the utility of cofactor analog II, two-fold because such fluorophore linkage may result in steric interference with the substrate and second, prelabeling limits the versatility of use to the pre-determined label.

Published U.S. Patent Applications 2002/0016003, 2003/0199084 and 2005/0148032, each hereby incorporated by reference in its entirety, describe a chemoselective ligation reaction that can be carried out under physiological conditions. This modified Staudinger reaction, the "Staudinger ligation" occurs between an azide and a phosphine in a stable reaction that does not interfere with cell processes to display markers on oligosaccharides present on cell membranes. As disclosed in the above patent applications, the Staudinger ligation, is, generally, directed to cell surface molecules for the purpose of attaching a phosphine-linked tag to the cell membrane.

The further development of compositions and methods to further elucidate the roles of methylation and methylases requires cofactor analogs that are more efficient to construct and have a greater facility of use such that they are compatible with existing technologies and can also be easily modified without affecting their ability to take the place of the native cofactor. For example, the identification of analogs that are easily synthesized and are stable for longer periods of time in storage while also being amenable to labeling with purification moieties and/or reporter moieties would greatly facilitate their use.

These and other features and advantages of various preferred embodiments of the compositions and methods according to this invention are described in, or are apparent from, the following detailed description of various exemplary embodiments of the methods according to this invention.

SUMMARY OF THE INVENTION

The present invention provides compounds and methods used to specifically target substrates of methylation by S-adenosyl-L-methionine (SAM)-dependent methyl transferases. The substrates can be peptides, single stranded nucleic acids or double stranded nucleic acids, including RNA, DNA and PNA or phospholipids. The compounds disclosed are SAM analogs that are modified at the C5' position such that the cofactor analog is specifically transferred to a methylation site by the methyltransferase. Once anchored to the methyltransferase substrate the compounds are further modified to include a reacting group that allows the facile addition of a detectable label. Such labels may also have incorporated a binding or affinity moiety to purify and/or identify specific residues that are physiological sites of methylation. In other embodiments, the detectable label may include a reporter moiety such as a fluorescent moiety, luminescent moiety, a chromophore moiety or radioactive moiety. In some embodiments, the detectable label can be used to cleave the substrate. When the substrate is cleaved, identification of the cleavage patterns forms a methylation footprint of the substrate. The invention can also be used, clinically, to determine methylation state of a gene or gene promoter such as those involved in imprinting and transcription. In other embodiments, when used with nucleic acid methyltransferases, the SAM analogs disclosed can be used as blockades to polymerases and/or exonucleases thus allowing for rapid identification for specific DNA or RNA residues that are typically methylated. In some preferred embodiments, the invention includes a kit, which includes one or more suitable SAM analogs and may include one or more detectable labels. In other preferred embodiments, the invention includes a pharmaceutical composition.

In one preferred embodiment, the invention comprises a cofactor analog of the formula III:

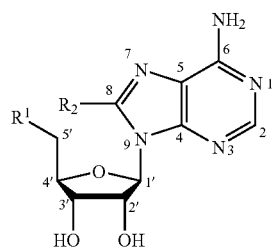

where $R_1$ is attached to C5' through a nitrogen atom and comprises: $NC_2H_4$, $XC_2H_4NH(CH_2)_{n2}C_2H$, $XC_2H_4NH(CH_2CH_2O)_{n1}C_2H$, $XC_2H_4NHCH_2C_2CH_3$, $XC_2H_4NHC_3H_5NH_3COOH$, and $X(CH_2)_2NR_3$, $X(CH_2)_2NH(CH_2)_{n2}CR_3$ and $X(CH_2)_2NH(CH_2CH_2O)_{n1}CR_3$ where $n_1$ is an integer from 1 to 10 inclusive and $n_2$ is an integer from 2-10, inclusive and X is a leaving group selected from the group consisting of a halide such as I, Br, Cl and F, or a tosylate (OTs), mesylate (OMs) or triflate (OTf) and $R_3$ is selected from the group consisting of:

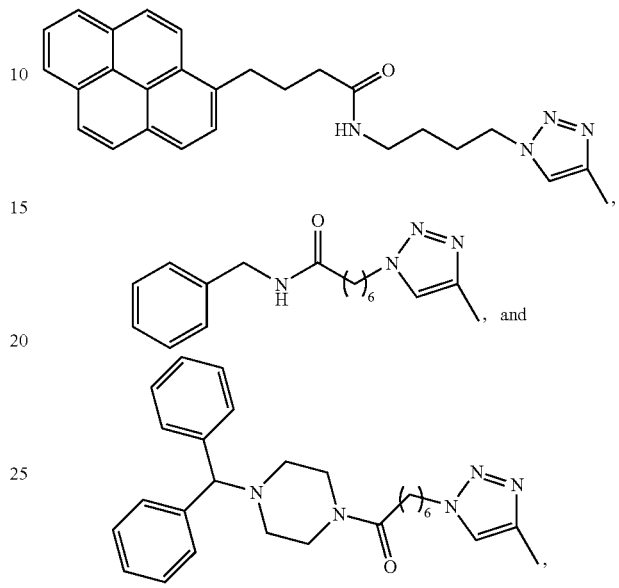

where $R_2$ is independently selected from H, $N_3$, $NH(CH_2)_{n2}N_3$, $NH(CH_2CH_2O)_{n1}N_3$, $NH(CH_2)_{n2}C_2H$, $NH(CH_2CH_2O)_{n1}C_2H$,

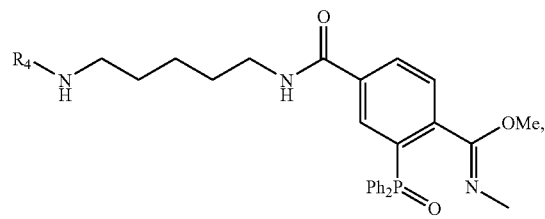

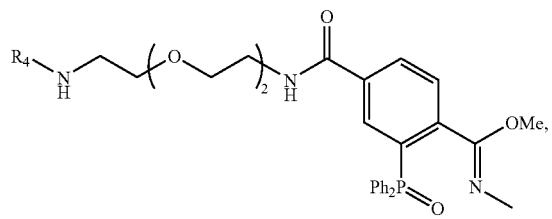

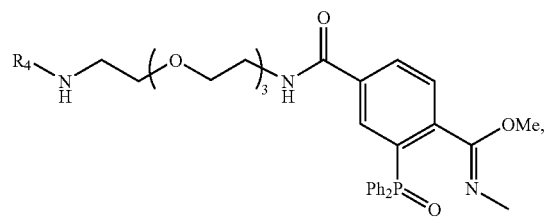

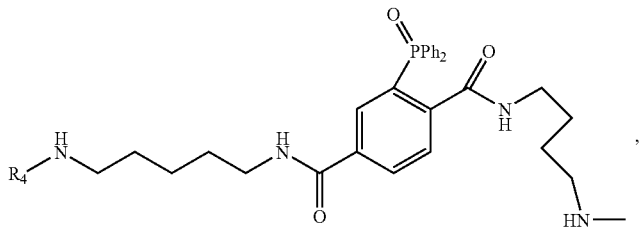

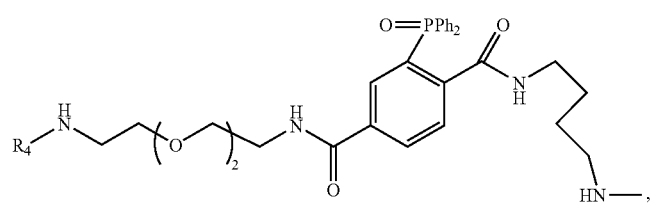

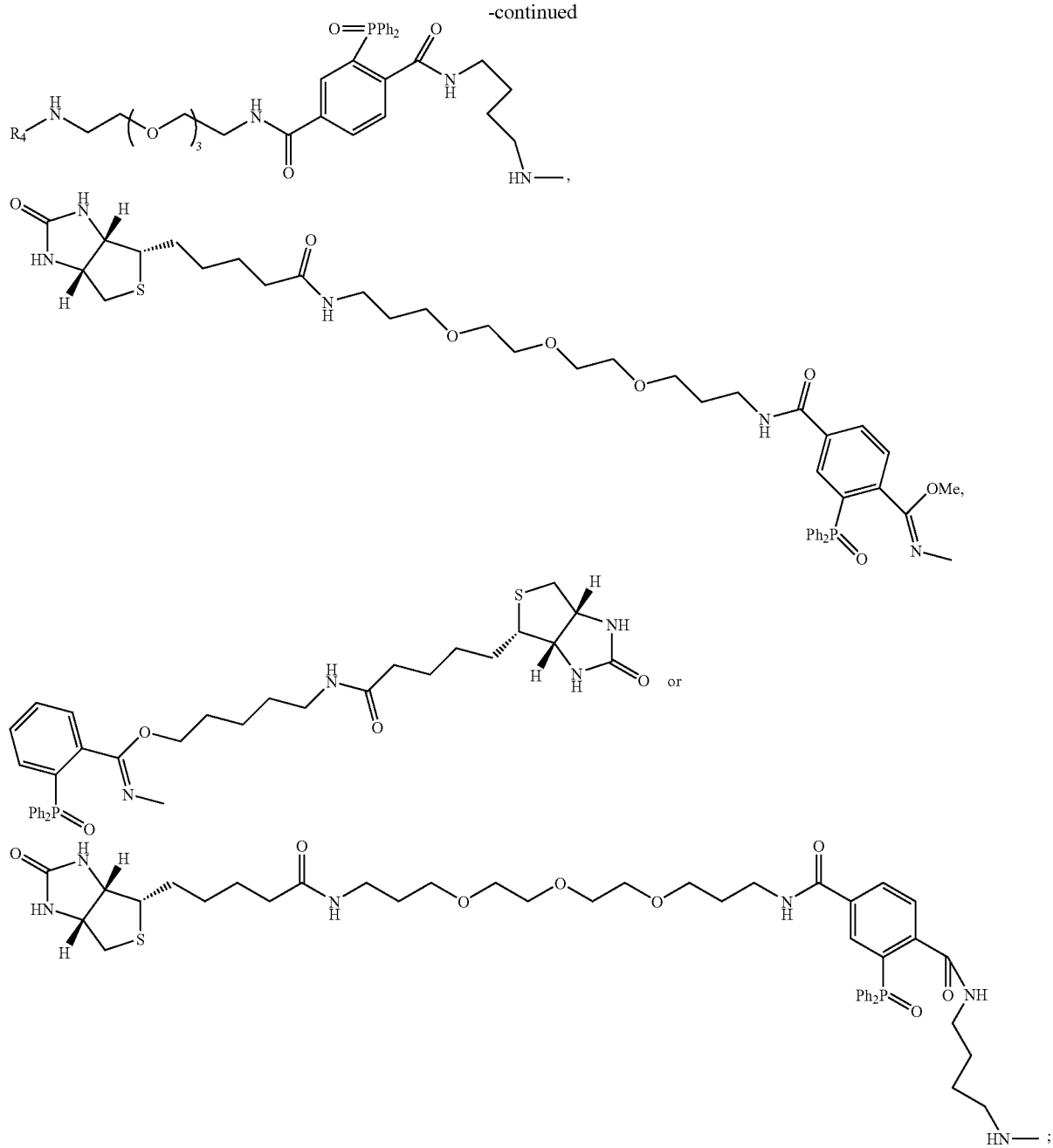

provided that when $R_1$ is $NC_2H_4$, $R_2$ is not $N_3$ or H; and where $R_4$ is H, $CH_3$ or

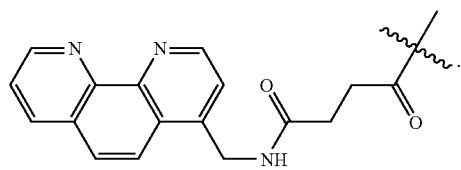

In some preferred embodiments, the triarylphosphine is a phenanthroline derivatized trialylphospine.

In other preferred embodiments, the cofactor analog is ligatable to a substrate by a methyltransferase. In some preferred embodiments, the substrate is a phospholipid, a peptide, a protein, a nucleic acid, a polynucleotide or a peptide nucleic acid (PNA). In other preferred embodiments, the cofactor analog is ligatable to an adenosyl residue or a cytosyl residue of the substrate. In some embodiments, the methyltransferase is selected from the group consisting of M.TaqI, M.EcoRI, M.HhaI, and M.SssI. However, it should be appreciated that the use of any methyltransferase capable of catalyzing the ligation is encompassed by the invention.

When the cofactor analog includes those shown in formula III, the analog may comprise a ligation product of an azide-containing first molecule with a carboxy-containing second molecule, wherein the ligation occurs between the azide moiety and the carboxy moiety. In these embodiments, the first molecule is selected from the group consisting of:
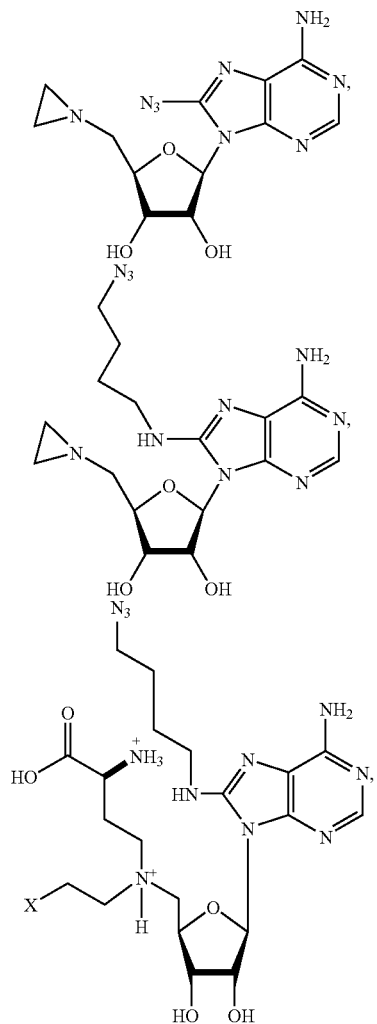
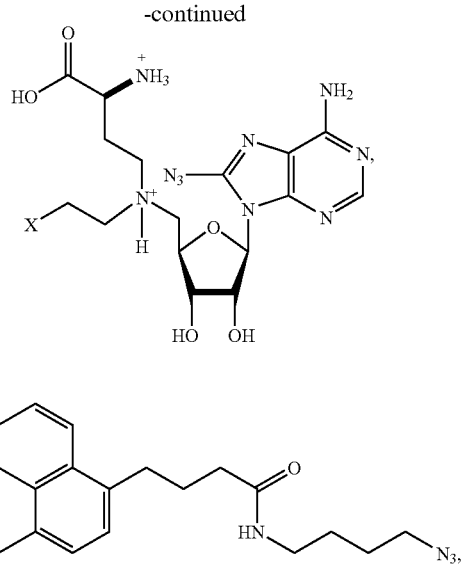
and the second molecule is selected from the group consisting of:
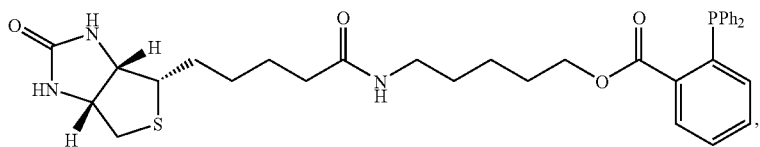
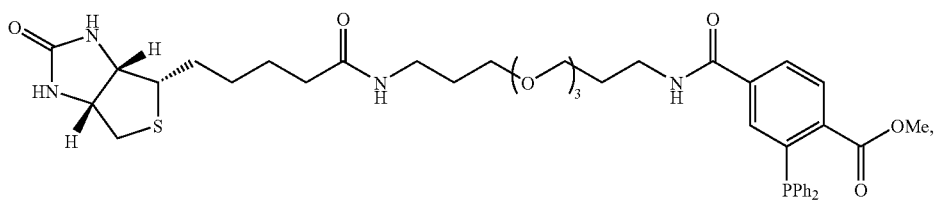

-continued

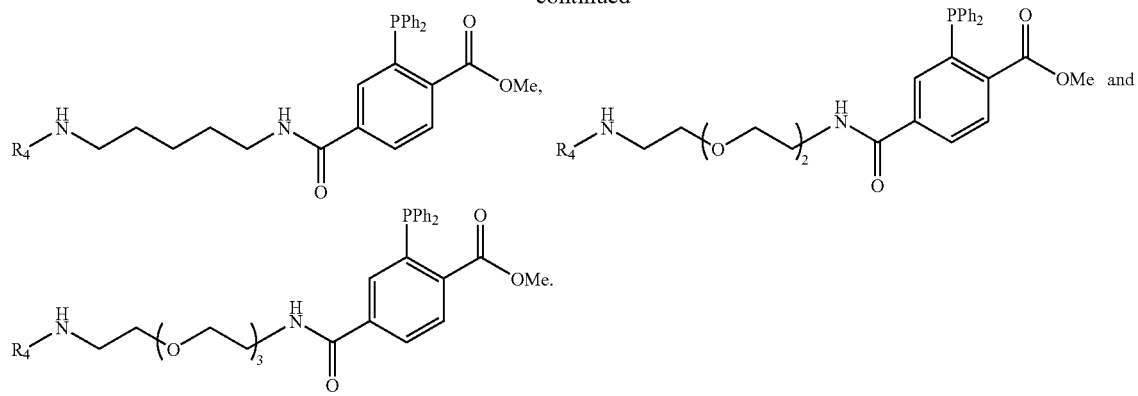

In these embodiments X is a leaving group selected from the group consisting of a halide such as F, Cl, Br and I and a tosylate (OTs), mesylate (OMs) or triflate (OTf) where $R_4$ is H, $CH_3$ or

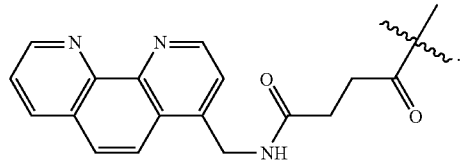

In some preferred embodiments, the triarylphosphine is a phenanthroline derivatized triarylphosphine.

In another preferred embodiment, the invention comprises a cofactor analog having the formula:

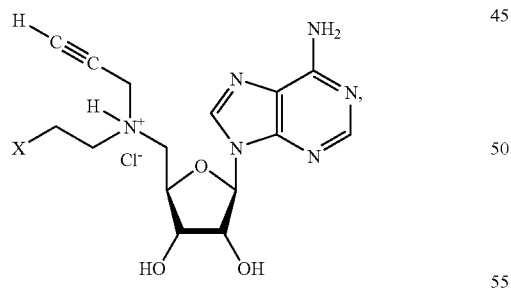

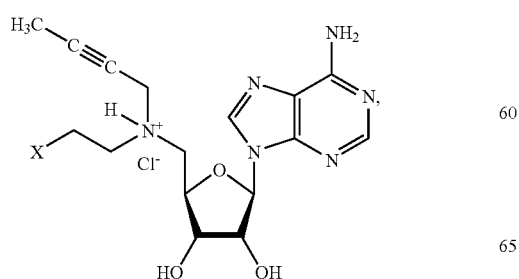

-continued

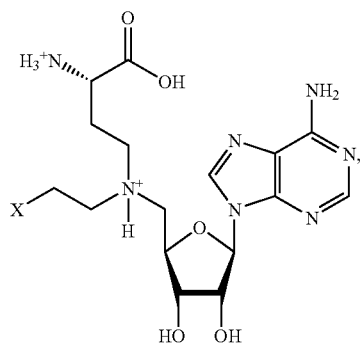

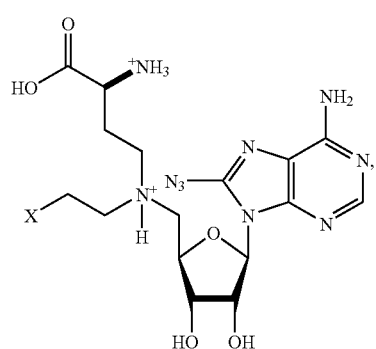

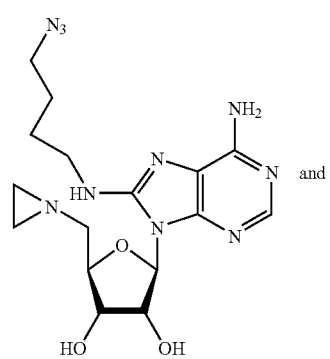

-continued

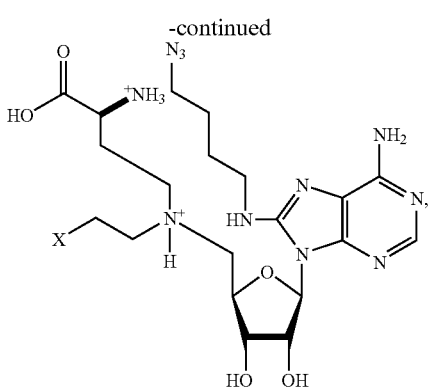

where X is a leaving group selected from the group consisting of a halogen such as F, Cl, Br, I or a tosylate (OTs), mesylate (OMs) or triflate (OTf).

In some preferred embodiments, the cofactor analog is selected from the group consisting of 8-azido-5'-aziridino-5'deoxy adenosine, 8-(4"-Azido-butylamino)-5'-aziridino-5'-deoxy adenosine, 5'-(diaminobutyric acid)-N-iodoethyl-5'deoxyadenosine ammonium chloride, 5'-(Nα-Boc diaminobutyric acid-O-tert-Butyl ester)-N-hydroxyethyl-5'-deoxy-2',3'-bis-(O-triethylsilyl)adenosine, 5'-(diaminobutyric acid)-N-iodoethyl-5'-deoxy-8-aminobutylazido adenosine (bis)hydrochloride and 5'-(diaminobutyric acid)-N-iodoethyl-5'-deoxy-8-azidoadenosine (bis)hydrochloride. In these preferred embodiments, the cofactor analog is attached to a substrate by a methyltransferase. In some preferred embodiments, the cofactor-linked substrate is a peptide, a protein, a phospholipid, a nucleic acid, a peptide nucleic acid, or a polynucleotide. In preferred embodiments, the cofactor analog is linked by the methylase to an adenosyl residue or a cytosyl residue of the substrate biopolymer. In some preferred embodiments, the methyltransferase is selected from the group consisting of M.TaqI, M.EcoRI, M.HhaI and M.SssI.

In other preferred embodiments, the invention comprises a cofactor analog according to formula III having a C-8 containing azido group that comprises a first reacting group allowing ligation of the analog with a carboxyphenylphosphine second reacting group. In these embodiments, the phosphine reacting group is selected from the group consisting of:

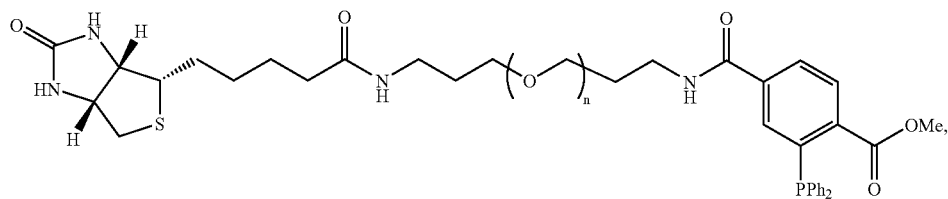

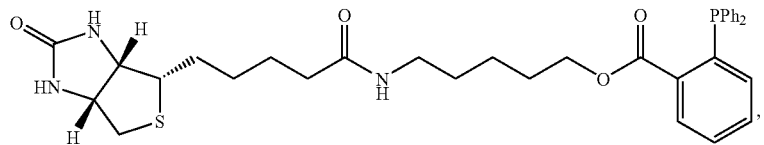

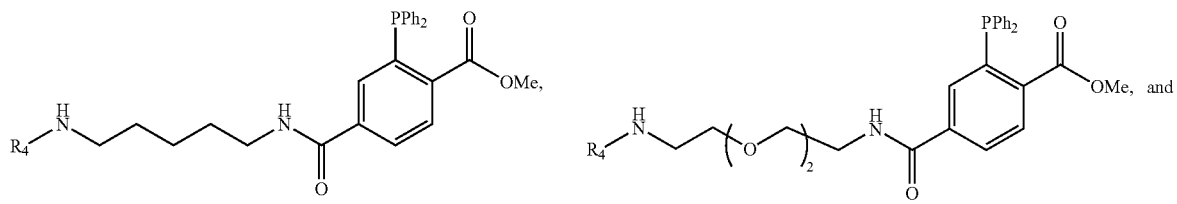

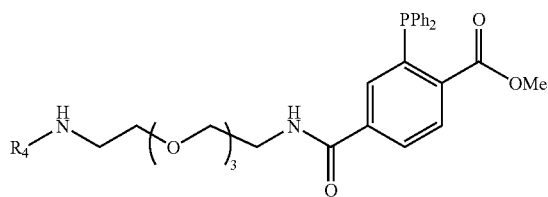

where n is 1, 2, 3 or 4 and $R_4$ is H, $CH_3$ or

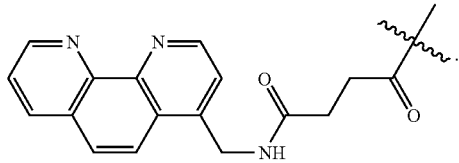

In other preferred embodiments, a C-5' linked carboxy group is a first reacting group allowing ligation with an azido-containing second reacting group. In these preferred embodiments, the azido-containing reacting group is selected from the group consisting of:

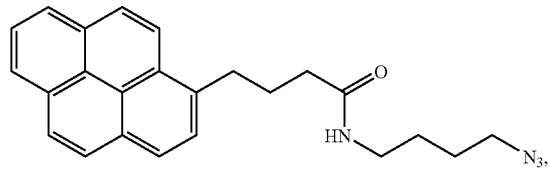

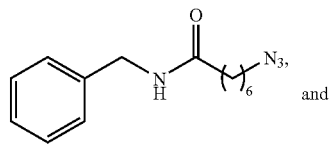
and

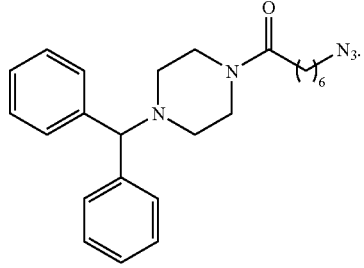

In another preferred embodiment, the invention comprises a cofactor analog ligated to a substrate having the formula:

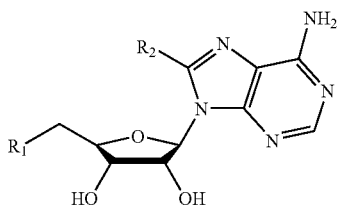

where $R_1$ is selected from the group consisting of: Su-$C_2H_4$NH, Su-$C_2H_4$NH$(CH_2)_{n2}C_2$H, Su-$C_2H_4$NH $(CH_2CH_2O)_{n1}C_2$H, Su-$C_2H_4$NHCH$_2C_2$CH$_3$, Su-$C_2H_4$NH $(CH_2)_2$NH$_3$CO$_2$H and Su- where $n_1$ is an integer from 1-10 inclusive and $n_2$ is an integer from 2-10 inclusive and where Su is a substrate selected from the group consisting of: a phospholipid, a nucleic acid, a polynucleotide, a peptide nucleic acid, a peptide, a polypeptide and a protein and where $R_2$ is independently selected from the group consisting of: $N_3$, NH$(CH_2)_{n2}N_3$, NH$(CH_2CH_2O)_{n1}N_3$, NH$(CH_2)_{n2}C_2$H, NH$(CH_2O)_{n1}C_2$H and H, provided that when $R_1$ is Su-$C_2H_4$NH, $R_2$ is not $N_3$ or H.

In some preferred embodiments, the cofactor analog is selected from the group consisting of:

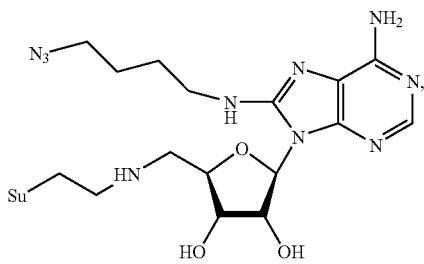

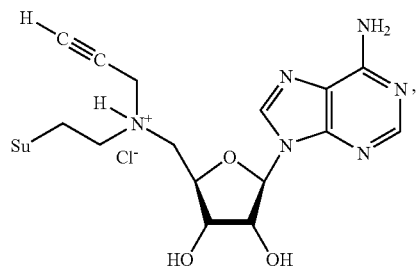

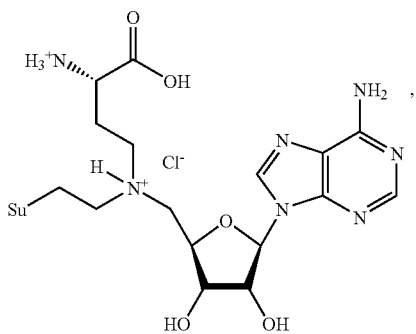

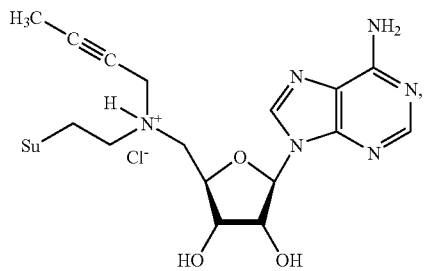

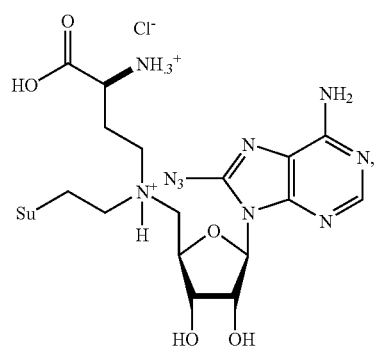
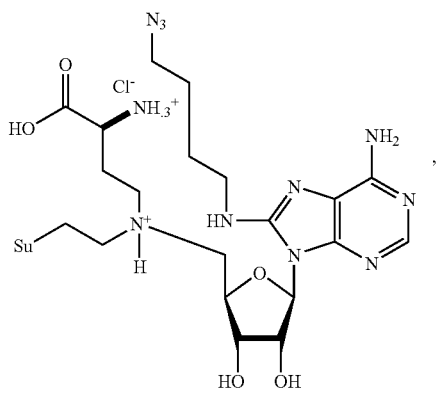
-continued
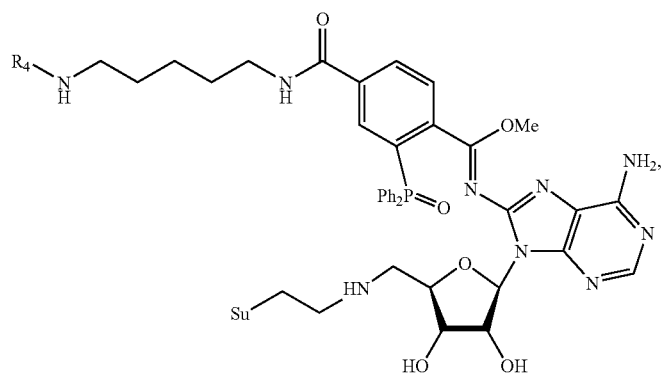
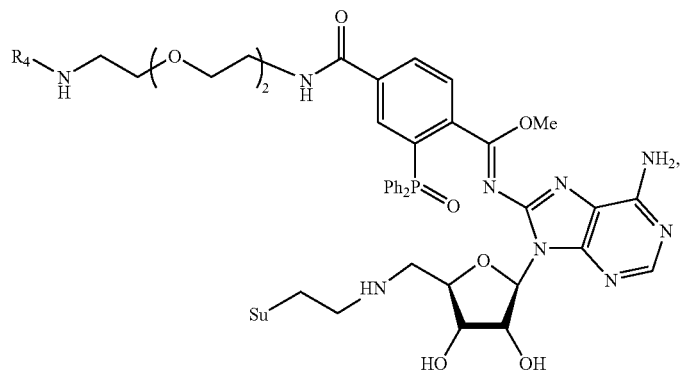
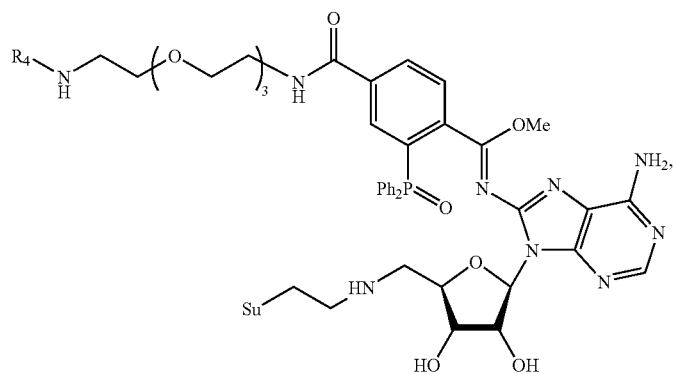

-continued
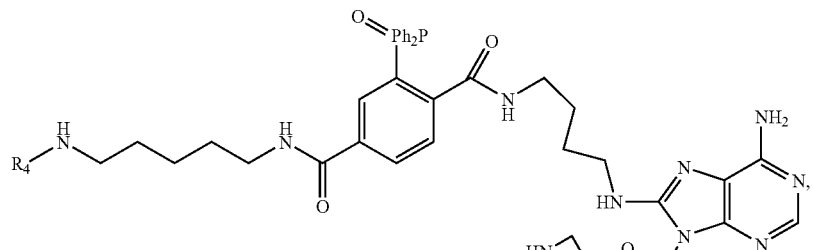
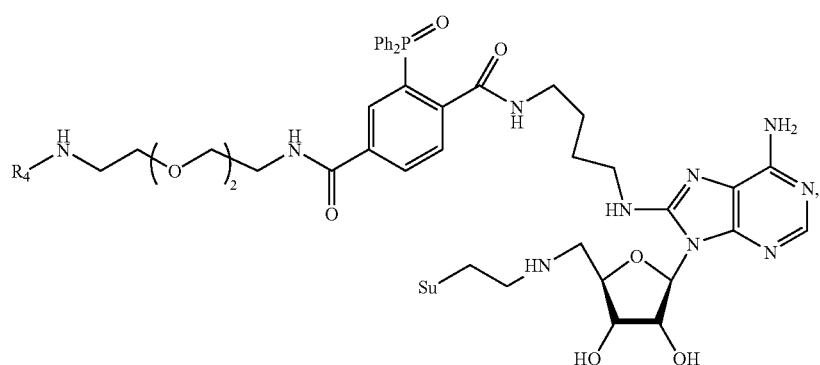
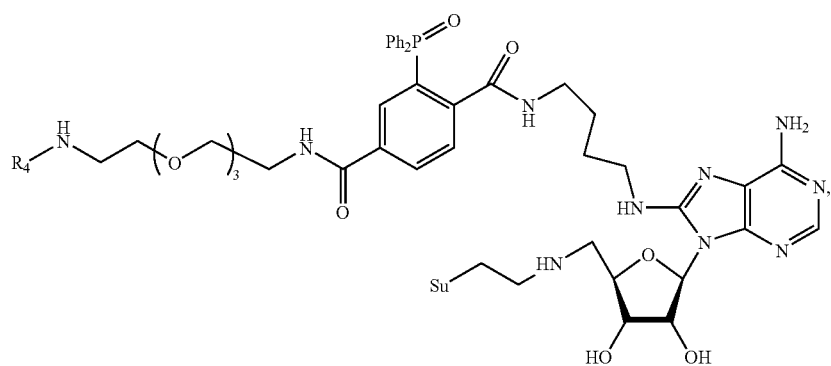
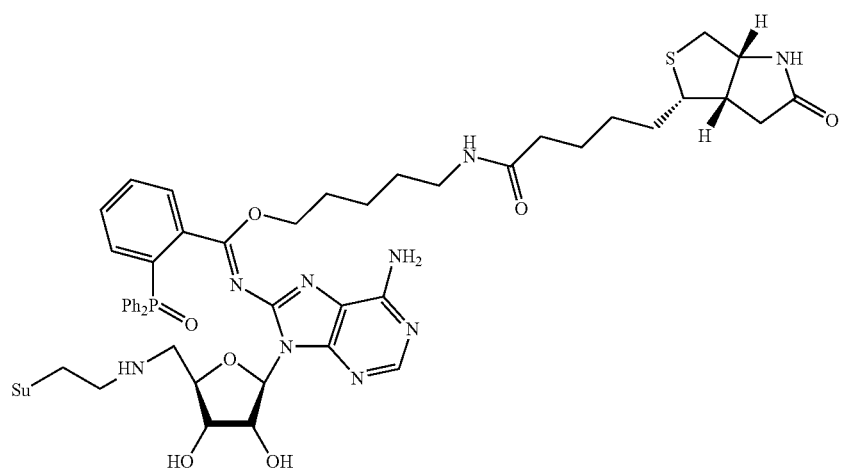

-continued
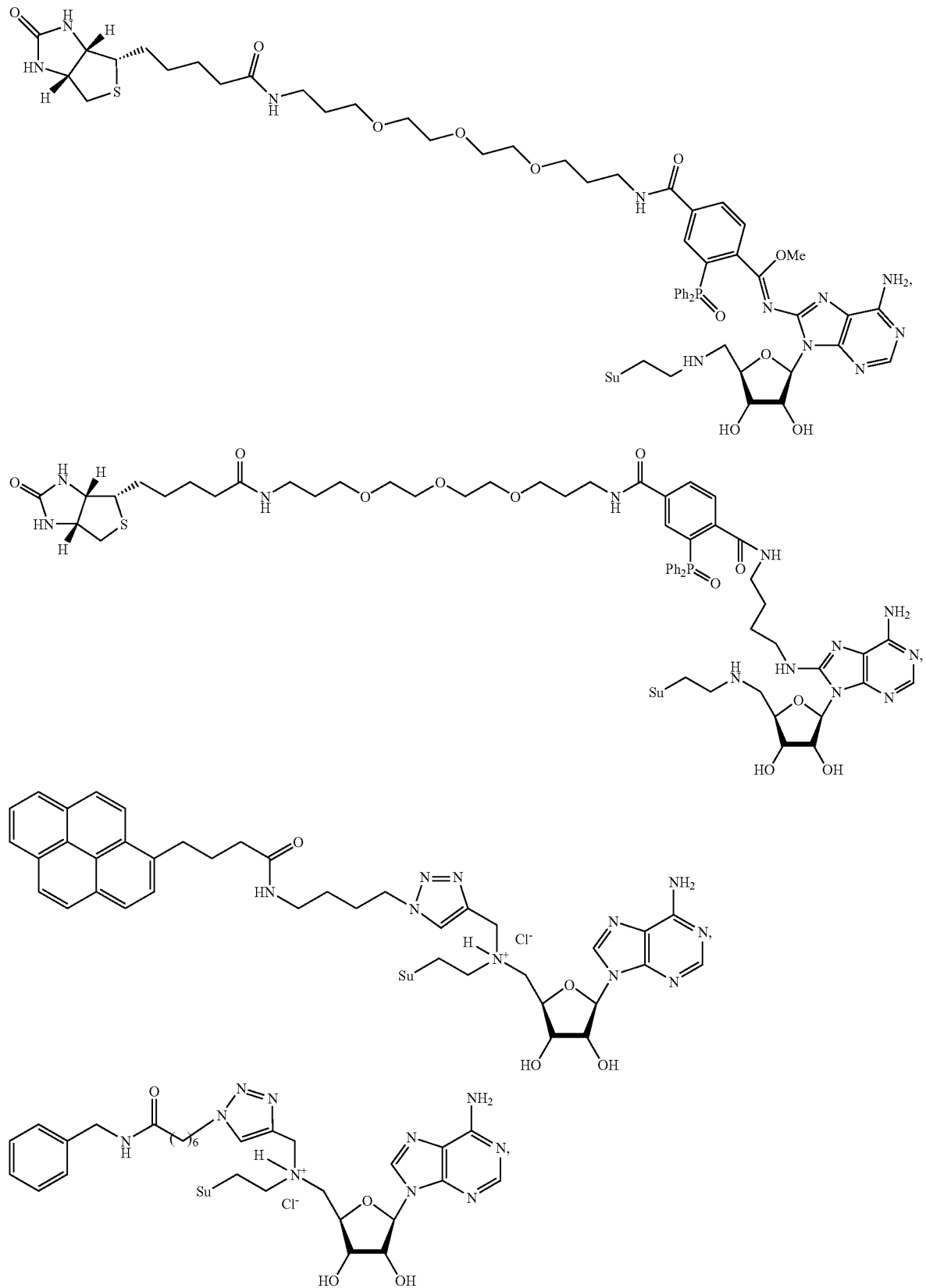

-continued
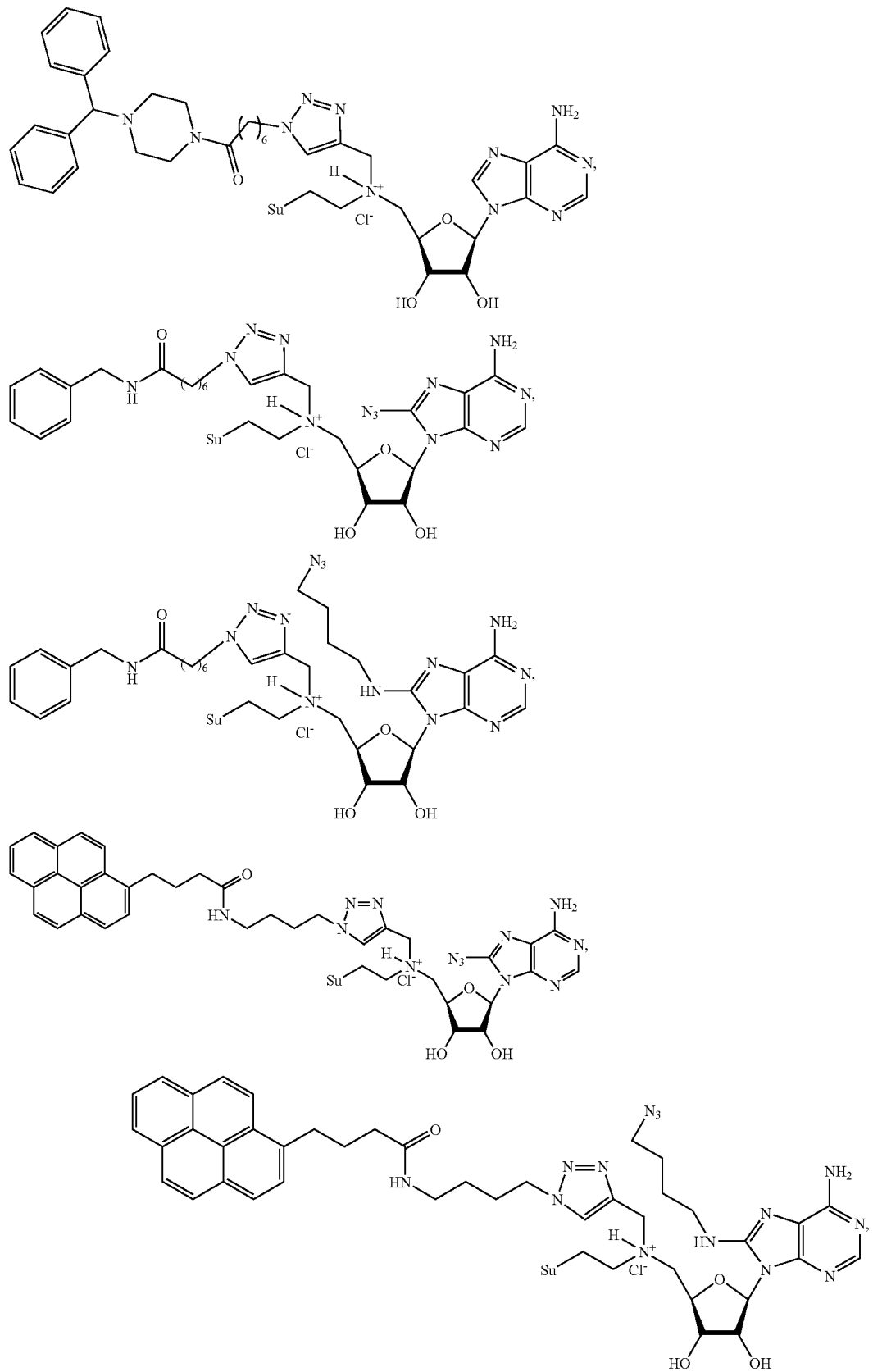

-continued
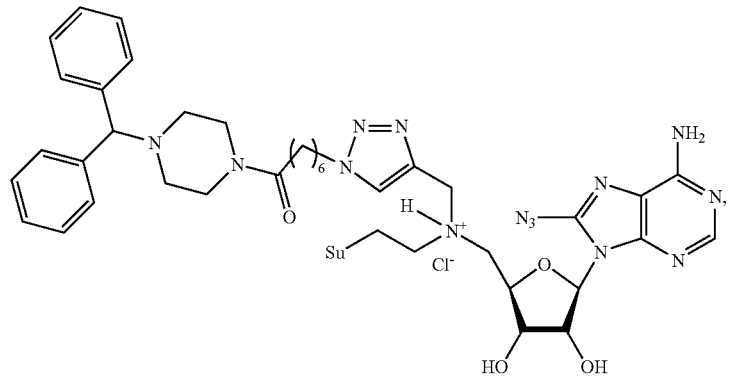
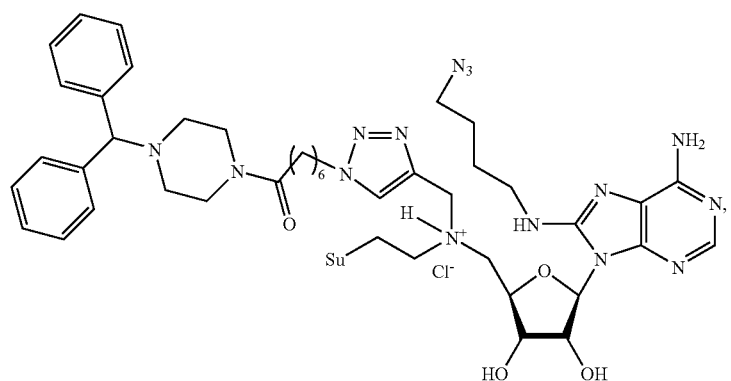
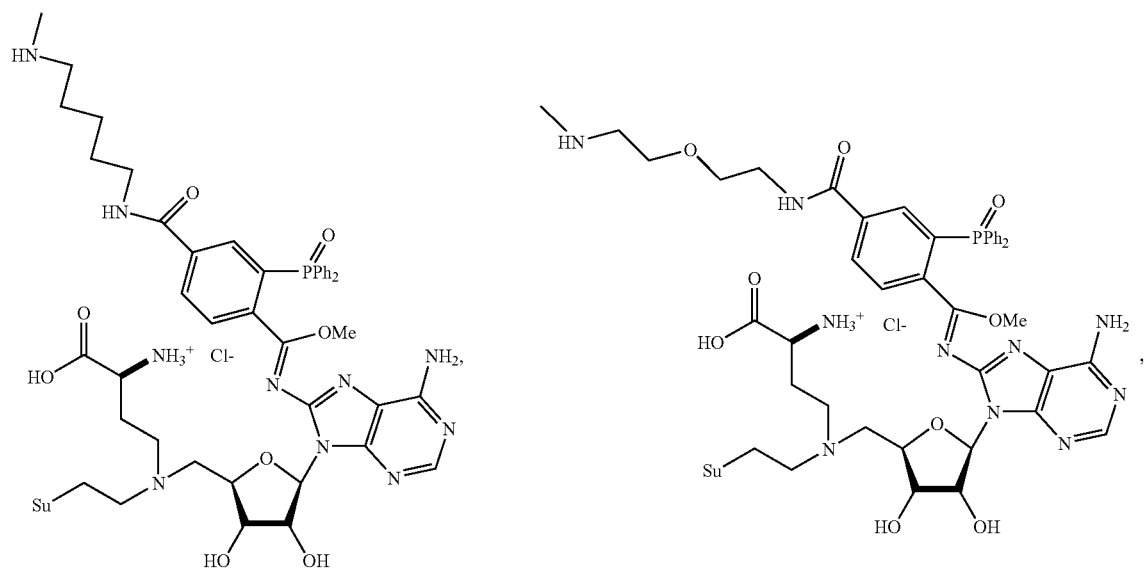

-continued
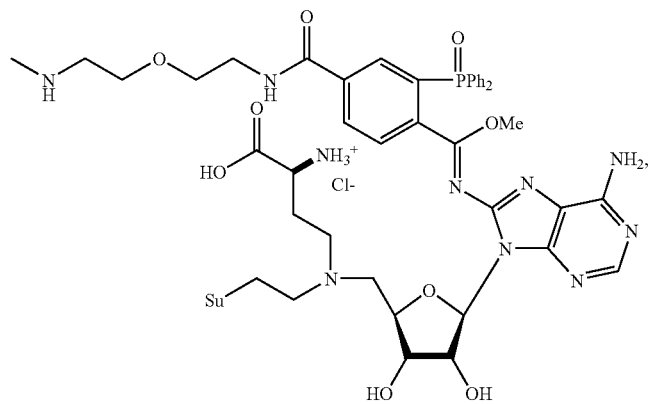
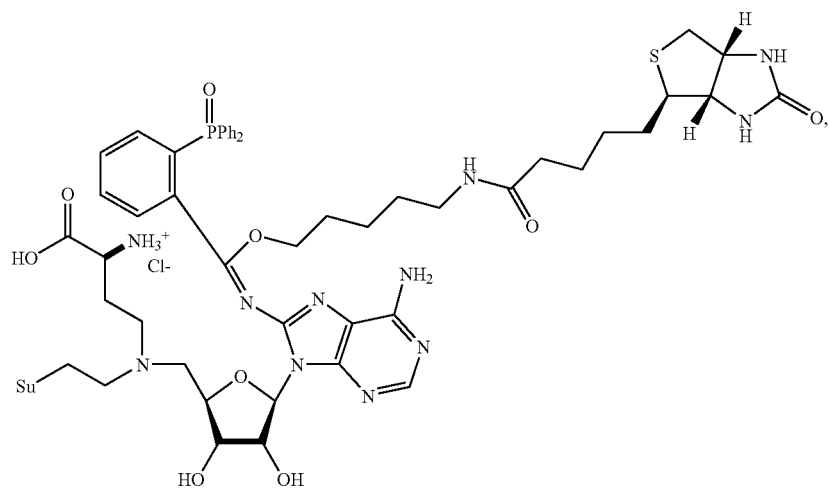
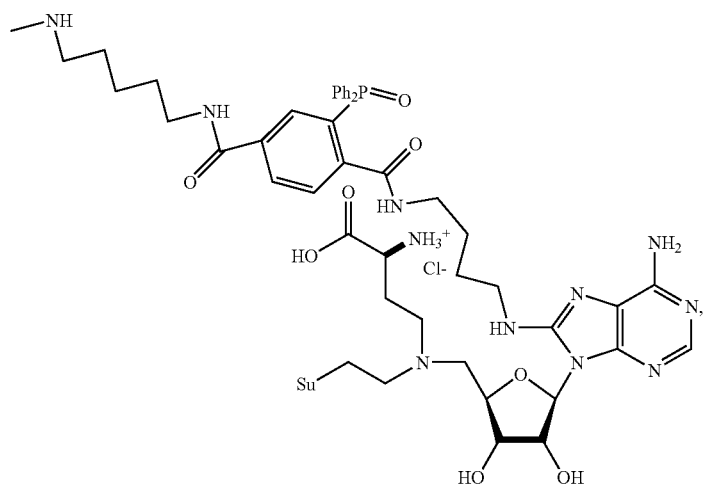

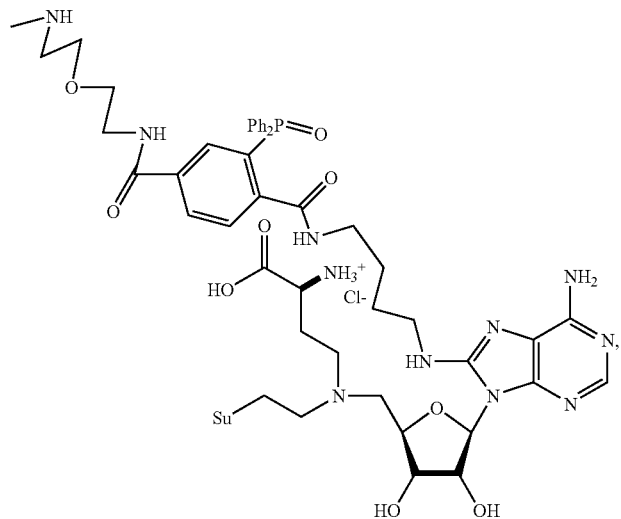
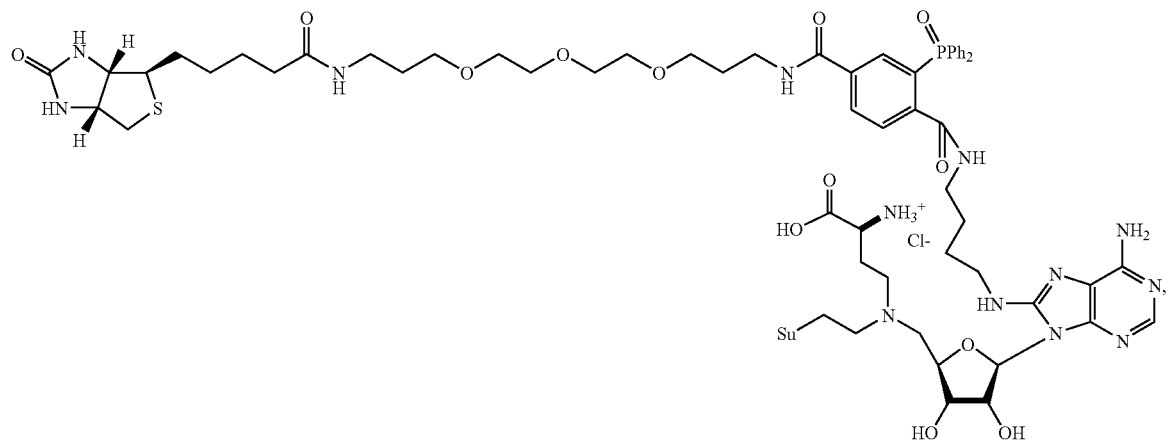
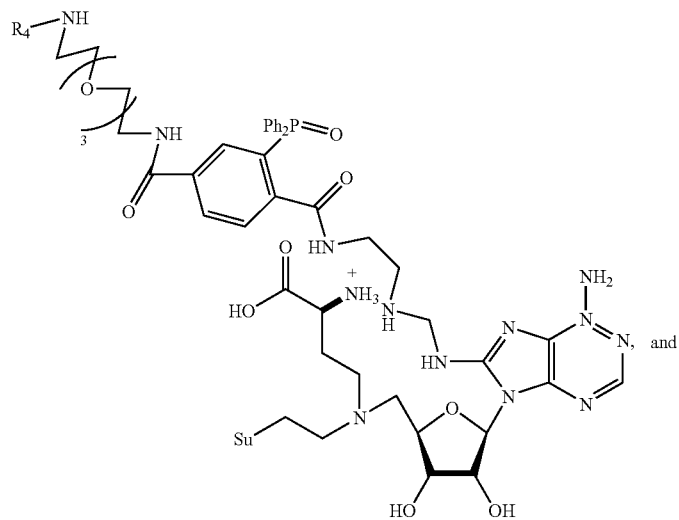

-continued

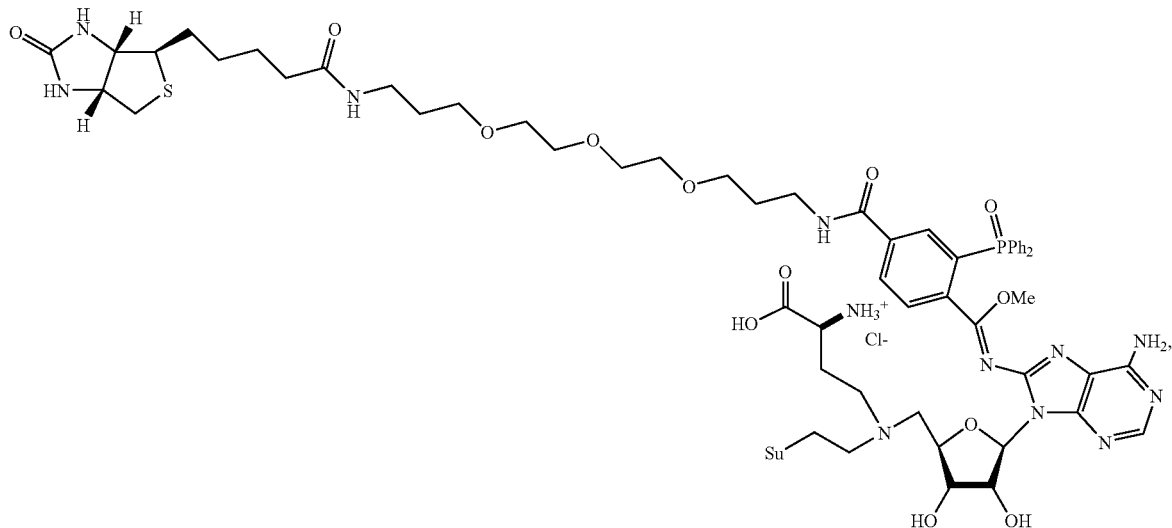

where $R_4$ is selected from the group consisting of H, $CH_3$ and

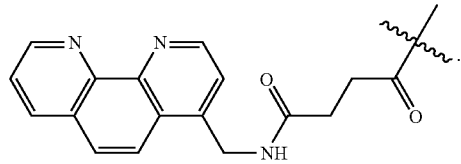

In other preferred embodiments, the invention comprises a method of derivatizing a methyl transferase substrate comprising: providing a methyltransferase substrate; providing a methyltransferase and providing a cofactor analog. In these preferred embodiments, the cofactor analog is modified at the 5' carbon atom to result in site-specific covalent ligation of the cofactor analog to the methyltransferase substrate by the methyltransferase. In these embodiments, the cofactor analog further includes at least one reacting group allowing for ligation of the cofactor analog to a detectable label. In these embodiments, the reacting group includes an azido moiety or a carboxy moiety.

In other preferred embodiments, the method further includes ligating a detectable label to the reacting group. In some versions of those embodiments, the cofactor analog is selected from the group consisting of:

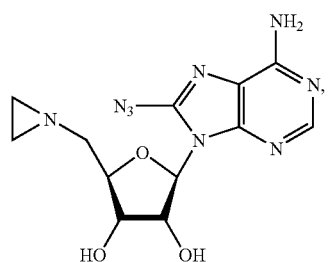

-continued

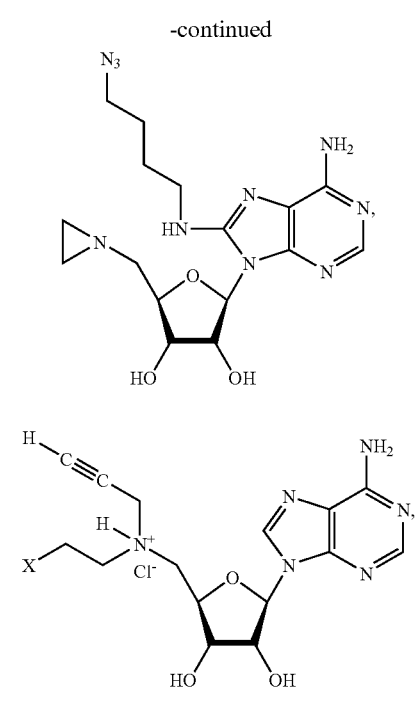

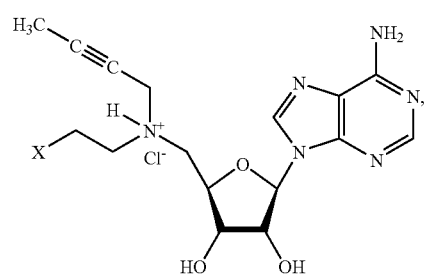

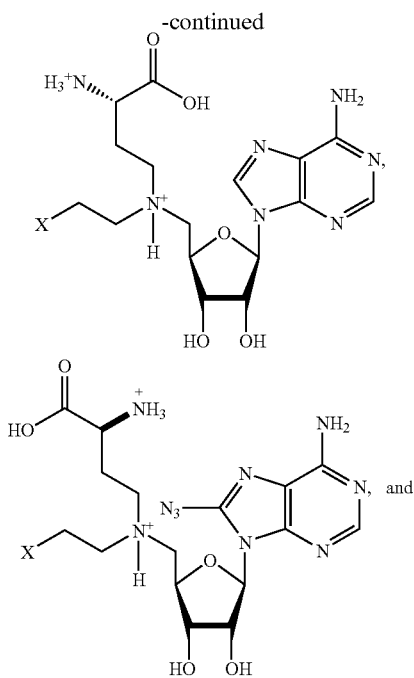
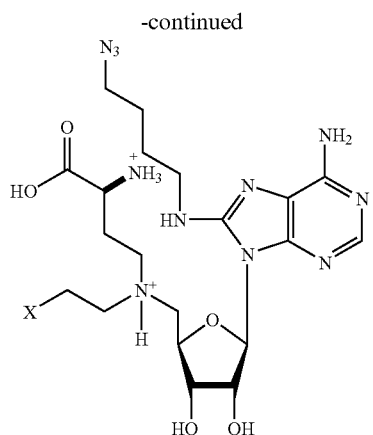
where X is a leaving group such as a halide selected from the group consisting of F, Cl, Br and I or a tosylate (OTs), mesylate (OMs) or triflate (OTf).
In preferred embodiments, where the invention includes a detectable label, the detectable label may be selected from the group consisting of:
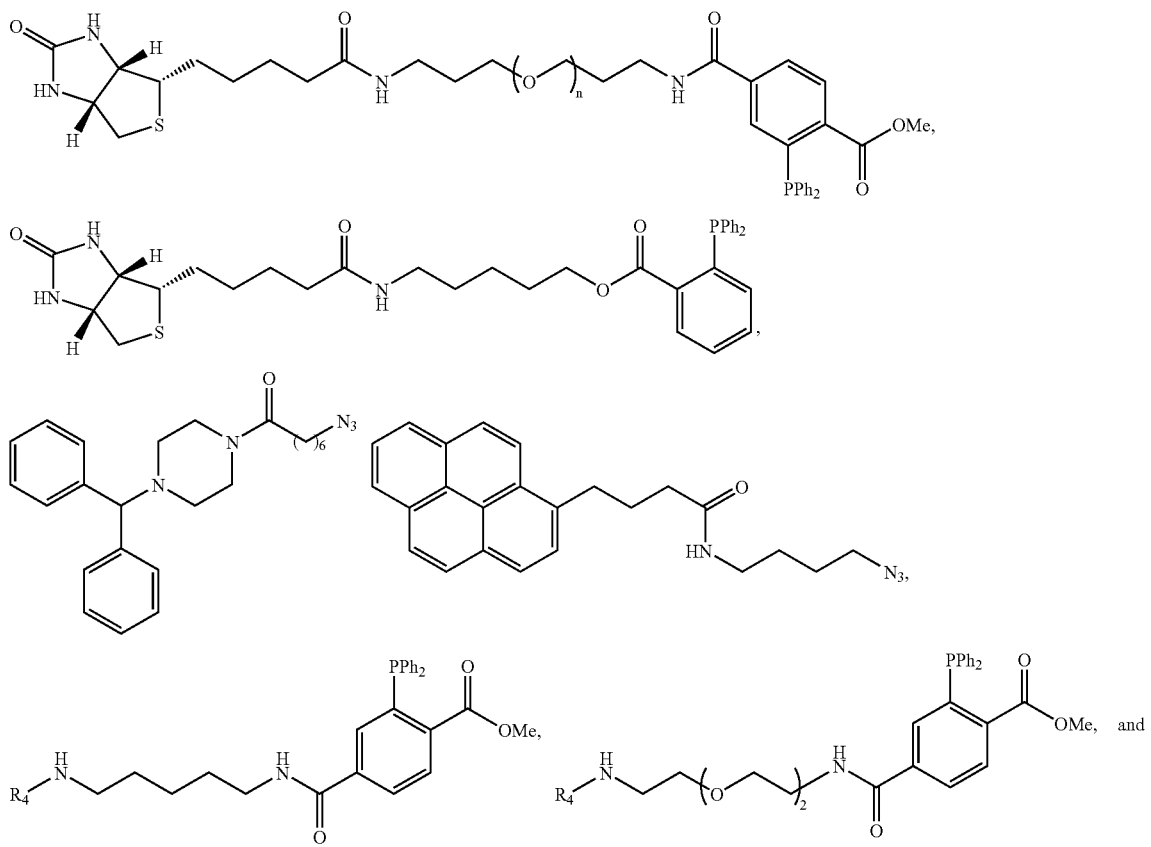

-continued

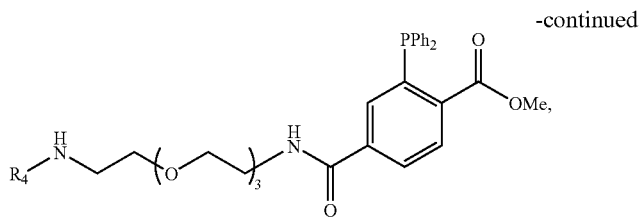

where n is 1, 2, 3 or 4 inclusive, and where $R_4$ is H, $CH_3$ or

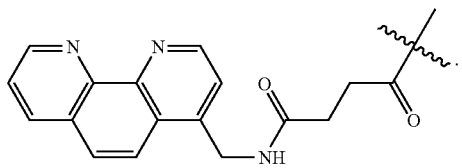

In some preferred embodiments, $R_4$ is a phenanthroline derivatized triarylphosphine.

In those preferred embodiments when $R_4$ is a triarylphosphine, the method further includes contacting the triarylphosphine-linked cofactor analog with Cu(I)—resulting in substrate scission. In these preferred embodiments, substrate scission occurs at a methylation site on the substrate.

In some preferred embodiments of the method, the ligation of the detectable label to the cofactor analog is the result of a modified Staudinger reaction comprising coupling of an azide and a carboxylic acid or a [2+3] cycloaddition reaction. In some preferred embodiments, where the detectable label includes a biotin moiety, the method further comprises the step of contacting the biotin moiety with an avidin-linked moiety. In some embodiments, the avidin-linked moiety includes a reporter moiety. In various preferred embodiments, the reporter moiety is selected from the group consisting of: a fluorescent moiety, a chromophore moiety, a radionuclide moiety or a quantum dot moiety.

In another preferred embodiment, the invention comprises a method of determining the methylation state of substrate comprising: providing a substrate and contacting the substrate with a cofactor analog, to create a mixture, contacting the mixture with a methyltransferase to create a complex; and detecting complex formation. In some preferred embodiments, complex detection is accomplished by gel electrophoresis, phosphorimaging, spectroscopy or photoluminescence.

In some preferred embodiments, the method further includes contacting the complex with Cu(I)—resulting in Haber-Weiss mediated cleavage of the substrate. In those embodiments, identification of the cleavage products provides a methylation footprint of the substrate. In some embodiments identification of the cleavage products is achieved by electrophoresis.

In other preferred embodiments, the invention also includes a kit comprising a cofactor analog according to formula III. In some versions of this embodiment, the kit also includes a detectable label. In particular versions, the detectable label includes a binding moiety. In some versions, the kit also includes a reporter group, the reporter group is linked to a binding partner of the binding moiety. In particular versions, the binding moiety is biotin and the binding partner is avidin or streptavidin. In some embodiments, the reporter group is a chromophore, a fluorophore, a radionuclide or a quantum dot. In other embodiments, a methyltransferase is also included in the kit.

In another preferred embodiment, the invention also includes a pharmaceutical composition comprising a cofactor analog according to formula III; and a pharmaceutically acceptable carrier.

These and other features and advantages of various exemplary embodiments of the compounds and methods according to this invention are described in, or are apparent from, the following detailed description of various preferred embodiments of the compositions and methods according to this invention.

BRIEF DESCRIPTION OF THE FIGURES

Various exemplary embodiments of the methods of this invention will be described in detail, with reference to the following figures, wherein:

FIGS. 1A and 1B show results of DNA alkylation reactions of R.EcoR I linearized pUC19 by aziridine cofactor analogs 3, 24a and 24b. Reaction mixtures were prepared by addition of appropriate stock solutions to a total volume of 20 µL containing 14.3 nM DNA buffered with 20 mM Tris-OAc (pH 6.0), 50 mM KOAc, 10 mM Mg(OAc)$_2$, 0.01% Triton-X100. The mixtures were analyzed on a 2% agarose gel run at 120 volts for 2 h. FIG. 1A: Increase in M.TaqI concentration. Lane 1: DNA; lane 2: DNA, 100 µM cofactor analog 3, R.Taq$^\alpha$ I; lane 3: DNA, 100 µM 1, 20 nM M.TaqI, R.Taq$^\alpha$ I; lane 4: DNA, 100 µM 3, 100 nM M.TaqI, R.Taq$^\alpha$ I; lane 5: DNA, 100 µM 3, 200 nM M.TaqI, R.Taq$^\alpha$ I; lanes 6-9: same as lanes 2-5, but with aryl azide cofactor analog 24a; lanes 10-13: same as 2-5, but with alkyl azide cofactor analog 24b; lane 14: DNA, R.Taq$^\alpha$ 1. FIG. 1B: Increase in cofactor analog concentration. Lane 1: DNA; lane 2: DNA, 200 nM M.TaqI, R.Taq$^\alpha$ I; lane 3: DNA, 10 µM cofactor analog 3, 200 nM M.TaqI, R.Taq$^\alpha$ I; lane 4: DNA, 50 µM 3, 200 nM M.TaqI, R.Taq$^\alpha$ I; lane 5: DNA, 100 µM 1, 200 nM M.TaqI, R.Taq$^\alpha$ I; lanes 6-9: same as lanes 2-5, but with aryl azide cofactor analog 24a; lanes 10-13: same as lanes 2-5, but with alkyl azide cofactor analog 24b; lane 14: DNA, R.Taq$^\alpha$ I.

FIG. 2A: reaction mixtures were prepared by addition of appropriate stock solutions to a total volume of 20 µL containing 1 µM DNA buffered with 20 mM Tris-OAc (pH 6.0), 50 mM KOAc, 10 mM Mg(OAc)$_2$, 0.01% Triton-X100, 100 µM specified cofactor analog, and 6 µM M.TaqI. FIG. 2B: Reaction mixtures were prepared by addition of appropriate stock solutions to a total volume of 20 µL containing 1 µM DNA buffered with 10 mM Tris-Cl (pH 7.4), 50 mM NaCl, 0.5 mM EDTA, 0.01% Triton-X100, 100 µM specified cofactor analog, and 2 µM M.EcoRI. Samples that were subjected to ligation conditions were brought to a final DNA concentration of 500 nM and contained a 20-fold excess of triarylphosphine. The mixtures were analyzed on a 20% DPAGE ran at 1800 V for 2 h. For the above FIGS. 2A and 2B, components that are present in the reaction are denoted by a '+'; components that are absent are denoted by a '−'.

FIGS. 3A and 3B show immobilization of DNA-biotin conjugates on streptavidin-agarose. Reaction mixtures were incubated for 1 h, followed by washing with 1M NaCl (×3). The amount of DNA retained was quantitated by scintillation counting. FIG. 3A: Binding reactions performed on 25a. Bar 1. 25a+DMF, Bar 2. 25a+41, Bar 3. 25a+43. FIG. 3B: Binding reactions performed on 5b. Bar 1. 5b+DMF, Bar 2. 25b+41, Bar 3. 25b+43.

FIG. 18A DNA modified with M.TaqI. Lane 1: DNA standard; Lane 2: duplex 6; Lane 3: duplex 6-72; Lane 4: duplex 6-73; Lane 5: duplex 6-74. FIG. 18B. DNA modified with M.HhaI. Lane 1: duplex 7; Lane 2: duplex 7-72; Lane 3: duplex 7-73; Lane 4: duplex 7-74.

DETAILED DESCRIPTION OF THE EXEMPLARY EMBODIMENTS

Figures 2A, 2B:
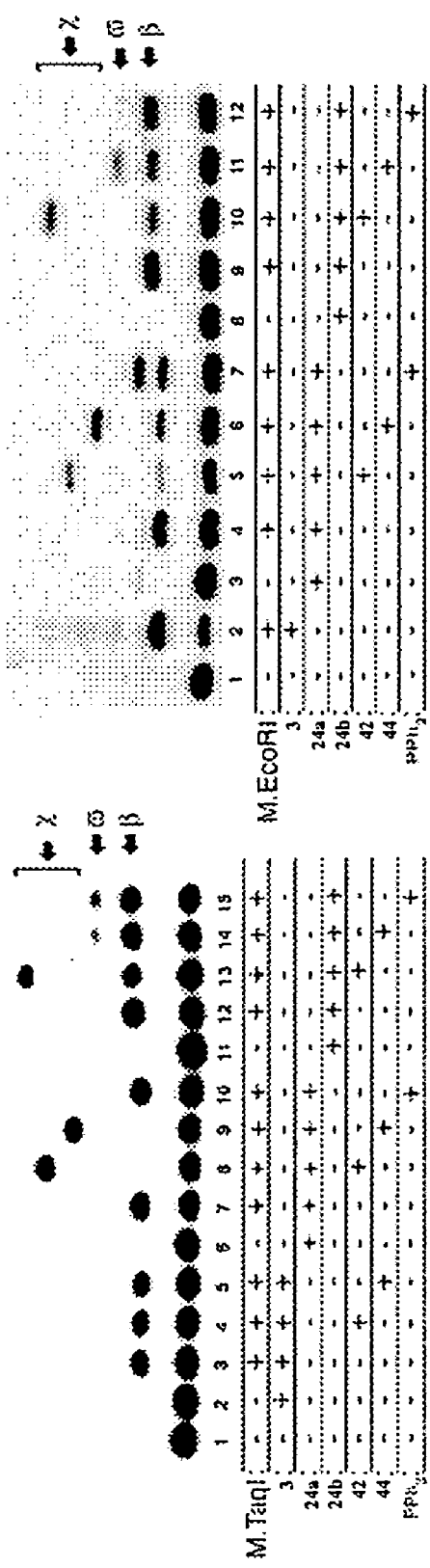
FIGS. 2A and 2B show the DNA alkylation reaction of a synthetic oligonucleotide by aziridine cofactor analogs 3, 24a and 24b and the Staudinger ligation of resulting alkylation products.

Before the present invention is described, it is understood that this invention is not limited to the particular methodology, protocols, nucleic acid sequences, and reagents described, as these may vary. It is also to be understood that the terminology used herein is for the purpose of describing particular embodiments only, and is not intended to limit the scope of the present invention which will be limited only by the appended claims.

As defined herein "incubating" and "incubation" means to maintain under specified conditions in a controlled or artificial environment. "Substrate" means a substance that is acted upon by an enzyme during a biochemical reaction. Contacting means that the components of the reaction used in the present invention are introduced to a substrate in a test tube, flask, tissue culture, chip, array, plate, microplate, capillary, or the like and incubated at a temperature and time sufficient to permit a reaction to occur. "Reacting group" means a chemical substance that takes part in a biochemical reaction. "Cleave" or "cleavage" means the rupture of a chemical bond in a molecule with the formation of a smaller molecule, e.g. "scission". "Ligate" means to join molecules or molecular fragments together with a bond. "Ligatable" means molecules that can be ligated. "Nucleic acid" means linear polymers of nucleotides linked by 3',5' phosphodiester bonds. The nucleic acids can be single stranded or double stranded and can be composed of deoxynucleotides or ribonucleotides. "Oligonucleotide" refers to a nucleic acid composed of up to 20 nucleotides. "Polynucleotide" refers to a nucleic acid polymer greater than 20 nucleotides. As used herein, "nucleic acid" includes oligonucleotides and polynucleotides. "Peptide nucleic acid" (PNA) refers to a molecule similar to DNA or RNA but its backbone is composed of repeating N-(2-aminoethyl)-glycine units linked by peptide bonds. PNA molecules are mimics of DNA.

As used herein, a "detectable label" has the ordinary meaning in the art and refers to an atom (e.g., radionuclide), molecule (e.g., fluorescein, chromophore), or molecular complex (e.g. biotin), that is or can be used to detect (e.g., due to a physical or chemical property), indicate the presence of a molecule or to enable binding of another molecule to which it is covalently bound or otherwise associated. The term "label" also refers to covalently bound or otherwise associated molecules (e.g., a biomolecule such as an enzyme) that act on a substrate to produce a detectable atom, molecule or complex. Detectable labels suitable for use in the present invention include any composition detectable by spectroscopic, photochemical, biochemical, immunochemical, electrical, electrophoretic, optical or chemical means.

As used herein reporter moieties means a chemical moiety that is directly or indirectly detectable. Examples of functional parts of reporter moieties are biotin; digoxigenin fluorescent proteins, chromophores, quantum dots, radioisotopes, chemiluminescent labels, spin labels, enzymes (such as peroxidases, alkaline phosphatases, beta-galactosidases, and oxidases), antigens, antibodies, haptens, etc. For example, reporter moieties useful in the present invention include biotin for staining with labeled streptavidin conjugate, magnetic beads (e.g., Dynabeads™), fluorescent dyes (e.g., fluorescein, Texas red, rhodamine, green fluorescent protein, enhanced green fluorescent protein, and the like), radiolabels (e.g., $^3H$, $^{125}I$, $^{35}S$, $^{14}C$, or $^{32}P$), enzymes (e.g., hydrolases, particularly phosphatases such as alkaline phosphatases, esterases and glycosidases, or oxidoreductases, particularly peroxidases such as horse radish peroxidase, and others commonly used in ELISAs), substrates, cofactors, inhibitors, chemiluminescent groups, chromogenic agents, and colorimetric labels such as colloidal gold or colored glass or plastic (e.g., polystyrene, polypropylene, latex, etc.) beads.

Patents teaching the use of detectable labels and reporter moieties include U.S. Pat. Nos. 3,817,837; 3,850,752; 3,939,350; 3,996,345; 4,277,437; 4,275,149; and 4,366,241. Means of reporter moieties are well known to those of skill in the art. Thus, for example, radiolabels and chemiluminescent labels may be detected using photographic film or scintillation counters, fluorescent markers may be detected using a photodetector to detect emitted light (e.g., as in fluorescence-activated cell sorting). Enzymatic labels are typically detected by providing the enzyme with a substrate and detecting the reaction product produced by the action of the enzyme on the substrate, and colorimetric labels are detected by simply visualizing the colored label. Thus, a reporter moiety is any composition detectable by spectroscopic, photochemical, biochemical, immunochemical, electrical, optical or chemical means. When quantum dots are the reporter moiety, different emission wavelengths may be selected for which the excitation energy is the same.

In the synthetic schemes disclosed herein, some of the steps illustrated require hydroxy-protecting groups. Hydroxy-protecting groups particularly shown include triethyl silyl (abbreviated, $Et_3Si$ or TES) and tert-butyldimethylsilane (TBS), both used for the temporary protection of hydroxy functions. In some cases the use of TBS and TES groups are interchangeable. Other groups commonly used for the temporary protection of hydroxy functions, include, for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatized or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

Recently, new methods have been identified to use non-biological chemical reactions to provide biological constructs with functional ligation products. Classically, phosphorus derivatives are often used to convert azides to amides by taking advantage of the Staudinger reaction (Staudinger, H. and J. Meyer, Helv. Chem. Acta. 2:619-635 (1919)). In this transformation, a phosphine or phosphite reacts with an azide to yield a phosphorimine (phosphazene). These nucleophilic phosphorus derivatives can be coupled with a carboxylic acid to give amide and phosphine oxide (Zaloom, J. et al., J. Org. Chem. 50:2601-2603 (1985); Homer, L. and A. Goss, Liebigs Ann. Chem. 591:117-134 (1955); Garcia, J. et al., Tetrahedron Lett. 25:4841-4844 (1984)). A modified Staudinger reaction termed the "Staudinger ligation" has been used to link phosphine groups to cell surface sugars bearing azide groups. Similarly, the (2+3) cycloaddition (sometimes referred to as a Huisgen cycloaddition) is the ligation of a dipolarophile with a 1,3-dipolar compound that leads to 5-membered heterocycles. Cycloaddition reactions can be defined as any reaction between two (or more) moieties (either intra or intermolecular) where the orbitals of the reacting atoms form a cyclic array as the reaction progresses (typically in a concerted fashion although intermediates may be involved) along the reaction coordinate leading to a product.

DNA interstrand cross-linking is one of the most potent and useful forms of DNA modification. Uses of DNA modification range from the pharmaceutical and clinical to diagnostic and research. For example, in chemotherapies cross-linking selectivity often results due to drug activation processes attributed to oxidizing or reducing environments characteristic of diseased cells. Indeed, gene therapy has been exploited as an effective means of attenuating drug action based upon overexpression of certain enzymes associated with these environmental conditions. In addition, many DNA sequence-selective targeting methods have been developed resulting in impressive selectivities and affinities. Surprisingly, the exploitation of enzymatic DNA modification mechanisms has received considerably less attention. Such an approach has advantages over traditional methods. First, the sequence specificity of DNA alkylation results not from a small molecule/DNA interaction, but rather a protein/DNA interaction making the reaction highly specific. Second, the association of a drug with the DNA modifying enzyme affords a drug trafficking mechanism potentially capable of shielding the drug from inactivating species such as cytosolic nucleophiles or oxidants. In diagnostic or research uses, DNA crosslinking is used method to measure methylation state or methyltransferase activity is through use of radiolabeled S-adenosyl-L methionine (SAM). However, radiolabeled reagents, while generally effective, are dangerous, costly and time-consuming to use.

The present invention exploits the ability of analogs of S-adenosyl-L-methionine to undergo specific covalent anchoring to biomolecules that are ordinarily methylated by methyltransferases. The disclosed cofactor analogs effectively convert biological methyltransferases into nucleoside transferases. Because the SAM analogs disclosed herein have an azide or alkyne moiety that is biologically inert, yet able to ligate with selected other substances, the biomolecules bearing azide or alkyne-linked cofactor analogs are amenable to facile isolation from complicated biological mixtures and identification and sequencing. This technology allows the isolation and identification of biological methyltransferase substrates in a way that is not currently available. Further, the cofactor analogs described herein are compatible with a wide range of biological methylases and the isolation step does not require the biasing use of antibodies.

Methylations at cytosine $C^5$ and $N^4$ and at adenosine $N^6$ play an integral role in prokaryotic defense mechanisms. In eukaryotes, a large body of data has revealed excellent correlation between DNA methylation and gene repression (Razin, A.; Cedar, H., 1991 Microbiol. Rev., 55, 451-458). Silenced genes are generally methylated in their regulatory regions whereas their expressed counterparts are unmethylated. Genes differentially expressed in different tissues are differentially methylated (Siegfried Z.; et al., 1999 Nat. Genet., 22, 203-206). Aberrant DNA methylation is inherent in a number of oncogenic processes and is thought, in some cases, to be a leading contributor to carcinogenesis. Thus, agents capable of taking part in or deterring Mtase-dependent transcriptional errors can be clinically important. For instance, regions of the genome that might be improperly repressed due to aberrant methylation of CpG units (a signature of numerous cancers) might be de-repressed by the replacement of DNA bound methyl groups with non-natural moieties. Indeed the concept of "cofactor mimicry" offers abundant chemotherapeutic opportunity through alterations of transcriptionally relevant molecular recognition processes, as well as from the simple standpoint of sequence specific DNA damaging moieties.

Various exemplary embodiments of methods according to this invention are described in the following illustrative examples. In these examples, specific products identified by Arabic numerals (e.g., 1, 2, 3, etc.) refer to the specific structures so identified in the following description and in SCHEMES I-XIX.

SCHEME I

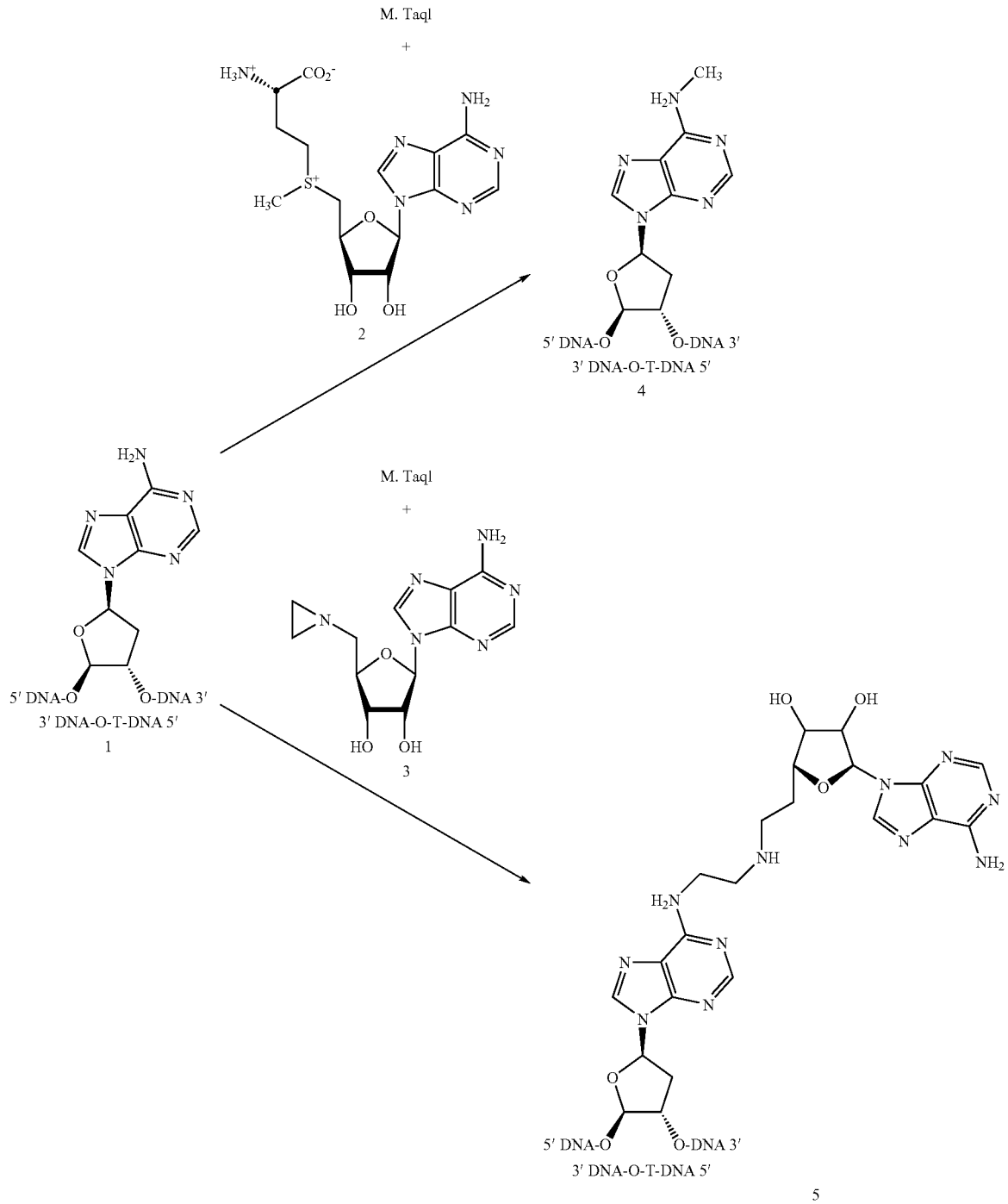

As shown in SCHEME I, the C-5' aziridine 3 affords a substitute for SAM 2 in the M.TaqI catalyzed alkylation of adenine within the recognition sequence 5'TCGA3' where 1 represents an unmethylated DNA residue, 2 represents the native SAM molecule and 4 represents a native adenine residue methylated at its $N^6$ position. When the synthetic cofactor analog 3 is used, instead of generating the $N^6$ methylated dA residue, substrate adenylation is accomplished via ring-opening of the aziridine generating a 3 conjugated adenine residue in a DNA strand 5. Importantly, the regiochemistry of DNA substrate modification is identical to the S-adenosyl-L-methionine 2 dependent methylation. Notably, a fluorescent analog of 3 has also been shown to substitute for SAM in the $C^5$ cytosine alkylation by M.HhaI DNA methyltransferase (Pignot, M.; et al., International Patent Pub. No. WO 00/06587, U.S. Pat. No. 6,875,750).

The stability of the free base 3 led the inventors to investigate whether such a cofactor analog structure may be amenable to conjugation with other DNA-reactive functionalities thus affording access to synthetic agents which derive biological activity (as a function of DNA sequence selectivity) from selected methyltransferases. The design and synthesis of such agents resulted in the development of a highly efficient route to "tetherable" analogs of 3 and the investigation and use of Gabriel-Cromwell aziridination for rapid access to the desired agents.

There are few examples of efficient N-alkylation of aziridines with alkyl halides and sulfonates; condensations with yields >90% typically involve benzyl halides (Tanner et al., Tetrahedron, 1998, 54, 14213-14232) and results in contamination of the synthesis products requiring further purification. This contamination, coupled with the anticipated limitations on possible coupling components, facilitated the development of alternative methodologies by which functionalized aziridines could be appended to adenosine at the 5' position. Critical to these other methodologies was an efficient means of obtaining on large scale, 5'-aminoadenosine or related congeners bearing suitable hydroxy protection at the 2' and 3' positions.

While it is shown here that both azide and alkyne-bearing cofactor analogs can be enzymatically linked to substrates, such as, for example, plasmid DNA and small oligodeoxynucleotides by methyltransferases, the inventors herein also show that azide and carboxy reacting groups present of the analogs also provide a convenient means to further modify such cofactor analogs. For example, azide or carboxy bearing cofactor analogs are readily amendable to a modified Staudinger or cycloaddition reaction with a suitable reacting group-bearing moiety, such as a detectable label. While derivatization of methyl transferase substrates by cofactor analogs is readily detectable by, for example, an electrophoretic shift, the presence of stably linked reacting groups on the cofactor provides a handle to further derivatized such analogs by the addition of reacting group-bearing moieties, such as, for example, a detectable label.

The derivatization of methylase substrates as described herein provides, at least, two very different uses for the cofactor analogs. First the label allows the direct identification of the site of cofactor analog linkage, e.g. the physiological site of substrate methylation. Such labeling allows the direct identification of methylated or non-methylated state of naturally occurring methylase substrates, rather than by inference as is currently the state of the art. Second, radiolabeled or chemo-labeled cofactor analogs may provide a site specific therapeutic in cases where aberrant methylation affects gene transcription. For example, results reported herein confirm that DNA which is conjugated with the cofactor analogs disclosed is not available for further methylation. Thus, gene transcription and expression may be directly altered.

Expression of nucleotide residues that have been de-methylated, and hence expressed, can be modulated by conjugation with a synthetic cofactor analog bearing a radiolabel. In such instances, the radiolabel is tethered directly to the gene, inhibiting gene translation while resulting in DNA damage. In addition, genes undergoing transcription are hemimethylated, allowing greater access for binding of the cofactor analog to the DNA. Consequently, this phenomenon results in greater inhibition and/or destruction of actively transcribed genes and provides a use for therapeutics resulting in DNA damage and/or altered gene transcription having direct application to gene silencing of oncogenes, tumorigenic gene products and disease states resulting from aberrant transcription. Further, recent research shows that compounds such as the various cofactor analogs described can function as competitive inhibitors of methyltransferases by competing with the native cofactor (Bjelakovic, G, et al., Competitive Inhibitors of Enzymes and their Therapeutic Application, (2002) FACTA Universities, 9(3) 201-206). Such cofactor analogs can function as "blockades" for polymerases and/or exonucleases and identify regions of methylation in nucleic acids and give single-nucleotide resolution without requiring a ligation step. In such instances, the large variety of cofactor analogs described here, while having potentially valuable therapeutic significance provide novel instruments with which to investigate enzyme mechanisms and identify metabolic pathways.

By identifying cofactor analogs that are amenable to ligation by native methyltransferases, the compounds described herein can also be used to monitor methyltransferase activity and/or substrate specificity in cell lysate studies. Such studies include identifying the presence of methylated nucleic acid residues implicated in a variety of developmental disorders and aberrant protein methylations which are diagnostic of malignant or cancerous disease states.

For example, when used to identify methylase substrates or methylation state of genomic material, use of the present invention would considerably simplify the methods taught in U.S. Pat. No. 6,617,434 and published U.S. Patent Application 2003/0082609 whereby multiple enzymes and/or pre-treatment steps are relied on to determine methylation state. The present invention allows determination of the overall methylation state by allowing a genomic digest to be contacted with the cofactor analogs of the present invention followed by a modified Staudinger reaction or (2+3) cycloaddition with a detectable label-bearing reacting group. In various exemplary embodiments, the reacting group may comprise a phosphine moiety allowing for a modified Staudinger reaction with the azide present on the cofactor analog. In other embodiments, the reacting group may include an azide moiety allowing for Huisgen cycloaddition with the alkyne present on the analog. In other exemplary embodiments, the detectable label may include an affinity tag or binding moiety, such as, for example, biotin or calmodulin binding protein (CBP) or bearing a reporter moiety such as a radiolabel, a fluorophore, a chromophore or a quantum dot. When an affinity tag is used, such as, for example biotin, the cofactor ligated substrate can easily be purified using an avidin-linked matrix. When a reporter moiety is used, such as, for example a radiolabel, a chromophore, a fluorophore or a quantum dot is used the presence of the reporter moiety can be detected by methods well established in the arts, such as, for example spectrophotometry, gel electrophoresis, autoradiograph or the like to directly visualize the site or sites of methylation present in a substrate.

Further, methylation state of specific genes can be determined by use of a reverse Southern blot. Such reverse Southern hybridizations are known in the art, for example, reverse Southern blots can be made on a solid substrate where specific probes are spotted on nylon membranes with a genomic digest layered on top (Herd, M. and Kocks, C., Infection and Immunity, 2001, 69: 3972-3979). Currently, probes specific to target nucleic acids may be as small as 15-25 nucleotides in length to allow specific hybridization with the target gene. As used with the instant invention, after washing to remove non-specifically bound DNA, cofactor analogs of the present invention can be contacted with the blot, in the presence of the desired MTase. Thus, the methylation state of specific genes can be determined following visualization of the bound synthetic cofactor analog by conjugation of a desired label using the modified Staudinger reaction or the (2+3) cycloaddition as described below. It should be appreciated that when a large number of genes are desired to be analyzed, DNA microchip arrays may be commercially obtained that provide a large number of specific probes for desired genes. Such arrays are commercially available such as those from Affymetrix, (Santa Clara, Calif.) and NimbleGen (Madison, Wis.), for example.

Various exemplary embodiments of compounds obtained as generally described above and methods according to this invention, will be understood more readily by reference to the following examples, which are provided by way of illustration and are not intended to be limiting of the invention in any fashion.

EXAMPLES

I. Synthesis of Aziridine-Based Cofactor Analogs

SCHEME II

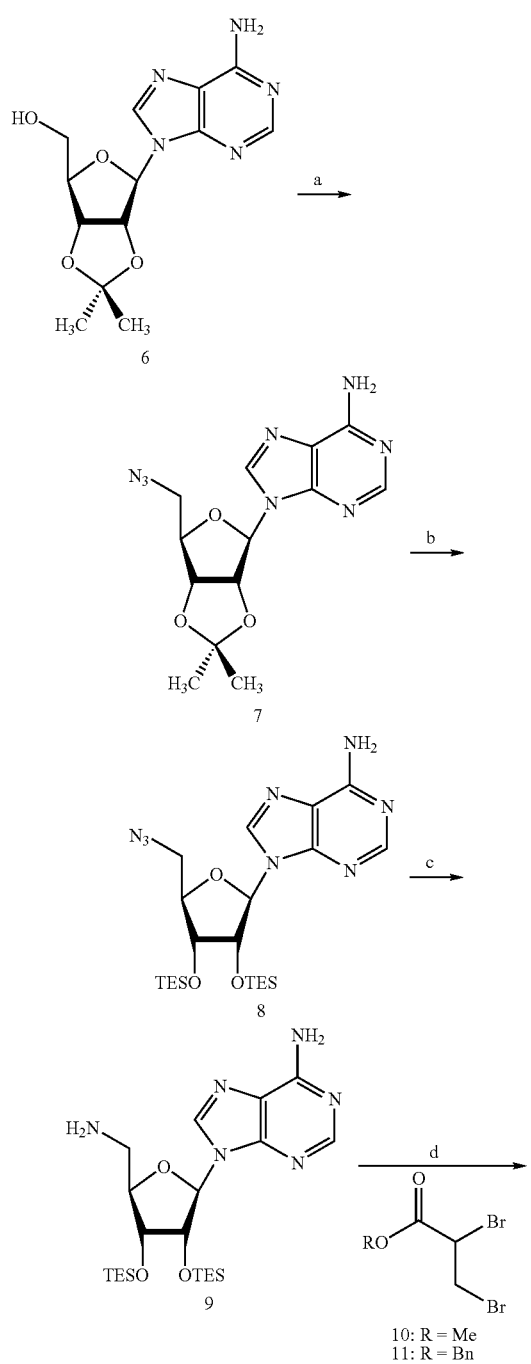

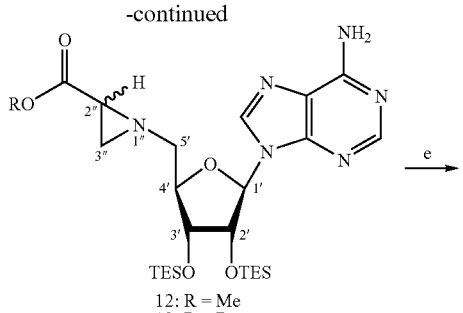

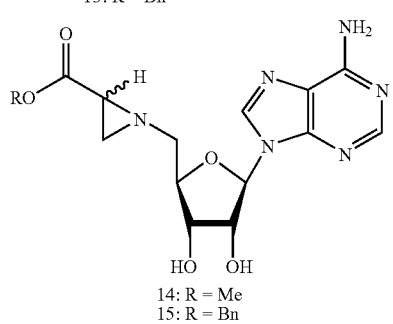

a. DPPA, PPh₃, DEAD, THF; b. 1. TFA/H₂O, 2. Chlorotriethylsilane, imidazole, DMF; c. PPh₃, THF, H₂O; d. 10 or 11, TEA, THF; e. tBu₄NF, dioxane Using a Mitsunobu variation of chemistry, the inventors found that the desired OH→NH₂ interconversion coupled with silylation of both the 2' and 3' alcohols could be most expeditiously effected by treatment of commercially available 6 with diphenylphosphoryl azide (DPPA), triphenylphosphine (PPh₃), diethylazodicarboxylate (DEAD) as shown in SCHEME II (Liu, F.; Austin, D. J., *J. Org. Chem.*, (2001) 66, 8643-8645). Azide installation in this manner proceeded in 73% yield. The azide 7 was highly amenable to acetonide cleavage with trifluoroacetic acid (Fei, L.; Austin, D. J., *Org. Lett.*, (2001) 3, 2273-2276) and subsequent 2',3' reprotection as the 2',3' bis(triethylsilyl ether) (Allerson, C. R.; Swaine, L.; Verdine, G. L., *J. Am. Chem. Soc.*, (1997) 119, 7423-7433). Disilylation permitted not only improved solubility traits throughout the remainder of the synthesis, but also allowed for a high degree of aziridine survival upon final diol deprotection. Staudinger reduction of the azide 8 ultimately afforded the highly versatile 5' amine 9 in 74% yield over three steps from azide 7 (Toyota, M.; Komori, C.; Ihara, M., *J. Org. Chem.*, (2000) 65, 7110-7113).

Although a host of chemistries have been used by the inventors to prepare such compounds, by far the most efficient hinges upon the reaction of 9 with α,β-unsaturated α-bromo carbonyl compounds. Of particular interest is the reaction of 9 with dibromopropionic methyl and benzyl esters 10 and 11. The products would present two avenues by which to conjugate DNA damaging moieties or drug delivery tools.

Treatment of amine 9 with dibromopropionates 10 or 11 in the presence of triethylamine in refluxing THF afforded diastereomeric mixtures of 5' aziridines in good (80-87%) yields. In these reactions, no protection of the adenine base is necessary. Following 5' aziridine construction, simple cleavage of the silyl ethers with TBAF affords a diastereomeric mixture of each SAM analog (Van der Wende, E. M.; et al., (1998) *J. Med. Chem.*, 41, 102-108)

In addition to enabling the rapid construction of diverse nucleoside aziridines this chemistry can generate stereodiverse populations of cofactor analogs. Diastereomeric mixtures of aziridine-based cofactor analogs were initially envisioned to be readily separable by HPLC. Although this was true in the case of the carbobenyloxy aziridines this was not the case for diastereomeric mixture 14 or its precursor 12. Efforts to remedy this entailed the exploitation of asymmetrically disposed dibromopropionate 18 and its antipode 19.

While a similar scheme has previously been employed for the synthesis of chiral benzyl aziridine-2-carboxylates the influence relies upon the ureadiyl moieties of 18 and 19. What was found was that the dibromopropionate auxiliaries ultimately afforded aziridines highly amenable to separation by conventional chromatography. Thus, although the ureadiyl moieties 18 and 19 serve partly as chiral auxiliaries for aziridination (in combination with the adenosine ribose) they also serve as separatory auxiliaries.

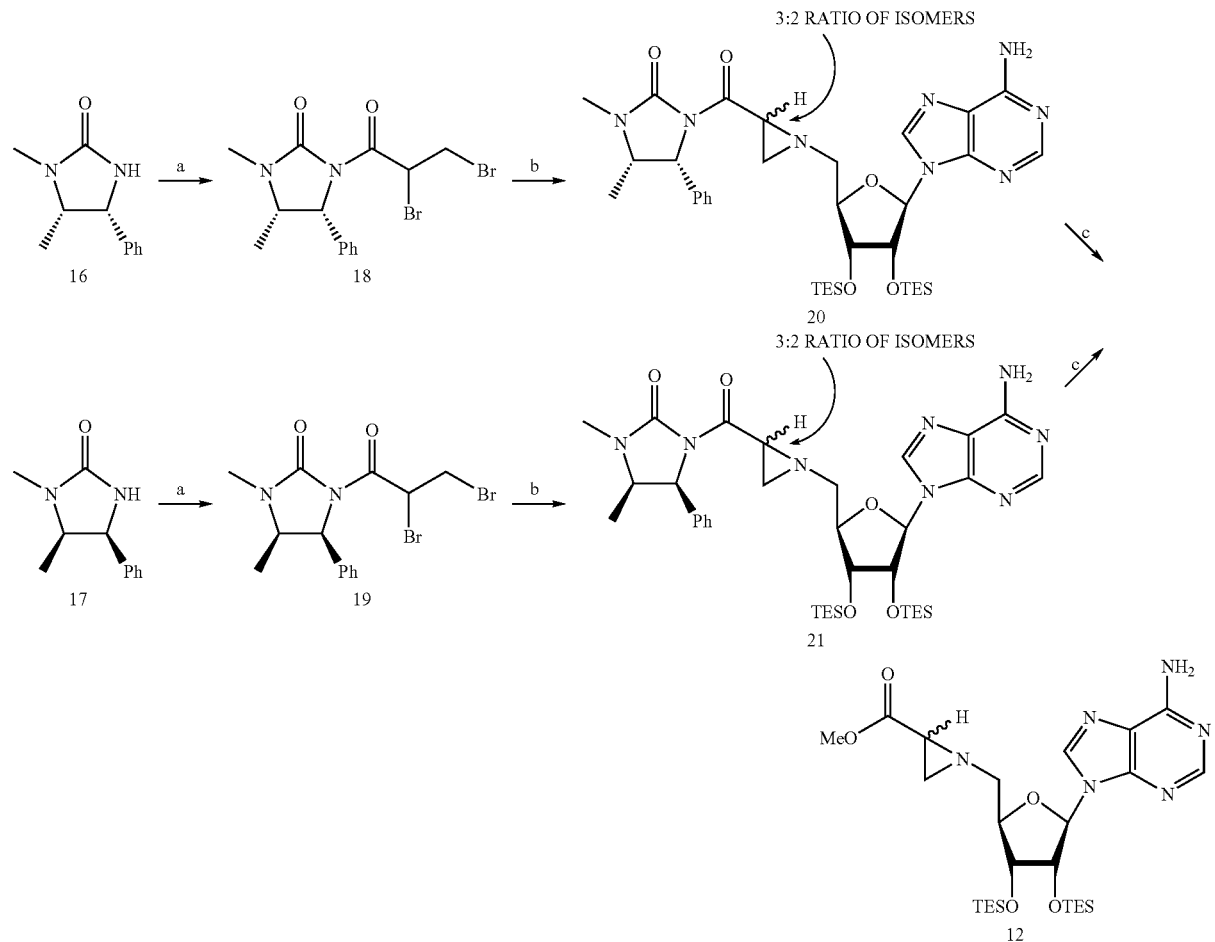

a. Dibromopropionyl Chloride, CH$_3$CN; b. TEA, THF, 4; c. TEA, MeOH aziridines reported here do not bear substituents at both aziridine carbons (Cardillo, G.; et al., (1996) *Tetrahedron: Asymmetry*, 7, 755-762). Initially, the inventors thought, on the basis of a chiral protonation step immediately following initial Michael-type addition to the transient bromoacrylate, that auxiliaries 16 and 17 might afford asymmetric induction at the brominated α carbonyl center. This was found not to be the case. Rather, regardless of dibromopropionate stereochemistry a 3:2 ratio of aziridine stereoisomers was consistently obtained. That a ratio of 1:1 is typically observed using non-chiral bromopropionates clearly indicates a stereochemical bias in the auxiliary-based system yet a mechanistic rationale for asymmetric induction regardless of auxiliary stereochemistry is not yet apparent. It is clear that the asymmetric environment of the adenosine ribose framework exerts influence upon the stereochemical outcome. However, this Having failed to assign stereochemical configuration to aziridines derived from Gabriel-Cromwell reactions with 9, the inventors sought the independent synthesis of each stereoisomer of hydroxymethyl aziridines. The conversion of methyl ester 12 to the hydroxymethyl analog was desirable for conjugation to other biologically relevant moieties. This, coupled with the ability to separate auxiliary modified aziridine stereoisomers 20 and 21 on large scale led to an important realization. As shown in SCHEME III, carboxyaziridines 20 and 21 are readily converted to methyl ester 12 upon exposure to methanolic triethylamine with 16 and 17 easily recovered intact. Exposure of each stereoisomer of 12 to LiAlH$_4$ at low temperature affords the corresponding primary alcohol 22 in 76% yield. Notably, introduction of the hydroxymethyl functionality at this point allows for selective modification of 22 with DNA modifying agents of choice, while leaving other potentially nucleophilic sites masked. Desilylation of 22 with TBAF affords 23 in 75% yield.

Finally, with a facile means by which to derive "tetherable" cofactor analogs in diastereomerically pure form, the inventors were able to assign aziridine stereochemistry. Each stereoisomer of 22 was synthesized via aminolysis of R-(+) and S-(−)O-benzyl glycidol respectively. Conversion of the resulting amino alcohols to their respective stereoisomerically pure aziridines was accomplished using Mitsunobu conditions and $^1$H-NMR chemical shifts compared with those of previously obtained Gabriel-Cromwell adducts. The synthesis of similarly substituted aziridines had been noted to be very difficult and the inventors' efforts substantiated this observation. Subjection of O-benzyl glycidol-derived amino alcohols to triphenylphosphine, and DEAD in refluxing THF afforded aziridines in ~40% yield after very careful chromatographic separation.

A remarkable difference in $^1$H chemical shifts of the C5' hydrogens based upon the aziridine stereochemistry had earlier been noted and this was again evident in the O-benzyl derived aziridines. Spectral analysis revealed the R aziridine to possess chemical shifts of 2.57 and 2.76 ppm for C5' Ha and Hb respectively. Alternatively, S aziridines demonstrate chemical shifts of 2.42 and 2.96 ppm for Ha and Hb. Using these observations the inventors assigned stereochemical configuration to all carboxy and hydroxymethyl functionalized aziridines. Further, the 3:2 ratio of Cromwell adducts obtained for compounds 20 and 21 indicates the preferred formation in both cases of the S aziridine over the R isomer.

A. General Experimental Procedures:

All reactions were carried out under an inert atmosphere of argon unless indicated otherwise. All reagents were obtained from available commercial sources and used without additional purification. Anhydrous THF was obtained from a J. T. Baker Cycle-Tainer (Mallinckrodt Baker, Phillipsburg, N.J.). Melting points were determined using a Mel-Temp apparatus and are uncorrected. NMR spectra were recorded on Varian ui400 and ui500 spectrometers (Varian, Inc., Palo Alto, Calif.) using solvent as the internal reference; the chemical shifts are reported in ppm, in δ units. Mass spectra were obtained from Colorado State University, Department of Chemistry Central Instrument Facilities using a Fisons VG Autospec spectrometer (Fisons Instruments, Manchester, UK).

Example 1

Synthesis of 5'-Azido-5'-deoxy-2',3'-Isopropylidene Adenosine 7

To 450 mL dry THF at 0° C. was added PPh$_3$ (21.5 g, 82.0 mmol). The solution was allowed to stir for ten min. and DEAD (14.2 g, 81.3 mmol) was added and the resulting mixture stirred for an additional ten min. The ice bath was removed and to the warming solution was added DPPA (22.6 g, 82.1 mmol) over a period of five min., followed by addition of 2',3'-isopropylidene-adenosine 6 (commercially available from Pharma Waldhof GmbH, Dusseldorf, GDR) (25.0 g, 81.5 mmol). The reaction was allowed to stir for 36 h sheltered from light. The resulting white precipitate was filtered and washed with petroleum ether. The solvent was evaporated in vacuo to reveal a thick orange oil. Column chromatography on silica gel (3:1:0.1 EtOAc/CH$_2$Cl$_2$/MeOH) afforded 7 as a gummy white solid (19.8 g, 73.1%). Mp 126-130° C. $^1$H NMR (CDCl$_3$) δ 8.40 (s, 1H), 7.95 (s, 1H), 6.12 (d, J=2.4 Hz, 1H), 5.62 (bs, 2H), 5.45 (dd, J=6.4, 2.4 Hz, 1H), 5.05 (dd, J=6.4, 3.6 Hz, 1H), 4.39 (m, 1H), 3.61 (dd, J=12.8, 6.0 Hz, 1H), 3.56 (dd, J=13.2, 6.0 Hz, 1H), 1.61 (s, 3H), 1.42 (s, 3H); $^{13}$C NMR (CDCl$_3$) δ 156.0, 153.8, 149.7, 140.0, 120.5, 114.8, 91.1, 86.1, 84.2, 82.0, 52.3, 27.6, 25.8. FAB-LRMS: calculated for C$_{13}$H$_{16}$N$_8$O$_3$ (M+H$^+$) 333.32, observed 333.2.

Example 2

5'-Azido-5'-deoxy-2',3'-bis-(O-triethylsilyl)adenosine 8

To 100 mL 10:1 TFA/H$_2$O at 0° C. was added 7 (15.3 g, 45.9 mmol). After 5 min., the reaction was allowed to warm to room temperature and stirred for an additional 20 min. The solution was evaporated in vacuo and co-evaporated repetitively with ethanol to render a gummy white foam. To the crude 5'-azidoadenylate (20.7 g, 70.8 mmol) in 100 mL dry dimethylformamide (DMF) at 0° C., was added imidazole (38.6 g, 566.8 mmol) and chlorotriethylsilane (19.8 g, 131.1 mol). The reaction was stirred for 2 h at room temperature. An aqueous workup was performed (NH$_4$Cl, EtOAc, brine), the combined organic layers dried over Na$_2$SO$_4$ and evaporated in vacuo. A crude light yellow solid, 8, was obtained which was taken directly forward.

Example 3

5'-Amino-5'-deoxy-2',3'-bis-(O-triethylsilyl)adenosine 9

To crude 8 (25.0 g, 48.0 mmol) in 300 mL dry THF, was added triphenylphosphine (18.9 g, 72.0 mmol) and the solution was stirred for 15 min. Water (11.2 g, 624 mmol) was added and the solution was heated at reflux for 1.5 h. The solvent was removed in vacuo. Column chromatography on silica pre-treated with 1% TEA (4:2:1 EtOAc/CH$_2$Cl$_2$/MeOH) gave 9 as white solid (16.8 g, 74.0%). Mp 164-167° C. $^1$H NMR (CDCl$_3$) δ 8.35 (s, 1H), 7.95 (s, 1H), 6.48 (bs, 2H), 5.86 (d, J=6.1 Hz, 1H), 5.15 (dd, J=5.9, 4.6 Hz, 1H), 4.28 (dd, J=4.4, 2.8 Hz, 1H), 4.09 (m, 1H), 3.08 (dd, J=13.5, 3.6 Hz, 1H), 3.02 (dd, J=13.3, 5.6 Hz, 1H), 2.25 (bs, 2H), 0.95 (t, J=8.0 Hz, 9H), 0.78 (t, J=8.1 Hz, 9H), 0.64 (q, J=8.0 Hz, 6H), 0.38 (qq, J=16.0, 8.0 Hz, 6H); $^{13}$C NMR (CDCl$_3$) δ 156.2, 153.6, 150.1, 141.1, 121.0, 90.0, 87.6, 74.0, 73.8, 44.0, 7.2, 6.9, 5.8, 5.5. FAB-LRMS: calculated for C$_{22}$H$_{42}$N$_6$O$_3$Si$_2$ (M+H$^+$) 495.78, observed 495.2.

Example 4

Methyl 2,3-dibromopropionate 10

Dibromopropionyl chloride (Alfa Aesar, Ward Hill, Mass.) (13.1 g, 52.3 mmol) in 25 mL dry THF was added to a suspension of methanol (3.35 g, 104.6 mmol) and potassium hydrogen carbonate (12.6 g, 125.5 mmol) in 25 mL dry THF at 0° C. over 10 min. The reaction was warmed to room temperature and stirred for two h. The reaction was then chilled to 0° C. and filtered. An aqueous workup was performed (H$_2$O, EtOAc, brine), dried over Na$_2$SO$_4$ and evaporated in vacuo. Column chromatography on silica (1:1:1 Pet Et/EtOAc/MeOH) rendered 10 as a clear oil (10.23 g, 79.5%). $^1$H NMR (CDCl$_3$) δ 4.46 (dd, J=11.2, 4.5 Hz, 1H), 3.94 (dd, J=11.2, 9.9 Hz, 1H), 3.85 (s, 3H), 3.68 (dd, J=9.9, 4.6 Hz, 1H); $^{13}$C NMR (CDCl$_3$) δ 168.2, 53.6, 40.9, 29.8.

Example 5

Benzyl 2,3-dibromopropionate 11

Dibromopropionyl chloride (8.72 g, 34.9 mmol) in 18 mL dry THF was added to a suspension of benzyl alcohol (3.15 g, 29.1 mmol) and potassium hydrogen carbonate (6.99 g, 69.8 mmol) in 22 mL dry THF at 0° C. over 10 min. The reaction was warmed to room temperature and stirred for two h. The reaction was then chilled to 0° C. and filtered. An aqueous workup was performed ($H_2O$, EtOAc, brine), dried over $Na_2SO_4$ and evaporated in vacuo. Column chromatography on silica (2:1 Pet Et/EtOAc) gave 11 as a clear oil (6.89 g, 73.6%). $^1$H NMR (CDCl$_3$) δ 7.35 (m, 5H), 5.25 (s, 2H), 4.47 (dd, J=11.2, 3.6 Hz, 1H), 3.93 (dd, J=10.8, 10.0 Hz, 1H), 3.66 (dd, J=10.0, 4.8 Hz, 1H); $^{13}$C NMR (CDCl$_3$) δ 167.6, 134.9, 128.88, 128.86, 128.53, 68.3, 41.3, 29.9.

Example 6

5'-Aziridino-5'-deoxy-(2"-carboxylmethyl)-2', 3'-bis-(O-triethylsilyl)adenosine 12

To 20a (0.600 g, 0.814 mmol) in 11 mL dry MeOH was added triethylamine (0.494 g, 4.885 mmol). The solution was heated at reflux for 2 h. The reaction was cooled and an aqueous workup was performed (EtOAc, $H_2O$, brine), dried over $Na_2SO_4$ and evaporated in vacuo. The crude was taken directly forward due to co-migration of the auxiliary. The signals due to 12a (S aziridine) could be discerned: $^1$H NMR (CDCl$_3$) δ 8.26 (s, 1H), 7.97 (s, 1H), 6.29 (s, 2H), 5.91 (d, J=5.6 Hz, 1H), 5.04 (dd, J=5.6, 4.4 Hz, 1H), 4.30 (m, 2H), 3.73 (s, 3H), 3.04 (dd, J=12.8, 3.6 Hz, 1H), 2.47 (dd, J=12.8, 6.4 Hz, 1H), 2.16 (dd, J=6.4, 3.2 Hz, 1H), 2.12 (dd, J=3.2, 1.2 Hz, 1H), 1.74 (dd, J=6.4, 1.2 Hz, 1H), 0.98 (t, J=8.0 Hz, 9H), 0.78 (t, J=8.0 Hz, 9H), 0.65 (q, J=8.0 Hz, 6H), 0.35 (qq, J=16.0, 8.0 Hz, 6H); $^{13}$C (CDCl$_3$) δ 170.21, 154.80, 151.77, 148.72, 119.47, 87.91, 83.81, 72.90, 72.87, 60.33, 51.25, 36.08, 33.61, 5.84, 5.53, 3.92, 3.50; FAB-HRMS: calculated for $C_{26}H_{46}N_6O_5Si_2$ (M+H$^+$) 579.31, observed 579.314.

A similar procedure was performed with 20b. The signals due to 12b (R aziridine) could be discerned: $^1$H NMR (CDCl$_3$) δ 8.28 (s, 1H), 7.98 (s, 1H), 6.29 (s, 2H), 5.91 (d, J=5.6 Hz, 1H), 5.05 (dd, J=5.2, 4.4 Hz, 1H), 4.41 (dd, J=4.4, 2.4 Hz, 1H), 4.25 (m, 1H), 3.67 (s, 3H), 2.96 (dd, J=12.8, 5.2 Hz, 1H), 2.51 (dd, J=12.8, 6.0 Hz, 1H), 2.23 (dd, J=6.4, 3.2 Hz, 1H), 2.18 (dd, J=3.2, 1.2 Hz, 1H), 1.65 (dd, J=6.4, 1.2 Hz, 1H), 1.00 (t, J=8.0 Hz, 9H), 0.80 (t, J=8.0 Hz, 9H), 0.67 (q, J=8.0 Hz, 6H), 0.37 (qq, J=16.0, 8.0 Hz, 6H); $^{13}$C (CDCl$_3$) δ 170.04, 154.81, 151.76, 148.62, 110.49, 88.21 83.35, 72.68, 72.65, 60.18, 51.11, 36.05, 33.50, 5.82, 5.55, 3.89, 3.45; FAB-HRMS: calculated for $C_{26}H_{46}N_6O_5Si_2$ (M+H$^+$) 579.31, observed 579.314.

The inventors have also found that 12 can be synthesized from 21a and 22b via the same procedure.

Example 7

5'-Aziridino-5'-deoxy-(2"-carboxylbenzyl)-2',3'-bis-(O-triethylsilyl)adenosine 13

To 11 (1.835 g, 5.701 mmol) in 40 mL dry THF was stirred for 15 min. at room temperature. 9 (2.848 g, 5.757 mmol) in 40 mL dry THF was added to the dibromide solution, followed by TEA (1.730 g, 17.099 mmol). The solution was heated at reflux for 16 h. The solution was cooled to 0° C., filtered and the residual Et$_3$N—HBr salts triturated with anhydrous Et$_2$O. The combination of organic layers was evaporated in vacuo followed by column chromatography on silica (4:2:1 EtOAc/CH$_2$Cl$_{21}$MeOH) to afford 13 as a mixture of diastereomers (3.012 g, 80.7%). $^1$H NMR (CDCl$_3$) δ 8.33 (s, 1H), 8.32 (s, 1H), 8.01 (s, 1H), 8.00 (s, 1H), 7.34 (m, 5H), 7.33 (m, 5H), 5.92 (d, J=7.5 Hz, 1H), 5.90 (d, J=7.5 Hz, 1H), 5.52 (bs, 2H), 5.51 (bs, 2H), 5.20 (d, J=5.5 Hz, 2H), 5.14 (d, J=5 Hz, 2H), 5.11 (dd, J=7, 5.5 Hz, 1H), 5.06 (dd, J=7, 5.5 Hz, 1H), 4.42 (dd, J=5.5, 4 Hz, 1H), 4.34 (dd, J=5, 3.5 Hz, 1H), 4.29 (m, 1H), 4.25 (m, 1H), 3.08 (dd, J=16, 5.5 Hz, 1H), 2.94 (dd, J=15.5, 7.5 Hz, 1H), 2.53 (dd, J=15.5, 3 Hz, 1H), 2.43 (dd, J=16, 8 Hz, 1H), 2.29 (dd, J=6.5, 3.5 Hz, 1H), 2.22 (dd, J=3.5, 1.5 Hz, 1H), 2.20 (dd, J=6.5, 3 Hz, 1H), 2.14 (dd, J=3, 1.5 Hz, 1H), 1.74 (dd, J=6.5, 1.5 Hz, 1H), 1.66 (dd, J=6.5, 1.5 Hz, 1H), 1.00 (t, J=8.0 Hz, 9H), 0.98 (t, J=8.0 Hz, 9H), 0.80 (t, J=8.0 Hz, 9H), 0.78 (t, J=8.0 Hz, 9H), 0.67 (q, J=8.0 Hz, 6H), 0.65 (q, J=8.0 Hz, 6H), 0.37 (qq, J=16.0, 8.0 Hz, 6H), 0.35 (qq, J=16.0, 8.0 Hz, 6H); $^{13}$C (CDCl$_3$) δ 170.83, 170.67, 156.03, 153.03, 149.98, 149.89, 140.92, 140.93, 135.74, 135.70, 128.73, 128.53, 128.52, 128.34, 120.73, 120.68, 89.44, 89.06, 84.93, 84.40, 74.24, 74.12, 74.03, 73.66, 67.14, 66.92, 61.48, 61.27, 37.41, 37.36, 35.01, 7.05, 6.76, 5.13, 4.76. FAB-HRMS: calculated for $C_{32}H_{50}N_6O_5Si_2$ (M+H$^+$) 655.34, observed 655.347.

General Procedure for 2',3' desilylation of 5'-Aziridino-5'-deoxyadenosine analogs: To the 2',3'-bis-(O-triethylsilyl)adenosine (0.1085 mmol) in 0.50 mL dry dioxane was added TBAF (0.2170 mmol) in 0.50 mL dry dioxane. The reaction was allowed to stir at room temperature for 30 min. and evaporated in vacuo to reveal a yellow oil. Purification by reverse-phase HPLC (C18-100 Å).

Example 8

5'-Aziridino-5'-deoxy-(2"-carboxylmethyl)adenosine 14

Purification of 5'-Aziridino-5'-deoxy-(2"-carboxylmethyl)adenosine 14 was performed by reverse-phase HPLC on a linear gradient (5-60% CH$_3$CN over 20 min.; retention time 15.0 min.).

14a (S aziridine) Yield: 34.9%. Mp 130° C. (dec). $^1$H NMR (D$_2$O) δ 8.30 (s, 1H), 8.29 (s, 1H), 6.08 (d, J=4.8 Hz, 1H), 4.59 (t, J=5.6 Hz, 1H), 4.30 (m, 1H), 3.59 (s, 3H), 3.02 (dd, J=13.6, 4.8 Hz, 1H), 2.61 (dd, J=13.6, 3.6 Hz, 1H), 2.33 (dd, J=6.8, 3.2 Hz, 1H), 2.10 (d, J=3.2 Hz, 1H), 1.88 (d, J=6.8 Hz, 1H); $^{13}$C NMR (D$_2$O) δ 172.79, 156.53, 152.22, 149.08, 140.23, 118.91, 87.76, 82.98, 73.38, 70.83, 58.55, 52.74, 37.91, 33.41. FAB-HRMS: calculated for $C_{14}H_{18}N_6O_5$ (M+H$^+$) 351.13, observed 351.143.

14b (R aziridine) Yield: 43.3%. Mp 132° C. (dec). $^1$H NMR (D$_2$O) δ 8.36 (s, 1H), 8.25 (s, 1H), 6.08 (d, J=5.6 Hz, 1H), 4.87 (t, J=5.2 Hz, 1H), 4.38 (t, J=5.2 Hz, 1H), 4.34 (m, 1H), 3.62 (s, 3H), 3.00 (dd, J=13.2, 4.0 Hz, 1H), 2.56 (dd, J=13.2, 7.6 Hz, 1H), 2.38 (dd, J=6.8, 3.2 Hz, 1H), 2.13 (d, J=3.2 Hz, 1H), 1.89 (d, J=6.8 Hz, 1H); $^{13}$C NMR (D$_2$O) δ 172.87, 155.07, 152.02, 149.01, 140.60, 119.06, 87.80, 83.54, 73.11, 71.44, 59.99, 52.77, 38.21, 33.05. FAB-HRMS: calculated for $C_{14}H_{18}N_6O_5$ (M+H$^+$) 351.13, observed 351.143.

Example 9

5'-Aziridino-5'-deoxy-(2"-carboxylbenzyl)adenosine 15

Purification of 5'-Aziridino-5'-deoxy-(2"-carboxylbenzyl)adenosine 15 was performed by reverse-phase HPLC on a linear gradient of MeOH (0-50% over 4 min., 50-80% over 18 min.; retention time 15.0, 16.2 min.). Yield: 53.8%. Mp 145° C. (dec).

15a (R aziridine) $^1$H NMR (DMSO) δ 8.39 (s, 1H), 8.15 (s, 1H), 7.29 (m, 5H), 5.90 (d, J=5.2 Hz, 1H), 5.47 (bs, 2H), 5.06 (ABq, J=12.4 Hz, 2H), 4.60 (dd, J=5.6, 4.8 Hz, 1H), 4.18 (dd=t, J=4.4 Hz, 1H), 4.03 (m, 1H), 2.73 (dd, J=12.8, 3.6 Hz, 1H), 2.52 (dd, J=12.8, 6.4 Hz, 1H), 2.34 (dd, J=6.4, 3.2 Hz, 1H), 1.97 (dd, J=3.2, 1.6 Hz, 1H), 1.70 (dd, J=6.4, 1.6 Hz, 1H); $^{13}$C (DMSO) δ 170.94, 156.77, 153.32, 150.16, 140.39, 136.60, 129.12, 128.66, 128.40, 119.81, 88.07, 84.13, 73.81, 71.92, 66.41, 61.47. FAB-HRMS: calculated for $C_{20}H_{22}N_6O_5$ (M+H$^+$) 427.43, observed 427.1733.

15b (S aziridine) $^1$H NMR (DMSO) δ 8.31 (s, 1H), 8.10 (s, 1H), 7.30 (m, 5H), 7.24 (s, 2H), 5.86 (d, J=5.2 Hz, 1H), 5.52 (d, J=5.6 Hz, 1H), 5.29 (d, J=5.2 Hz, 1H), 5.05 (ABq, J=12 Hz, 2H), 4.56 (ddd=q (observed), J=5.2 Hz, 1H), 4.17 (ddd=q (observed), J=5.2 Hz, 1H), 3.97 (m, 1H), 2.80 (dd, J=12.8, 4.0 Hz, 1H), 2.38 (dd, J=12.8, 3.2 Hz, 1H), 2.22 (dd, J=6.4, 3.2 Hz, 1H), 1.93 (dd, J=3.2, 1.2 Hz, 1H), 1.70 (dd, J=6.4, 1.2 Hz, 1H); $^{13}$C (DMSO) δ 170.98, 156.72, 153.33, 150.14, 140.19, 136.49, 129.12, 128.79, 119.66, 87.83, 84.02, 73.82, 71.87, 66.62, 61.39, 36.92, 34.89. FAB-HRMS: calculated for $C_{20}H_{22}N_6O_5$ (M+H+) 427.43, observed 427.1733.

Example 10

(4R,5S)-1,5-dimethyl-4-phenylimidazolidin-2-one-3-(2',3'-dibromopropionate) 18

To 16 (0.250 g, 1.315 mmol) in 2.5 mL dry acetonitrile was added dibromopropionyl chloride (0.395 g, 1.578 mmol) at room temperature. The solution was heated at reflux for 2 h. Upon cooling to 0° C., the reaction was diluted with 5% MeOH/CH$_2$Cl$_2$. An aqueous workup was performed (H$_2$O, 5% MeOH/CH$_2$Cl$_2$, brine), the resulting organic layer dried over Na$_2$SO$_4$ and solvent removed in vacuo to yield a pink oil. Column chromatography on silica gel (1:1 Pet Ether/EtOAc) yielded 18 as a mixture of diastereomers (0.436 g, 82.1%). Mp 112-114° C. $^1$H NMR (CDCl$_3$) δ 7.25 (m, 10H), 6.35 (dd, J=11.5, 4 Hz, 1H), 6.24 (dd, J=11.5, 3.5 Hz, 1H), 5.39 (d, J=9.0 Hz, 1H), 5.36 (d, J=9.0 Hz, 1H), 4.00 (m, 4H), 3.66 (m, 2H), 2.89 (s, 6H), 0.83 (d, J=6.5 Hz, 6H); $^{13}$C (CDCl$_3$) (166.70, 165.83, 154.73, 154.63, 135.74, 135.45, 128.77, 128.75, 128.73, 128.70, 128.60, 128.53, 60.14, 60.08, 54.00, 53.94, 40.04, 39.53, 29.84, 29.28, 28.52, 28.48, 15.31, 15.17; FAB-HRMS: calculated for $C_{14}H_{16}Br_2N_2O_2$(M+H+) 404.96, observed 404.962.

Example 11

(4S,5R)-1,5-dimethyl-4-phenylimidazolidin-2-one-3-(2',3'-dibromopropionate) 19

To 17 (0.500 g, 2.639 mmol) in 5 mL dry acetonitrile was added dibromopropionyl chloride (ABCR Chemicals, Karlsruhe, GDR) (0.790 g, 3.156 mmol) at room temperature. The solution was heated at reflux for 2 h. Upon cooling to 0° C., the reaction was diluted with 5% MeOH/CH$_2$Cl$_2$. An aqueous workup was performed (H$_2$O, 5% MeOH/CH$_2$Cl$_2$, brine), dried over Na$_2$SO$_4$ and evaporated in vacuo to yield a pink oil. Column chromatography on silica gel (1:1 Pet Ether/EtOAc) gave 19 as a mixture of diastereomers (0.690 g, 64.9%). Mp 113-115° C. $^1$H NMR (CDCl$_3$) δ 7.25 (m, 10H), 6.34 (dd, J=11.5, 4 Hz, 1H), 6.21 (dd, J=11.5, 3.5 Hz, 1H), 5.38 (d, J=9.0 Hz, 1H), 5.35 (d, J=9.0 Hz, 1H), 4.00 (m, 4H), 3.65 (m, 2H), 2.89 (s, 6H), 0.83 (d, J=6.5 Hz, 6H); $^{13}$C (CDCl$_3$) δ 166.74, 165.86, 154.76, 154.74, 135.76, 135.46, 128.81, 128.74, 128.73, 128.64, 128.57, 127.26, 60.17, 59.59, 54.03, 53.97, 40.05, 39.54, 29.86, 29.30, 28.55, 28.51, 15.35, 15.20; FAB-HRMS: calculated for $C_{14}H_{16}Br_2N_2O_2$ (M+H$^+$) 404.96, observed 404.962.

Example 12

(4'''R,5'''S)-5'-aziridino-5'-deoxy-[2''-carboxyl(1''', 5'''-dimethyl-4'''-phenylimidazolidin-2'''-one)]-2',3'-bis-(O-triethylsilyl)adenosine 20

To 18 (0.125 g, 0.310 mmol) in 10 mL dry THF was added 9 (0.155 g, 0.313 mmol) in 10 mL dry THF. The reaction was allowed to stir for 15 min. Upon addition of TEA (0.094 g, 0.931 mmol), the solution was heated at reflux for 16 h. The precipitate was triturated with anhydrous Et$_2$O and the organic removed in vacuo to yield a solid. Column chromatography on silica (5:2:1 EtOAc/CH$_2$Cl$_2$/MeOH) gave 20 as two diastereomers. Yield (0.091 g, 0.061 g, 66.5%). Mp 184° C. (dec).

20a (S aziridine) $^1$H NMR (CDCl$_3$) δ 8.36 (s, 1H), 8.22, (s, 1H), 7.28 (m, 5H), 6.18 (s, 2H), 6.02 (d, J=6.4 Hz, 1H), 5.47 (d, J=8.4 Hz, 1H), 4.99 (dd, J=6, 4.4 Hz, 1H), 4.32 (dd, J=4.4, 2.4 Hz, 1H), 4.25 (m, 1H), 3.89 (dq, J=8.4, 6.8 Hz, 1H), 3.87 (dd, J=6.4, 3.2 Hz, 1H), 3.31, (dd, J=12.8, 3.6 Hz, 1H), 2.82 (s, 3H), 2.43 (dd, J=12.8, 5.6 Hz, 1H), 2.14 (dd, J=2.8, 1.2 Hz, 1H), 1.71 (dd, J=6.4, 1.2 Hz, 1H), 0.98 (t, J=8.0 Hz, 9H), 0.78 (t, J=8.0 Hz, 9H), 0.75 (d, J=6.8 Hz, 3H), 0.65 (q, J=8.0 Hz, 6H), 0.35 (qq, J=16.0, 8.0 Hz, 6H); $^{13}$C (CDCl$_3$) δ 169.41, 156.17, 153.25, 150.29, 140.79, 136.63, 128.75, 128.34, 127.39, 120.15, 88.15, 85.62, 75.34, 74.19, 61.76, 59.40, 54.34, 36.89, 35.97, 28.38, 15.14, 7.13, 6.80, 5.17, 4.72. FAB-HRMS: calculated for $C_{36}H_{56}N_8O_5Si_2$ (M+H$^+$) 737.40, observed 737.397.

20b (R aziridine) $^1$H NMR (CDCl$_3$) δ 8.35 (s, 1H), 8.25 (s, 1H), 7.24 (m, 5H), 6.10 (s, 2H), 6.01 (d, J=6.4 Hz, 1H), 5.35 (d, J=8.8 Hz, 1H), 4.77 (dd, J=6, 4.4 Hz, 1H), 4.41 (dd, J=4.4, 2.4 Hz, 1H), 4.22 (m, 1H), 3.90 (dq, J=8.4, 6.4 Hz, 1H), 3.84 (dd, J=6.4, 3.2 Hz, 1H), 2.94 (dd, J=12.8, 4.8 Hz, 1H), 2.82 (s, 3H), 2.63 (dd, J=12.8, 4.0 Hz, 1H), 2.17 (dd, J=2.8, 1.2 Hz, 1H), 1.68 (dd, J=6.4, 1.2 Hz, 1H), 1.00 (t, J=8.0 Hz, 9H), 0.80 (t, J=8.0 Hz, 9H), 0.75 (d, J=6.8 Hz, 3H), 0.67 (q, J=8.0 Hz, 6H), 0.37 (qq, J=16.0, 8.0 Hz, 6H); $^{13}$C (CDCl$_3$) δ 169.33, 156.17, 153.34, 149.91, 140.26, 136.61, 128.61, 128.19, 127.38, 120.07, 89.01, 83.48, 75.71, 72.76, 60.39, 59.66, 54.51, 37.19, 37.01, 28.39, 15.15, 7.02, 6.81, 5.15, 4.90. FAB-HRMS: calculated for $C_{36}H_{56}N_8O_5Si_2$ (M+H$^+$) 737.40, observed 737.397.

Example 13

(4'''S,5'''R)-5'-aziridino-5'-deoxy-[2''-carboxyl(1''', 5'''-dimethyl-4'''-phenylimidazolidin-2'''-one)]-2',3'-bis-(O-triethylsilyl)adenosine 21

To (4S,5R)-1,5-dimethyl-4-phenylimidazolidin-2-one-3-(2',3'-dibromopropionate) (19) (0.129 g, 0.320 mmol) in 10 mL dry THF was added 9 (0.160 g, 0.323 mmol) in 10 mL dry THF. The reaction was allowed to stir for 15 min. Upon addition of TEA (0.097 g, 0.961 mmol), the solution was heated at reflux for 16 h. The precipitate was triturated with anhydrous Et$_2$O and the organic was evaporated in vacuo to yield a solid. Column chromatography on silica (5:2:1 EtOAc/CH$_2$Cl$_2$/MeOH) gave 21 as two diastereomers. Yield (0.061 g, 0.087 g, 62.8%). Mp 210° C. (dec).

21a (R aziridine) $^1$H NMR (CDCl$_3$) δ 8.34 (s, 1H), 8.11, (s, 1H), 7.29 (m, 5H), 6.18 (d, J=5.2 Hz, 1H), 5.75 (s, 2H), 5.29 (d, J=8.4 Hz, 1H), 4.93 (dd, J=6, 4.4 Hz, 1H), 4.40 (dd, J=4.4, 2.4 Hz, 1H), 4.25 (m, 1H), 3.88 (dq, J=8.4, 6.8 Hz, 1H), 3.82 (dd, J=6.4, 3.2 Hz, 1H), 2.89 (dd, J=12.8, 5.2 Hz, 1H), 2.81 (s, 3H), 2.73 (dd, J=12.8, 5.2 Hz, 1H), 2.23 (dd, J=3.2, 1.2 Hz, 1H), 1.63 (dd, J=6.4, 1.2 Hz, 1H), 0.98 (t, J=8.0 Hz, 9H), 0.80 (t, J=8.0 Hz, 9H), 0.79 (d, J=6.8 Hz, 3H), 0.66 (q, J=8.0 Hz, 6H), 0.41 (qq, J=16.0, 8.0 Hz, 6H); $^{13}$C (CDCl$_3$) δ 168.99, 156.13, 153.11, 150.01, 140.48, 136.45, 128.70, 128.34, 127.30, 120.44, 89.02, 84.29, 74.88, 73.50, 61.56, 59.57, 54.31, 37.29, 35.83, 38.34, 15.15, 7.09, 6.82, 5.09, 4.81. FAB-HRMS: calculated for C$_{36}$H$_{56}$N$_8$O$_5$Si$_2$ (M+H$^+$) 737.40, observed 737.397.

21b (S aziridine) $^1$H NMR (CDCl$_3$) δ 8.35 (s, 1H), 8.09 (s, 1H), 7.24 (m, 5H), 5.99 (s, 2H), 5.93 (d, J=6.4 Hz, 1H), 5.33 (d, J=8.4 Hz, 1H), 4.99 (dd, J=6, 4.4 Hz, 1H), 4.30 (m, 1H), 4.20 (dd, J=4.4, 2.4 Hz, 1H), 3.94 (dq, J=8.4, 6.4 Hz, 1H), 3.80 (dd, J=6.4, 2.8 Hz, 1H), 3.38 (dd, J=12.4, 4 Hz, 1H), 2.86 (s, 3H), 2.36 (dd, J=12.4, 7.2 Hz, 1H), 2.10 (dd, J=2.8, 1.2 Hz, 1H), 1.81 (dd, J=6.4, 1.2 Hz, 1H), 0.97 (t, J=8.0 Hz, 9H), 0.81 (d, J=6.8 Hz, 3H), 0.76 (t, J=8.0 Hz, 9H), 0.63 (q, J=8.0 Hz, 6H), 0.34 (qq, J=16.0, 8.0 Hz, 6H); $^{13}$C (CDCl$_3$) δ 169.29, 155.85, 153.05, 149.90, 141.14, 136.29, 128.60, 128.23, 127.25, 120.68, 89.07, 85.38, 74.45, 74.26, 61.61, 59.75, 54.53, 36.97, 36.11, 28.32, 15.06, 7.05, 6.73, 5.14, 4.68. FAB-HRMS: calculated for C$_{36}$H$_{56}$N$_8$O$_5$Si$_2$ (M+H$^+$) 737.40, observed 737.397.

SCHEME IV

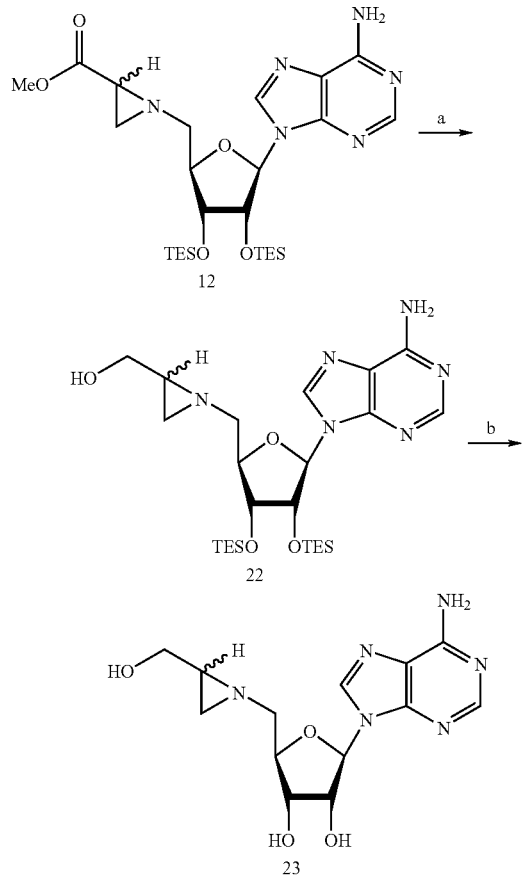

a. LiAlH$_4$, THF, -20° C. b. tBu$_4$NF, dioxane

Example 14

5'-Aziridino-5'-deoxy-(2"-hydroxymethyl)-2',3'-bis-(O-triethylsilyl)adenosine 22

Synthesis of 5'-Aziridino-5'-deoxy-(2"-hydroxymethyl)-2',3'-bis-(O triethylsilyl)adenosine 22 was accomplished according to the steps shown in SCHEME IV. To 12a (0.499 g, 0.862 mmol) in 10 mL dry THF at −10° C. was added a 1M solution of LiAlH$_4$ in THF (0.948 mL, 0.948 mmol) dropwise. The reaction was warmed slowly and stirred for an additional 10 min. The reaction was quenched with NaHCO$_3$ and extracted into EtOAc. The organic layer was washed with water and brine, dried over Na$_2$SO$_4$, and evaporated in vacuo. Silica gel chromatography (5:2:1 EtOAc/CH$_2$Cl$_2$/MeOH) afforded 22a (R aziridine) (0.296 g, 66.0%). Mp 129-132° C. $^1$H NMR (CDCl$_3$) δ 8.24 (s, 1H), 8.02 (s, 1H), 6.82 (s, 2H), 5.83 (d, J=6.0 Hz, 1H), 5.06 (dd, J=5.5, 4.5 Hz, 1H), 4.51 (s, 1H), 4.28 (dd, J=4.0, 3.5 Hz, 1H), 4.19 (m, 1H), 3.74 (dd, J=11.5, 2.5 Hz, 1H), 3.34 (dd, J=11.5, 6.0 Hz, 1H), 2.85 (dd, J=13.0, 3.5 Hz, 1H), 2.47 (dd, J=13.0, 7.0 Hz, 1H), 1.72 (m, 1H), 1.67 (d, J=3.5 Hz, 1H), 1.39 (d, J=6.5 Hz, 1H), 0.92 (t, J=8.0 Hz, 9H), 0.72 (t, J=8.0 Hz, 9H), 0.59 (q, J=8.0 Hz, 6H), 0.34 (qq, J=16.0, 8.0 Hz, 6H); $^{13}$C NMR (CDCl$_3$) δ 156.25, 153.00, 149.77, 141.08, 120.58, 89.45, 85.29, 74.12, 74.06, 63.13, 62.11, 40.28, 32.04, 7.03, 6.74, 5.14, 4.74. FAB-HRMS: calculated for C$_{25}$H$_{46}$N$_6$O$_4$Si$_2$ (M+H$^+$) 551.31, observed 551.319.

A similar procedure was performed with 12b to obtain 22b (S aziridine) Yield: 0.231 g, 66.0%. Mp 130-132° C. $^1$H NMR (CDCl$_3$) δ 8.09 (s, 1H), 7.81 (s, 1H), 6.10 (s, 1H), 5.82 (d, J=7.0 Hz, 1H), 5.62 (dd, J=7.0, 4.0 Hz, 1H), 4.15 (d, J=10.5 Hz, 1H), 4.08 (d, J=4.0 Hz, 1H), 4.03 (t, J=11.0 Hz, 1H), 3.86 (d, J=12.0 Hz, 1H), 3.17 (dd, J=12.5, 9.0 Hz, 1H), 1.92 (m, 1H), 1.81 (d, J=12.5, 2.0 Hz, 1H), 1.69 (d, J=3.5 Hz, 1H), 1.32 (d, J=6.5 Hz, 1H), 1.02 (t, J=8.0 Hz, 9H), 0.72 (t, J=8.0 Hz, 9H), 0.68 (q, J=8.0 Hz, 6H), 0.28 (qq, J=16.0, 8.0 Hz, 6H); $^{13}$C NMR (CDCl$_3$) δ 155.38, 152.46, 148.95, 141.39, 120.56, 90.28, 85.85, 75.18, 72.60, 53.38, 62.66, 41.91, 30.94, 7.08, 6.66, 5.17, 4.60. FAB-HRMS: calculated for C$_{25}$H$_{46}$N$_6$O$_4$Si$_2$ (M+H$^+$) 551.31, observed 551.319.

Example 15

5'-Aziridino-5'-deoxy-(2"-hydroxymethyl)adenosine 23

Purification of 5'-Aziridino-5'-deoxy-(2"-hydroxymethyl) adenosine 23 was performed by reverse-phase HPLC on a linear gradient of CH$_3$CN (5-100% over 11 min.; retention time 5.7 min.). Yield: 39.5%. Mp 140° C. (dec).

23a (R aziridine) $^1$H NMR (D$_2$O) δ 8.23 (s, 1H), 8.07 (s, 1H), 5.98 (d, J=4.8 Hz, 1H), 4.71 (dd=t (observed), J=5.2 Hz, 1H), 4.32 (dd=t (observed), J=5.2 Hz, 1H), 4.28 (m, 1H), 3.58 (dd, J=12.0, 4.8 Hz, 1H), 3.40 (dd, J=12.0, 2.8 Hz, 1H), 2.77 (dd, J=13.2, 4.0 Hz, 1H), 2.66 (dd, J=13.2, 7.2 Hz, 1H), 1.91 (m, 1H), 1.72 (d, J=4.0 Hz, 1H), 1.61 (d, J=6.4 Hz, 1H); $^{13}$C NMR (D$_2$O) δ 155.53, 152.90, 148.81, 140.11, 118.82, 87.86, 83.72, 73.59, 71.52, 63.47, 60.89, 39.89, 31.82. FAB-HRMS: calculated for C$_{13}$H$_{18}$N$_6$O$_4$ (M+H$^+$) 323.14, observed 323.147.

23b (S aziridine) $^1$H NMR (D$_2$O) δ 8.31 (s, 1H), 8.22 (s, 1H), 6.07 (d, J=5.2 Hz, 1H), 4.40 (dd=t (observed), J=5.2 Hz, 1H), 4.29 (m, 1H), 3.58 (dd, J=12.0, 4.8 Hz, 1H), 3.39 (dd, J=12.0, 2.8 Hz, 1H), 2.77 (dd, J=13.2, 3.6 Hz, 1H), 2.67 (dd, J=13.2, 6.8 Hz, 1H), 1.93 (m, 1H), 1.69 (d, J=4.0 Hz, 1H), 1.60 (d, J=6.8 Hz, 1H); $^{13}$C NMR (D$_2$O) δ 155.68, 152.99, 148.98, 140.13, 118.95, 87.80, 83.60, 73.61, 71.50, 63.49, 60.71, 40.65, 31.00. FAB-HRMS: calculated for $C_{13}H_{18}N_6O_4$ (M+H$^+$) 323.14, observed 323.147.

Thus, the inventors have described and disclosed herein the highly efficient synthesis of S-adenosyl-L-methionine analogs bearing differentially tetherable functionalities. Synthesis of the 5' amine core, followed by Gabriel-Cromwell aziridination affords carboxyaziridines capable of facile reduction to the hydroxymethyl analogs. Silyl ether cleavage from both 2' and 3' alcohols using TBAF affords aziridine-based cofactor analogs of interest. Stereochemical assignment of the resulting SAM analogs has been achieved through independent stereocontrolled synthesis of each stereoisomer of O-benzyl 22. Cofactor analogs thus obtained are currently being evaluated for compatibility with a host of DNA and protein methyltransferases.

II. Conversion of DNA Methyltransferases into Azido-nucleosidyl Transferases Via Synthetic Cofactor Analogs As previously described, the 5'-aziridine adenylate 3 is a substitute for SAM in the M.TaqI catalyzed alkylation of adenine within the recognition sequence d(TCGA) as depicted in SCHEME I. Although previous SAM analogs have been used to label nucleic acid residues the possibilities afforded by C8 of the adenosine base has not been appreciated.

The development of cofactor analogs related to 3 as universal cofactor analogs required that the core structure of 3 have a handle to which any desired molecule (DNA damaging moiety, affinity matrix handle, fluorophore, etc.) could be appended following MTase-dependent anchoring. Such a handle would present a minimal disruption to cofactor-MTase interactions and be capable of rapid couplings to other reagents under physiological conditions. These requirements suggested the use of the Staudinger ligation of azides and ortho-methoxycarbonyl functionalized triarylphosphines to provide a reaction as illustrated in SCHEME V.

SCHEME V

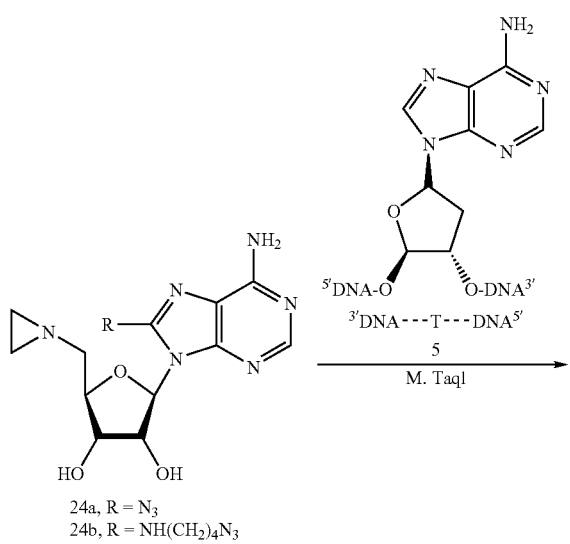

24a, R = N$_3$
24b, R = NH(CH$_2$)$_4$N$_3$

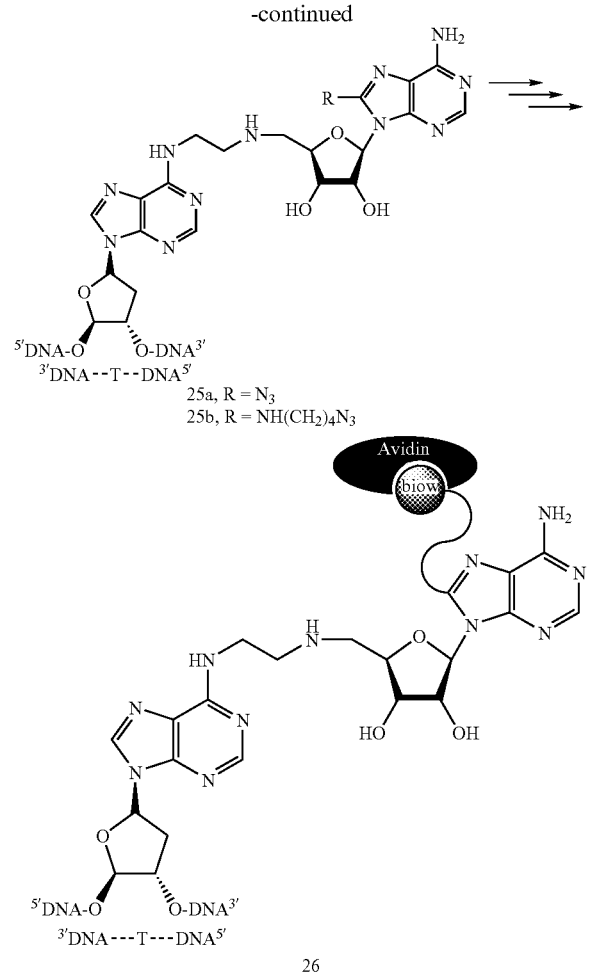

Many azides have been shown to be highly active participants in [2+3] Huisgen cycloadditions. These "Click chemistry" reactions also are compatible with biological conditions (Speers, A. E., et al., (2003) J. Am. Chem. Soc., 125, 4686-4687;). The synthetic cofactor analogs can take part in or act as a platform for click chemistry reaction to label or tag desirable substrates, for example, as shown in SCHEME V.

A. General Experimental Methods

All reactions were carried out under an inert atmosphere of argon unless indicated otherwise. All reagents were obtained from commercial suppliers and used as received unless otherwise noted. The silica gel used in column flash chromatography was Merck no. 9385, 60 Å, 230-400 mesh (Sigma Aldrich, St. Louis, Mo.). Analytical TLC was conducted on EM Science silica gel plates (Alltech, Inc. Deerfield Ill.) with detection by ninhydrin and/or UV light. Tetrahydrofuran (THF) was distilled over Na and benzophenone. TEA was dried over KOH and then distilled; 2,6-lutidine was distilled from AlCl$_3$; DIEA was distilled from ninhydrin, and then from KOH; Br$_2$ was distilled from KBr, and then from P$_2$O$_5$. The $^1$H-NMR and $^{13}$C-NMR spectra were recorded on Varian UI400 and UI500 spectrometers using solvent as the internal reference. Chemical shifts are reported in ppm, in δ units. High-resolution matrix-assisted laser desorption ionization (MALDI) was performed at the University of Wisconsin-Madison, School of Pharmacy.

pUC19 and all enzymes (unless indicated) were obtained from New England Biolabs. The DNA MTase reactions with M.TaqI were run in buffer A (20 mM Tris-OAc (pH 6.0), 50 mM KOAc, 10 mM Mg(OAc)$_2$, 0.01% Triton-X100). The DNA MTase reactions with M.EcoRI were run in buffer B (10 mM Tris-Cl (pH 7.4), 50 mM NaCl, 0.5 mM EDTA, 0.01% Triton-X100). All agarose gels were prepared with a High-melt agarose in 1× TAE containing 0.05 µg/µL ethidium bromide. Following electrophoresis, gels were de-stained for 20 min. (1 mM MgSO$_4$, 10 mM 2-mercaptoethanol) prior to visualization. Bands were visualized at 300 nm using a photo-documentation system. Synthetic oligonucleotides were obtained from Sigma-Genosys and gel purified prior to use (Sigma-Genosys, The Woodlands, Tex.). The concentration of the oligonucleotide was determined at 260 nm using the following molar extinction coefficients: 15400 (A), 11500 (G), 8700 (T), 7400 (C). The immobilized Streptavidin pull-down assay was performed in buffer C (1 M NaCl, 1 mM EDTA, 10 mM sodium phosphate, pH 7.5).

Example 16

Synthesis of the Alkyl Azide Cofactor Analogs

The synthesis of the aryl azide cofactor analog, 24a was accomplished by following the steps illustrated in SCHEME VI (Comstock, L. R. and Rajski, S. R. (2004), *J. Org. Chem.*, 69, 1425-1428).

SCHEME VI

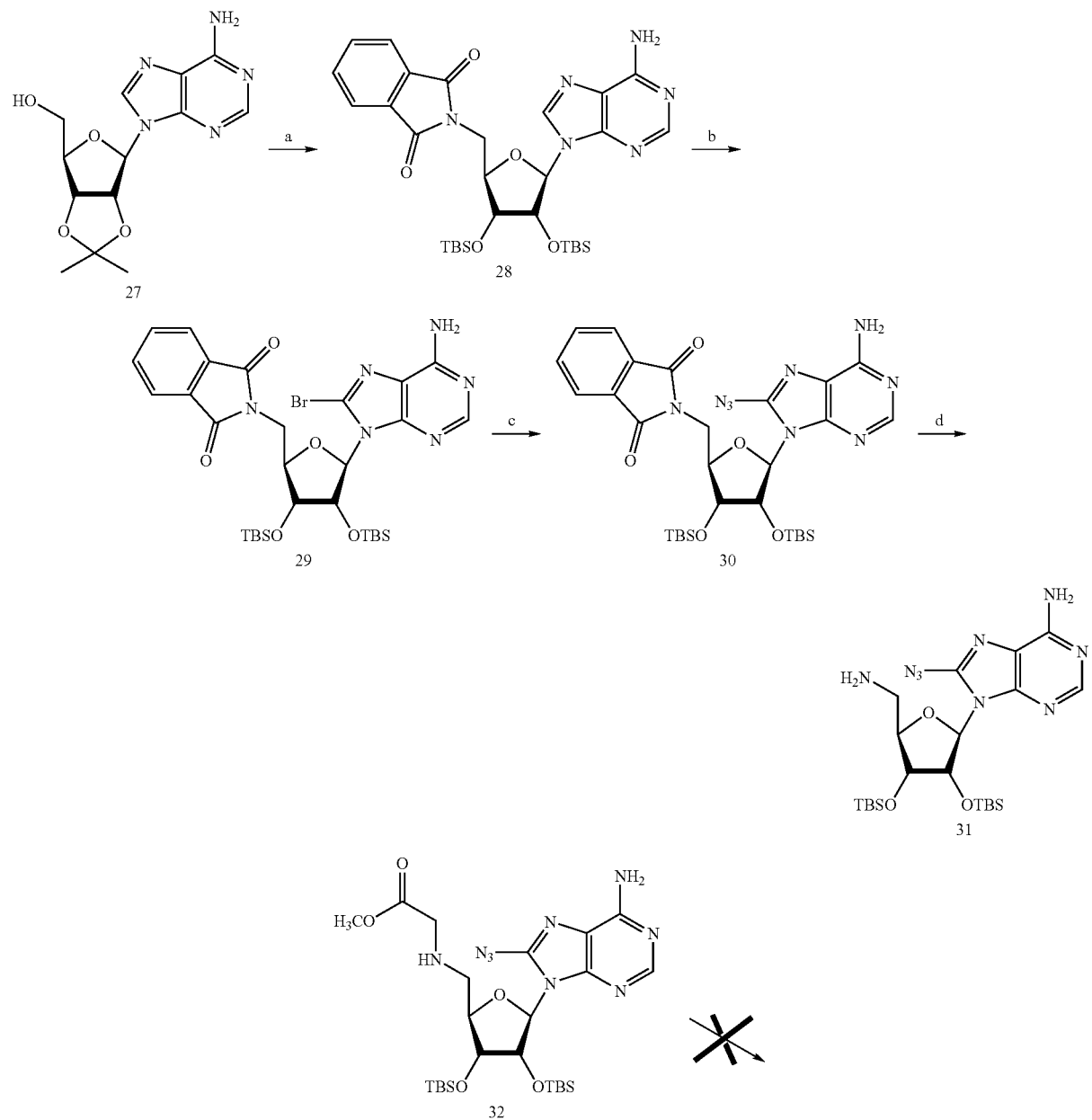

-continued

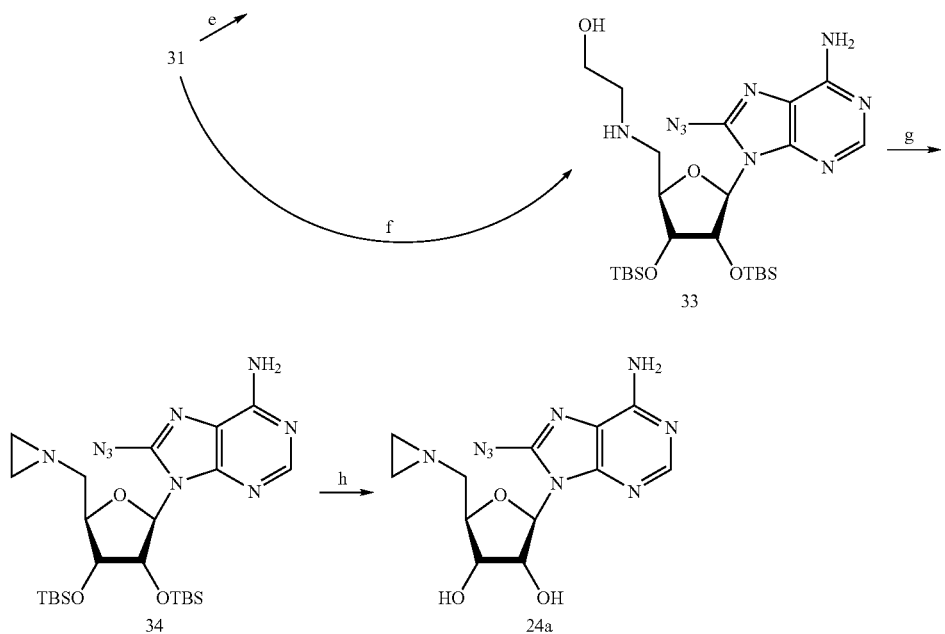

(a) (1) phthalimide, PPh3, DEAD, THF, rt,
(2) 3:1:1 TFA/H2O/THF, rt,
(3) TBSCl, imidazole, DMF, rt 60% three steps;
(b) Br2, 0.5M NaOAc (pH 5.3), dioxane, rt, 79%;
(c) NaN3, DMSO, 70° C., 90%
(d) ethylenediamine, EtOH, 70° C., 81%
(e) Methyl bromoacetate, TEA, THF, rt, 80%;
(f) 2iodoethanol, toluene, 70° C., 34%;
(g) PPh3, DEAD, THF, reflux, 58%;
(h) Bu4NF, THF, 0° C., 60%

Briefly, commercially available 2',3'-isopropylidene adenosine 27 (R.I. Chemical, Orange, Calif.) was converted to the bis-silyl ether 28 using Mitsunobu chemistry (Kolb, M et al., (1982) J. Med. Chem. 25(5)550-6) and subsequent isopropylidene cleavage with aqueous TFA (Fei, L.; Austin, D. L., (2001) Org. Lett. 3, 2273) was followed by reaction with TBSCl and imidazole. (Allerson, C. R. et al., J. Am. Chem. Soc. 119, 7423 (1997). Phthalimide 28 was derived from 27 in 60% overall yield in a method not requiring chromatography. Bromination at the 8-position was accomplished with Br$_2$ (Urata, H. et al., (1999) J. Chem. Soc. Perkin Trans. 1, 1833) under mildly acidic conditions in 79% yield to render 29, which was then converted to azide 30 in 90% yield. Interestingly, phthalimide cleavage efforts using hydrazine hydrate and other well known procedures failed to produce primary amine 31 with suitable efficiencies. An alternative procedure utilizing ethylenediamine afforded the versatile C8 azido 5'-amine 31 in 81% yield. Next, 31 was alkylated with 2-iodoethanol to yield ethanolamine adenylate 33. Optimization of the reaction was necessary to avoid undesired bis-alkylated material and careful control of time, solvent, and number of equivalents of iodoethanol proved vital to the success of this transformation. The yield for alkylation is low (34%), but is partly offset by facile recovery and recycling of 31 (37%) following column chromatography. Having successfully obtained 33, aziridination was accomplished using Mitsunobu chemistry to yield 34 in a 58% yield. Finally, TBS ether cleavage was effected using nBu$_4$NF to yield the 8-azido-5'-aziridino-5'-deoxyadenosine 24a in 60%.

SCHEME VII

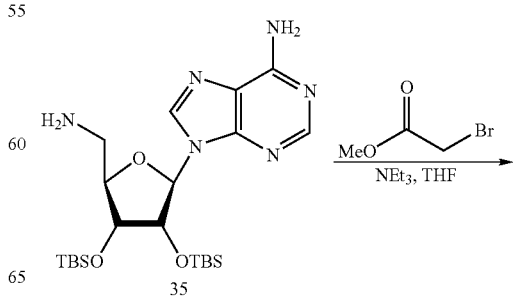

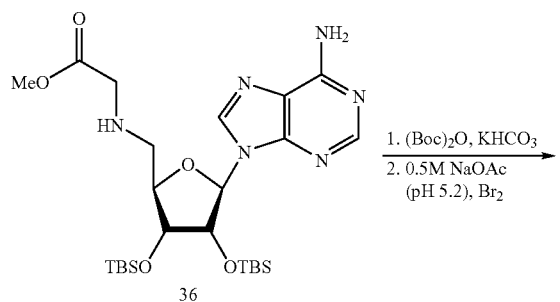

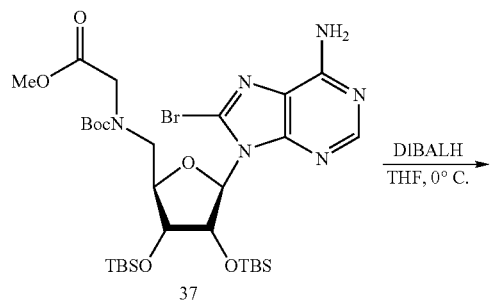

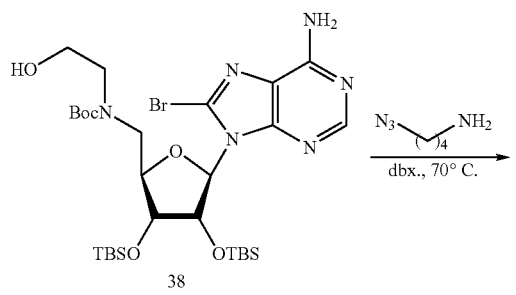

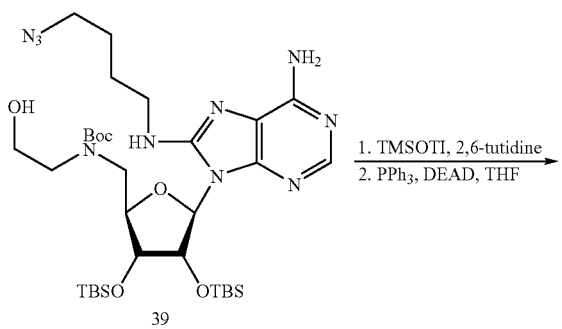

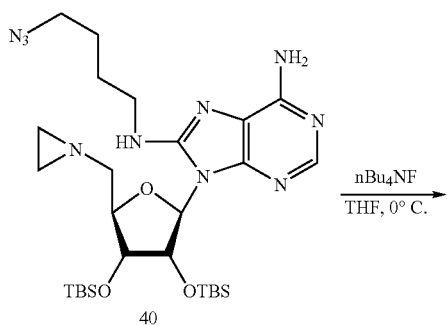

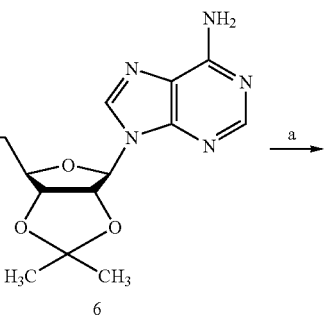

The structure and corresponding construction of alkyl azide cofactor analog 24b SCHEME VII, differs significantly from that of aryl azide 24a (SCHEME VI). Installation of the azide capped butane moiety dictated C5' elaboration prior to base modification. Beginning with an intermediate previously described in EXAMPLE 3, (Comstock, L. R. and Rajski, S. R. (2002) Expeditious synthesis of aziridine based cofactor analogs. *Tetrahedron*, 58, 6019-6026), the primary amine 35 was alkylated with the methyl bromoacetate to provide 36 in 85% yield. Due to anticipated difficulties in achieving effective C8 bromination, the secondary amine functionality of 36 was protected as the t-Butyl carbamate (Kolb, M. and Barth, J. (1985) *Liebigs Ann. Chem.*, 1036-1040). Subsequent bromination under mildly acidic conditions (Urata, H., et al. (1999) *J. Chem. Soc. Perkin Trans.* 1, 1833-1838) yielded 37 in 89% yield from 36. Reduction of the methyl ester to the primary alcohol 38 with DIBALH (Gano, K. W., et al. (2001) *Tetrahedron Lett.*, 42, 2249-2251) occurred with a yield of 81%, followed by $S_NAr$ reaction with 4-Azido-butylamine (Lee, J. W., et al., (2001) *Tetrahedron Lett.*, 42, 2709-2711), to yield guanidine 39 in 49% yield. Following Boc deprotection using TMSOTf (Sakaitani, M. and Ohfune, Y. (1990) *J. Org. Chem.*, 55, 870-876), the crude 5' ethanolamine was converted to aziridine 40 utilizing Mitsunobu conditions (Lindstrom, U. M. and Somfai, P. (1998) *Synthesis*, 109-117) in 54% over the two steps. Finally, the silyl ethers were removed with nBu₄NF (Van der Wende, E. M., et al. (1998) *J. Med. Chem.*, 41, 102-108) to yield the desired alkyl azide cofactor analog 24b, in 60% yield.

Example 17

5'-Amino-5'-deoxy-2',3'-bis-(O-tert-butyldimethylsilyl)adenosine (35)

SCHEME VIII

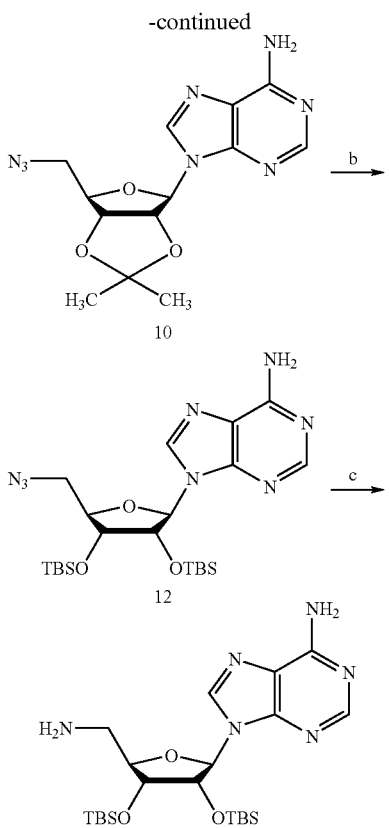

a. DPPA, PPh₃, DEAD, THF; b. 1. TFA/H₂O, 2. Chlorotriethylsilane, imidazole, DMF; c. PPH₃, THF, H₂O; d. 10 or 11, TEA, THF; e. tBu₄NF, dioxane 5'-Amino-5'-deoxy-2',3'-bis-(O-tert-butyldimethylsilyl) adenosine (35) was synthesized by the method previously described by the inventors (Comstock, L R and Rajski, S R, Tetrahedron 58 (2002) 6019-6026) and shown in SCHEME VIII. Briefly, using a Mitsunobu variation of chemistry previously reported, the inventors found that the desired OH→NH₂ interconversion coupled with silylation of both the 2' and 3' alcohols could be most expeditiously effected by treatment of commercially available 2',3'-Isopropylidene adenosine 6 with diphenylphosphoryl azide (DPPA), triphenylphosphine (PPh₃), diethylazodicarboxylate (DEAD). Azide installation in this manner proceeded in 73% yield. The azide 10 was highly amenable to acetonide cleavage with trifluoroacetic acid (Fei, L.; Austin, D. J., Org. Lett., 2001, 3, 2273-2276) and subsequent 2',3' reprotection as the 2',3' bis (O-tert-butyldimethylsilyl ether. Allerson, C. R.; Swaine, L.; Verdine, G. L., J. Am. Chem. Soc., 1997, 119, 7423-7433. Disilylation permitted not only improved solubility traits throughout the remainder of the synthesis, but also allowed for a high degree of aziridine survival upon final diol deprotection. Staudinger reduction of the azide 12 ultimately afforded the highly versatile 5' amine 35 in 74% yield over three steps from azide 10.

An NMR analysis was performed where: $^1$H NMR (CDCl₃) δ 8.33 (s, 1H), 7.95 (s, 1H), 5.99 (bs, 2H), 5.84 (d, J=6.0 Hz, 1H), 5.00 (dd, J=6.0, 4.8 Hz, 1H), 4.30 (dd, J=4.8, 3.2 Hz, 1H), 4.13 (m, 1H), 3.11 (dd, J=13.6, 3.6 Hz, 1H), 3.01 (dd, J=13.6, 5.6 Hz, 1H), 0.95 (s, 9H), 0.79 (s, 9H), 0.12 (s, 6H), −0.06 (s, 3H), −0.36 (s, 3H); $^{13}$C NMR (CDCl₃) δ 155.9, 153.0, 149.8, 141.0, 121.1, 90.0, 87.3, 74.2, 73.3, 43.8, 26.0, 25.9, 18.3, 18.0, −4.2, −4.4, −4.4, −5.1. HRMALDI: calculated for C₂₂H₄₂N₆O₃Si₂ (M+H⁺) 495.29, observed 495.285.

Example 18

5'-Amino-acetic acid methyl ester-5'-deoxy-2',3'-bis-(O-tert-butyldimethylsilyl)adenosine (36)

5'-Amino-acetic acid methyl ester-5'-deoxy-2',3'-bis-(O-tert-butyldimethylsilyl) adenosine (36) was synthesized by the method shown in SCHEME VII. To 5'-Amino-5'-deoxy-2',3'-bis-(O-tert-butyldimethylsilyl)adenosine (35) (6.664 g, 13.48 mmol) in 66.3 mL THF at 0° C. was added triethylamine (Sigma, St. Louis, Mo. Cat. No. 90335) (1.637 g, 16.17 mmol). To this solution was added methyl bromoacetate (2.474 g, 16.17 mmol) in 38.0 mL THF, drop wise. The reaction was stirred at room temperature for 16 h. The resulting precipitate was filtered off and triturated with anhydrous diethyl ether. The organic was evaporated in vacuo. Column chromatography (4:2:1 EtOAc/CH₂Cl₂/MeOH) gave 36 as a white solid (6.47 g, 85%).

An NMR analysis was performed where: $^1$H NMR (CDCl₃) δ 8.26 (s, 1H), 7.94 (s, 1H), 6.45 (bs, 2H), 5.81 (d, J=6.0 Hz, 1H), 4.94 (dd, J=6.0, 4.8 Hz, 1H), 4.22 (dd, J=4.8, 3.2 Hz, 1H), 4.17 (m, 1H), 3.67 (s, 3H), 3.45 (s, 2H), 2.97 (dd, J=12.8, 3.2 Hz, 1H), 2.87 (dd, J=12.8, 6.0 Hz, 1H), 0.88 (s, 9H), 0.73 (s, 9H), 0.05 (s, 6H), −0.13 (s, 3H), −0.38 (s, 3H); $^{13}$C NMR (CDCl₃) δ 172.7, 156.1, 152.9, 149.6, 140.5, 120.8, 89.8, 85.4, 74.2, 73.7, 51.8, 51.1, 50.9, 25.9, 25.8, 18.1, 17.9, −4.3, −4.6, −4.6, −5.2. HRMALDI: calculated for C₂₅H₄₆N₆O₅Si₂ (M+H⁺) 567.31, observed 567.309.

Example 19

8-Bromo-5'-(N-Boc)-amino-acetic acid methyl ester-5'-deoxy-2',3'-bis-(O-tert-butyldimethylsilyl)adenosine (37)

8-Bromo-5'-(N-Boc)-amino-acetic acid methyl ester-5'-deoxy-2',3'-bis-(O-tert-butyldimethylsilyl)adenosine (37) was synthesized by the method shown in SCHEME VII. Briefly, to 5'-Amino-acetic acid methyl ester-5'-deoxy-2',3'-bis-(O-tert-butyldimethylsilyl) adenosine (36) (3.276 g, 5.779 mmol) in 23.4 mL 1:1 CHCl₃/H₂O was added KHCO₃ (0.579 g, 5.779 mmol) and (Boc)₂O (1.262 g, 5.779 mmol). The reaction was stirred at room temperature for 5 h and followed by an aqueous workup (H₂O, CHCl₃). The organic was dried over Na₂SO₄ and evaporated in vacuo. To the crude material in 110 mL 9:4 dioxane/0.5 M NaOAc (pH 5.2) was added Br₂ (1.85 g, 11.558 mmol). After stirring at room temperature for 3 h, the reaction was washed (Na₂S₂O₃, EtOAc, and brine). The organic was dried over Na₂SO₄ and evaporated in vacuo. Column chromatography (2:1 EtOAc/Pet Ether) afforded 37 as a light yellow solid (3.83 g, 89%).

The product 37, was analyzed in DMSO-d6 at 90° C. The resulting NMR spectra indicated the resulting product as a mixture of rotomers, signals obtained in the spectra were broad and very little splitting was observed. Therefore, it was concluded that the mixture observed in CDCl₃ at 25° C. was due to a rotomeric mixture. The NMR spectra was: $^1$H NMR (CDCl₃) δ 8.12 (s, 1H), 8.10 (s, 1H), 6.81 (bs, 4H), 5.93 (d, J=6.4 Hz, 1H), 5.91 (d, J=6.4 Hz, 1H), 5.38 (m, 2H), 4.17 (bs, 4H), 4.06 (m, 2H), 3.90 (m, 2H), 3.78 (m, 2H), 3.58 (s, 3H), 3.57 (s, 3H), 3.39 (m, 2H), 1.40 (s, 9H), 1.33 (s, 9H), 0.89 (s, 9H), 0.88 (s, 9H), 0.70 (s, 9H), 0.68 (s, 9H), 0.09 (s, 3H), 0.08 (s, 3H), 0.07 (s, 3H), 0.06 (s, 3H), −0.17 (s, 3H), −0.18 (s, 3H), −0.52 (s, 3H), −0.53 (s, 3H); $^{13}$C NMR (CDCl₃) δ 175.8, 170.72, 170.70, 166.6, 155.4, 155.2, 154.9, 154.8, 152.4, 150.6, 150.5, 128.6, 120.5, 90.5, 90.3, 86.4, 86.0, 80.6, 80.2, 73.9, 71.8, 71.7, 68.6, 66.3, 62.6, 51.7, 50.1, 50.0, 49.2, 28.5, 28.2, 25.9, 25.7, 25.6, 25.4, 18.08, 18.06, 17.8, 17.7, −4.42, −4.45, −4.49, −4.5, −4.6, −4.7, −5.3, −5.4. HRMALDI: calculated for C₃₀H₅₃BrN₆O₇Si₂ (M+H⁺) 744.27, observed 747.270.

Example 20

8-Bromo-5'-(N-Boc)-ethanolamine-5'-deoxy-2',3'-bis-(O-tert-butyldimethylsilyl)adenosine (38)

8-Bromo-5'-(N-Boc)-ethanolamine-5'-deoxy-2',3'-bis-(O-tert-butyldimethylsilyl)adenosine (38) was synthesized by the method shown in SCHEME VII. Briefly, to 8'-Bromo-5'-(N-Boc)-amino-acetic acid methyl ester-5'-deoxy-2',3'-bis-(O-tert-butyldimethylsilyl)adenosine (37) (0.710 g, 0.952 mmol) in 16.2 mL dry THF at 0° C. was added DIBALH (4.760 mmol). The reaction was warmed to room temperature and stirred for an additional 5 h. 10 mL saturated potassium sodium tartrate tetrahydrate (Rochelle's salt) was added to the reaction and stirred vigorously overnight. The organic was washed (saturated Rochelle's salt, $H_2O$, EtOAc, brine), dried over $Na_2SO_4$ and evaporated in vacuo. Column chromatography (6:1 EtOAc/$CH_2Cl_2$) provided 38 (0.550 g, 81%). The resulting NMR spectra indicated the resulting product as a mixture of rotomers. This compound was analyzed in DMSO-$d_6$ at 90° C. The obtained signals in the spectra were broad and very little splitting was observed. Thus, the inventors concluded that the mixture observed in CDCl$_3$ at 25° C. was due to a rotomeric mixture. The peaks were very broad and often overlapping. The correct number of protons (at an appropriate chemical shift) was present in the spectra. HRMALDI: calculated for $C_{29}H_{53}BrN_6O_6Si_2$ (M+H$^+$) 717.27, observed 717.272.

Example 21

8-(4"-Azido-butylamino)-5'-(N-Boc)-ethanolamine-5'-deoxy-2',3'-bis-(O-tert-butyldimethylsilyl)adenosine (39)

8-(4"-Azido-butylamino)-5'-(N-Boc)-ethanolamine-5'-deoxy-2',3'-bis-(O-tert-butyldimethylsilyl)adenosine (39) was synthesized by the method shown in SCHEME VII. Briefly, to 8'-Bromo-5'-(N-Boc)-ethanolamine-5'-deoxy-2',3'-bis-(O-tert-butyldimethylsilyl)adenosine (38) (0.546 g, 0.761 mmol) in 9.36 mL dioxane at 70° C. was added 4-Azido-butylamine (0.869 g, 7.610 mmol). The reaction was stirred at this temperature for 2 d. The organic was washed (NaHCO$_3$, EtOAc, brine), dried over Na$_2$SO$_4$ and evaporated in vacuo. Column chromatography (6:1 EtOAc/CH$_2$Cl$_2$→1:1 Pet Ether/4:2:1 EtOAc/CH$_2$Cl$_2$/MeOH) yielded 39 (0.279 g, 49%). The resulting NMR spectra indicated the resulting product as a mixture of rotomers. This compound was analyzed in DMSO-$d_6$ at 90° C. The obtained signals in the spectra were broad and very little splitting was observed. Thus, it was concluded that the mixture observed in CDCl$_3$ at 25° C. was due to a rotomeric mixture. The peaks were very broad and often overlapping. The correct number of protons (at an appropriate chemical shift) was present in the spectra. HRMALDI: calculated for $C_{33}H_{62}N_{10}O_6Si_2$ (M+H$^+$) 751.44, observed 751.445.

Example 22

8-(4"-Azido-butylamino)-5'-aziridino-5'-deoxy-2',3'-bis-(O-tert-butyldimethylsilyl)adenosine (40)

8-(4"-Azido-butylamino)-5'-aziridino-5'-deoxy-2',3'-bis-(O-tert-butyldimethylsilyl)adenosine (40) was synthesized by the method shown in SCHEME VII. Briefly, to 8'-(4"-Azido-butylamino)-5'-(N-Boc)-ethanolamine-5'-deoxy-2',3'-bis-(O-tert-butyldimethylsilyl)adenosine (39) (0.118 g, 0.158 mmol) in 1.6 mL anhydrous CH$_2$Cl$_2$ was added 2,6-lutidine (0.084 g, 0.788 mmol) and TMSOTf (0.140 g, 0.630 mmol). The reaction was stirred for 45 min. and quenched via addition of 2 mL MeOH and 2 mL 200 mM Citric Acid (pH 4); stirring at room temperature for an additional hour ensued. The organic was washed (NaHCO$_3$, CH$_2$Cl$_2$), dried over Na$_2$SO$_4$ and evaporated in vacuo. The crude material was taken directly forward. To PPh$_3$ (0.062 g, 0.236 mmol) in 2.36 mL dry THF at 0° C. was added DEAD (0.041 g, 0.236 mmol). The components were stirred until TLC indicated complete consumption of PPh$_3$. The mixture was added to the crude adenosine in 2.1 mL dry THF. The reaction was warmed to room temperature and heated at reflux for 2.5 hours. An aqueous workup was performed (NaHCO$_3$, EtOAc, brine), the organic was dried over Na$_2$SO$_4$ and evaporated in vacuo. Column chromatography (6:1 EtOAc/CH$_2$Cl$_2$→1:1 Pet Ether/4:2:1 EtOAc/CH$_2$Cl$_2$/MeOH) afforded 40 (0.054 g, 54%).

An NMR spectra was performed where: $^1$H NMR (CDCl$_3$) δ 8.12 (s, 1H), 7.41 (t, J=5.6 Hz, 1H), 6.20 (d, J=7.6 Hz, 1H), 5.31 (bs, 2H), 4.77 (dd, J=7.6, 4.8 Hz, 1H), 4.26 (m, 1H), 4.10 (m, 1H), 3.35 (m, 2H), 3.28 (m, 2H), 3.21 (dd, J=13.2, 3.2 Hz, 1H), 1.90 (dd, J=13.2, 2.4 Hz, 1H), 1.85 (m, 2H), 1.62 (m, 4H), 1.38 (m, 1H), 1.27 (m, 1H), 0.90 (s, 9H), 0.69 (s, 9H), 0.11 (s, 3H), 0.06 (s, 3H), −0.13 (s, 3H), −0.40 (s, 3H); $^{13}$C NMR (CDCl$_3$) δ 152.1, 151.6, 151.3, 149.4, 117.9, 85.9, 85.6, 73.3, 71.3, 62.5, 51.3, 42.5, 30.0, 26.9, 26.6, 26.3, 26.0, 25.8, 18.3, 17.9, −4.2, −4.52, −4.55, −5.3. HRMALDI: calculated for $C_{28}H_{52}N_{10}O_3Si_2$ (M+H$^+$) 633.38, observed 633.381.

Example 23

8-(4"-Azido-butylamino)-5'-aziridino-5'-deoxy adenosine (24b)

8-(4"-Azido-butylamino)-5'-aziridino-5'-deoxy adenosine (24b) was synthesized as shown in SCHEME VII. Briefly, to 8'-(4"-Azido-butylamino)-5'-aziridino-5'-deoxy-2',3'-bis-(O-tert-butyldimethylsilyl)adenosine (40) (0.076 g, 0.120 mmol) in 3.3 mL THF at 0° C. was added nBu$_4$NF (0.263 mmol). The reaction was stirred at 0° C. for 1 h and evaporated in vacuo. Immediate chromatography (2:1:1 EtOAc/CH$_2$Cl$_2$/MeOH) yielded product (0.0290 g, 60%). $^1$H NMR (DMSO-$d_6$) δ 7.90 (s, 1H), 7.65 (t, J=4.8 Hz, 1H), 6.41 (bs, 2H), 5.94 (d, J=5.2 Hz, 1H), 5.33 (bs, 1H), 5.21 (bs, 1H), 4.72 (bs, 1H), 4.26 (m, 1H), 4.00 (m, 1H), 3.36 (m, 2H), 3.30 (m, 2H), 2.99 (dd, J=10.4, 2.4 Hz, 1H), 2.25 (dd, J=10.4, 2.4 Hz, 1H), 1.72 (m, 2H), 1.56 (m, 4H), 1.41 (m, 1H), 1.31 (m, 1H); $^{13}$C NMR (DMSO-$d_6$) δ 152.1, 151.2, 150.2, 148.5, 116.9, 85.9, 84.0, 71.0, 69.9, 61.7, 50.5, 41.7, 28.7, 26.2, 25.8, 25.6. HRMALDI: calculated for $C_{16}H_{24}N_{10}O_3$ (M+H$^+$) 405.20, observed 405.209.

Stock concentrations were determined using UV/Vis spectroscopy (260 nm). The concentration of 3 was determined as previously described. The molar extinction coefficients were determined to be 6633 for the aryl azide cofactor analog, 24a, and 8900 for the alkyl azide cofactor analog, 24b.

B. Synthesis and Characterization of Biotinylated Triarylphosphine and Intermediates In order to determine the efficacy of the Staudinger ligation of labeled reacting groups to synthetic cofactor analogs 24a and 24b biotinylated triarylphosphine reacting groups were synthesized for use in the Staudinger ligation.

Example 24

N-(3-{2-[2-(3-tert-Butoxycarbonylamino-propoxy)-ethoxy]-ethoxy}-propyl)-2-diphenylphosphanyl-terephthalamic acid methyl ester (41)

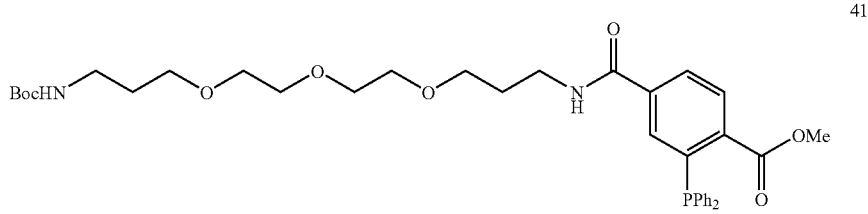

41

Synthesis of N-(3-{2-[2-(3-tert-Butoxycarbonylamino-propoxy)-ethoxy]-ethoxy}-propyl)-2-diphenylphosphanyl-terephthalamic acid methyl ester (41). To 2-Diphenyl-phosphanyl-terephthalic acid 1-methyl ester (Saxon, E. and Bertozzi, C. R. (2000) Science, 287, 2007-2010) (0.493 g, 1.352 mmol) in 4.75 mL THF was added CDI (0.263 g, 1.623 mmol). After stirring for 1 h, Boc-(4,7,10-trioxa-1,13-tridecanediamine) (2) (0.520 g, 1.623 mmol) in 4.9 mL THF was added and the mixture allowed to stir at ambient temperature for an additional hour. The organic was washed (NH$_4$Cl, EtOAc, brine), dried over Na$_2$SO$_4$, and evaporated in vacuo. Column chromatography (5:1 EtOAc/Pet Ether) yielded 41 as a yellow solid (0.733 g, 81%). An NMR analysis was performed where: $^1$H NMR (CDCl$_3$) δ 8.01 (dd, J=8, 3.6 Hz, 1H), 7.71 (dd, J=8, 1.2 Hz, 1H), 7.37 (dd, J=3.6, 1.2 Hz, 1H), 7.30-7.23 (m, 10H), 6.88 (bs, 1H), 4.99 (bs, 1H), 3.69 (s, 3H), 3.58-3.45 (m, 8H), 3.45-3.40 (m, 6H), 3.14 (m, 2H), 1.75 (p, J=6 Hz, 2H), 1.67 (p, J=6 Hz, 2H), 1.39 (s, 9H); $^{31}$P NMR (CDCl$_3$) δ -2.66; $^{13}$C NMR (CDCl$_3$) δ 166.7, 166.2, 156.0, 141.55, 141.3, 137.7, 137.3, 137.2, 136.5, 136.3, 134.0, 133.8, 133.1, 130.7, 129.0, 128.7, 128.6, 126.4, 70.5, 70.3, 70.1, 69.5, 52.2, 38.7, 38.5, 29.7, 28.8, 28.5. HRMALDI: calculated for C$_{36}$H$_{47}$N$_2$O$_8$P (M+H$^+$), 667.31, observed 667.303.

Example 25

2-Diphenylphosphanyl-N-(3-{2-[2-(3-Biotin)-propoxy)-ethoxy]-ethoxy}-propyl)-terephthalamic acid methyl ester (42)

Synthesis of 2-Diphenylphosphanyl-N-(3-{2-[2-(3-Biotin)-propoxy)-ethoxy]-ethoxy}-propyl)-terephthalamic acid methyl ester (42). To 41 (0.234 mmol) was added 2.4 mL 4N HCl/dioxane. After stirring at room temperature for 2 h, the solvent was evaporated and co-stripped with 1:1 EtOAc/MeOH twice. The resulting crude material was dried under vacuum before further use and taken directly forward without purification. Biotin (0.048 g, 0.195 mmol) was dissolved in 650 µL dry DMF by heating and magnetic stirring (3). The solution was cooled to ambient temperature and CDI (0.038 g, 0.234 mmol) in 65 µL dry DMF was added to give a white precipitate. After stirring at room temperature for 1 h, DIEA (0.076 g, 0.584 mmol) and deprotected 41 (0.133 g, 0.234 mmol) in 530 µL dry DMF was added and stirred overnight. The organic was evaporated and dried under vacuum. The crude material was brought up in CH$_2$Cl$_2$, washed with H$_2$O, dried over Na$_2$SO$_4$, and evaporated in vacuo. Column chromatography (10:1 CH$_2$Cl$_2$/MeOH) afforded 42 (0.110 g, 71%).

An NMR analysis was performed on 42 where: $^1$H NMR (CDCl$_3$) δ 8.05 (dd, J=8, 3.6 Hz, 1H), 7.78 (dd, J=8, 1 Hz, 1H), 7.42 (dd, J=3.6, 1 Hz, 1H), 7.34-7.25 (m, 10H), 7.23 (t, J=5.6 Hz, 1H), 6.74 (t, J=5.6 Hz, 1H), 6.41 (s, 1H), 5.61 (s, 1H), 4.45 (dd, J=7.6, 4.8 Hz, 1H), 4.25 (dd, J=7.6, 5.2 Hz, 1H), 3.72 (s, 3H), 3.60-3.42 (m, 14H), 3.28 (q, J=6.4 Hz, 2H), 3.12-3.08 (m, 1H), 2.86 (dd, J=12.8, 4.8 Hz, 1H), 2.70 (d, J=12.8 Hz, 1H), 2.15 (t, J=7.6 Hz, 2H), 1.79 (p, J=6.4 Hz, 2H), 1.72 (p, J=6.4 Hz, 2H), 1.66-1.57 (m, 4H), 1.40 (p, J=6.4 Hz, 2H); $^{31}$P NMR (CDCl$_3$) δ -2.63; $^{13}$C NMR (CDCl$_3$) δ 173.3, 166.9, 166.4, 164.2, 141.5, 141.2, 137.6, 137.3, 137.2, 136.6, 136.4, 134.0, 133.8, 133.2, 130.7, 129.0, 128.7, 128.6,

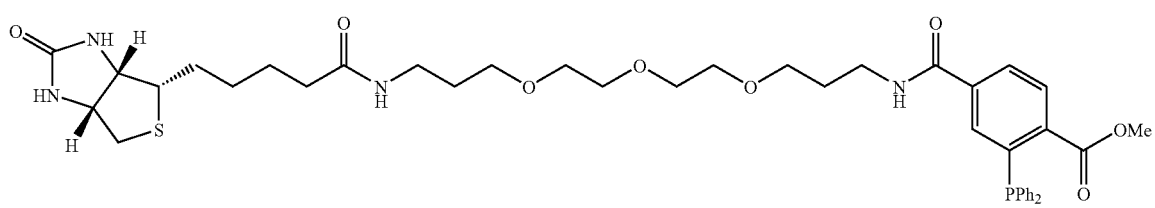

42

126.5, 70.45, 70.39, 70.2, 70.0, 69.96, 69.7, 61.8, 60.2, 55.8, 52.3, 40.5, 38.5, 37.5, 36.1, 29.7, 29.1, 28.9, 28.4, 28.2, 25.8. HRMALDI: calculated for $C_{41}H_{53}N_4O_8PS$ (M+H$^+$), 793.33, observed 793.325.

Example 26

2-Diphenylphosphanyl-benzoic acid 5-(biotin)-pentyl ester (44)

44

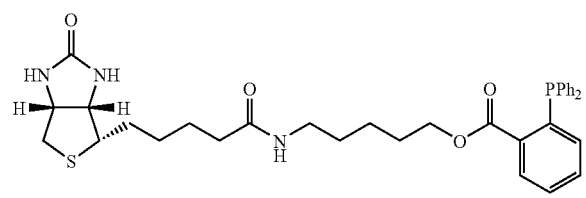

Synthesis of 2-Diphenylphosphanyl-benzoic acid 5-(biotin)-pentyl ester (44). To 2-Diphenylphosphanyl-benzoic acid 5-(Boc-amino)-pentyl ester (Restituyo et al., 2003, Org. Lett., 5, 4357-4360) (0.295 g, 0.689 mmol) was added 10 mL 4N HCl/dioxane. After stirring at room temperature for 2 h, the solvent was evaporated and co-stripped with 1:1 EtOAc/MeOH twice. The resulting crude material was dried under vacuum before further use and taken directly forward without purification. Biotin (0.160 g, 0.655 mmol) was dissolved in 4 mL of a 5:1:1 THF/H$_2$O/DMF solution, along with DIEA (0.237 g, 1.837 mmol) and O—(N-Succinimidyl)-N,N,N',N'-tetramethyl-uronium tetrafluroborate (TSTU) (0.240 g, 0.797 mmol). After stirring for 2 h, an additional aliquot of DIEA (0.519 g, 4.02 mmol) was added, followed by the crude phosphine (0.689 mmol) in 10 mL THF. The mixture was stirred for an additional 12 h and the organic was evaporated. The crude material was resuspended in CHCl$_3$ and washed (NH$_4$Cl, NaHCO$_3$, CHCl$_3$, brine), the organic was dried over Na$_2$SO$_4$ and evaporated in vacuo. Column chromatography (4:4:1 EtOAc/CH$_2$Cl$_2$/MeOH) provided 44 (0.200 g, 49%).

An NMR analysis was performed on product 44 where: $^1$H NMR (DMSO-d$_6$) δ 7.98-7.94 (m, 1H), 7.73 (t, J=5.6 Hz, 1H), 7.52-7.50 (m, 2H), 7.38-7.37 (m, 6H), 7.19-7.15 (m, 4H), 6.86-6.82 (m, 1H), 6.42 (s, 1H), 6.35 (s, 1H), 4.28 (dd, J=6.4, 5.2 Hz, 1H), 4.10 (dd, J=6.4, 5.2 Hz, 1H), 4.04 (t, J=6.4 Hz, 2H), 3.10-3.05 (m, 1H), 3.00 (q, J=6.4 Hz, 2H), 2.80 (dd, J=12.0, 4.8 Hz, 1H), 2.57 (d J=12.0 Hz, 1H), 2.04 (t, J=7.2 Hz, 2H), 1.63-1.56 (m, 1H), 1.52-1.42 (m, 5H), 1.38-1.15 (m, 6H); $^{31}$P NMR (CDCl$_3$) δ −3.74; $^{13}$C NMR (CDCl$_3$) δ 173.3, 166.9, 146.4, 140.1, 139.8, 137.9, 134.6, 134.4, 134.3, 133.8, 133.6, 131.9, 130.5, 128.6, 128.44, 128.38, 128.2, 65.1, 61.7, 60.3, 60.2, 55.8, 40.4, 39.2, 35.9, 29.1, 28.2, 28.1, 25.8, 23.3. HRMALDI: calculated for $C_{34}H_{40}N_3O_4PS$ (M+H$^+$), 618.25, observed 618.248.

C. Modified Staudinger Reaction with Enzymatically Azidated Oligonucleotide

Example 27

DNA Labeling and Duplex Formation

The synthetic oligonucleotide utilized for M.TaqI reactions having the sequence d(5'-TGAATCTCGAGCACCC-3') (SEQ. ID. 1). The 5'-$^{32}$P-labeled oligonucleotide was prepared with T4 Polynucleotide Kinase and [γ-$^{32}$P]ATP using standard methods (Sambrook, J. and Russell, D. (2001) Molecular Cloning: A Laboratory Manual. Cold Spring Harbor Laboratory Press, Cold Spring Harbor, N.Y., 9.68-9.69). The labeled oligonucleotide was desalted and unincorporated [γ-$^{32}$P]ATP removed via Sephadex G-25 spin column (Amersham, Piscataway, N.J.). The labeled strand was annealed to its complement d (3'-GGGTGCTCGAGATTCAAA-5') (SEQ. ID. 2) in 1× TE buffer by heating to 80° C. (5 min) and cooling to 4° C. over 4 h. A similar procedure to prepare the synthetic oligonucleotide for M.EcoRI was followed, but utilized the sequence d(5'-TGAATGAATTCGACCC-3') (SEQ. ID. 3) and its complement d (3'-GGGTCGAATTCATTCAAA-5') (SEQ. ID. 4).

D. Restriction/Protection Assay

Example 28

M.TaqI-Mediated DNA Alkylation

Commercially available pUC19 (New England Biolabs, Ipswich, Mass.) was linearized with R.EcoR I according to manufacturer's protocol (final concentration of 0.2 μg/μL or 114 nM). R.EcoR I was heat inactivated at 65° C. for 15 min. prior to further plasmid use. Reaction mixtures were prepared by the addition of appropriate stock solutions to a total volume of 20 μL (in buffer A). The final DNA concentration was 14.3 nM; the final concentrations of the cofactor analogs and the M.TaqI varied upon the specific reaction sequence. All reactions were heated at 65° C. for 4 h, followed by cooling to 0° C. The extent of methyltransferase dependent DNA alkylation was analyzed by the addition of R.TaqI (2 U in an additional 10 μL buffer A), followed by incubation at 65° C. for 1 h. Upon cooling to 0° C., Proteinase K (Ambion, Austin, Tex.) (0.02 U in 5 μL H$_2$O) was added to each reaction and incubated at 37° C. for 1 h. The extent of alkylation (as indicated by protection from endonuclease cleavage) was visualized by electrophoresis on a 2% agarose gel shown in FIG. 1A shows the protective effect of increasing the concentration of M.TaqI while FIG. 1B shows the protective effect of increasing cofactor analog. In both FIGS. 1A and 1B linearized pUC19 is shown in lane 1 with faster migrating restriction fragments seen in the following lanes.

E. M.TaqI-Mediated DNA Alkylation

A restriction/protection assay previously described (Pljevaljcic, G., et al., (2004) Sequence-specific methyltransferase-induced labeling of DNA (SMILing DNA). Chem Bio Chem, 5, 265-269) was utilized to analyze the extent of MTase-dependent DNA alkylation by the unsubstituted aziridine cofactor analog 3 and the two azido-based cofactor analogs 24a and 24b. FIG. 1A illustrates the effect of increasing M.TaqI concentration on the extent of DNA alkylation. In comparing lanes 3-5, 7-9, and 11-13 for the three cofactor analogs at 100 μM, an increase in the amount of DNA alkylation is observed with a gradient ranging from 20 to 200 nM M.TaqI as reflected by the increased protection from the R.TaqI digestion indicated by the decrease in intensity of the faster migrating restriction fragments. Significantly, in the absence of M.TaqI, no protection of the DNA is observed (lanes 2, 6, and 10); none of the cofactor analogs tested thus appeared to inhibit R.TaqI nor was non-specific DNA alkylation by any of the cofactor analogs sufficient to render protection from R.TaqI-mediated plasmid scission. Similar trends were observed with an increase in the amount of cofactor analogs shown in FIG. 1B. Increasing cofactor analog concentration from 10 to 100 μM coincided with increased protection from R.TaqI as seen in lanes 3-5, 7-9, and 11-13. As indicated by lanes 2, 6, and 10, R.TaqI is not inhibited by the methyltransferase.

Example 29

M.TaqI and M.EcoRI Reactions with Synthetic Oligonucleotide

Reaction mixtures were prepared by the addition of appropriate stock solutions to a total volume of 20 μL in either buffer A or buffer B. The final DNA concentration was 1 μM; final concentration of cofactor analog was 100 μM; the final concentrations of M.TaqI and M.EcoRI were 6 μM and 2 μM respectively. All reactions were incubated at 37° C. for 18 h, followed by cooling to 0° C. Proteinase K (0.02 U in 2 μL $H_2O$) was added to each reaction and digestions were carried out for 1 h at 37° C. The resulting alkylated and proteolyzed samples were then processed as indicated below.

Example 30

Modified Staudinger Reaction with Cofactor Analog-Linked 32P-Labeled Oligonucleotide An aliquot (5.5 μL, 5 pmol) of cofactor analog-linked $^{32}$P-labeled duplex was combined with 2.5 μL $H_2O$, 1 μL 50 mM NaOH, and 1 μL 10 mM Biotin-linked phosphine 42 or 44 (in DMF) as shown in SCHEME IX. The final concentration of DNA in the ligation reaction was 500 nM. Additional control reactions were also prepared (containing DMF only). The samples were incubated at 37° C. for 14 h. The ligation reaction was either analyzed by DPAGE or ethanol precipitated (Sambrook, J. and Russell, D. (2001) Molecular Cloning: A Laboratory Manual. Cold Spring Harbor Laboratory Press, Cold Spring Harbor, N.Y., 9.68-9.69) with 39 μg tRNA (*E. coli*, Type XX, Strain W) before subsequent processing and data acquisition.

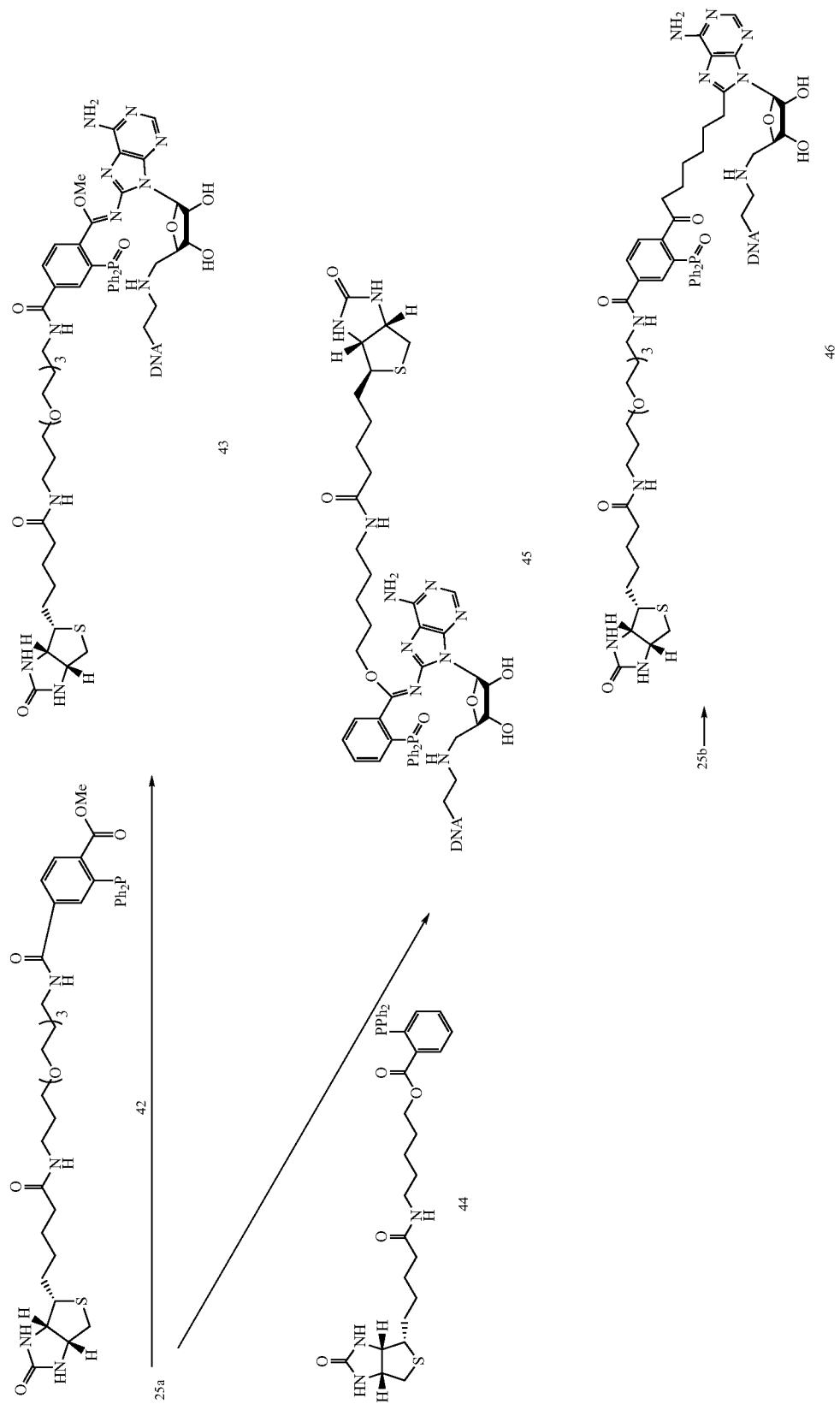

Example 31

Immobilized Streptavidin Pull-Down Assay

ImmunoPure® Immobilized Streptavidin (Pierce Biotechnology, Rockford, Ill.) was prepared by washing twice with 1M NaCl (total slurry volume of 30 μL). The washed agarose was added to the ligation reaction in a total volume of 20 μL buffer C. The slurry was gently mixed at room temperature for 1 h. The material was transferred to a micro-spin column and unbound DNA was washed away by subsequent resuspension in 1M NaCl and centrifugation (3×50 μL). The extent of radiolabeled DNA retention on the streptavidin-linked agarose was determined by liquid scintillation counting of the micro-spin column matrices.

Example 32

Staudinger Ligation with Enzymatically Azidated Oligonucleotide

Biotin linked triarylphosphines 42 and 44 (SCHEME IX) were synthesized to assess the effectiveness of Staudinger ligations with cofactor analog modified DNA. See EXAMPLES 24-36 for experimental procedures and corresponding spectral data. Based upon previous results, the ortho-methoxycarbonyl functionalized triarylphosphine 42 was expected to ligate with both the aryl and alkyl azide adducts, as depicted in SCHEME IX. Alternatively, ester-linked phosphine 44 was anticipated to couple only with the aryl azide modified DNA based upon previous findings (Restituyo, J. A., et al., (2003) *Org. Lett.*, 5, 4357-4360). These expectations were predicated on the knowledge that aryl azides react with ortho-alkoxycarbonyl triarylphosphines to afford highly stable imidate structures such as 43 or 45. In marked contrast, alkyl azides react with such phosphines to produce amide-linked materials. Alkyl azide reactions with such phosphines invoke dissociation of the ester-derived alkoxide moiety from the ligated species.

As shown in FIG. 2A, a pronounced shift of the DNA mobility in the presence of the three cofactor analogs and M.TaqI (lanes 3, 7, and 12) highlights the covalent attachment to the synthetic oligonucleotide. It is important to note that non-specific alkylation is not visible for the three cofactor analogs tested here (lanes 2, 6, and 11). Subjection of 25a to biotinylated triarylphosphine 42 produced a significant reduction in DNA mobility (lanes 8 and 13) consistent with triarylphosphine ligation. Additionally, the biotinylated triarylphosphine 44 only ligated to the product derived from 25a, as seen in lane 9 versus 14. The observation of a new band is evident in lane 14 (reaction of 25b with 44) and is likely the product resulting from the reduction of the azide to the primary amine. This is consistent with the fact that 44 does not ligate to alkyl azides, but rather effects their water dependent reduction (Restituyo, J. A., et al., (2003) *Org. Lett.*, 5, 4357-4360). Indeed, the product obtained from treatment with 44 migrates with that formed by treatment of 25b with triphenylphosphine (lane 15). Importantly, no shift of 3 occurs in the presence of either phosphine (lanes 4 and 5) and indicates that the observed shift resulting from the addition of the triarylphosphines is, in fact, due to the Staudinger ligation involving the azides of 24a and 24b. In the presence of the phosphines tested here, no alteration in the band mobility occurs for either the DNA or the non-specific alkylation controls.

The attachment of cofactor analogs 3, 24a and 24b to DNA is not restricted to the M.TaqI system. FIG. 2B shows the results of investigations into the ability of the enzyme M.EcoRI to transfer these cofactor analogs to a radiolabeled synthetic oligo duplex having the sequence d(5'-GAATTC-3') (SEQ. ID. 5). As evidenced by investigation of lane 2, M.EcoRI is clearly capable of transferring 3. As assessed by independent analysis the slow mobility material observed in lane 2 moves with a different mobility than that observed in the absence of M.EcoRI and the amount of alkylation observed with enzyme is far greater than that observed in the absence of enzyme (data not shown). Perhaps more intriguing is that the mobility pattern of products formed in lanes 3-12 of FIG. 2B are very similar to those of lanes 6-15 in FIG. 2A. The activity of M.EcoRI with cofactor analogs 24a and 24b closely parallels that observed with M.TaqI. Careful analysis of FIG. 2B, lane 5 clearly indicates, however, that Staudinger ligation of the 24a modified M.EcoRI substrate does not proceed with the same efficiency observed with the analogous M.TaqI case. Also noteworthy is that treatment of the 24a-linked M.EcoRI substrate with PPh$_3$, unlike the case seen in lane 10 of FIG. 2A, affords a band with altered mobility relative to the 24a-linked strand (lane 7, FIG. 2B). These subtle differences may result from DNA sequence moderated hydrogen-bonding networks made available in the M.TaqI versus M.EcoRI products. Although slight differences exist between M.TaqI and M.EcoRI-derived reactions and products, these results show that multiple DNA methyltransferases are active with both 24a and 24b.

Example 33

Label Functionality

Initial efforts to couple biotinylated reagents 42 and 44 with azide-linked pUC19 failed to yield discernible ligation via the streptavidin pull-down assay. Two hypotheses were developed to explain this shortcoming: the first involved the low DNA concentration and the second took into account the sterics imparted by the larger piece of DNA. Thus, a synthetic oligonucleotide duplex was used to perform the MTase-dependent alkylations, followed by the modified Staudinger reaction. To verify the structural and functional integrity of biotin following the modified Staudinger reaction, a pull down assay utilizing agarose-immobilized streptavidin was performed using products derived from M.TaqI reactions. As shown in FIG. 3A, scintillation counting of the 5'-end labeled modified strands revealed a high degree of radioisotopic retention to the streptavidin-agarose in those reactions involving 4a and either 42 or 44 relative to a DMF control devoid of phosphine. Additionally, FIG. 3B illustrates the retention of radioactivity for the ligation product of 25b with 42. This observation supports the notion that 25b did not ligate to 44 (lane 14, FIG. 2A), consistent with previous efforts by the inventors demonstrating that ester linked triarylphosphines, such as 44, form stable ligation products with aryl azides but not alkyl azides. This approach not only allowed the ligations to be performed at a higher DNA concentration, but subtle structural differences between DNA adducts could also be readily visualized with denaturing polyacrylamide gel electrophoresis.

M.TaqI and M.EcoR I both promote DNA azidation upon presentation with an appropriate substrate and either 24a or 24b. Qualitative analysis of M.TaqI promoted alkylation of linearized pUC19 can be made by observing the intensity and location of modified and/or unmodified DNA bands shown in FIGS. 1A and 1B. In comparing the efficiency of M.TaqI dependent DNA alkylation with the three cofactor analogs, it appears that 24a and 24b are better cofactor analogs for M.TaqI than is the unsubstituted cofactor analog 3. This can be deduced from the almost complete disappearance of the smaller restriction fragments in reactions containing 24a and 24b, relative to 3. Using a small synthetic oligonucleotide, it was possible to assess the activity of M.EcoRI with 3, 24a and 24b. As noted previously, M.EcoRI, like M.TaqI, is highly amenable to DNA modification with all three cofactor analogs. These results implicate both 24a and 24b as potentially powerful tools by which to modify both known and unknown biological substrates of adenine MTases.

Notably, azide bearing cofactor analogs are not restricted to use by adenine methyltransferases. In addition to M.TaqI and M.EcoR I, the inventors examined two cytosine $C^5$ methyltransferases, M.HhaI and M.HpaII. Of the two enzymes, M.HhaI catalyzed the transfer of both the aryl azide 24a and alkyl azide 24b analogs, albeit with a lower efficiency than M.TaqI. M.HpaII was compatible with the unsubstituted cofactor analog 3, but was not able to catalyze the transfer of either azido-based cofactor analog. Thus, the nucleic acid chemistry of azide bearing cofactor analogs is not restricted to adenine methyltransferases, but is consistent throughout for SAM utilizing methyltransferases. This result led the inventors to study whether azide-bearing DNA substrates undergo ligation chemistries similarly.

Initial ligation model studies focused on the ability of cofactor analog precursors with aryl and alkyl azides to undergo the modified Staudinger reaction and Huisgen [2+3] cycloaddition reactions under biological conditions (Restituyo, J. A., et al., (2003) *Org. Lett.*, 5, 4357-4360). HPLC analysis of an aryl azide derivative indicated fast reaction times and high yields with triarylphosphines bearing the core of 42 and 44. The alkyl azide derivative also underwent ligation to a terminal alkyne in a similarly facile manner. However, the aryl azide was incompatible with alkyne ligations under a wide array of reaction conditions. Thus, it was concluded that the aryl azide cofactor analog, 24a, would be well suited for the Staudinger ligation, whereas the alkyl azide cofactor analog, 24b, would be compatible with both the Staudinger ligation (although not as fast as 24a) and click chemistry.

Recent applications of Cu(I)-catalyzed click chemistry emphasize the reliable Huisgen dipolar cycloaddition between an azide and alkyne. This coupling has become an important method for coupling subunits together with a high thermodynamic driving force. Applications have ranged from modifications of enzyme active sites to the cell surfaces of *E. coli* and continue to evolve on an almost daily basis (Link, A. J. and Tirrell, D. A. (2003) *J. Am. Chem. Soc.*, 125, 11164-11165; Speers, A. E., et al., (2003) *J. Am. Chem. Soc.*, 125, 4686-4687). Although the methodology has been successful with non-nucleic acid substrates, the Cu(I)-catalyzed cycloaddition in the presence of DNA leads to rapid destruction of nucleic acids via Fenton-Haber Weiss chemistry (Kanan, M. W., et al., (2004) *Nature*, 431, 545-549; Erdem, G., et al., (1994) *J. BioscL*, 19, 9-17). As a result, emphasis was placed on the modified Staudinger reaction.

The ability of the ortho-methoxycarbonyl functionalized triarylphosphine 42 and the triarylphosphine 44 to undergo the modified Staudinger reaction with DNA modified with the two azido cofactor analogs has been demonstrated herein. Based upon previous observations and mechanistic rationale the ability of 42 to couple with both the alkyl and aryl azide cases was validated. As expected, the extent of ligation to the alkyl azide modified DNA was lower than that observed with the aryl azide. This is perhaps best rationalized when one considers the significantly greater electron density (and thus, reduced electrophilic character) of alkyl azides relative to the more electron poor aryl azides. Also noteworthy is that formation of the imidate structures characteristic of purported ligation adducts 44 and 45 (SCHEME IX) calls for a significantly abbreviated mechanistic pathway than that involved in formation of amide structures like 46 (Restituyo, J. A. et al., (2003) *Org. Lett.*, 5, 4357-4360). Although phosphine 44 is compatible only with aryl azides, its ligation to azide-modified DNA is remarkably efficient. One of the principal advantages to 44 lies in its ease of preparation. Unlike the phosphine developed by Bertozzi, which requires multiple synthetic manipulations and tedious recrystallizations to purify intermediates (Saxon, E. and Bertozzi, C. R. (2000) *Science*, 287, 2007-2010), 44 can be readily produced from a commercially available triphenylphosphinic acid via attachment to one's linker of choice through simple esterification procedures (Restituyo, J. A., et al., (2003) *Org. Lett.*, 5, 4357-4360).

Having validated the hypothesis that enzymatically azidated DNA was compatible with the Staudinger ligation, the inventors next demonstrated the utility of this methodology in identifying and isolating biological molecules as demonstrated in EXAMPLES 28 and 29. The high binding affinity between avidin and biotin prompted the choice of this affinity matrix handle to demonstrate this methodology. One could easily exploit the avidin-biotin interaction by performing an electrophoretic mobility shift (gel shift) assay or by one of several technologies based on the strength of this interaction. For this investigation, the inventors opted to use an immobilized streptavidin that would allow unbound molecules to be washed away, leaving the biotinylated product bound to the agarose. Selective 5'-end labeling of the DNA duplex allowed the application of liquid scintillation counting for detection of avidin bound materials. The results obtained reveal the cofactor analog, methylase and ligation-dependent retention of radiolabeled DNA to the immobilized agarose relative to the DMF control. Thus, these investigations show that synthetic cofactor analogs described here can be used to specifically identify and isolate methylation substrates.

The results not only validate the integrity of the azido-based cofactor analogs following enzymatic transfer to substrate DNA, but also verifies that affinity tagged triarylphosphines can undergo ligation to azide linked DNA under biological conditions. These results show that biological methylases can be converted into azidonucleosidyl transferases using cofactor analogs. Further, the cofactor analogs can undergo post-substrate modification to be further modified by ligating a handle of choice to the substrate complex. Thus, the reactions described can be used to both purify and quantify the modified substrates.

The ability of 8-azidoadenosine (and aryl azides in general) to undergo the Staudinger ligation with triarylphosphines coupled with the ability of C8 azido-SAM analog to retain its cofactor reactivity led to the inventors previously reported synthesis of azido cofactor analog 24a (Comstock, L. R., J Org Chem. 2004 Feb. 20; 69(4):1425-8). However, until now, it has not been shown that such a cofactor analog could be used by DNA methyltransferases or used as an anchoring point for biomolecule labeling, such as with biotin or radiolabels. These investigations illustrate that both 24a and 24b are very effective in their role as a synthetic cofactor analog and that DNA modified with this substance undergoes facile Staudinger ligation with a biotinylated reagent as shown in rather generic fashion by SCHEME V.

The production of synthetic cofactor analogs similar in structure to SAM but allowing for elaborate post-enzymatic modifications permits site specific modification of biomolecules in a way not previously known. Importantly, MTase-dependent azidation of large biomolecular substrates may be used not only to modify known substrates of methylation, but also to aid in the isolation and identification of currently unknown substrates of methylation, be they nucleic acids or proteins. Indeed, as attention at the chemistry biology interface continues to intensify on understanding the roles of DNA and protein methylation, particularly in the realm of transcriptional regulation, synthetic agents capable of intervening in biosynthetic processes will become attractive tools by which to more readily answer biological questions.

III. DNA Methyltransferase Click Chemistry

Success in using cofactor analogs to transfer specific components to receiving groups led to investigations in synthesizing similar cofactor analogs that could be used in click chemistry. Success in the use of methyltransferases as azidonucleosidyl transferases led the inventors to investigate whether click chemistry could be an available route for the synthesis of cofactor analogs.

Manifolds for the sequence-specific recognition and modification of DNA have proven vital for structural and functional studies of DNA, as well as the pursuit of rationally designed therapeutic agents. Successful strategies for sequence-selective targeting of DNA include triplex forming oligodeoxyribonucleotides (ODNs), designer zinc finger proteins and most notably, synthetic polyamides. The mechanisms of recognition in each of these examples are unique but are contingent upon a series of temporary interactions between modifying agent and substrate. Therefore, the inventors designed a series of experiments to identify a method or methods for covalent site-specific DNA alkylation, mediated by methyltransferases. Such methods should also enable subsequent chemoselective ligation via cycloaddition reactions such as the Huisgen [2+3] cycloaddition reaction. Success in this goal would provide an ability to easily, quickly and specifically tag DNA moieties followed by click chemistry (cycloaddition) labeling.

A. Chemistry

All reactions were carried out under an atmosphere of argon unless indicated otherwise. All reagents were obtained from available commercial sources and used without further purification unless otherwise noted. NMR spectra were acquired on Varian Unity Inova 400 MHZ and 500 MHz spectrometers using TMS, 3-(trimethylsilyl)-propionic-2,2, 3,3-$d_4$ acid sodium salt, or solvent as internal reference; the chemical shifts are reported in ppm, in δ units.

Example 34

Synthesis of Ethanolamine Adenylate (54)

SCHEME X

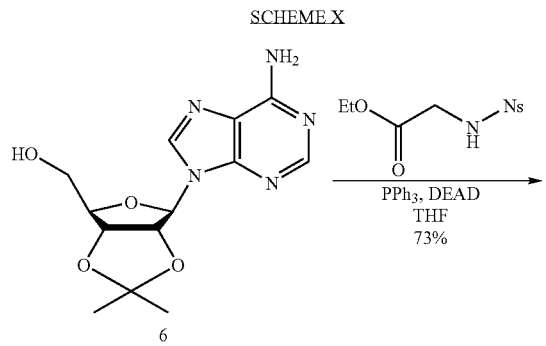

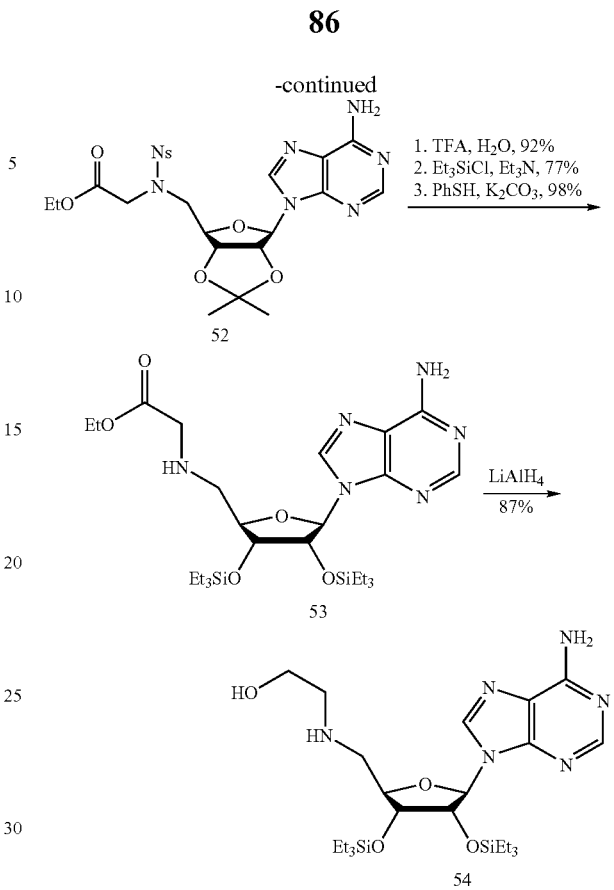

Ethanolamine Adenylate (54) was synthesized as shown in SCHEME X. Briefly, commercially available 2',3'-isopropylidene adenosine 6 (Acros Organics, Geel, BE, Cat. No. 122720050) was coupled with nosylate 51 in the presence of triphenylphosphine (PPh$_3$) and diethylazodicarboxylate (DEAD) in THF. Ethyl ester 52 was obtained in purified form in 73% yield. Acetonide cleavage followed by 2',3' reprotection as the di-TES ether and almost quantitative cleavage of the o-NBS moiety provided 53, which was amenable to ester reduction with LiAlH$_4$ to yield 54. Interestingly, 54 can also serve as a precursor to 3 through aziridination at the 5' position with triphenylphosphine and DEAD in THF in modest yields, followed by deprotection of the silyl groups with Bu$_4$NF.

Example 35

Synthesis of 5'-Propargylethanolamine-5'-Deoxy-2', 3'-Bis(O-Triethylsilyl)Adenosine (55)

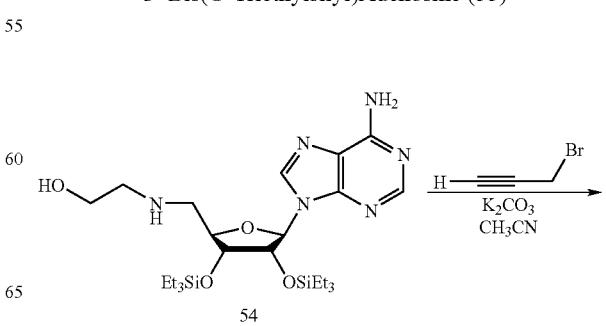

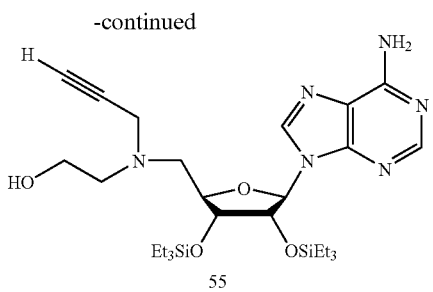

5'-propargylethanolamine-5'-deoxy-2',3'-bis(O-triethylsilyl)adenosine (55) was synthesized by the method shown above. To 56.6 mg of ethanolamine adenylate 54 (0.105 mmol.) was added 0.5 mL anhydrous CH₃CN. To the stirring solution was added 17.5 mg K₂CO₃ (0.127 mmol., 1.2 eq.) at room temperature. To the basic solution was then added 15 mg. (9.5 µL, 0.126 mmol., 1.2 eq.) propargyl bromide (Alfa Aesar) diluted with 0.5 mL anhydrous CH₃CN. The reaction was stirred at room temperature for 18 h after which time the reaction was filtered through a glass wool plug, solvent evaporated in vacuo and off-white solid 55 isolated via preparative thin layer chromatography (PTLC) (2:2:1 CH₂Cl₂: EtOAc:MeOH) (29 mg, 46%). m.p. 140-142° C.

An NMR analysis of 55 was performed where: $^1$H NMR (400 MHz, CDCl₃) δ 8.34 (s, 1H), 7.92 (s, 1H), 5.84, (d, J=5.2 Hz, 1H), 5.53 (bs, 1H), 5.14 (dd, J=5.2, 4.4 Hz, 1H), 4.21-4.17 (m, 2H), 3.62-3.58 (m, 2H), 3.52 (d, J=0.4 Hz, 2H), 3.02-2.93 (m, 2H), 2.81-2.76 (m, 2H), 2.22 (t, J=2.0 Hz, 1H), 1.00 (t, J=8.0 Hz, 9H), 0.81 (t, J=8.0 Hz, 9H), 0.67 (q, J=7.6 Hz, 6H), 0.50-0.33 (m, 6H); $^{13}$C NMR (400 MHz, CDCl₃) δ 155.8, 153.0, 149.6, 141.0, 120.9, 90.1, 83.7, 78.6, 74.6, 73.5, 59.2, 56.7, 55.8, 42.9, 29.9, 7.1, 6.8, 5.2, 4.7, 1.2. HRMS (MALDI) calculated for C₂₇H₄₈N₆O₄Si₂ (M+H): 577.3354, measured: 577.3344.

Example 36

5'-[(iodoethyl)propargyl)amino]-2',3'-5'-deoxyadenosine hydrochloride (56)

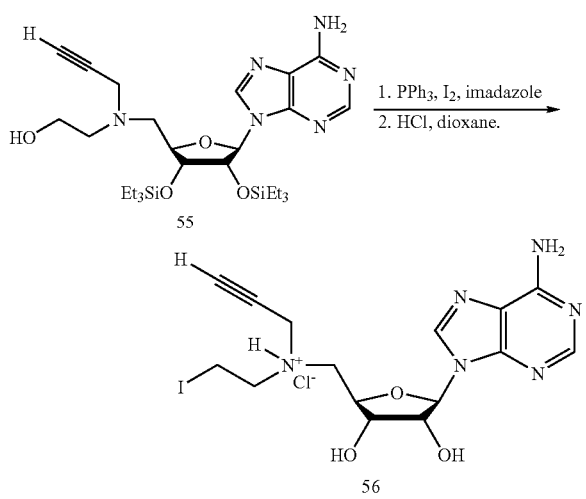

5'-[(iodoethyl)propargyl)amino]-2',3'-5'-deoxyadenosine hydrochloride (56) was synthesized as shown above. Briefly, to 20.5 mg triphenylphosphine (0.0780 mmol, 1.5 eq) and 5.7 mg imidazole (0.0780 mmol, 1.5 eq) in 200 µL CH₂Cl₂ at 0° C. was added 19.8 mg I₂ (0.0780 mmol, 1.5 eq). 30 mg propargyl amino alcohol 55 (0.0520 mmol, 1 eq) was then added in 200 µL CH₂Cl₂ and the reaction stirred for 1 h. The reaction was diluted with ice-chilled CH₂Cl₂ and H₂O and the organic layer washed two times with H₂O before being placed back under argon and chilled to 0° C. 100 µL 4N HCl-dioxane (7.7 eq) was added and the reaction stirred for 1 h. Ice chilled H₂O was added and the aqueous layer extracted three times with CH₂Cl₂ before lyophilization to afford iodo alkyne 56 as an off-white solid (17.5 mg, 74%). Decomposition starting at 145° C.

An NMR analysis of 56 was performed where: $^1$H NMR (400 MHz, D₂O) δ 8.46 (s, 1H), 8.45 (s, 1H), 6.16 (d, J=4.0 Hz, 1H), 4.86 (t, J=4.4 Hz, 1H), 4.56-4.49 (m, 2H), 4.20 (d, J=2.0 Hz, 2H), 3.82-3.77 (m, 4H), 3.46-3.34 (m, 2H), 3.11 (t, J=2.4 Hz, 1H); $^{13}$C NMR (500 MHz, D₂O) δ 155.8, 154.3, 150.3, 150.2, 126.9, 126.8, 97.2, 88.2, 88.1, 86.0, 85.9, 80.5, 80.4, 79.3, 78.8, 63.4, 62.6, 62.2, 51.2, 50.7, 45.2, 4.6. HRMS (MALDI) calculated. for C₁₅H₂₀N₆O₃I (M): 459.0642, measured: 459.0628.

Example 37

4-(1-pyrenyl)propanylamide butyl azide (62)

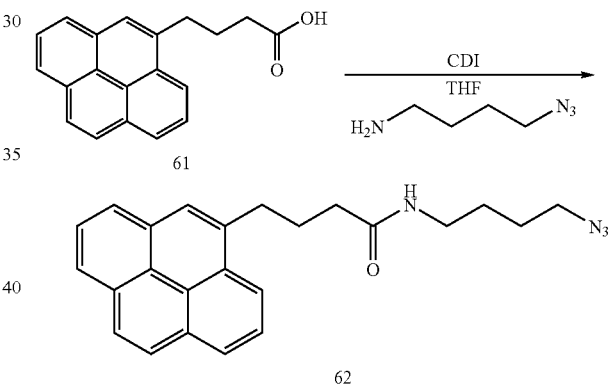

4-(1-pyrenyl)propanylamide butyl azide (62) was synthesized as shown above. Briefly, to 400 mg of 1-pyrenebutyric acid (61) (Sigma, St Louis, Mo., Cat. No. 82655) (1.39 mmol) was added 2 mL anhydrous THF. To the stirring solution was added 247 mg (1.52 mmol, 1.1 eq) N,N'-Carbonyldiimidazole (CDI) (Lancaster Synthesis, Windham, N.H.) at room temperature. Gas was rapidly evolved as the yellow slurry became transparent. The yellowish solution was stirred at room temperature for 1 h followed by the addition of 240 mg of azido butyl amine (2 mmol, 1.5 eq) (see, Menes-Arzate, M. et al., J. Org. Chem. 69, 4002-4004, (2004). The reaction was stirred at room temperature for 12 h followed by removal of solvent in vacuo, redissolution into 5 mL CH₂Cl₂ and silica gel chromatography (4:1 CH₂Cl₂:EtOAc) to render azido pyrene 62 as a light yellow powder (270 mg, 50%). m.p. 85-87° C.

An NMR analysis was performed where: $^1$H NMR (500 MHz, CDCl₃) δ 8.29 (d, J=9.0 Hz, 1H), 8.17 (dd, J=7.5, 3.0 Hz, 2H), 8.12-8.10 (m, 2H), 8.03-7.98 (m, 3H), 7.85 (d, J=7.5 Hz, 1H), 5.37 (bs, 1H), 3.39 (t, J=7.5 Hz, 2H), 3.27-3.21 (m, 4H), 2.27-2.18 (m, 4H), 1.59-1.48 (m, 4H); $^{13}$C NMR (400 MHz, CDCl₃) δ 172.7, 135.9, 131.4, 130.9, 129.9, 128.7, 127.5, 127.4, 127.3, 126.7, 125.9, 125.0, 124.9, 124.8, 123.4, 51.0, 38.8, 35.9, 32.7, 27.4, 26.9, 26.2. HRMS (ESI) calculated. for $C_{24}H_{24}N_4O$ (M+Na): 407.1848, measured: 407.1862.

Example 38

7-Azidoheptanoic Acid (64)

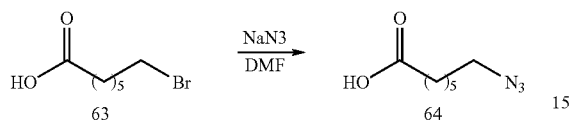

7-azidoheptanoic acid (64) was synthesized from 7-bromoheptanoic acid 63 as shown above. To 914 mg of 7-bromoheptanoic acid (63) (commercially available from Matrix Scientific, Columbia, S.C.) (4.4 mmol) was added 15 mL anhydrous DMF. To the stirring solution was added 914 mg $NaN_3$ (14 mmol, 3.2 eq) at room temperature. The clear solution was warmed to 60° C. for a period of 6 h. The solution was then cooled to room temperature and diluted with 50 mL $CH_2Cl_2$. The organic layer was washed with cold 1N HCl (7×50 mL) and brine (2×50 mL), then dried over anhydrous $Na_2SO_4$. Filtration and removal of solvent afforded 709 mg crude 7-azidoheptanoic acid 64 in 94% yield which was of suitable purity for continued progression enroute to materials 65 and 66. An NMR analysis was performed where: $^1H$ NMR (400 MHz, $CDCl_3$) δ 11.55 (bs, 1H), 3.14 (t, J=6.8 Hz, 2H), 2.22 (t, J=7.2 Hz, 2H), 1.56-1.45 (m, 4H), 1.30-1.24 (m, 4H); $^{13}C$ NMR (400 MHz, $CDCl_3$) δ 178.3, 51.1, 33.7, 28.5, 28.4, 26.2, 24.4. HRMS (ESI) calculated. for $C_7H_{13}N_3O_2$ (M−H): 170.0930, measured: 170.0930.

Example 39

7-azido-N-(phenylmethyl)heptanamide (65)

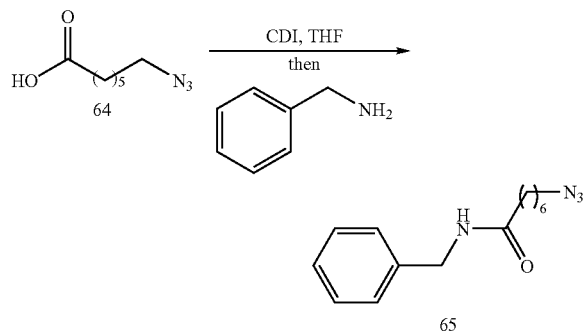

7-azido-N-(phenylmethyl)heptanamide (65) was synthesized from 7-zidoheptanoic acid (64) as shown above. To 120 mg crude 7-azidoheptanoic acid (64) (0.7 mmol, 1.0 eq) was added 1 mL anhydrous THF. To the stirring solution was added 120 mg CDI (0.74 mmol, 1.06 eq) at room temperature. $N_2$ was rapidly evolved from the yellowish slurry. The resulting transparent solution stirred at room temperature for 0.5 h. To the solution was then added 82.5 mg benzylamine (0.77 mmol, 1.1 eq). The solution was stirred 2 h at room temperature followed by solvent removal in vacuo and silica gel chromatography (2:2:1; petroleum ether:$Et_2O$:EtOAc) to render 65 in as a waxy solid (108 mg, 60%). Lyophilization from 50% aqueous $CH_3CN$ afforded a fluffy white powder. m.p. slightly above ambient temperature.

An NMR analysis of 65 was performed where: $^1H$ NMR (400 MHz, $CDCl_3$) δ 7.35-7.25 (m, 5H), 5.95 (bs, 1H), 4.41 (d, J=6.0 Hz, 2H), 3.24 (t, J=6.8 Hz, 2H), 2.20 (t, J=7.6 Hz, 2H), 1.66 (q, J=7.6 Hz, 2H), 1.58 (q, J=8.0 Hz, 2H), 1.39-1.31 (m, 4H); $^{13}C$ NMR (400 MHz, $CDCl_3$) δ 172.9, 138.6, 128.8, 127.9, 127.6, 51.5, 43.7, 36.6, 28.9, 28.8, 26.6, 25.7. HRMS (ESI) calculated for $C_{14}H_{20}N_4O$ (M+Na): 283.1535, measured: 283.1522.

Example 40

7-azido-N-((N-diphenylmethyl)-piperazino)heptanamide (66)

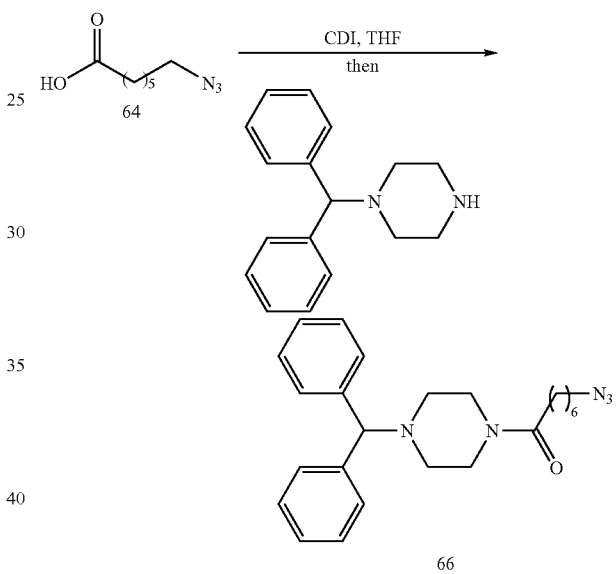

7-azido-N-((N-diphenylmethyl)-piperazino)heptanamide (66) was synthesized from 7-azidoheptanoic acid (64) as shown above. To 170 mg crude 7-azidoheptanoic acid (64) (1 mmol, 1 eq) was added 1.5 mL anhydrous THF. To the stirring solution was added 169 mg CDI (1.04 mmol, 1.04 eq) (Lancaster Synthesis, Windham, N.H.) at room temperature. $N_2$ was rapidly evolved and the resulting transparent solution stirred at room temperature for 0.5 h. To the solution was then added 276 mg 1-(diphenylmethyl)-piperazine (1.1 mmol, 1.1 eq). The solution was stirred overnight at room temperature followed by solvent removal in vacuo and silica gel chromatography (2:2:1; petroleum ether:$Et_2O$:EtOAc) to render 66 as a colorless oil (312 mg, 73%).

An NMR analysis of 66 was performed where: $^1H$ NMR (400 MHz, $CDCl_3$) δ 7.42 (d, J=7.6 Hz, 4H), 7.29 (t, J=7.2 Hz, 4H), 7.20 (t, J=7.2 Hz, 2H), 4.25 (s, 1H), 3.63 (t, J=4.8 Hz, 2H), 3.45 (t, J=4.4 Hz, 2H), 3.25 (t, J=6.8 Hz, 2H), 2.38 (bs, 4H), 2.29 (t, J=7.2 Hz, 2H), 1.67-1.56 (m, 4H), 1.40-1.34 (m, 4H); $^{13}C$ NMR (400 MHz, $CDCl_3$) δ 171.4, 142.3, 128.7, 128.0, 127.2, 76.1, 52.2, 51.7, 51.5, 45.8, 41.8, 33.1, 29.0, 28.8, 26.6, 25.1. HRMS (ESI) calculated for $C_{24}H_{31}N_5O$ (M+H): 406.2607, measured: 406.2601.

B. Biology

Ethanol precipitation was performed by addition of tRNA (40 mg/reaction, first round only), H₂O of a volume appropriate to bring the total aqueous volume of the reaction to 100 µL, 15 µL 3M NaOAc, and 250 µL absolute ethanol. The reactions were chilled over dry ice for a minimum of 15 min, spun down for 8 min. at 14,000 rpm, and the supernatant removed. The second round of precipitation was completed in the same manner, with 100 µL H₂O, 30 µL 3M NaOAc, and 420 µL absolute ethanol, followed by drying of the pellet in vacuo. Methylase-mediated reactions were buffered in the following unless otherwise noted: (M.TaqI) 20 mM Tris-OAc (pH 6.0), 50 mM KOAc, 10 mM Mg(OAc)₂, 0.01% Triton-X100; (M.EcoRI) 10 mM Tris (pH 7.4), 5 mM NaCl, 0.5 mM EDTA and 0.01% Triton X-100. DNA target and complementary strands were purchased from Sigma-Genosys. The 5'-end of the target strand was labeled with ³²P, gel purified and annealed to the corresponding complementary ODN (M.TaqI ODN=5'-TGAATCTCG$\underline{A}$GCACCC-3' (SEQ. ID. 6), complementary ODN=3'-AAACTTAG$\underline{A}$GCTCGTGGG-5' (SEQ. ID. 7), M.EcoRI ODN=5'-TGAATGA$\underline{A}$TTCGACCC-3' (SEQ. ID. 8), complementary ODN=3'-AAACTTACTT$\underline{A}$AGCTGGG-5' (SEQ. ID. 9).

C. DNA Duplex Alkylation

Alkylation reaction mixtures contained 0.5 µM duplex DNA (10 µM stock in corresponding MTase buffer), 1 µM M.TaqI or M.EcoRI, and 1, 10, 50, or 100 µM 3 or 50 (0.01, 0.1, 0.5, or 1.0 mM stock in H₂O for 3 or 2.5 mM H₂SO₄ for 50). All reaction mixtures were incubated at 37° C. for 12 h and analyzed (following EtOH precipitation) on a 20% DPAGE gel run at 40 mA for 4 h.

D. Regioselectivity Experiments

Large scale stock solutions of SAM-modified DNA and pre-incubated control DNA (DNA only, DNA+M.Tase, DNA+MTase+SAH) were prepared for both EcoR1 or Taqa1 target strands by incubation of 0.5 µM DNA duplex (either EcoRI or TaqI target strands), 1 µM.EcoRI or M.TaqI, and 50 µM SAM or S-adenosyl-L-homocystiene (SAH) (2 mM stocks in H₂O). Each reaction was incubated at 37° C. for 12 h, ethanol precipitated, and the pellet dissolved in 25 µL H₂O for a 2 µM stock solution.

Example 41

DNA Methyltransferase Identification of Methylation State

SCHEME XI

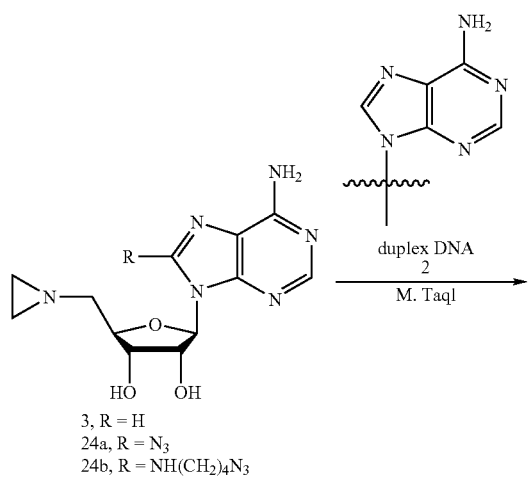

3, R = H
24a, R = N₃
24b, R = NH(CH₂)₄N₃

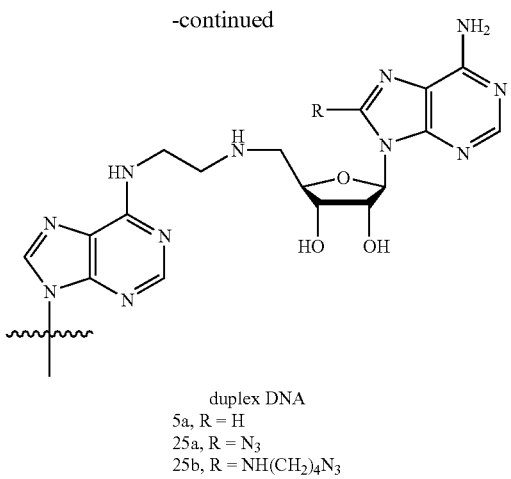

duplex DNA
5a, R = H
25a, R = N₃
25b, R = NH(CH₂)₄N₃

DNA MTases combine sequence-specific recognition with covalent modification to act as molecular "third parties", directing delivery of the new alkyl group through association with individual target sequences. The transferred methyl group is derived from S-adenosyl-L-methionine (SAM). SAM is routinely coined "mother nature's methyl iodide" for good reason. The agent is a potent and potentially non-specific alkylating agent. However, under the direction of MTases, SAM is a highly selective alkylating agent capable not only of DNA modification but also an avid participant in protein modification, RNA methylation and as a biosynthetic tool for secondary metabolite production. Indeed, SAM-dependent methylation of DNA and proteins is now a major theme in epigenomics. Understanding the role that biological methylation plays, particularly in gene transcription, has been hampered by a general lack of tools for identification of MTase substrates. The largest impediment arguably stems from the methyl group's relative absence of functionality, which renders it difficult to identify in complex biological environments. Therefore, the ability to ligate detectable labels directly to the site of methylation provides the ability to directly identify sites of biological importance in methylation, as well as, provides a powerful tool to identify the methylation state of substrates for diagnostic and clinical purposes.

Aziridine adenylates 3, 24a and 24b take part in MTase-dependent DNA alkylations. The ability of 5'-aziridine adenylates to act as MTase-dependent DNA modifying agents is illustrated in SCHEME XI. Pignot, M.; et al., Angew. Chem., Int. Ed. 1998, 37, 2888-2891; Pignot, M., et al., (2000) European patent WO 00/06587; Comstock, L. R.; Rajski, S. R. Nucleic Acids Res. 2005, 33, 1644-1652. Moreover, Azido adenylates 24a and 24b allow the conversion of DNA MTases into azidonucleoside transferases. Comstock, L. R.; Rajski, S. R. Nucleic Acids Res. 2005, 33, 1644-1652. Substrates of azidation are the same as those ordinarily acted upon by MTases. Unlike the methyl group, azides provide a chemically unique handle to which other probes (radioisotopes, affinity matrix handles, etc.) can be linked under biologically amenable conditions. The sequence selectivity of DNA azidation accomplished by DNA MTases and substrates modified with either 24a or 24b and elaborated post enzymatically via Staudinger ligation chemistry as was demonstrated in EXAMPLES 27-30.

Aziridines 3, 24a and 24b are believed to undergo quaternization of the 5' amine followed by MTase binding, delivery to the site of methylation and subsequent aziridinium ring opening with concomitant substrate alkylation. Initial generation of the positively charged aziridinium is consistent not only with activation towards nucleophiles, but also cation-π interactions between cofactor analogs and MTase, which are hallmarks of SAM-MTase complexes (Fauna, E. B.; et al. Cheng, X., Blumenthal R. M., Eds.: World Scientific: Singapore, 1999; pgs. 1-13). The inventors sought to exploit this phenomenon in the design of a novel synthetic cofactor analog devoid of the inherently labile aziridine moiety of 3, 24a and 24b. Hydrochloride salt 56 was envisioned to rapidly form aziridinium 57 in situ, thus avoiding synthetic difficulties associated with intact aziridines. The proposed aziridinium ion formation is illustrated in SCHEME XII. This intermediate was expected to be more reactive and more amenable to MTase promoted chemistry by virtue of 5' amine quaternization via aziridination instead of a potentially reversible protonation (as has been proposed for compounds such as 3, 24a and 24b). Iodide 56 was designed with the propargyl substituent to allow for possible bioconjugation of the DNA substrate post-alkylation.

In evaluating the hypothesis that 56 (and related agents) could serve as an effective cofactor analogs for MTases, the inventors were initially highly skeptical due to the unknown impact of the alkynyl substituent upon cofactor analog: MTase interactions. Indeed, 56 has so far proven to be completely devoid of DNA-damaging activity in the presence of the cytosine $C^5$ MTase M.HhaI. However, in contrast, the inventors have found that 56 is highly amenable to use by two different $N^6$ adenine MTases.

Example 42

Regioselectivity Experiments

SCHEME XII

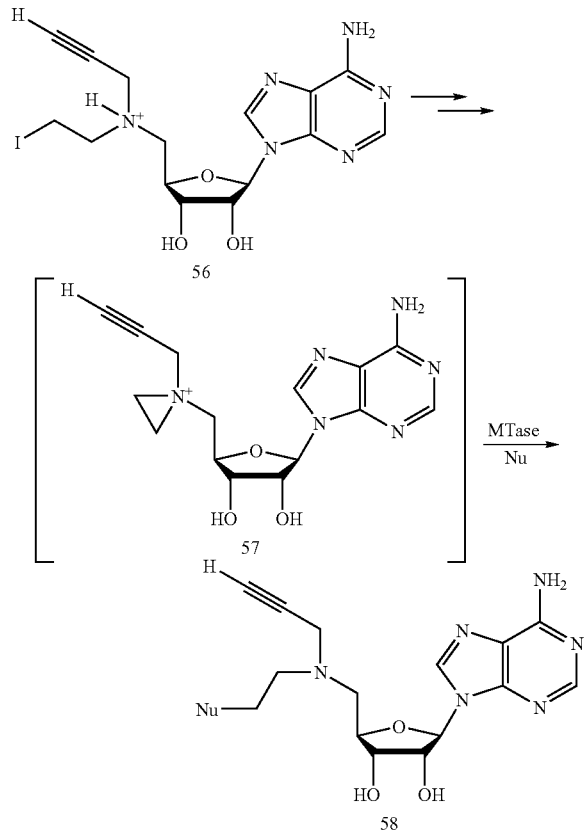

Large scale stock solutions of SAM-modified DNA and pre-incubated control DNA (DNA only, DNA+M.Tase, DNA+MTase+SAH) were prepared for both EcoRI or TaqI target strands by incubation of 0.5 μM DNA duplex (either EcoRI or TaqI target strands), 1 μM M.EcoRI or M.TaqI, and 50 μM SAM or S-adenosyl-L-homocysteine (SAH) (2 mM stocks in $H_2O$). Each reaction was incubated at 37° C. for 12 h, ethanol precipitated, and the pellet dissolved in 25 μL $H_2O$ for a 2 μM stock solution.

Figure 4:
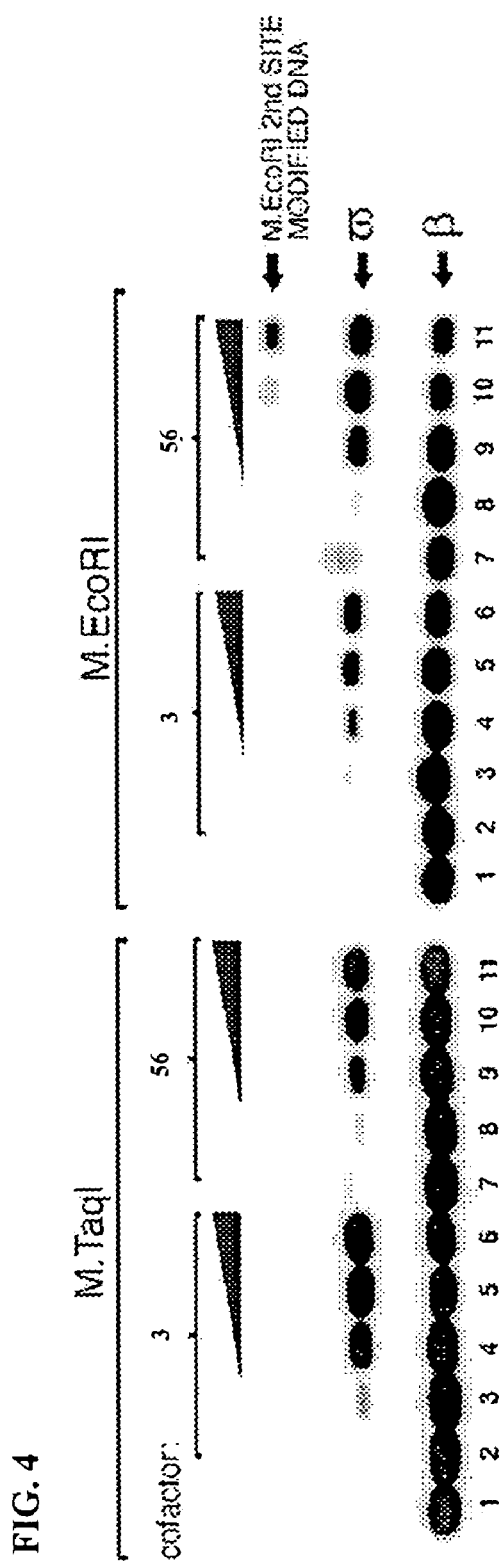
FIG. 4 shows a denaturing polyacrylamide gel electrophoresis (DPAGE) of DNA alkylation reactions with synthetic oligonucleotides and 50 (relative to 3). β=native unmodified DNA and $\overline{\omega}$=DNA alkylated with 3 or 56. Each series of reactions/lanes 1-11 are as follows: 1: DNA-only control; 2: DNA+100 µM 3 (no enzyme added); 3: DNA+1 µM 3+M.TaqI (to 1 µM); 4: DNA+10 µM 3+M.TaqI; 5: DNA+50 µM 3+M.TaqI; 6: DNA+100 µM 3+M.TaqI; lanes 7-11 same as 2-6 except using alkyne cofactor analog 56. Right hand panel lanes are identical in loading to left hand loadings with the exception that M.EcoRI was used instead of M.TaqI. Note that for all reactions the concentration of enzyme used was 1 µM. Controls accounting for cofactor analog solvent and/or appropriate MTase resulted in no slower mobility materials.

FIG. 4 shows that the activity of 56 closely parallels that of 3 with both M.TaqI and M.EcoRI. To evaluate M.TaqI activity, the ODN 5'-TGAATCTCGAGCACCC-3' (SEQ. ID. 10) was 5'-end labeled with $^{32}P$, gel purified and annealed to complementary ODN 3'-AAACTTAGAGCTCGTGGG-5' (SEQ. ID. 11). M.TaqI ordinarily methylates each adenine $N^6$ (underlined) within the bold-faced palindromic sequence shown in bold. Evaluation of M.EcoRI activity called for 5'-end labeling of 5'-TGAATGAATTCGACCC-3' (SEQ. ID 12) followed by gel purification and annealing to the complement 3'-AAACTTACTTAAGCTGGG-5' (SEQ. ID. 13). M.EcoRI ordinarily methylates each adenine $N^6$ (underlined) within the bold-faced palindrome. Duplex substrates were incubated with the corresponding enzyme and either the aziridine 3 or hydrochloride 56. Incubations were then quenched via addition of tRNA (40 μg/reaction) and repetitive EtOH precipitation. Notably, a second, more slowly moving DNA adduct is observed in reactions of M.EcoRI. This observation is consistent with work previously reported by Jeltsch and co-workers in which M.EcoRI was found to display significant promiscuity (Jeltch et al., (1999) J. Biochem., 274: 19538-19544). The precise origin and sequence selectivity of modification of this much slower mobility product is under active investigation.

Example 43

Confirmation of Regiospecificity

To ensure the regiochemistry of DNA alkylation with 56 is the same as that normally observed for SAM-dependent methylation, we performed experiments involving pre-methylated substrates. Alkylation reactions involving 56 were carried out on duplexes enzymatically methylated with SAM prior to treatment with fresh MTase and 56. Confirmation that methylation of both M.TaqI and M.EcoRI sequence bearing duplexes had taken place was accomplished by subjection of these DNAs to R.TaqI and R.EcoR I, their respective restriction endonuclease partners. DNAs subjected to SAM and MTase failed to act as sites of endonucleolytic cleavage; all other DNAs did, thus, confirming the integrity of substrate methylation. Similarly, methylated duplexes failed to undergo reaction when presented with fresh MTase and 50 μM 56. That substrate DNA methylation precluded alkylation by 56 indicates that MTase-driven substrate alkylations by 56 and SAM share the same regiochemistry. This efficient and predictable site-specific alkylation of nucleic acids paved the way for novel elaboration of the modified sites by virtue of the propargyl substituent of 56.

Figure 5:
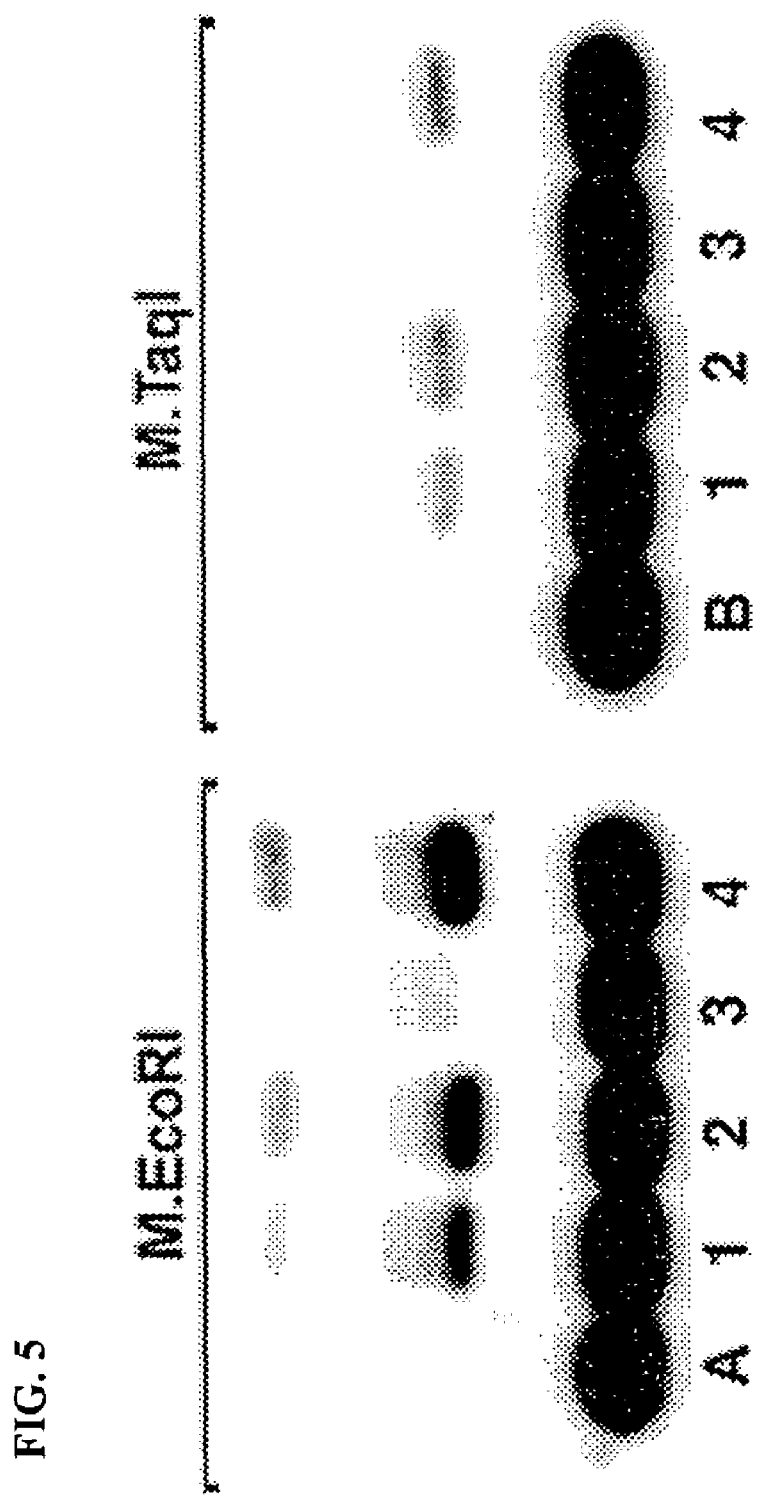
FIG. 5 shows the results of a DPAGE analysis of DNA alkylation reactions with synthetic oligonucleotides and 56 following methylation with SAM. Reactions with 56 were performed identically to those of FIG. 4. For each panel of lanes/reactions, the MTase and corresponding restriction enzymes used are so indicated. Lanes A and B correspond to unmodified DNA bearing each enzyme's recognition sequence. Prior to reaction with 56, synthetic DNAs were treated either with nothing (lane 1), MTase alone (lane 2), SAM and MTase (lane 3) or MTase and SAM (lane 4). Following first round incubation, DNAs were isolated by repetitive EtOH precipitation, dried in vacuo and resuspended for subsequent analysis by restriction enzyme digestion to ensure proper methylation (data not shown).

FIG. 5 shows the results of small scale restriction enzyme digestions completed to check for full methylation in the reactions containing SAM and no-methylation in controls. Digestion reactions contained 0.05 μM alkylated DNA (M.EcoRI or M.TaqI target strands) and either 157.7 units R.EcoRI or 6.51 units R.TaqI (enough for a 10:1 overdigestion). R.EcoRI reactions were buffered using NEB buffer 4. Reactions were incubated at 37° C. for 12 h, an aliquot diluted 1:1 with loading buffer and analyzed on 20% DPAGE (data not shown). Alkylation reactions contained 0.5 μM duplex DNA (EcoRI or M.TaqI target strands), 1 μM M.EcoRI or M.TaqI, and 50 μM 56 (0.5 mM stock in $H_2SO_4$). Each reaction was incubated at 37° C. for 12 h, ethanol precipitated and analyzed on 20% DPAGE. Results are shown in FIG. 5.

Example 44

Aqueous Huisgen (2+3) Cycloaddition Reactions

Large scale (~0.2 nmoles of each duplex sample) stock solutions of 56-modified DNA and control DNA (DNA+

MTase, DNA+MTase+3) were prepared for use in subsequent cycloaddition reactions. Alkylation reactions contained 0.5 µM DNA (M.EcoRI target strand), M.EcoRI (1 µM), and 100 µM 3 or 5 µM 56. All reactions were incubated at 37° C. for 8 h, ethanol precipitated and the pellet dissolved in 25 µL H$_2$O for a 2 µM stock solution. Each DNA stock was analyzed for purity on 20% DPAGE prior to use in click reactions. Standard cycloaddition reaction mixtures contained 80 nM DNA duplex, 1 mM CuSO$_4$-TTA ligand complex (50 mM stock in 4:1 tert-butanol:H$_2$O), 2 mM tris(carboxyethyl-)phosphine (TCEP) (50 mM stock in H$_2$O), 2.5 mM azide (50 mM in dioxane), 20 mM NaHCO$_3$ (pH ~8.5 unadjusted) and 5% tert-butyl alcohol. All solvents and stock solutions were degassed prior to use by bubbling argon through the solution for a minimum of 30 min. Reactions were run at room temperature for 1-2 h, ethanol precipitated and analyzed on 20% DPAGE. When aliquots were removed from each reaction at earlier time points, the aliquots were frozen over dry ice immediately after removal, then thawed and ethanol precipitated all together.

Bioconjugation via alkyne moieties is ideally suited to the Huisgen [2+3] cycloaddition. This chemoselective ligation of azides and alkynes affords highly stable triazole moieties under biologically relevant conditions. The reaction has been extensively used in a number of biological motifs; the most effective incarnation calls for the use of Cu(I) and a unique tris-triazaloylamine (TTA) ligand along with either ascorbate or tris-carboxyethylphosphine (TCEP) as reductants for CuSO$_4$. The number of examples with nucleic acids is still relatively small presumably because of the well known role that Cu(I) can play in Haber-Weiss redox cycling to produce hydroxyl radical. However, it was not obvious that the Cu(I)-TTA complex can promote Haber Weiss redox cycling. Moreover, if Cu(I)-TTA does permit hydroxyl radical formation it is likely that t-BuOH present in the reaction would immediately sequester radical intermediates thus circumventing DNA strand scission. Because of these concerns, the inventors envisioned the scenario in SCHEME XIII, illustrating proposed Huisgen cycloaddition with alkyne modified DNA, where DNA lesion 59 could render triazole 60 following reaction with alkyl azides.

SCHEME XIII

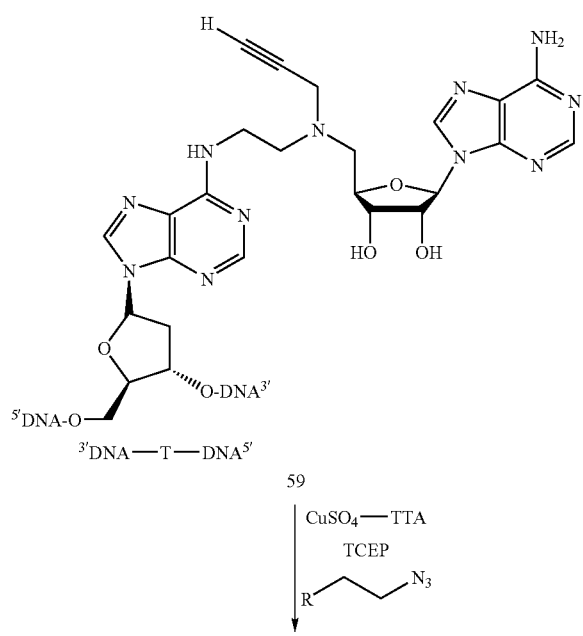

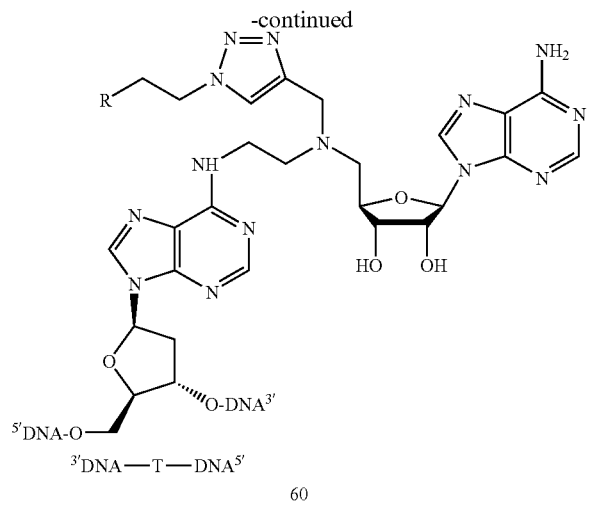

60

Figure 6:
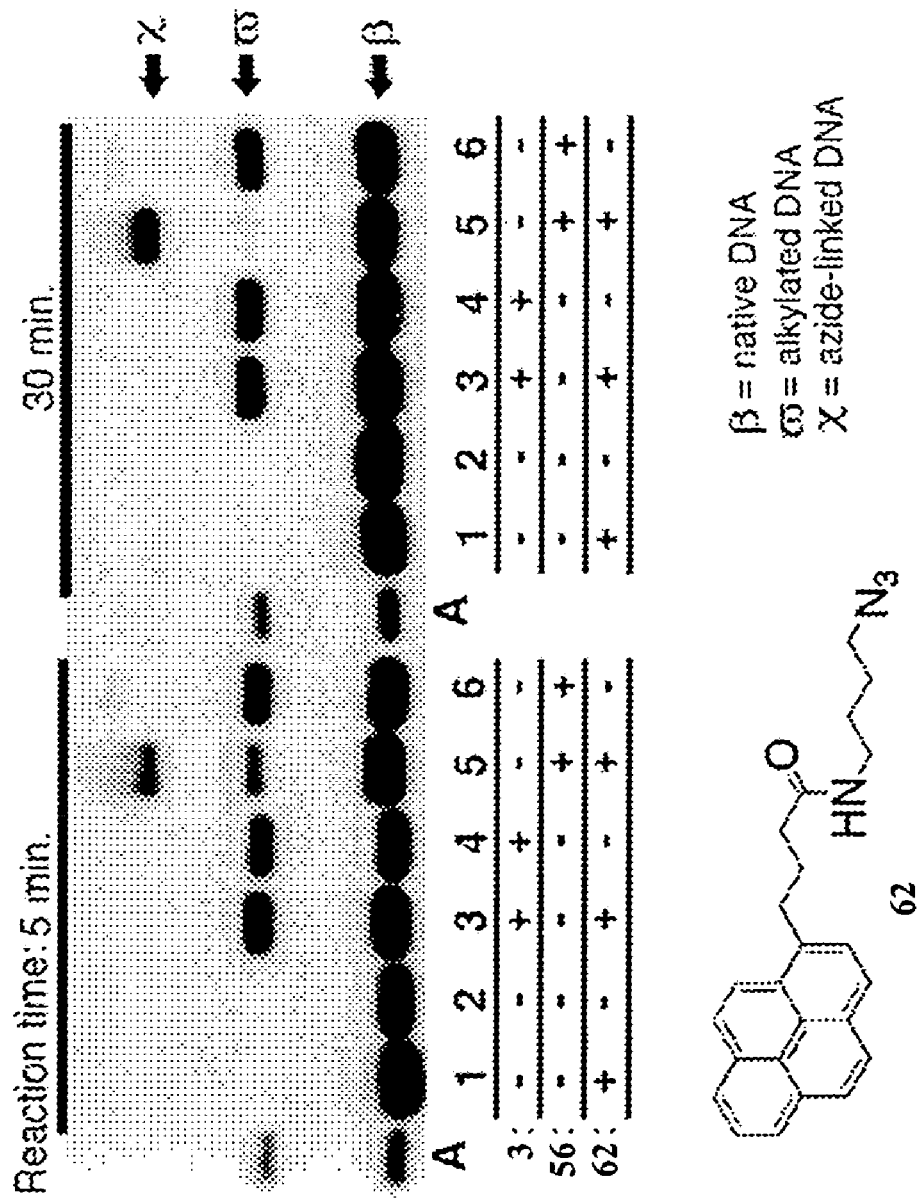
FIG. 6 shows the results of a DPAGE analysis of click reactions between pyrene azide 62 and synthetic oligonucleotides modified either with 3 or 56. Lane A is a DNA-56 conjugate control. Lanes 1 and 2 are reactions of DNA treated with M.EcoRI but no cofactor analog. Lanes 3 and 4 are reactions involving DNA subjected to M.EcoRI and 3. Lanes 5 and 6 are reactions using DNA treated with M.EcoRI and alkyne cofactor analog 56. Reactions assayed in lanes 1-6 all contained 80 nM DNA duplex, 20 mM NaHCO$_3$, 1 mM CuSO$_4$:TTA complex, 2 mM TCEP, 5% t-BuOH. All reactions were conducted at room temperature and time of reaction is noted above each series of lanes. Reactions monitored in odd numbered lanes contained 2.5 mM azide 62; even numbered lanes/reactions lacked azide. In this manner it was deduced that the generation of slow mobility material designated with χ is azide dependent.
Figure 7:
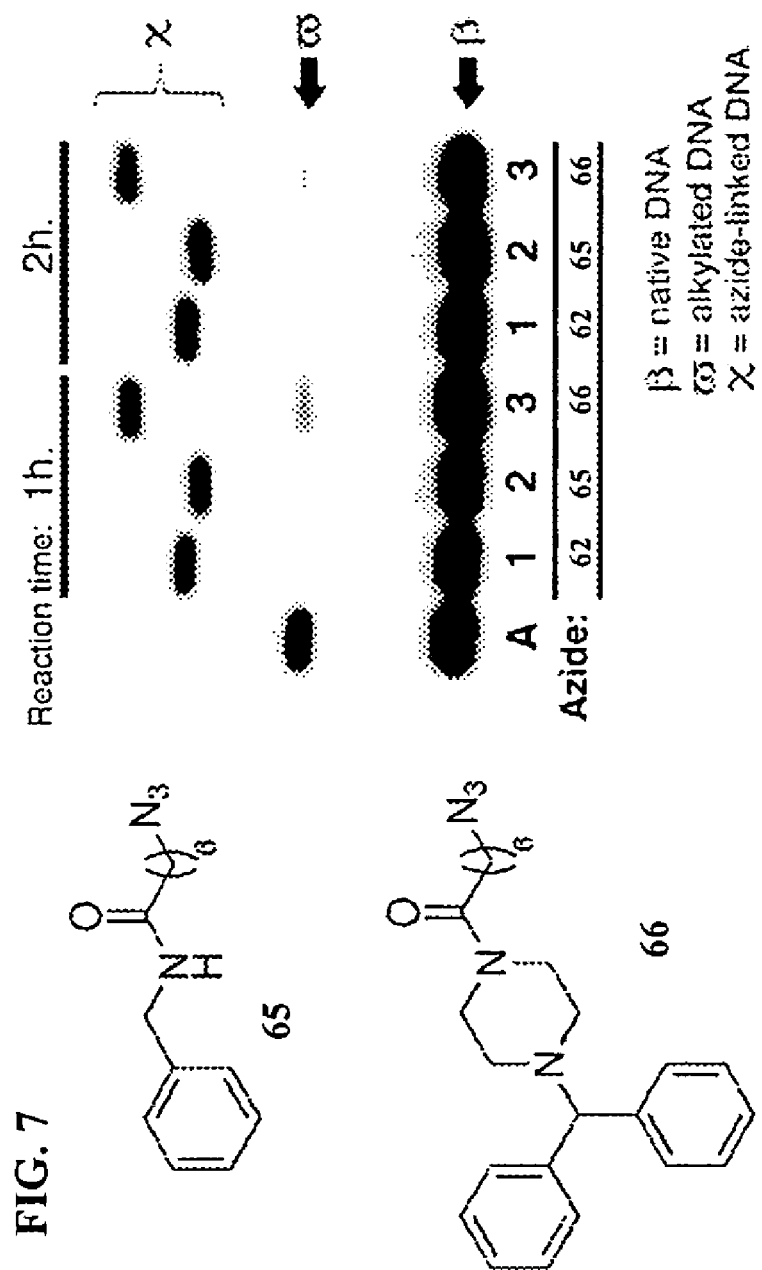
FIG. 7 shows the results of a DPAGE analysis of click chemistry reactions of 56-modified DNA and azides 62, 65 and 66. Lane A is DNA-56 conjugate standard lane and lanes 1-3 are reactions of 56-modified DNA with 2.5 mM 62, 65 and 66 respectively.

The viability of the coupling indicated by SCHEME XIII is shown by the data illustrated in FIG. 6. FIG. 6 shows that DNA modified with 56 (in M.EcoRI-dependent fashion) underwent extremely facile coupling to azide 62 under aqueous conditions. The slow mobility product formed (χ) is proposed to be the result of Huisgen [2+3] cycloaddition since the product is not apparent in reactions lacking alkyne or azide. This is best reflected in comparing lanes 3 to 5 and then 5 to 6 for both timepoints. Subjection of DNA modified with 3 to azide gave a 1:1 complex of Cu-TTA and TCEP afforded no new radiolabeled product. The same conditions applied to DNA modified with alkyne 56 and rendered the new DNA product noted by χ. Similarly, subjection of DNA modified with 56 to reaction conditions lacking 62 failed to render χ. To the inventors knowledge, this is the first entirely solution phase example of nucleic acid based click chemistry that does not call for extensive heating or templating effects. It is significant that during the course of EtOH precipitations following cycloaddition there was no observed isotope loss to supernatant consistent with little or no Cu(I)-mediated DNA strand scission. This, in combination with the appearance of very clean DNA bands indicates that, DNA can serve as an effective participant in Cu(I)-catalyzed click chemistry. This has not previously been suggested and shows that bioconjugation of DNA is an effective means to label specific residues. Further, the inventors also noted that ascorbate can be effectively substituted for TCEP without appreciable nucleic acid degradation (data not shown).

Coupling of alkyne-modified DNA and 62 proceeded very quickly as evidenced by the amount of product observed in lane 5 of FIG. 5. Preliminary experiments suggested this is largely a function of Cu(I) availability. For solubility reasons, the inventors generated a 1:1 complex of TTA ligand and CuSO$_4$ prior to cycloaddition. This contrasts with most click chemistry examples in which TTA and Cu(I) source are added independently. As used by the inventors, the independent addition of CuSO$_4$ and TTA had a profoundly detrimental impact on coupling efficiency relative to the use of pre-mixed CuSO$_4$:TTA.

The generality of the cycloaddition is depicted in FIG. 6. Azides 65 and 66 were prepared with the expectation that size and charge differences would result in visible mobility differences among the variously modified DNAs. Subsequent click reactions performed with 65 and 66 versus 62 afforded products again denoted by "χ" in lanes 1-3. Particularly striking is that coupled product bearing the piperazine moiety of 66 has a significantly slower electrophoretic mobility than products formed with 62 or 65; protonation of the piperazine nitrogen during electrophoresis is the likely cause of this pronounced mobility difference. Comparison of the same reactions carried out for shorter times revealed very similar rates of product formation (data not shown). Importantly, these results refute the possibility that the data from FIG. 5 were dependent upon the pyrene moiety of 62 and potential redox activities of the polycyclic moiety.

These experiments result in several important findings. First, synthetic cofactor analogs are not restricted to 5'-aziridines. The inventors have demonstrated the viability of N-mustards such as 56, as biochemical tools for use in click chemistry. It is significant that 56 has been used very effectively to protect linearized pUC19 DNA from R.TaqI digestion following brief treatments with M.TaqI (unpublished data). This protective effect of cofactor analogs was also illustrated in FIGS. 1A and 1B. Thus, MTase-dependent delivery of 56 to DNA is not restricted to small duplexes but, MTase-specific bioconjugation can be accomplished between the cofactor analog and large molecules. Second, DNA can take part in click chemistry, which allows specific and rapid delivery of cofactor analog transferred compounds directly to the target. These results show that synthetic cofactor analog 56 represents a novel means by which to do click chemistry in a sequence selective manner. In addition, this data indicates that N-mustard adenylates like 56 can be used as cofactor analogs to protect methylation sites from further conjugation by MTases IV. Design, Synthesis and Biological Evaluation of a DNA Methyl Transferase-Directed Alkylating Agent DNA binding/damaging agents often derive sequence selectivity from a finite set of specific contacts between the molecule of interest and select nucleotides. Tse, W. C.; Boger, D. L. Chem. Biol. 2004, 11, 1607-1617. Many such agents are of great interest due to their association with medicinally useful properties, although for many of these substances it remains unclear that all relevant mechanisms of action have been fully elucidated. In the context of DNA damage however, it can be invoked that damage at certain sites is expected to have greater impact than at other sites. At the heart of DNA sequence selectivity is the resounding impact of a finite set of interactions between target nucleotides and the small molecule of interest. In context of the inventors' research, an effort was made to determine how else sequence selectivity of DNA damage by a small molecule might be derived. Following this reasoning, the inventors designed experiments to determine whether DNA alkylation selectivity can be derived, not from associations of the small molecule with its target DNA site, but rather from the extensive contacts between a DNA modifying enzyme and its recognition site.

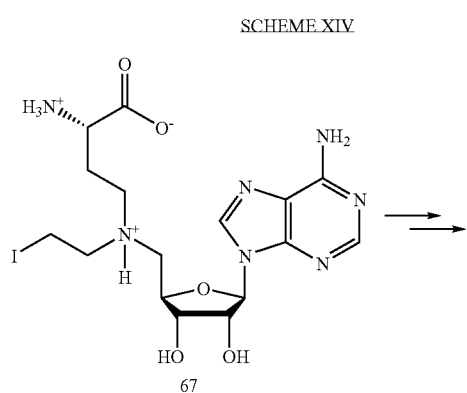

SCHEME XIV

67

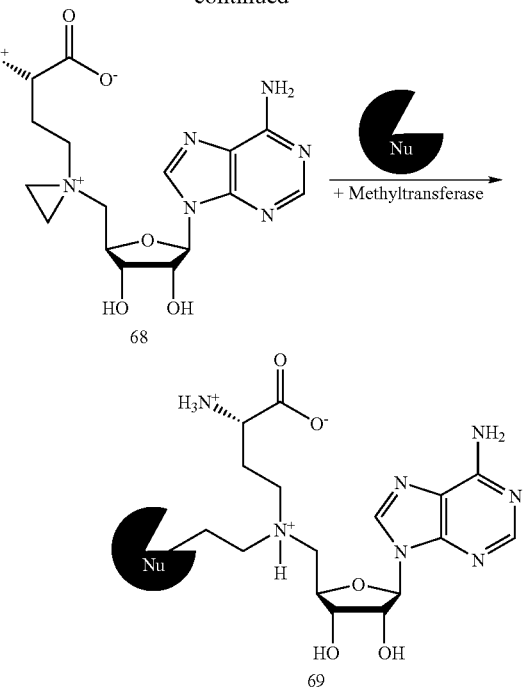

68

69

-continued

Difficulties associated with the construction of 5'-aziridine adenylates have limited the degree to which structural similarity to SAM could be achieved and have also been a deterrent to their further development. The inventors have identified and synthesized a 5'-N-mustard adenylate 67 that also serves as a highly efficient MTase-dependent DNA alkylating agent, presumably via the agency of an aziridinium ion. Without being held to any particular theory, the inventors hypothesized mechanism is illustrated in SCHEME XIV. 67 bears a pendant amino acid resulting in significant structural similarity to SAM. This, along with the use of N-mustard chemistry, results in a substance that is compatible with a number of different MTases and whose DNA alkylation efficiency surpasses that of other 5'-aziridine based cofactor analogs.

A. General Chemistry

All reactions were carried out under an atmosphere of argon unless indicated otherwise. All reagents were obtained from available commercial sources and used without further purification unless otherwise noted. NMR spectra were acquired on Varian Unity Inova 400 MHZ and 500 MHz spectrometers using TMS or solvent as internal reference; the chemical shifts are reported in ppm, in δ units.

Example 45

Synthesis of an N-Mustard SAM-Analog

As an extension of the inventors findings, reported above, an effort was made to synthesize other MTase analogs. To this end, the inventors synthesized a novel N-mustard which, as shown in EXAMPLE 48 and FIG. 10, proceeds to the aziridinium ion 68, a structure highly homologous with SAM 2.

SCHEME XV

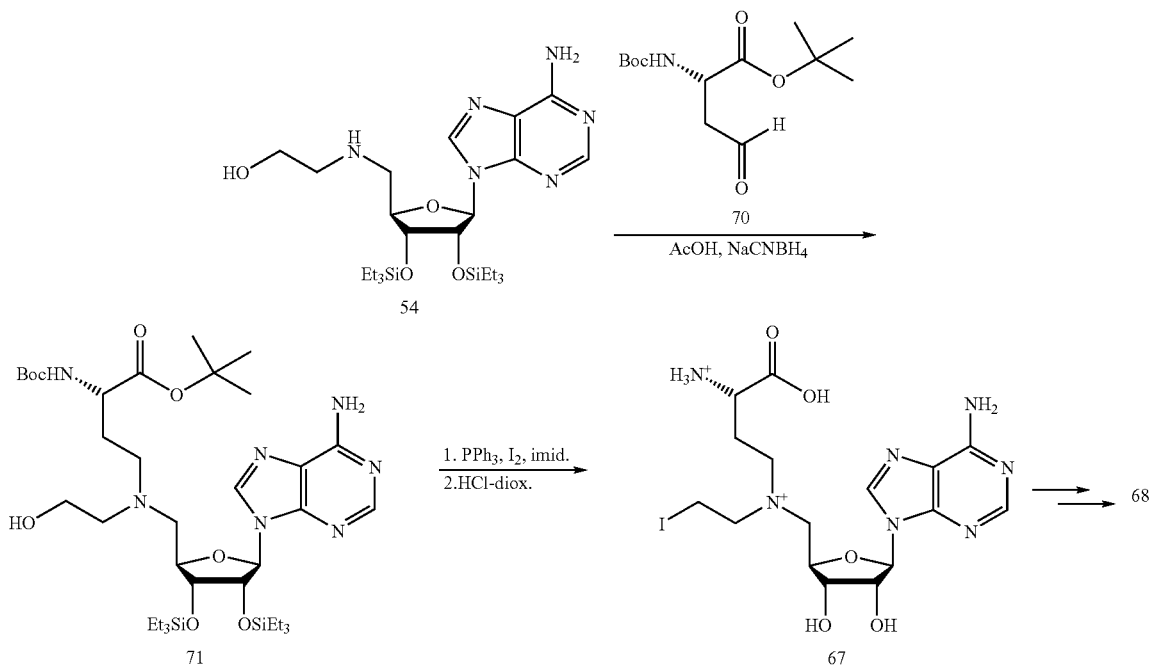

Aziridinium ion 68 bears a structural similarity to SAM 2. Because of the highly reactive nature of 68, the inventors postulated that the a more favorable strategy might lie in the synthesis of the reasonably stable N-mustard 5'-(diaminobutyric acid)-N-iodoethyl-5'-deoxyadenosine ammonium hydrochloride 67, which likely forms the aziridinium ion 68 in situ. The route of the synthesis is illustrated in SCHEME XV. Aldehyde 70 was produced from α-tert-Butyl(S)-N-Boc aspartate using the Rapoport sequence of thioester formation and subsequent triethylsilane/Pd/C reduction. Rapoport, H. *J. Org. Chem.* 1993, 58, 2369-2376. Convergence of 70 and adenylate 54 (Petersen, S. G.; Rajski, S. R. *J. Org. Chem.* 2005, 70, 5833-5839) proceeded smoothly to provide amino alcohol 71 in 65% yield. The iodination and deprotection sequence also proceeded smoothly to provide N-mustard 67 in 84% yield over two steps.

Example 46

5'-(N-Boc diaminobutyric acid-O-tert-Butyl ester)-N-hydroxyethyl-5'-deoxy-2',3'-bis-(O-triethylsilyl) adenosine (71)

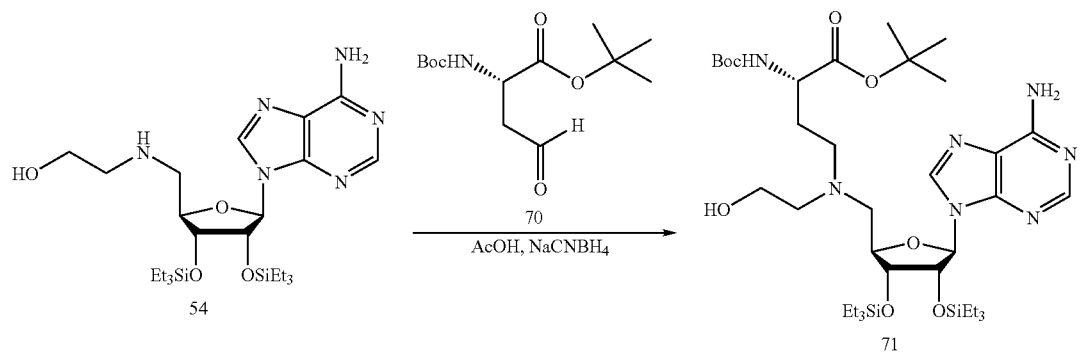

5'-(N-Boc diaminobutyric acid-O-tert-Butyl ester)-N-hydroxyethyl-5'-deoxy-2',3'-bis-(O-triethylsilyl)adenosine (71) was synthesized as shown above. To 28.5 mg of aldehyde 70 (0.1043 mmol) in 0.5 mL anhydrous MeOH was added 61.8 mg ethanolamine adenylate 54 (0.1147 mmol, 12.1 eq). To the stirring solution was added 9.8 mg NaBH$_3$CN (0.1560 mmol., 1.5 eq.) and 6 μL glacial acetic acid (0.1043 mmol, 1 eq). The reaction was stirred at room temperature overnight before dilution with EtOAc and NaHCO$_3$. The organic layer was washed once more with NaHCO$_3$, dried over Na$_2$SO$_4$ and the solvent evaporated in vacuo. White solid 71 was isolated via silica gel preparative thin layer chromatography (PTLC) (2:2:0.5 CH$_2$Cl$_2$:EtOAc:MeOH) (54 mg, 65%), m.p. 45-47° C.

Figure 8:
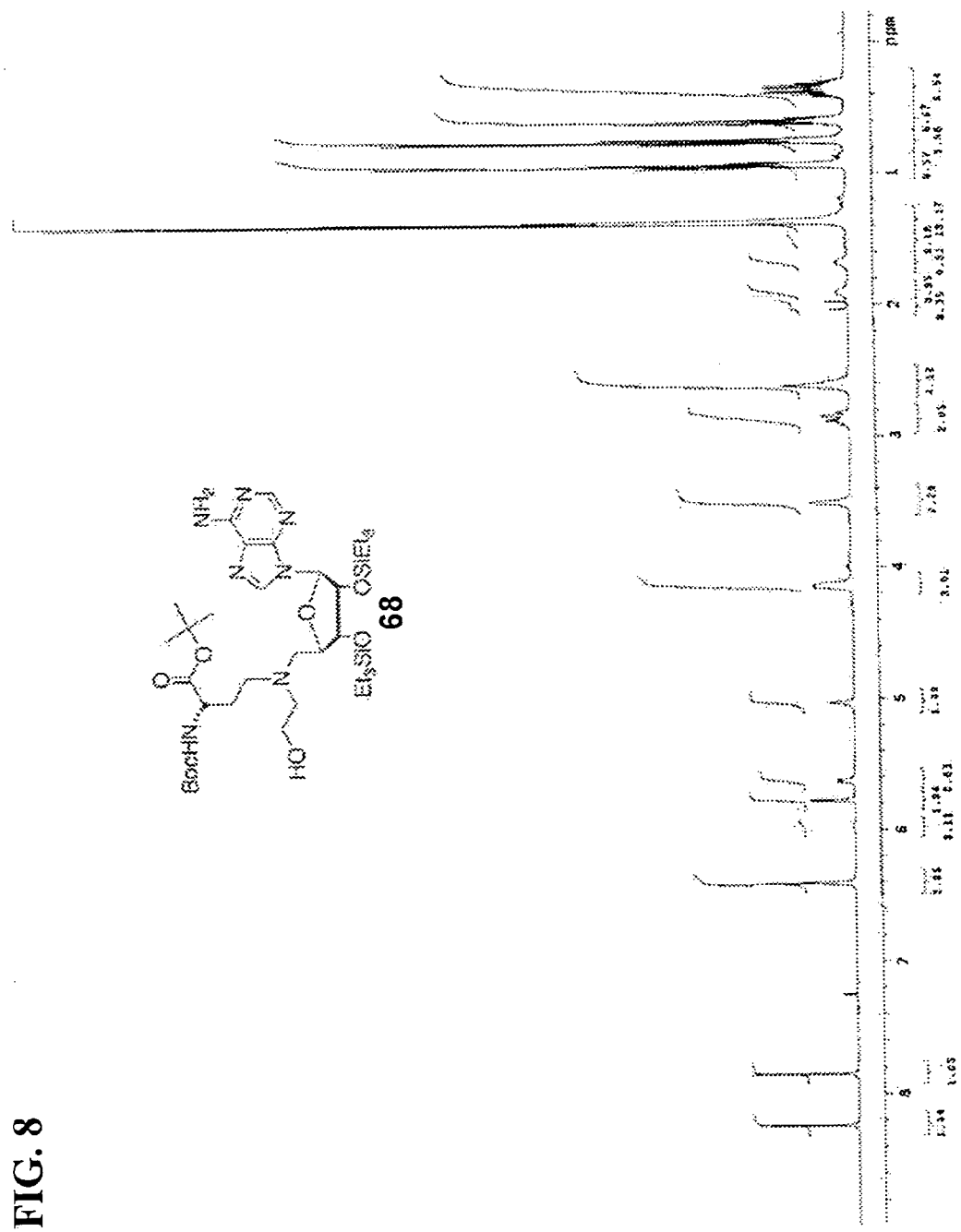
FIG. 8 is an NMR spectrum of 68.

An NMR analysis of 71 was performed and the spectrum is shown in FIG. 8 where: $^1$H NMR (500 MHz, CDCl$_3$) δ 8.23 (s, 1H), 7.84 (s, 1H), 6.40, (s, 2H), 5.77 (d, J=5.0 Hz, 1H), 5.62 (d, J=5.0 Hz, 1H), 5.04-5.00 (m, 1H), 4.15-4.12 (m, 3H), 3.52-3.48 (m, 2H), 2.91-2.81 (m, 2H), 2.64-2.56 (m, 4H), 1.94-1.86 (m, 1H), 1.71-1.62 (m, 1H), 1.36 (s, 9H), 1.35 (s, 9H), 0.92 (t, J=10.0 Hz, 9H), 0.74 (t, J=8.0 Hz, 9H), 0.59 (q, J=7.5 Hz, 6H), 0.42-0.28 (m, 6H); $^{13}$C NMR (500 MHz, CDCl$_3$) δ 172.1, 156.0, 155.7, 152.9, 149.5, 140.7, 120.7, 89.9, 83.2, 81.9, 79.6, 74.6, 73.7, 59.3, 56.7, 56.6, 52.9, 50.7, 29.8, 28.4, 28.0, 6.9, 6.8, 6.7, 5.1, 4.9, 4.8, 4.6. HRMS (MALDI) calculated for C$_{37}$H$_{69}$N$_7$O$_8$Si$_2$ (M+H): 796.4824, measured: 796.4894.

Example 47

5'-(Diaminobutyric Acid)-N-Iodoethyl-5'-Deoxyadenosine Ammonium Hydrochloride (67)

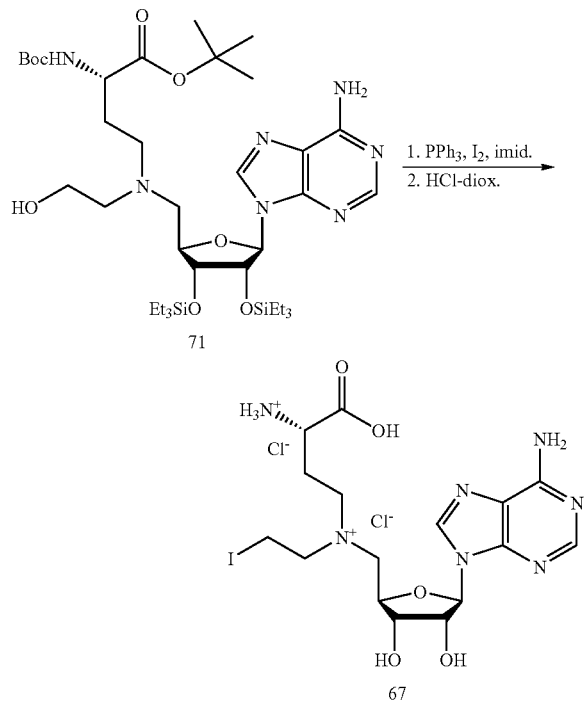

5'-(diaminobutyric acid)-N-iodoethyl-5'-deoxyadenosine ammonium hydrochloride (67) was synthesized as shown. To 19.8 mg triphenylphosphine (0.0754 mmol, 1.5 eq) and 5.2 mg imidazole (0.0754 mmol, 1.5 eq) in 200 μL CH$_2$Cl$_2$ at 0° C. was added 19.8 mg I$_2$ (0.0780 mmol, 1.5 eq). 40 mg amino alcohol 71 (0.0524 mmol, 1 eq) was then added in 200 μL CH$_2$Cl$_2$ and the reaction stirred for 1 h. The reaction was diluted with ice-chilled CH$_2$Cl$_2$ and H$_2$O and the organic layer washed two times with H$_2$O before being placed back under argon and chilled to 0° C. 300 μL 4N HCl-dioxane (23 eq) was added and the reaction stirred for 1 h. Ice chilled H$_2$O was added and the aqueous layer extracted three times with CH$_2$Cl$_2$ before lyophilization to afford an off-white solid. This was dissolved in methanol and ethyl acetate was added dropwise to precipitate 67 as a white solid (22 mg, 84%), decomposition starting at 130° C.

Figure 9:
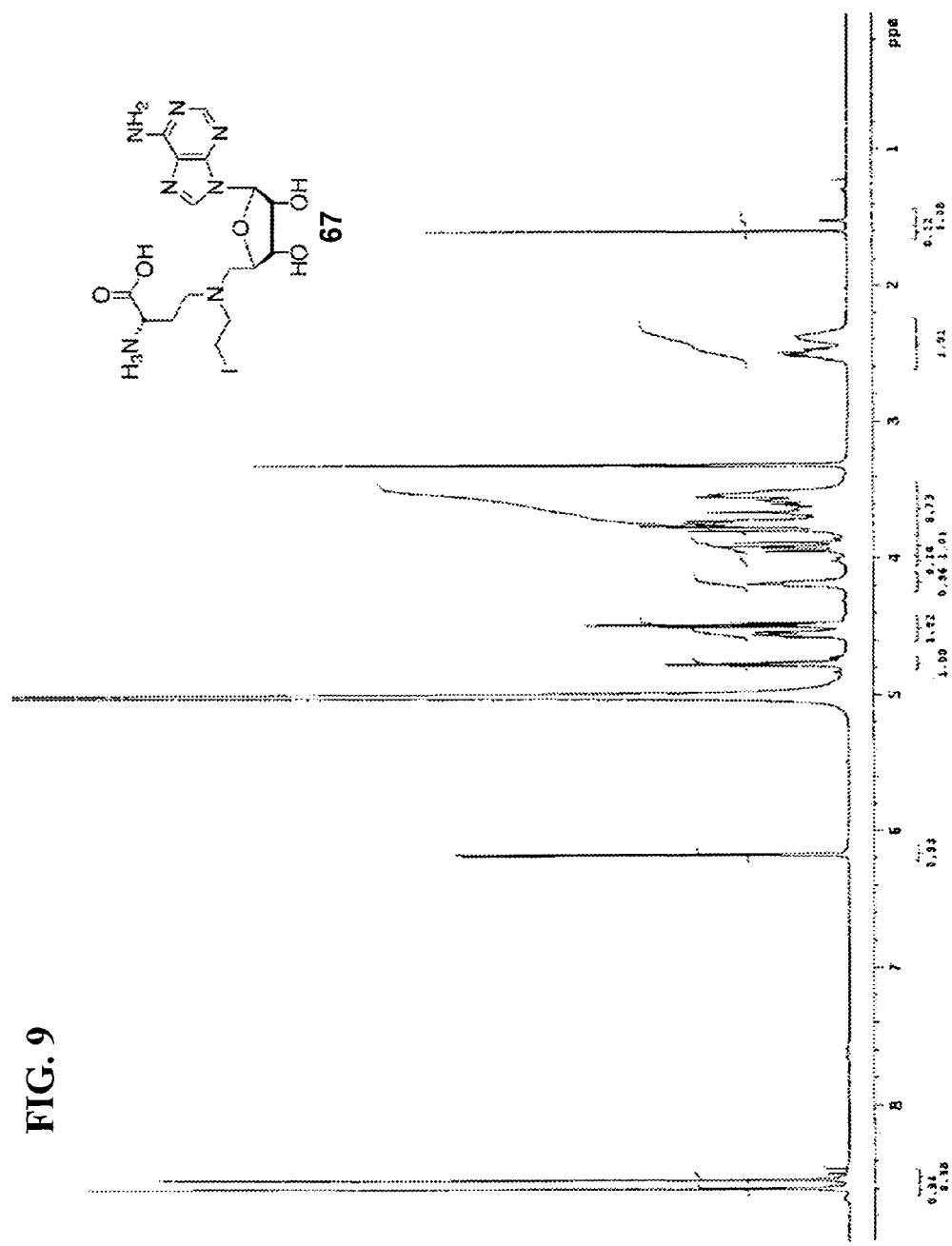
FIG. 9 is an NMR spectrum of 69.

An NMR analysis was performed and the spectrum is shown in FIG. 9 where: $^1$H NMR (400 MHz, methanol-d$_4$) δ 8.69 (s, 1H), 8.54 (s, 1H), 6.17 (d, J=4.4 Hz, 1H), 4.77 (t, J=4.8 Hz, 1H), 4.58-4.52 (m, 3H), 4.49 (t, J=5.6 Hz, 1H), 4.19 (t, J=5.6 Hz, 1H), 3.92 (dd, J=14, 10 Hz, 1H), 3.80-3.71 (m, 3H), 3.69-3.48 (m, 4H), 2.55-2.46 (m, 1H), 2.45-2.32 (m, 1H). $^{13}$C NMR (500 MHz, methanol-d$_4$) δ 170.5, 151.8, 149.9, 145.7, 145.1, 121.2, 92.1, 80.3, 74.6, 73.5, 57.6, 56.3, 51.5, 50.0, 26.0, −8.2. HRMS (MALDI) calculated for C$_{16}$H$_{25}$N$_7$O$_5$I (M): 522.0962, measured: 522.0982. For the purposes of biological experiments, solutions of purified 67 were made up using cold 2.5 mM H$_2$SO$_4$ and the concentration of these samples determined by UV-Vis measurement of optical density at 260 nm. Using the absorption values obtained at 260 nm and the molar extinction constant of 15,400M$^{-1}$ cm$^{-1}$ (for adenosine), stock solution concentrations were calculated using Beer's law. Stock solutions were stored at −80° C. and used within 2 weeks of dissolution.

B. General Biology

Ethanol precipitation was performed by addition of tRNA (40 μg/reaction, first round only), H$_2$O of a volume appropriate to bring the total aqueous volume of the reaction to 100 μL, 15 μL 3M NaOAc, and 250 μL absolute ethanol. The reactions were chilled over dry ice for a minimum of 15 min, spun down for 8 min. at 14,000 rpm, and the supernatant removed. The second round of precipitation was completed in the same manner, with 100 μL H$_2$O, 30 μL 3M NaOAc, and 420 μL absolute ethanol, followed by drying of the pellet in vacuo. Methyltransferase-mediated reactions were buffered in the following unless otherwise noted: (M.TaqI) 20 mM Tris-OAc (pH 6.0), 50 mM KOAc, 10 mM Mg(OAc)$_2$, 0.01% Triton-X100; (M.EcoRI, M.HhaI, M.SssI) 10 mM Tris (pH 7.4), 5 mM NaCl, 0.5 mM EDTA and 0.01% Triton X-100. DNA target and complementary strands were purchased from Sigma-Genosys. The 5'-end of the target strand was labeled with $^{32}$P, gel purified and annealed to the corresponding complementary ODN (M.TaqI ODN=5'-TGAATCTCGAGCACCC-3' (SEQ. ID. 14), complementary ODN=3'-AAACTTAGAGCTCGTGGG-5' (SEQ. ID. 15); M.EcoRI ODN=5'-TATATGAATTCTTAAA-3' (SEQ. ID. 16), complementary ODN=3'-AAATACTTAAGAATTTCT-5' (SEQ. ID. 17); M.HhaI ODN=5'-TGTCAGCGCATGA-3' (SEQ. ID. 18), complementary ODN=3'-ACAGTCGCGTACT-5' (SEQ. ID. 19); M.SssI ODN=5'-TGAATCTCGAGCACCC-3' (SEQ. ID. 20), complementary ODN=3'-AAACTTAGAGNTCGTGGG-5' (SEQ. ID. 21). (N=methylated cytosine)

C. DNA Duplex Alkylation

Figure 10:
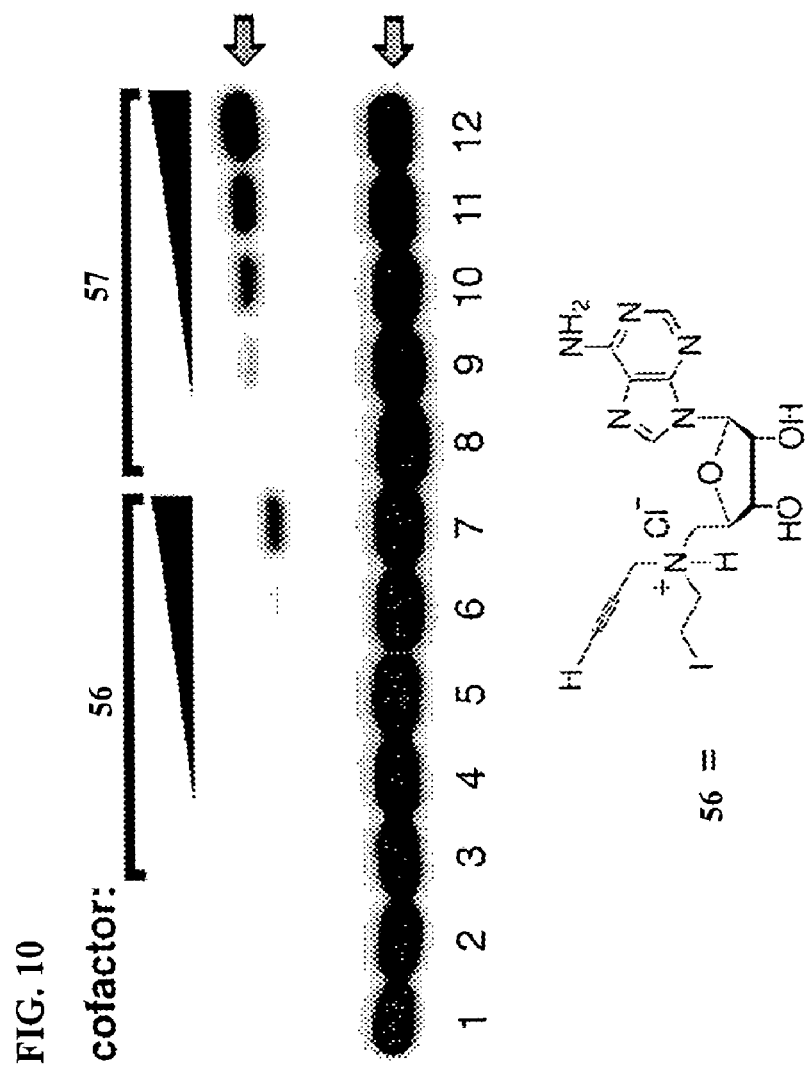
FIG. 10 shows a denaturing polyacrylamide gel electrophoresis (DPAGE) of DNA alkylation reactions. All reactions were 0.5 µM in duplex. For each panel of loadings the reaction contents are as follows: Lane 1: DNA only; Lane 2: MTase, no cofactor analog; Lane 3: 2 µM 56, no MTase; Lane 4: MTase+ 0.04 µM 56; Lane 5: MTase+0.2 µM 56; Lane 6: MTase+0.4 µM 56; Lane 7: MTase+2 µM 56; Lane 8: 2 µM 67, no MTase; Lane 9: MTase+0.04 µM 67; Lane 10: MTase+0.2 µM 67; Lane 11: MTase+0.4 µM 67; Lane 12: MTase+2 µM 67. Reactions were incubated at 37° C. for 10 h followed by repetitive EtOH precipitation workup. The upper arrow highlights alkylation products whereas the lower arrow indicates native unmodified DNA.

Alkylation reaction mixtures shown in FIG. 10 contained 0.5 μM duplex DNA (10 μM stock in TE buffer), 0.4 μM M.EcoRI, and 0.04, 0.2, 0.4, or 2 μM 67 or 56 (0.4, 2, 4, or 20 μM stock solutions in 2.5 mM H$_2$SO$_4$). Alkylation reaction mixtures shown in FIG. 11 contained 0.5 μM duplex DNA (10 μM stock in TE buffer), 0.6 μM M.EcoRI, M.SssI, or M.HhaI and 0.1, 0.5, 1, or 5 μM 67 (1, 5, 10, or 50 μM stock in 2.5 mM H$_2$SO$_4$). To compensate for the 37° C. incubation needed because of duplex sizes, the amount of M.TaqI used was ~1.2 μM. Normally, M.TaqI requires incubation at 65° C. that was not possible in these experiments. All reaction mixtures were incubated at 37° C. for 8-10 h and analyzed (following EtOH precipitation) on a 20% DPAGE gel run at 40 mA for 3 h.

Example 48

MTase-Dependent Alkylation by N-Mustard 5'-(di-aminobutyric acid)-N-iodoethyl-5'-deoxyadenosine ammonium hydrochloride 67

Studies of MTase-dependent DNA alkylation by 67 initially focused on M.EcoRI. The ability of M.EcoRI to enzymatically transfer propargylated adenylate 56 to duplexes bearing the MTase recognition site 5'-GAATTC-3' (the base ordinarily methylated is shown in bold-face) was described in EXAMPLES 34-44 and illustrated in FIGS. 4, 5 and 6. The resulting DNA readily takes part in subsequent "click" chemistry as described above. See also, Weller, R. L.; Rajski, S. R. *Organic Letters* 2005, 7, 2141-2144. These examples also show that 5'-aziridine adenylates permit DNA azidation and subsequent MTase-dependent Staudinger ligations. See also, Comstock, L. R.; Rajski, S. R., (2005) *Nucleic Acids Res.*, 33, 1644-1652. The inventors have attributed the success of this MTase-driven alkylation to the 5' N-mustard scaffold. Based on this success, this moiety was incorporated in the design of L-amino acid bearing substance 67. It was hypothesized that the amino acid of 67 would allow for significantly enhanced M.EcoRI-mediated DNA alkylation.

FIG. 10 shows the results of DNA alkylation using either compound 67 or 56. The superior efficiency of DNA alkylation with 67 as compared to that of 56 is evident by noting the formation of slower migrating species (shown by the upper arrow) at dose dependent concentration down to 0.04 µM of 67. The extent of alkylation in lanes 7 vs. 12 and 6 vs. 11 delineate this difference, although the most dramatic distinction in cofactor analog activities is illustrated in lanes 5 vs. 10. At this cofactor analog concentration (200 nM) alkyne 56 is not active at all, whereas subjection of DNA and M.EcoRI to 67 renders a significant amount of slow mobility DNA (highlighted with red arrow). Notably, 67 is active at concentrations as low as 40 nM, as shown in lane 9. Replacement of the alkyne in 56 with the amino acid moiety of 67 clearly has a pronounced impact on the ability of M.EcoRI to induce sequence-selective DNA damage to the duplex bearing its recognition site. These results have led the inventors to investigate whether the amino acid incorporation might increase the breadth of utility not only the efficiency, of such synthetic cofactor analogs.

Figure 11:
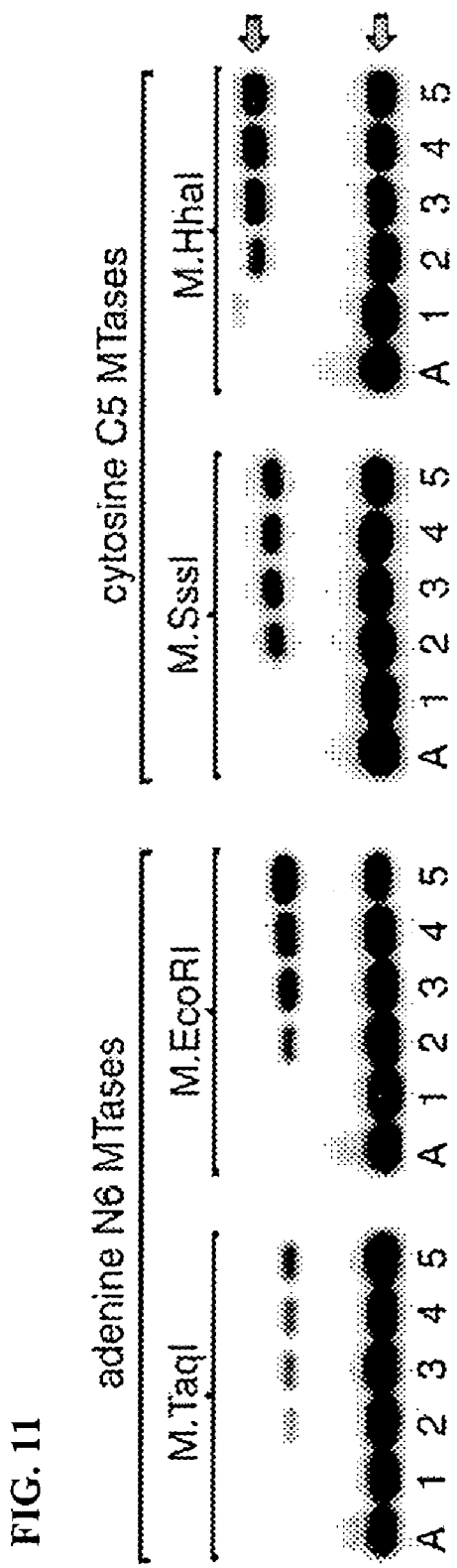
FIG. 11 shows results of DPAGE analysis of DNA alkylation reactions with 67 and various MTases. All enzymes and their corresponding DNA substrates (0.5 µM in duplex) were incubated with increasing concentrations of 67 for 10 h at 37° C. This is reflected by lanes 1-5 for each enzyme noted. Lane A for each series of sample loadings is a DNA duplex standard devoid of enzyme and cofactor analog. For each panel of loadings the reaction contents are as follows: Lane 1: DNA+5 µM 67 without MTase, Lane 2: MTase+0.1 µM 67; Lane 3: MTase+0.5 µM 67; Lane 4: MTase+1.0 µM 67; Lane 5: MTase+5 µM 67. Following incubation, reactions were processed as described for FIG. 10. Slow mobility alkylation products are highlighted with the upper arrow whereas native unmodified DNA is indicated with the lower arrow.

The ability of other MTases to transfer 67 to synthetic duplexes bearing the appropriate recognition sequences was next investigated. In addition to M.EcoRI, the inventors examined M.TaqI, M.SssI and M.HhaI (FIG. 11). For each panel of MTase reactions lane A represents only the duplex substrate. Lane 1 corresponds to nonspecific alkylation controls containing the highest concentration of cofactor analogs (5 µM), but no MTase. For all other reactions (with enzyme) the concentration of 67 was ramped from 100 mM to 5 µM as indicated. All MTases were able to transfer 67 to their respective DNA substrates, albeit with differing efficiencies. Percent yields for lane 2-5 reactions for each of the following enzymes were as follows: M.TaqI: 6, 9, 13, 12%; M.EcoRI: 7, 20, 28, 53%; M.SssI: 20, 25, 25, 26%; M.HhaI, 15, 38, 41, 42%. For all enzymes, yields of MTase-independent alkylation were <1% and margin of error=±3%. These values were obtained by phosphorimaging of the gels shown in FIG. 11 gels and subsequent data analysis with ImageQuant 2.0 software. This is to be expected since reaction conditions and concentrations for all enzymes were kept as uniform as possible so as to minimally alter DNA and/or cofactor analog integrity from one enzyme series to another. All reactions evaluated in FIG. 11 were incubated at 37° C. M.TaqI, however, has an optimum temperature of 65° C.; it displays markedly lower activity at 37° C. This likely explains the much lower yields of DNA alkylation with 67 by M.TaqI relative to other MTases under study.

Significantly, little or no non-specific alkylation is apparent in lane 1 for each MTase, yet yields for MTase-dependent alkylation are significant when compared to the maximum theoretical yield of 50%. Once attached to one of the two strands, 67 very likely prohibits further enzymatic processing of the complementary strand. Because both strands have an equal probability of being the first to react with 67, a theoretical yield (of radiolabeled and alkylated) of 50% is proposed. It is noteworthy that a variant of 68 devoid of the amino acid moiety was completely inactive with each MTase under identical reaction conditions (data not shown). This "control" compound has been previously described and is active with both M.TaqI, M.EcoRI albeit at much higher concentrations than those investigated here (Pignot, M; Seithoff, C.; Linscheid, M.; Weinhold, E. *Angew. Chem. Int. Ed. Engl.* 1998, 37, 2888-2891). That MTase-directed alkylation with 67 and SAM share the same regiochemistry was supported by the lack of base labile lesions in DNA modified with 67. Furthermore, duplexes bearing a 5-MeC for C substitution at the target base (for M.SssI and M.HhaI) failed to undergo alkylation by 67 as shown below. Taken together, these data show that 67, a very close structural analog of SAM, is a new type of potent MTase-directed DNA damaging agent. Further, the results show, that as in nature, methylation of the residue prior to treatment with the SAM analogs protects the residue from further methyltransferase action.

Example 49

Regioselectivity Experiments

Figure 12:
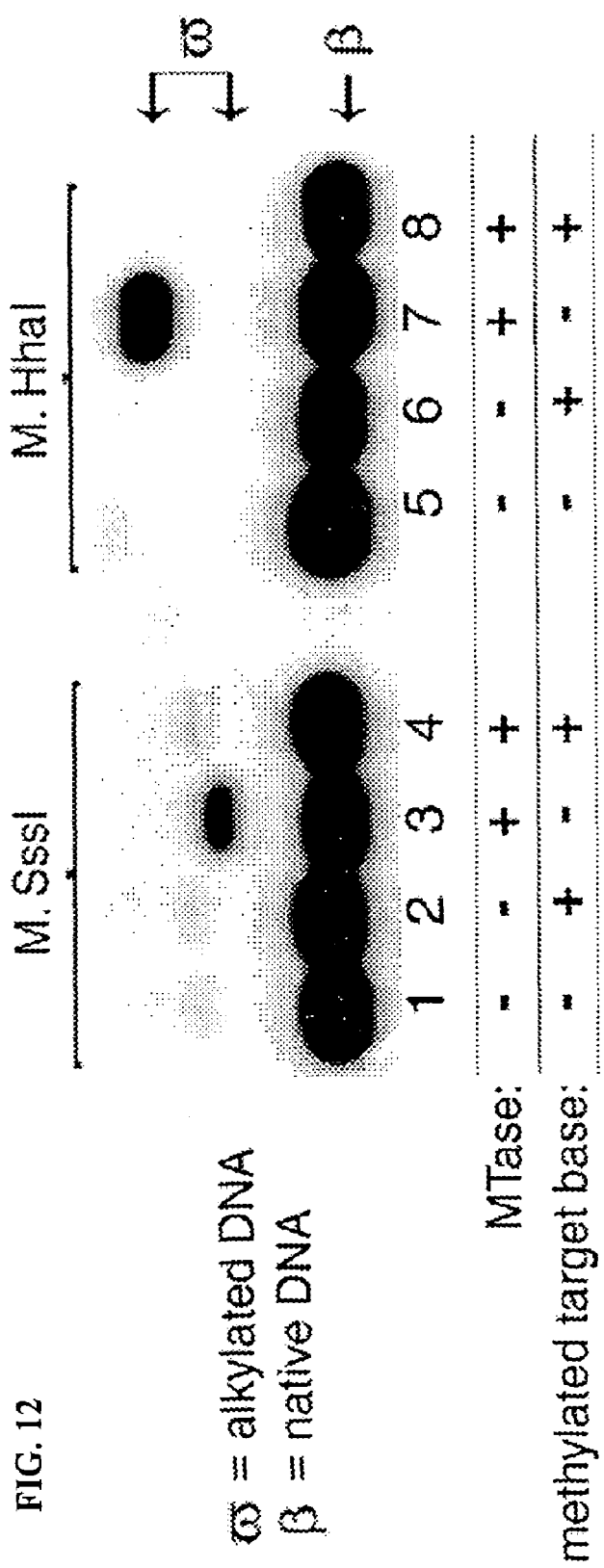
FIG. 12 shows results of regiospecificity experiments. Alkylation mixtures contained 0.5 µM duplex DNA (10 µM stock in TE buffer), 2 µM 67 (20 µM stock in 2.5 mM H$_2$SO$_4$), and indicated lanes contained 0.4 µM M.SssI or M.HhaI. All reaction mixtures were incubated at 37° C. for 8 h and analyzed (following EtOH precipitation) on a 20% denaturing polyacrylamide gel run at 40 mA for 3 h.

Alkylation reaction mixtures contained 0.5 µM duplex DNA (10 µM stock in TE buffer), 2 µM 67 (20 µM stock in 2.5 mM $H_2SO_4$), and indicated lanes contained 0.4 µM M.SssI or M.HhaI. All reaction mixtures were incubated at 37° C. for 8 h and analyzed (following EtOH precipitation) on a 20% denaturing polyacrylamide gel run at 40 mA for 3 h. These experiments show that the DNA in which the target base was methylated does not yield slower mobility material following reaction with MTase and 67 indicating that DNA alkylation by SAM and 67 proceeds with the same regiochemistry. Slow mobility DNA bands observed upon reaction with 67 are not the result of simple enhancements in base reactivity once flipped out of the DNA duplex by the MTase used. It is very well known that DNA methyltransferases bind to duplexes bearing completely nonmethylated, partially methylated, and fully methylated duplex recognition sequences. DNA base methylation does not prohibit enzyme binding nor is enzyme-promoted DNA base flipping (needed for covalent modifications) prohibited. Thus, the lack of reaction of methylated substrates with 67 is not a function of diminished enzyme binding. The results, shown in FIG. 12, indicate that methods similar to those disclosed herein are amenable for determining the methylation state of DNA sequences.

Experiment 50

Piperidine Digestion Reactions

In order to confirm that the alkylation was occurring at the specific position targeted by each methyl transferase, piperidine digestions, a standard digestion method for methylphosphonate oligomers, were performed on the DNA alkylated by 67. Prior to DPAGE analysis all alkylation reactions were carried out in the suitable MTase reaction buffers as previously indicated. Reactions were incubated at 37° C. for a period of 8 h followed by EtOH precipitation in the presence of ~40 μg tRNA.

Figure 13:
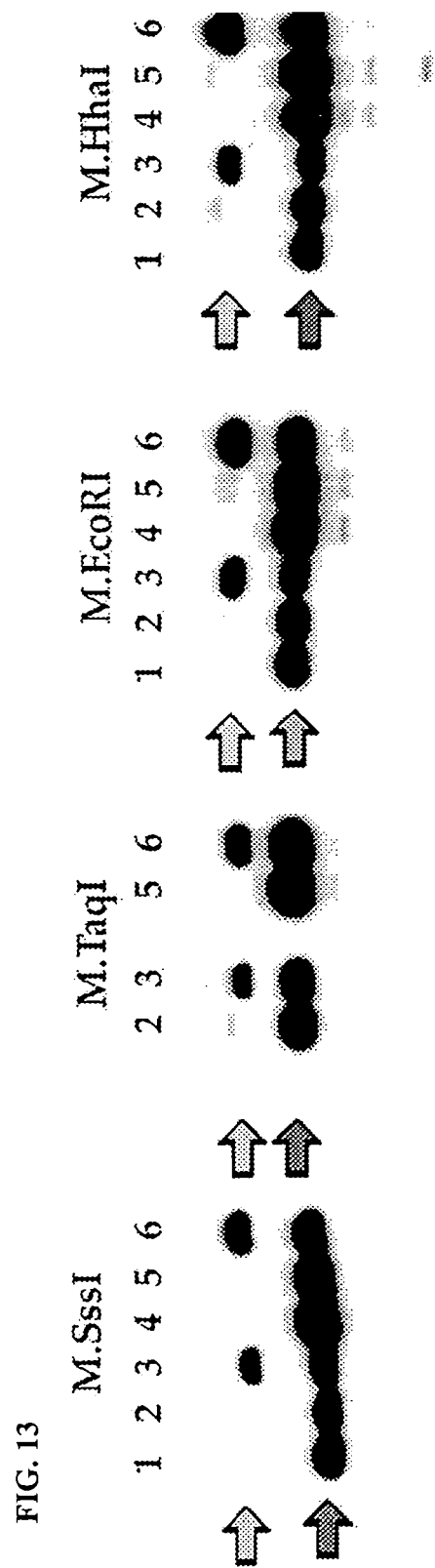
FIG. 13 shows DPAGE analysis of piperidine digestions of DNA alkylated by 67. Above each series of 6 lanes is indicated the MTase used. Upper arrows indicate slow mobility DNA products and lower arrows indicate position of native, radiolabeled unmodified DNA strands. Reaction/lane contents were as follows: Lane 1: 0.5 µM DNA duplex+MTase; Lane 2: 0.5 µM DNA duplex+5 µM 67; Lane 3: 0.5 µM DNA duplex+5 µM 67+MTase. Lanes 4-6 had the identical contents of reactions 1-3 with the notable exception that following EtOH precipitation workup the reactions were resuspended in 100 µL 0.5M piperidine and heated to 90° C. for 30 min followed by repetitive lyophilization prior to electrophoretic analysis. Lanes/reactions 1 and 4 for M.TaqI-containing samples are not shown. These samples were analyzed independent of the current analysis. In neither case was piperidine-promoted DNA cleavage observed consistent with reactions devoid of an electrophilic cofactor analog.

It is noteworthy that piperidine digestions (FIG. 13) did not lead to significant cleavage events specific to reactions inclusive of both MTase and 67. Any cleavage observed in the 67+ MTase reactions was also observed in corresponding 67 only and/or MTase only control lanes. These data refute the possibility that cofactor analog 67 alkylates the typically nucleophilic N7 and/or N3 positions of either A or G bases. Moreover, the retention of slow mobility, analog-dependent adducts in lane 6 for each reaction series supports the notion that DNA alkylation by 67 and S-adenosyl-L-methionine share the same regiochemistry, neither of which involves formation of base labile lesions. Indeed, it is somewhat surprising that the adducts formed by reaction of DNA with 67 easily withstand the brutal heating and pH conditions typically employed for Maxam-Gilbert sequencing.

After 58, this is the second reported structure to exploit an electrophilic N-mustard moiety en route to MTase-dependent DNA alkylation. That this new cofactor analog is effective with both adenine and cytosine MTases suggests a wide scope of utility compared to that of other reported SAM analogs. The amino acid moiety and resulting homology with SAM make this cofactor analog the most likely to show activity with other SAM-dependent methyltransferases. Additionally, the agent's high degree of activity indicates that this scaffold could be tolerant of a diverse range of substitution patterns.

The experimental results described here illustrate several important findings. First, a novel N-mustard 67 has been synthesized which likely proceeds (under biological conditions) to the aziridinium ion 68, a structure highly homologous with SAM. Secondly, the inventors have found this new cofactor analog to be remarkably efficient at methyltransferase (MTase)-driven DNA alkylation as shown in SCHEME XIV. Representatives of two classes of DNA MTases can effectively chaperone this small molecule to DNA in a highly selective way, just as they do S-adenosyl-L-methionine (SAM) en route to DNA methylation. Further, this new cofactor analog is compatible with an array of enzymes including M.TaqI and M.EcoRI (both adenine $N^6$ MTases), as well as cytosine $C^5$ MTases M.HhaI and M.SssI.

V. Methyl Transferase Directed DNA Strand Scission

The study of prokaryotic DNA methyltransferases (MTases) has provided significant insight into eukaryotic MTases and the important role that methylation plays in mammalian biology. The prokaryotic enzymes M.TaqI, M.EcoRI and M.HhaI are all capable of using 5'-aziridine adenylate 24a in place of S-adenosyl-L-methionine in MTase-dependent DNA alkylation reactions (Comstock, L. R.; Rajski, S. R., (2004) *J. Org. Chem.*, 69, 1425). By virtue of the C8 azide, 24a is significant because it is capable of converting these DNA MTases into azidonucleoside transferases. Not surprising, DNA modified with 24a is capable of undergoing very efficient Staudinger ligation with biotinylated triarylphosphines as described previously and schematically illustrated in SCHEME V. Although the inventors have already shown the use of 24a as a means of isolating various MTase substrates from complex mixtures, it was expect that 24a might be very useful for identifying, in a rapid way, regions of DNA hypermethylation.

As previously described, there are many methods currently used by which to determine methylation state. However, these methods are only useful for detection of 5-methylcytosine (5-MeC) and not other modified nucleosides and require multiple steps to perform. It was hypothesized that aziridines such as 24a do not have these limitations. The inventors realized that 24a could be used to "display" regions of DNA methylation. The inventors show here that DNA strand scission mediated through Haber-Weiss redox cycling represents an ideal means of identifying regions of DNA methylation. As was shown above in EXAMPLES 27-30, the site ordinarily methylated is modified by 24a, which allows the C-8 azide to undergo a Staudinger ligation with a phosphine moiety. The inventors hypothesized that the resulting conjugated phosphine could be converted into a DNA strand cleaving moiety via well-established phenanthroline (OP)-Cu(I) chemistry (Martelli, A.; et al., *Tetrahedron* 2002, 58, 4291). This strategy is schematically illustrated in SCHEME XVI.

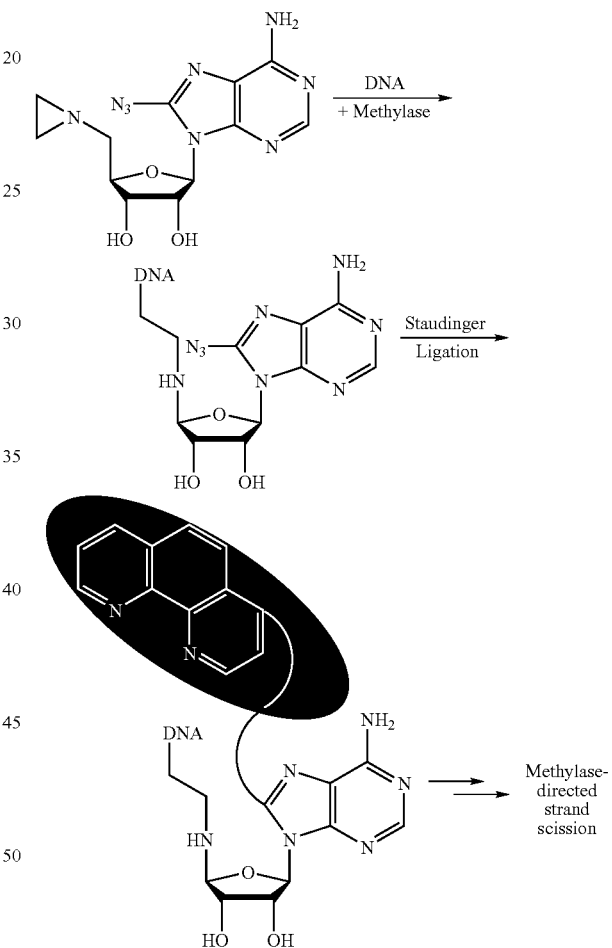

SCHEME XVI

With this goal in mind, the inventors designed and synthesized several phosphine compounds for investigation of their use with the Staudinger Ligation. One goal of this synthesis was to provide phosphine compounds of differing linker length to determine the steric requirements for Cu binding.

Of these compounds, it was found that triarylphosphines 72-74 SCHEME XVII readily undergo the Staudinger ligation with DNA enzymatically modified with 24a, and that subsequent presentation with $CuSO_4$ and the reductant 3-mercaptopropionic acid (MPA), induces sequence selective DNA strand scission. Variation of linker lengths in 72-74 was undertaken because of uncertainties related to copper binding and steric accessibility requirements. It was determined that DNA strand scission is highly localized to the DNA base ordinarily methylated.

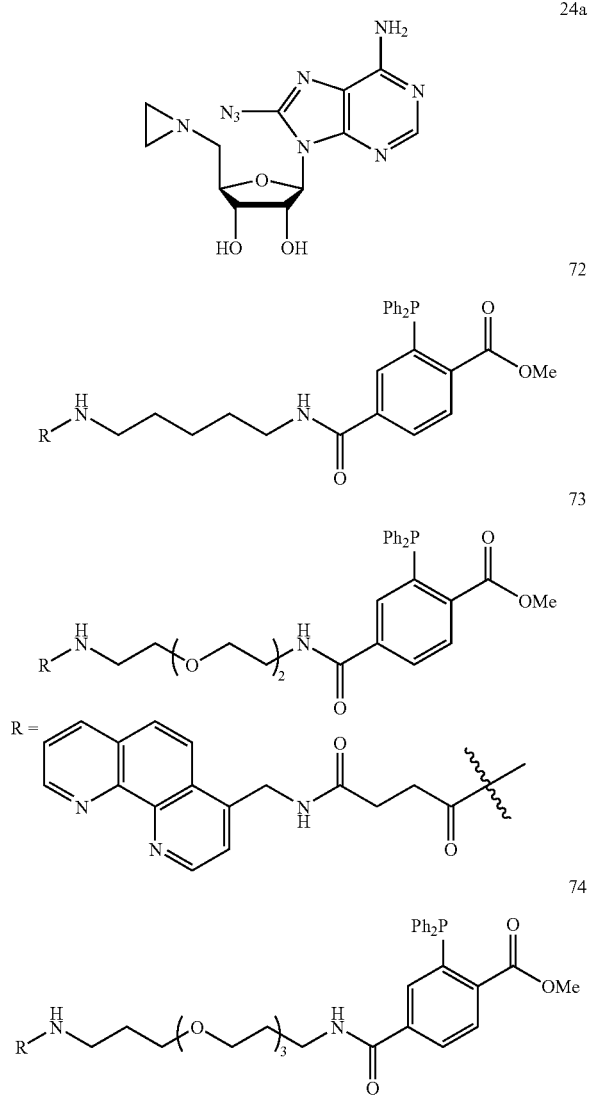

A. General Experimental Procedures

All reactions were carried out under an inert atmosphere of argon unless indicated otherwise. All reagents were obtained from commercial suppliers and used as received unless otherwise noted. Column chromatography was performed on basic aluminum oxide ($Al_2O_3$), Fisher no. A-941, 80-200 mesh. Analytical TLC was conducted on EM Science silica gel plates with or without indicator; material was detected by ninhydrin and/or UV light. Dichloromethane ($CH_2Cl_2$) and dimethylformamide (DMF) were obtained from an anhydrous solvent delivery system. TEA was dried over KOH and then distilled; DIEA was distilled from ninhydrin, and then from KOH. The $^1$H-NMR and $^{13}$C-NMR spectra were recorded on Varian ui400 and ui500 spectrometers using solvent as the internal reference. Chemical shifts are reported in ppm, in δ units. High-resolution matrix-assisted desorption/ionization (MALDI) data was obtained from the University of Wisconsin-Madison, School of Pharmacy. High-resolution electron spray ionization data was obtained from the University of Wisconsin-Madison, Department of Chemistry.

Example 51

4-(1,10-Phenanthroline-4-Methylamino)-4-Oxobutanoic Acid 75

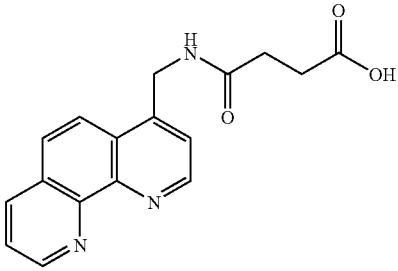

Synthesis of 4-(1,10-phenanthroline-4-methylamino)-4-oxobutanoic acid (75) was performed as follows: To succinic anhydride (0.050 g, 0.498 mmol) in 2.6 mL dry $CH_2Cl_2$ was added TEA (0.104 g, 1.030 mmol). After stirring for a few minutes, 1,10-phenanthroline-4-methanamine (0.101 g, 0.484 mmol) was added and stirred at a gentle reflux overnight. The reaction was dried down and washed with $CH_2Cl_2$ and $Et_2O$; the resulting solid was dried under vacuum (0.120 g)—contains TEA salts (75% by NMR).

An NMR analysis of 75 was performed where: $^1$H NMR (DMSO-$d_6$) δ 9.06 (d, J=3 Hz, 1H), 8.98 (d, J=5 Hz, 1H), 8.65 (bs, 1H), 8.45 (d, J=9.5 Hz, 1H), 8.12 (d, J=11.5 Hz, 1H), 7.98 (d, J=11.5 Hz, 1H), 7.73 (dd, J=9.5, 5.5 Hz, 1H), 7.62 (d, J=4.5 Hz, 1H), 4.82 (d, J=6 Hz, 1H), 2.47 (m, 4H); $^{13}$C NMR (DMSO-$d_6$) δ 174.0, 171.5, 150.0, 149.5, 145.6, 145.3, 144.9, 136.0, 127.9, 126.6, 126.2, 123.2, 122.0, 121.1, 45.3, 30.2, 29.4. ESI-HRMS: calculated for $C_{17}H_{15}N_3O_3$ (M+H$^+$) 308.1035, observed 308.1021.

B. General Procedure for Phenanthroline Coupling

To 4-(1,10-phenanthroline-4-methylamino)-4-oxobutanoic acid (75) (0.077 mmol) in 1.25 mL dry DMF was added 1-ethyl-3-[3-(dimethylamino)propyl]carbodiimide (0.155 mmol) (Pierce Biotechnology Inc. Rockford, Ill., Cat. No. 22980) and hydroxybenzotriazole (0.1546 mmol) (Sigma-Aldrich Chemicals, St. Louis, Mo., Cat. No. 362441). After stirring for 45 min., the amino-phosphine (pretreated with DIEA—0.124 mmol) in 375 μL DMF was added and stirred overnight. The solvent was evaporated, brought back up in $CH_2Cl_2$, washed (dilute $NH_4Cl$, $CH_2Cl_2$), dried over $Na_2SO_4$, and evaporated in vacuo. The compounds were chromatographed on basic $Al_2O_3$ (0 to 2% MeOH in $CH_2Cl_2$). Yield: 48%.

Example 52

2-Diphenylphosphanyl-N-(5-[1,10-Phenanthrolin-4-Oxobutanamido]-Pentyl)-Terephthalamic Acid Methyl Ester (72)

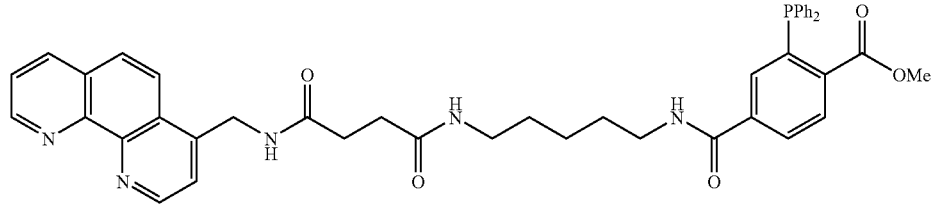

Synthesis of 2-Diphenylphosphanyl-N-(5-[1,10-phenanthrolin-4-oxobutanamido]-pentyl)-terephthalamic acid methyl ester (72) was accomplished as described above phenanthroline coupling.

An NMR analysis of 72 was performed where: $^1$H NMR (CDCl$_3$) δ 9.10 (dd, J=4, 1.6 Hz, 1H), 9.00 (d, J=4.4 Hz, 1H), 8.19 (dd, J=8, 1.6 Hz, 1H), 8.03 (dd, J=8, 3.6 Hz, 1H), 7.88 (d, J=9.2 Hz, 1H), 7.82 (dd, J=8, 1.6 Hz, 1H), 7.73 (d, J=9.2 Hz, 1H), 7.59 (m, 2H), 7.48 (d, J=4.4 Hz, 1H), 7.29 (m, 11H), 6.47 (t, J=5.6 Hz, 1H), 6.27 (t, J=5.6 Hz, 1H), 4.86 (d, J=6 Hz, 2H), 3.71 (s, 3H), 3.19 (q, J=6.4 Hz, 2H), 3.10 (q, J=6.4 Hz, 2H), 2.60 (m, 2H), 2.52 (m, 2H), 1.35 (m, 6H); $^{31}$P NMR (CDCl$_3$) δ −2.64; $^{13}$C NMR (CDCl$_3$) δ 172.7, 172.4, 166.9, 166.8, 150.6, 150.1, 146.4, 146.3, 144.0, 141.7, 141.5, 137.6, 137.4, 137.3, 136.8, 136.6, 136.1, 134.2, 134.0, 132.8, 131.9, 131.8, 131.0, 129.2, 128.84, 128.78, 128.4, 127.9, 127.0, 126.8, 126.7, 123.4, 121.8, 121.7, 52.4, 40.5, 39.8, 39.4, 31.84, 31.79, 29.0, 28.9, 23.9. HRMALDI: calculated for C$_{43}$H$_{42}$N$_5$O$_5$P (M+H$^+$), 740.29, observed 740.271.

Example 53

2-Diphenylphosphanyl-N-(2-{2-[2-(1,10-Phenanthrolin-4-Oxobutanamido)-Ethoxy]-Ethoxy}-Ethyl)-Terephthalamic Acid Methyl Ester (73)

2-Diphenylphosphanyl-N-(2-{2-[2-(1,10-phenanthrolin-4-oxobutanamido)-ethoxy]-ethoxy}-ethyl)-terephthalamic acid methyl ester (73) was synthesized as described: Yield: 60%. An NMR analysis was performed where: $^1$H NMR (CDCl$_3$) δ 9.14 (dd, J=4, 1.6 Hz, 1H), 9.04 (d, J=4.8 Hz, 1H), 8.20 (dd, J=8, 1.6 Hz, 1H), 8.01 (dd, J=8, 3.6 Hz, 1H), 7.92 (d, J=9.2 Hz, 2H), 7.74 (dd, J=8, 1.6 Hz, 1H), 7.62 (dd, J=8, 4.4 Hz, 1H), 7.49 (d, J=4.4 Hz, 1H), 7.29 (m, 12H), 6.68 (t, J=4.8 Hz, 1H), 6.38 (t, J=5.2 Hz, 1H), 4.90 (d, J=6 Hz, 2H), 3.70 (s, 3H), 3.49 (m, 10H), 3.35 (q, J=5.2 Hz, 2H), 2.61 (m, 2H), 2.55 (m, 2H); $^{31}$P NMR (CDCl$_3$) δ −2.64; $^{13}$C NMR (CDCl$_3$) δ 172.7, 172.4, 166.84, 166.80, 150.5, 150.0, 146.3, 146.0, 144.2, 141.7, 141.5, 137.4, 137.3, 136.9, 136.8, 136.1, 134.1, 134.0, 133.0, 131.9, 131.8, 130.92, 130.91, 129.1, 128.82, 128.77, 128.4, 127.0, 126.9, 126.8, 126.7, 123.4, 121.8, 121.7, 70.4, 70.3, 69.74, 69.68, 52.4, 40.5, 40.0, 39.4, 31.84, 31.78. HRMALDI: calculated for C$_{44}$H$_{44}$N$_5$O$_7$P (M+H$^+$), 786.30, observed 786.302.

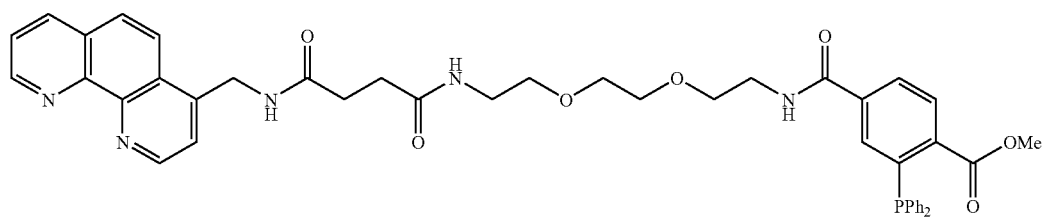

Example 54

2-Diphenylphosphanyl-N-(3-{2-[2-(3-{1,10-phenanthrolin-4-oxobutanamido}-propoxy)-ethoxy]-ethoxy}-propyl)-terephthalamic acid methyl ester (74)

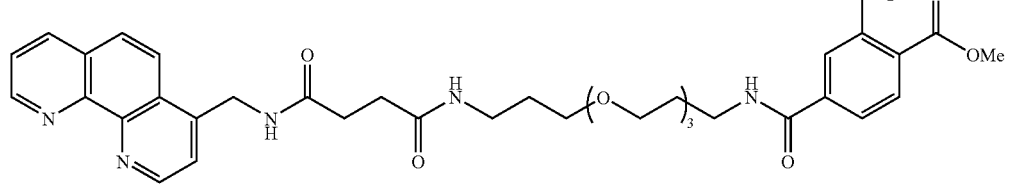

2-Diphenylphosphanyl-N-(3-{2-[2-(3-{1,10-phenanthrolin-4-oxobutanamido}-propoxy)-ethoxy]-ethoxy}-propyl)-terephthalamic acid methyl ester (74) was synthesized as described above. An NMR analysis was performed where: Yield: 50%. $^1$H NMR (CDCl$_3$) δ 9.17 (d, J=2.4 Hz, 1H), 9.06 (d, J=4.4 Hz, 1H), 8.22 (d, J=6.8 Hz, 1H), 8.01 (m, 1H), 7.94 (d, J=8.8 Hz, 1H), 7.75 (m, 2H), 7.62 (dd, J=8, 4 Hz, 1H), 7.53 (d, J=4.8 Hz, 1H), 7.40 (m, 1H), 7.29 (m, 11H), 7.04 (m, 11H), 6.66 (m, 11H), 4.91 (d, J=6 Hz, 2H), 3.69 (s, 3H), 3.53 (m, 8H), 3.42 (m, 6H), 3.27 (m, 2H), 2.61 (m, 2H), 2.55 (m, 2H), 1.75 (p, J=5.6 Hz, 2H), 1.66 (p, J=5.6 Hz, 2H); $^{31}$P NMR (CDCl$_3$) δ −2.69; $^{13}$C NMR (CDCl$_3$) δ 172.9, 172.3, 167.0, 166.5, 150.6, 150.2, 146.5, 146.3, 144.0, 141.6, 141.4, 137.7, 137.4, 137.3, 136.7, 136.6, 136.1, 134.2, 134.0, 133.3, 131.8, 131.7, 130.9, 130.4, 129.2, 128.83, 128.77, 138.4, 126.9, 126.8, 126.6, 123.3, 121.8, 121.7, 70.5, 70.3, 70.2, 70.11, 70.08, 52.4, 40.5, 38.7, 38.3, 32.0, 31.8, 29.1, 28.9. HRM-ALDI: calculated for C$_{48}$H$_{52}$N$_5$O$_8$P (M+H$^+$), 858.36, observed 858.322.

With the appropriate compounds synthesized, the inventors devised biological investigations to test the ability of using the Staudinger ligation to provide substrates for directed strand scission.

C. General Biological Methods and Procedures

All enzymes (unless indicated) were obtained from New England Biolabs (Ipswich, Mass.). The DNA MTase reactions with M.TaqI were run in buffer A (20 mM Tris-OAc (pH 6.0), 50 mM KOAc, 10 mM Mg(OAc)$_2$, 0.01% Triton-X100). The DNA MTase reactions with M.HhaI and M.SssI were run in buffer B (10 mM Tris-Cl (pH 7.4), 50 mM NaCl, 0.5 mM EDTA, 0.01% Triton-X100). DNA strand scission reactions were performed in buffer C (50 mM Tris, pH 8). Synthetic oligonucleotides were obtained from Sigma-Genosys (The Woodlands, Tex.) and gel purified prior to use. The concentration of the oligonucleotide was determined at 260 nm using the following molar extinction coefficients: 15,400 M$^{-1}$ cm$^{-1}$ (A); 11,500 M$^{-1}$cm$^{-1}$ (G); 8,700 M$^{-1}$cm$^{-1}$ (T); 7,400 M$^{-1}$ cm$^{-1}$ (C).

Example 55

Synthesis of Model Substrates

The inventors designed and constructed an oligonucleotide duplex (duplex 5) containing the recognition sequences for the MTases M.TaqI and M.HhaI. The synthetic oligonucleotide had the sequence d(5'-TGAACTGACCGTTCAGAATTCTA CTTCGATAAG GCGCCTAACGTACCTGAATCAA-3') (SEQ. ID. 22). The 5'-$^{32}$P-labeled oligonucleotide was prepared with T4 Polynucleotide Kinase and [γ-$^{32}$P]ATP using standard methods. The labeled oligonucleotide was gel purified on an analytical 20% DPAGE and desalted via Sephadex G-25 spin column (Amersham). The labeled strand was annealed to its complement d(3'-TTTTTGATTCAGGTACGTTAGG*CGCCTT ATCGAAGTAGAATTCTGAACGGTCAGTTCA-5') (SEQ. ID. 23) in 1× TE buffer by heating to 90° C. (5 min) and cooling to 4° C. over 4 h to afford 55 mer duplex 5. The synthetic oligonucleotide utilized for M.SssI reactions had the sequence d(5'-TGAATCTCGAGCACCC-3') (SEQ. ID. 24) and its complement d(3'-GGGTGCT*CGAGATTCAAA-5') (SEQ. ID. 25). The duplex containing only native DNA bases was assigned the number duplex 8; the duplex in which the *C=5-MeC was assigned the number duplex 9. Both duplexes were 5'-end-labeled on the strand with the underlined recognition site 5'-CG-3'. M.TaqI recognizes the duplex sequence 5'-TCG A-3' and M.HhaI recognizes the sequence 5'-GCGC-3' within duplex 5, where the base normally modified is underlined.

Example 56

Methyl Transferase Reactions with Synthetic Oligonucleotides

M.TaqI, M.HhaI, and M.SssI Reactions with synthetic oligonucleotides: reaction mixtures were prepared by the addition of appropriate stock solutions to a total volume of 40 µL in either buffer A or buffer B. The final DNA concentration was 1 µM; final concentration of cofactor analog 24a was 100 µM; the final concentrations of M.TaqI were 6 µM and both M.HhaI and M.SssI were 2 µM. All reactions were incubated at 37° C. for 18 h, followed by cooling to 0° C. Proteinase K (Ambion, Austin, Tex.) (0.04 U in 4 µL H$_2$O) was added to each reaction and digestions were carried out for 2 h at 37 µC. The resulting alkylated and proteolyzed samples were then used in the reactions described below.

Example 57

Staudinger Ligation with Cofactor Analog-Linked 32P-Labeled Oligonucleotide

Figure 14:
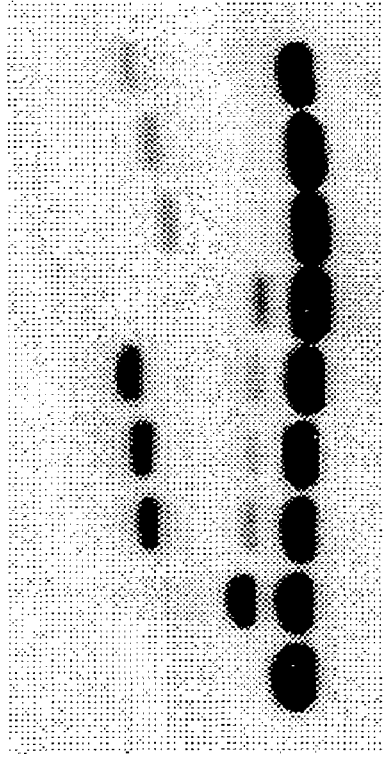
FIG. 14 shows the results of the DNA alkylation reactions of 55 bp oligonucleotide duplex 5 by aziridine cofactor analog 24a, and subsequent Staudinger ligations with phosphines 72, 73, and 74. Reaction mixtures were prepared by addition of appropriate stock solutions to a total volume of 20 μL containing 1 μM DNA (in duplex), 100 μM 24a, and 2 μM M.HhaI or 6 μM M.TaqI. M.HhaI reactions were buffered with 10 mM Tris-HCl (pH 7.4), 50 mM NaCl, 0.5 mM EDTA, and 0.01% Triton X-100. M.TaqI reactions were buffered with 20 mM Tris-OAc (pH 6.0), 50 mM KOAc, 10 mM Mg(OAc)$_2$, and 0.01% Triton X-100. Samples that were subjected to ligation conditions were brought to a final DNA concentration of 444 nM and contained 20-fold excess of triarylphosphine. The mixtures were analyzed on a hot 20% DPAGE ran at 90 W for 5 h. For the above figure, components that are present in the reaction are denoted by a '+'; components that are absent are denoted by a '−'.

An aliquot (11 µL, 10 pmol) of cofactor analog-linked $^{32}$P-labeled duplex was combined with 7.75 µL H$_2$O, 1.5 µL 100 mM NaOH, and 2.25 µL 10 mM each of phenanthroline-linked phosphine 72-74 (in DMF). The final concentration of DNA in the ligation reaction was 444 nM. Additional control reactions were also prepared (containing DMF only). The samples were incubated at 37° C. for 14 h. The ligation reaction was either analyzed by DPAGE or ethanol precipitated with 39 µg tRNA (E. coli, Type XX, Strain W) before subsequent processing and data acquisition. The dried pellet was resuspended in 30 µL buffer C for further use. The results of the Staudinger ligation with cofactor analog 24a modified 55 bp oligonucleotide duplex 5 and phosphines 72, 73 or 74 are illustrated in FIG. 14. The shift in lanes 2 and 6 shows that both M.HhaI and M.TaqI effectively catalyze the transfer of 24a to the 55-mer duplex 5. Further, the supershift in lanes 3-5 and 7-9 indicates addition of each of the phosphine groups to the modified oligonucleotide duplex 5. Further, it should be noted that while M.TaqI appears slightly less efficient in transferring 24a to the oligonucleotide duplex 5, there was little unmodified duplex remaining after the Staudinger ligation.

Example 58

DNA Strand Scission with Phenanthroline-Linked 32P-Labeled Oligonucleotide

The ligation partners 72-74 were found to undergo facile Staudinger ligation to both M.TaqI and M.HhaI modified 55 mer duplexes bearing the pendant aryl azide derived from 24a (FIG. 14). An aliquot (6.5 µL, 2.2 pmol) of phenanthroline-linked $^{32}$P-labeled duplex was combined with 1.5 µL buffer C, 1 µL 200 µM $CuSO_4$ (20 µM final concentration), and 1 µL 58 mM 3-MPA (5.8 mM final concentration). The reactions were incubated at 37° C. for 2 h and then stopped with EtOH precipitation. The pellets were dried under vacuum, brought up in dye, and analyzed by DPAGE (~5000 cpm/µL). Maxam-Gilbert sequencing reactions were run to identify base-specificity of strand scission.

Figure 15:
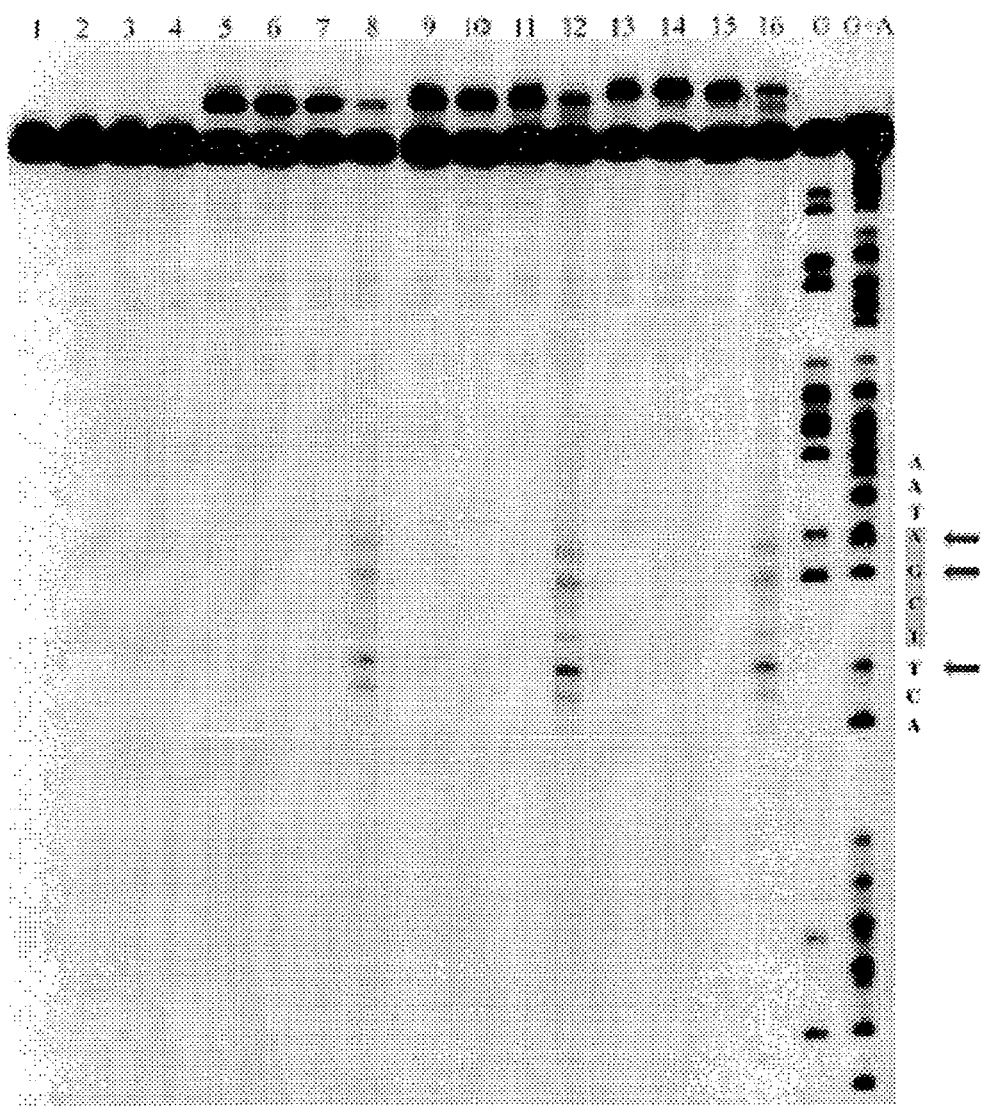
FIG. 15 illustrates sequence selective DNA strand scission via Cu(I)-mediated Haber-Weiss chemistry. Strand scission reactions were carried out on duplex 6 (55 bp oligonucleotide duplex 5 after modification with 24a by M.TaqI). Reactions were performed in 50 mM Tris buffer (pH 8) for 2 hours at 37° C. The methylase recognition site is boxed and major sites of DNA damage are indicated with an arrow. Scission sites were determined by comparison to Maxam-Gilbert sequencing reactions (Lanes G and G+A). Lane 1: duplex 6; Lane 2: duplex 6+20 μM CuSO$_4$; Lane 3: duplex 6+5.8 mM MPA; Lane 4: duplex 6+20 μM CuSO$_4$+5.8 mM MPA; Lane 5: duplex 6-72; Lane 6: duplex 6-72+20 μM CuSO$_4$; Lane 7: duplex 6-72+5.8 mM MPA; Lane 8: duplex 6-72+20 μM CuSO$_4$+5.8 mM MPA; Lane 9: duplex 6-73; Lane 10: duplex 6-73+20 μM CuSO$_4$; Lane 11: duplex 6-73+5.8 mM MPA; Lane 12: duplex 6-73+20 μM CuSO$_4$+5.8 mM MPA; Lane 13: duplex 6-74; Lane 14: duplex 6-74+20 μM CuSO$_4$; Lane 15: duplex 6-74+5.8 mM MPA; Lane 16: duplex 6-74+20 μM CuSO$_4$+5.8 mM MPA.

FIG. 15 shows the results of carrying out strand scission on duplex 6 (55 mer duplex 5 after modification with TaqI). The methyl transferase recognition site is shown by the box while the arrows indicate major sites of DNA damage. Note that only lanes 8, 12 and 16 having all the components for effective Haber-Weiss chemistry show the presence of faster migrating nucleotides.

Figure 16:
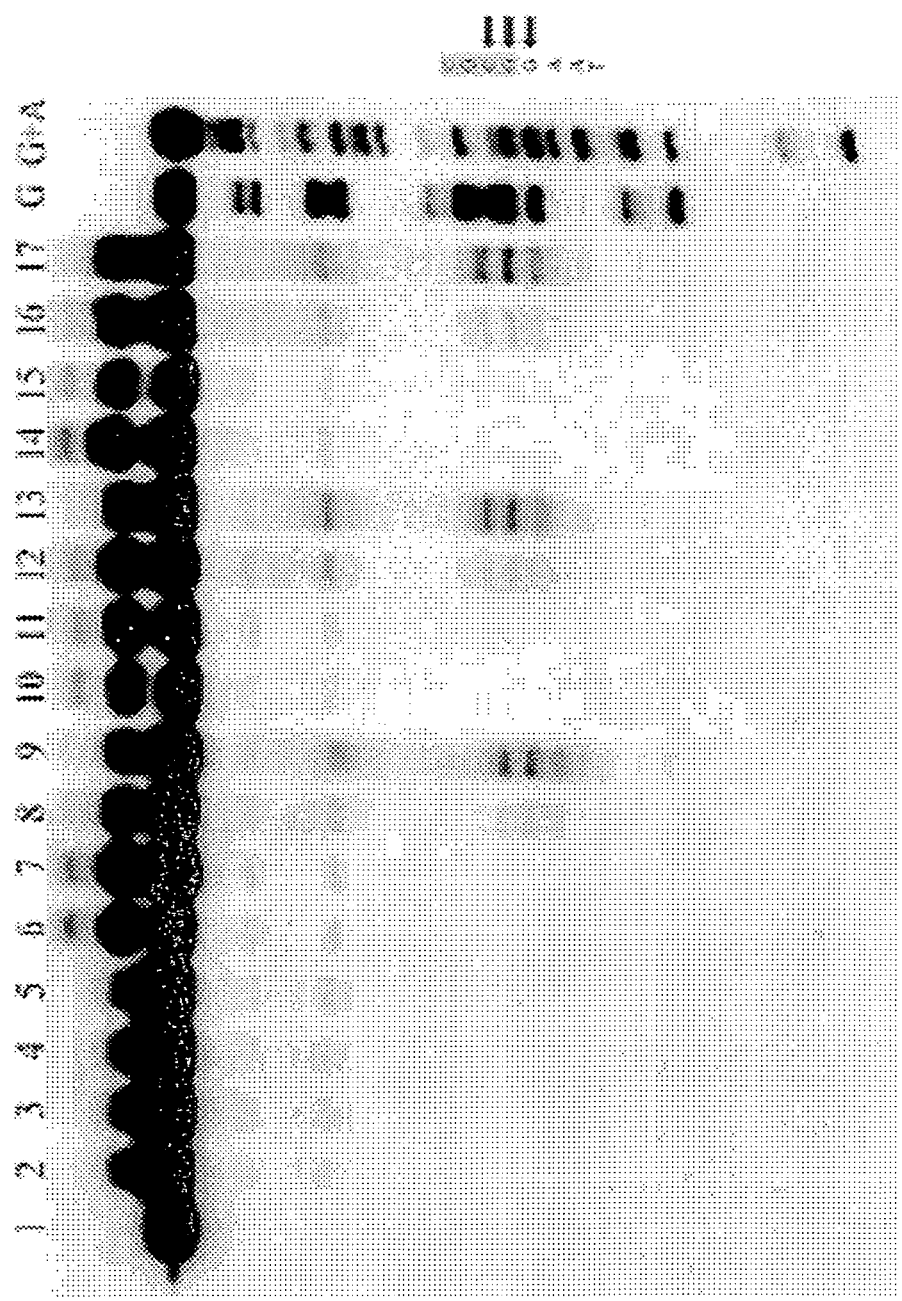
FIG. 16 shows the sequence selective DNA strand scission via Cu(I)-mediated Haber-Weiss chemistry. Strand scission reactions were carried out on duplex 7 (55 bp duplex 5 following M.HhaI-mediated alkylation with 24a). Reactions were performed in 50 mM Tris buffer (pH 8) for 2 hours at 37° C. The methylase recognition site is boxed in blue and major sites of DNA damage are indicated with an arrow. Scission sites were determined by comparison to Maxam-Gilbert sequencing reactions (Lanes G and G+A). Lane 1: DNA standard; Lane 2: duplex 7+20 μM CuSO$_4$; Lane 3: duplex 7+5.8 mM MPA; Lane 4: duplex 7+10 μM CuSO$_4$+2.9 mM MPA; Lane 5: duplex 7+20 μM CuSO$_4$+5.8 mM MPA; Lane 6: duplex 7-72+20 μM CuSO$_4$; Lane 7: duplex 7-72+5.8 mM MPA; Lane 8: duplex 7-72+10 μM CuSO$_4$+2.9 mM MPA; Lane 9: duplex 7-72+20 μM CuSO$_4$+5.8 mM MPA; Lane 10: duplex 7-73+20 μM CuSO$_4$; Lane 11: duplex 7-73+5.8 mM MPA; Lane 12: duplex 7-73+10 μM CuSO$_4$+2.9 mM MPA; Lane 13: 7-73+20 μM CuSO$_4$+5.8 mM MPA; Lane 14: duplex 7-74+20 μM CuSO$_4$; Lane 15: duplex 7-74+5.8 mM MPA; Lane 16: duplex 7-74+10 μM CuSO$_4$+2.9 mM MPA; Lane 17: duplex 7-74+20 μM CuSO$_4$+5.8 mM MPA.

FIG. 16 shows the results of Haber-Weiss strand scission carried out on duplex 7 the M.HhaI modified oligonucleotide duplex 5. Consistent with the presence of Staudinger ligated phosphine groups, DNA strand scission is seen only in the presence of complete reaction mixture. Further it should be noted that strand scission is apparent in a dose-response relationship where lanes 8, 12 and 16 show less DNA damage than lanes 9, 13 and 17 having twice the reactants present. The box on the right indicates the HhaI recognition sequence showing the specificity of the reaction.

Figure 17:
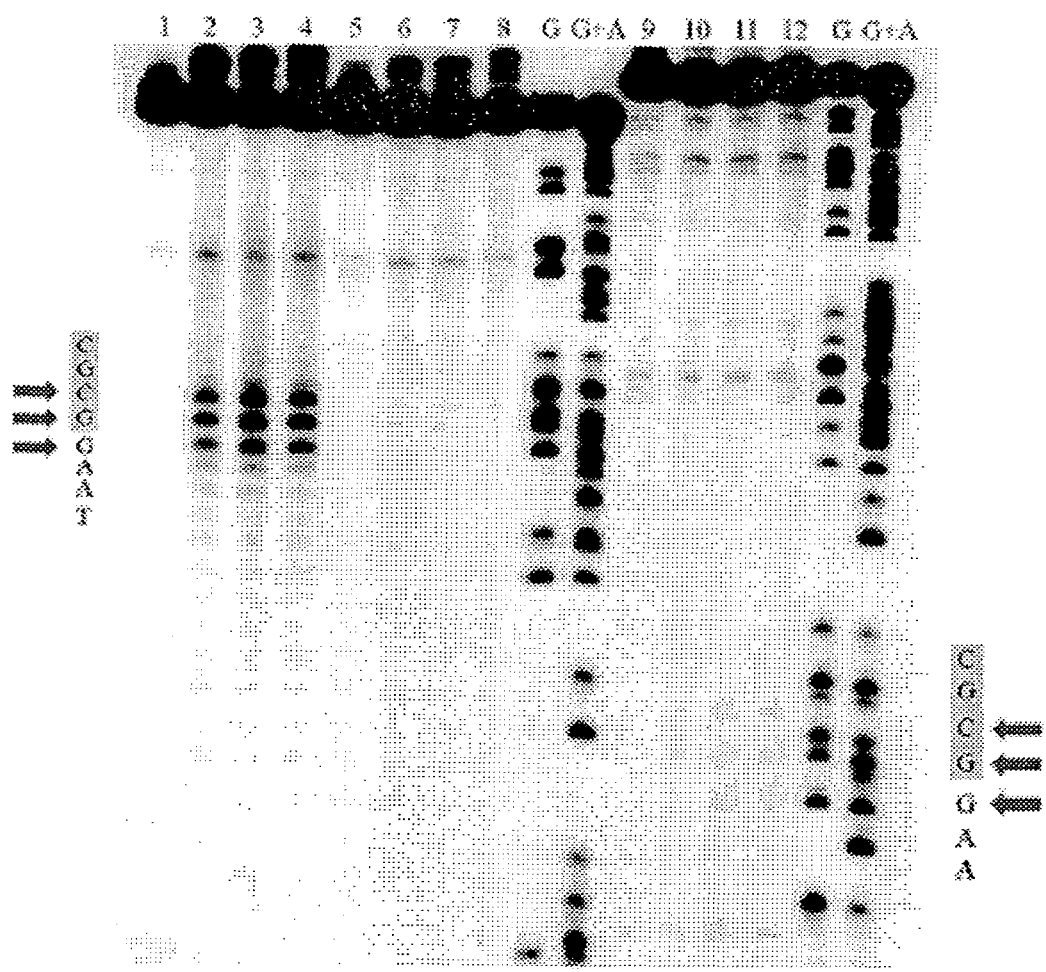
FIG. 17 shows the sequence selective DNA strand scission via Cu(I)-mediated Haber-Weiss chemistry. Strand scission reactions were carried out on 7 (55 bp oligonucleotide duplex 5 modified with 24a by M.HhaI). Additionally, duplex 12 (hemimethylated version of 55 mer duplex 5 following M.HhaI-mediated alkylation with 24a) was examined. Each lane was incubated with CuSO$_4$ and MPA (20 μM and 5.8 mM final concentration, respectively) in 50 mM Tris buffer (pH 8) for 2 hours at 37° C. The methylase recognition site is highlighted in blue and sites of DNA damage are indicated with an arrow. Scission sites were determined by comparison to Maxam-Gilbert sequencing reactions for both duplexes (Lanes G and G+A). Lanes 9-12 contain duplex 12 that are 5'-$^{32}$P-labeled on the methylated complementary oligonucleotide. Lane 1: duplex 7; Lane 2: duplex 7-72; Lane 3: duplex 7-73; Lane 4: duplex 7-74; Lane 5: duplex 12; Lane 6: duplex 12-72; Lane 7: duplex 12-73; Lane 8: duplex 12-74; Lane 9: duplex 12; Lane 10: duplex 12-72; Lane 11: duplex 12-73; Lane 12: duplex 12-74.

FIG. 17 shows the results of Haber-Weiss chemistry mediated strand scission carried out on duplex 7 (duplex 5 modified with I by M.HhaI) lanes 1-4 and duplex 12 (hemimethylated duplex 5 modified with 24a). In this experiment, all lanes (with the exception of control lanes 1, 5 and 9) contained all Haber-Weiss reactants. Consistent with prior results faster migrating oligonucleotide fragments are seen at the area of the methylase recognition site as shown by the boxed residues.

Figures 18A, 18B:
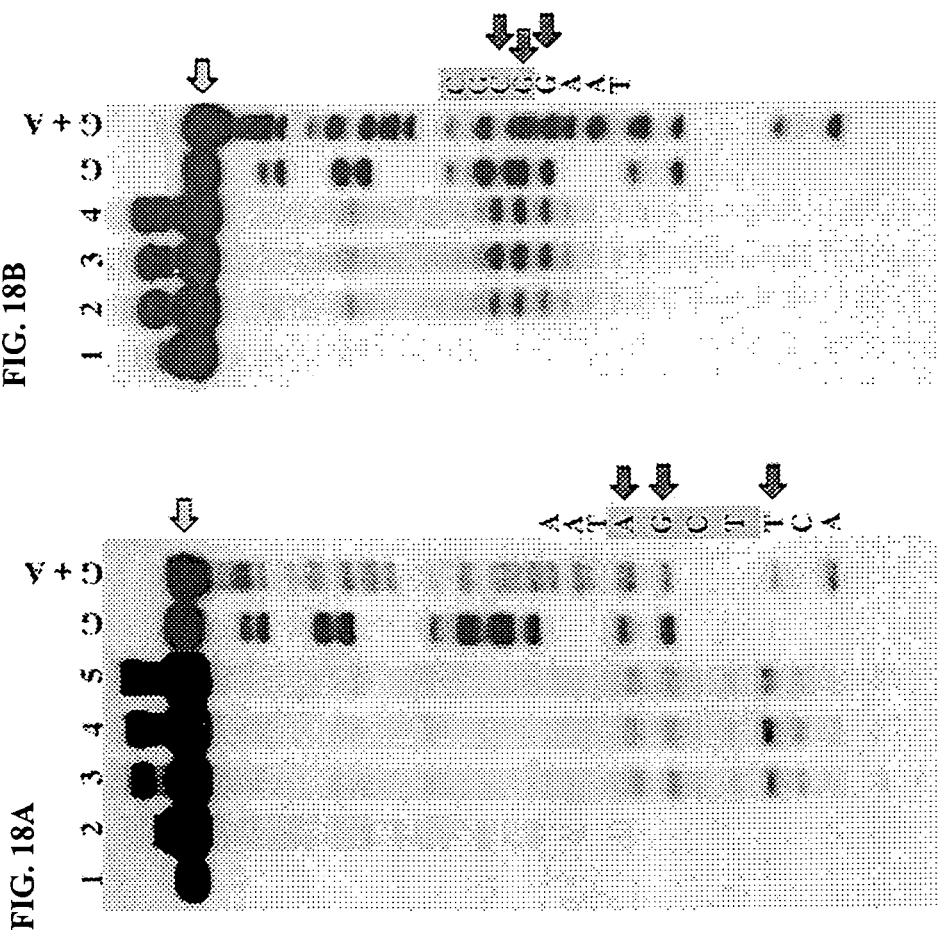
FIGS. 18A and 18B show MTase-directed DNA strand scission via Cu(I)-mediated Haber-Weiss chemistry. Strand scission reactions were carried out on duplex 6 (duplex 5 modified with 24a by M.TaqI) and duplex 7 (duplex 5 modified with 24a by M.HhaI). Each reaction/lane contained 20 μM CuSO$_4$ and 5.8 mM MPA in 50 mM Tris buffer (pH 8) and was incubated for 2 hours at 37° C. MTase recognition sites are boxed and major sites of damage are indicated with arrows. Scission sites were determined by comparison to Maxam-Gilbert sequencing reactions (Lanes G and G+A) and native unmodified DNA is at the top of the gel indicated with an arrow.

FIGS. 18A and 18B show the effect of Haber-Weiss mediated strand scission on duplex 6 M.TaqI modified duplex 5 (FIG. 18A) and duplex 7, M.HhaI modified duplex 5 (FIG. 18B). Addition of $CuSO_4$ and MPA induced DNA strand scission proximal to the MTase recognition site as determined by comparison to Maxam-Gilbert sequencing lanes (lanes G and G+A). As shown in FIG. 18A, DNA modified with 24a by M.TaqI produced several scission products; the major adducts corresponding to scission at the A and G residues within the M.Taq recognition sequence (on the 5'-end labeled strand), as well as the T residue immediately 5' of the recognition site. Phosphorimaging and data processing with ImageQuant revealed the yields for the three major scission products to be 12% (A), 13% (G), and 15% (T). Values are relative to all scission products observed. Several other products were observed, but are clearly minor contributors to the assortment of 5'-radiolabeled products. As with other experiments, linker length variation among the OP-phosphine conjugates exerts little, if any, change in product distribution across lanes 3, 4, and 5.

Examination of FIG. 18B reveals that M.HhaI-mediated DNA alkylation with 24a followed by ligation and copper treatment renders a distinctive pattern of damage. Strand scission products correlate to the 5'-GC-3' half of the M.HhaI site and, as with M.TaqI, extensive damage is seen immediately 5' of the enzyme recognition sequence. The scission yields for the three major scission products are 15% (C), 16% (G), and 13% (G). These data were obtained in a fashion identical to those related to M.TaqI. Importantly, a significant reduction in scission products is observed as distance from the modified base increases. Again, varying the linker length between the phosphine and OP does not appear to shift the scission site.

Figure 19:
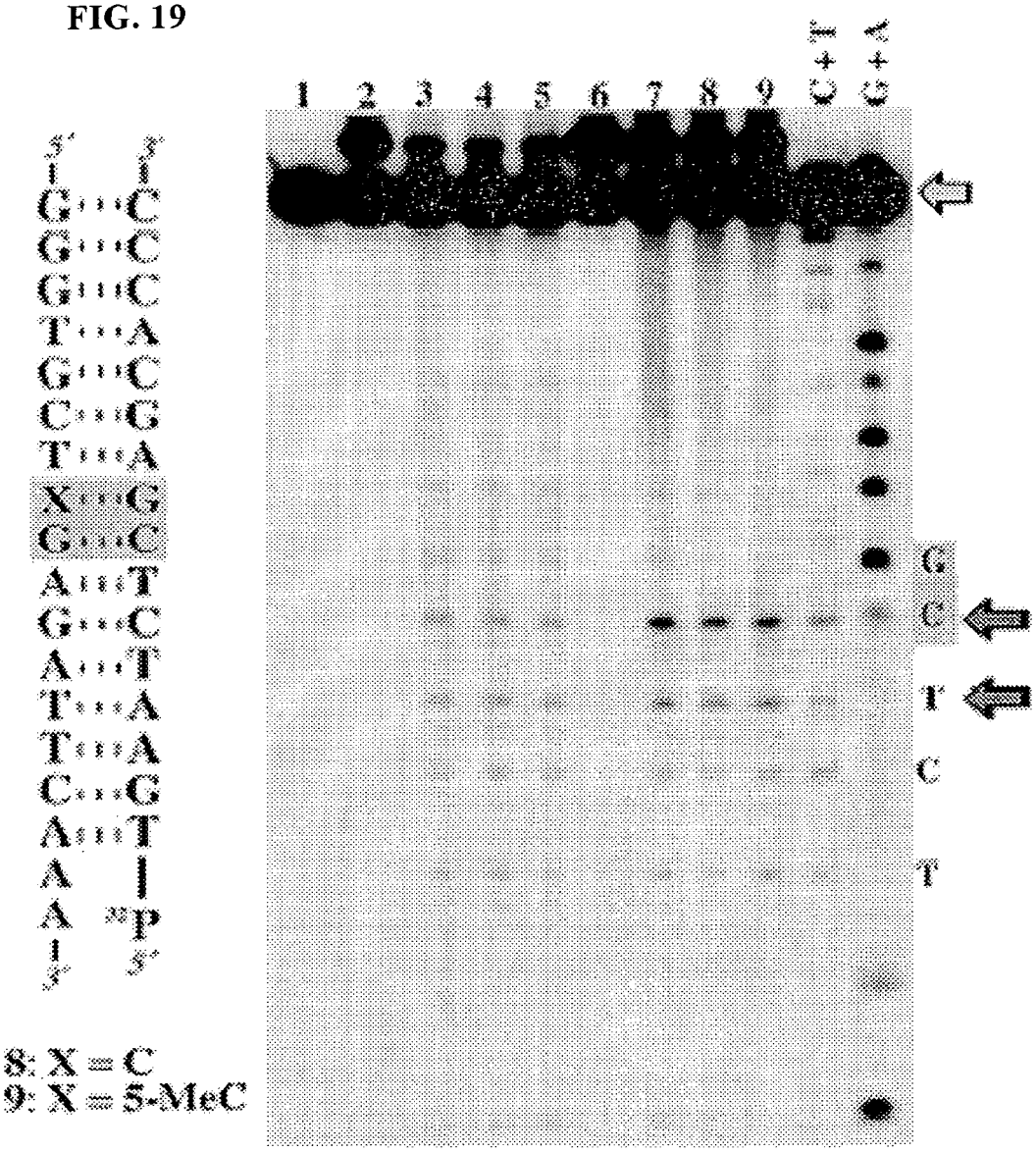
FIG. 19 shows M.SssI directed DNA strand scission via Cu(I)-mediated Haber-Weiss chemistry. Strand scission reactions were carried out on duplexes 8 and 9 following modification with cofactor analog 24a by M.SssI. Each lane/reaction contained CuSO$_4$ and MPA (20 μM and 5.8 mM final concentration respectively) in 50 mM Tris buffer (pH 8) and was incubated for 2 hours at 37° C. The MTase recognition site is boxed and major sites of DNA damage are indicated with red arrows. Native DNA is indicated with the arrow. Lane 1: DNA standard; Lane 2: duplex 10; Lane 3: duplex 10-72; Lane 4: duplex 10-73; Lane 5: duplex 10-74; Lane 6: duplex 11; Lane 7: duplex 11-72; Lane 8: duplex 11-73; Lane 9: duplex 11-74.

In addition to examining M.TaqI and M.HhaI, the inventors evaluated the ability of M.SssI to use compounds 24a and 72-74 with two 16 bp duplexes containing its 5'-CG-3' recognition site (FIG. 19). As shown in FIG. 19, one duplex (duplex 8) bore completely native DNA bases while duplex 9 was "hemimethylated" by virtue of 5-MeC incorporation. This experiment shows that M.SssI readily transfers 24a to its recognition sequence and that subsequent ligation yields with phosphines 72-74 are high. Notably, M.SssI mediated DNA alkylation by 24a is significantly more efficient for hemimethylated duplex 9 (to afford duplex 11) than for unmethylated duplex 8 (to afford modified duplex 10). For both modified DNA duplexes, the addition of $CuSO_4$ and MPA leads to strand scission principally at the cytosine that is ordinarily methylated by M.SssI. As with the preceding M.HhaI and M.TaqI examples, significant strand scission is induced at the base to the 5' side of the enzyme recognition sequence. In comparing cleavage of unmethylated duplex 10 (lanes 2-5) to that of hemimethylated duplex 11 (lanes 6-9), a dramatic difference is apparent. DNA damage with the hemimethylated duplex is significantly more pronounced than with unmethylated duplex. The yields for the major scission products of azide-linked duplex 10 (FIG. 19) are 17% (C) and 13% (T). The same sites are cleaved in duplex 11 with yields of 22% (C) and 13% (T). These data were obtained in a fashion identical to those related to M.TaqI and M.HhaI. Yields for M.SssI directed damage take into account the formation of apparent phosphoglycolate products that move slightly faster than each phosphate product highlighted.

Figure 20:
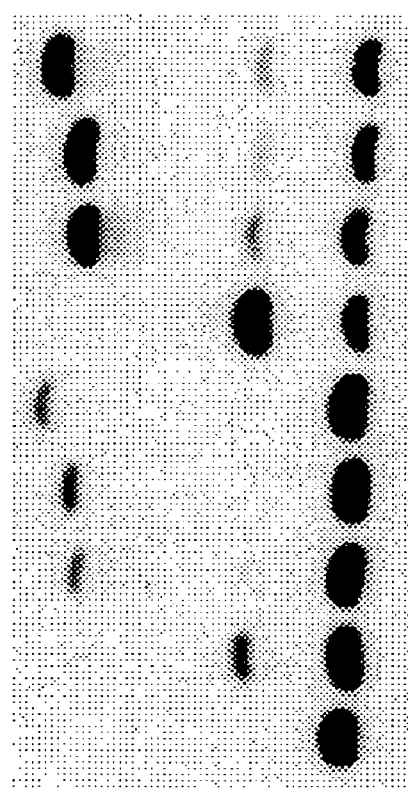
FIG. 20 shows M.SssI mediated DNA alkylation reactions of 16 bp oligonucleotide duplexes 8 and 9 with aziridine cofactor analog 24a and subsequent Staudinger ligations with phosphines 72, 73, and 74. T-C corresponds to duplex 8 where a native cytosine residue is on the complementary strand. T-MeC corresponds to duplex 9 where the complementary strand bears a methylcytosine residue within the M.SssI recognition sequence 5'-CG-3'. Reaction mixtures were prepared by addition of appropriate stock solutions to a total volume of 20 μL containing 1 μM DNA (in duplex) buffered with 10 mM Tris-HCl (pH 7.4), 50 mM NaCl, 0.5 mM EDTA, and 0.01% Triton X-100, 100 μM 24a, and 2 μM M.SssI. Samples that were subjected to ligation conditions were brought to a final DNA concentration of 444 nM and contained 20-fold excess of triarylphosphine. The mixtures were analyzed on a 20% DPAGE ran at 80 W for 2 h. For the above figure, components that are inclusive in the reaction are denoted by a '+'; components that are exclusive are denoted by a '−'.

Without being held to any particular mechanism, the inventors experiments indicate that the enhanced cleavage of duplex 11 does not result from structural aspects of 5-MeC incorporation in the unlabeled complementary strand. Rather, the improved cleavage of duplex 11 relative to duplex 10 is attributable to the much better coupling efficiency of duplex 9 with 24a relative to the same reaction involving unmethylated duplex 8. This effect is shown in FIG. 20. In other words, there are more substrates, in the form of synthetic cofactor analogs conjugated to the hemimethylated duplex target and available for Staudinger ligation with phosphine moieties and providing access to Haber-Weiss chemistry and consequent DNA strand cleavage than for the unmethylated duplex targets.

FIG. 20, shows the effect of methylated cytosine residues on the efficiency of synthetic cofactor analog conjugation. As shown, lanes 2-5 show DNA alkylation of non-methylated duplex 8 by M.SssI with compounds 24a and 72-74. In contrast, lanes 6-9 show the effect of DNA alkylation of an identical duplex 9 having a methylcytosine residue. As illustrated by the slower migrating, upper bands, there is considerable more alkylation by 24a (lane 6) and concomitantly greater products of Staudinger ligation incorporation of each of 72, 73 and 74 (lanes 7, 8 and 9) respectively. These data support the concept that the greater DNA damage seen in FIG. 19 is the result of an increase number of Haber-Weiss compatible substrates.

Figure 21:
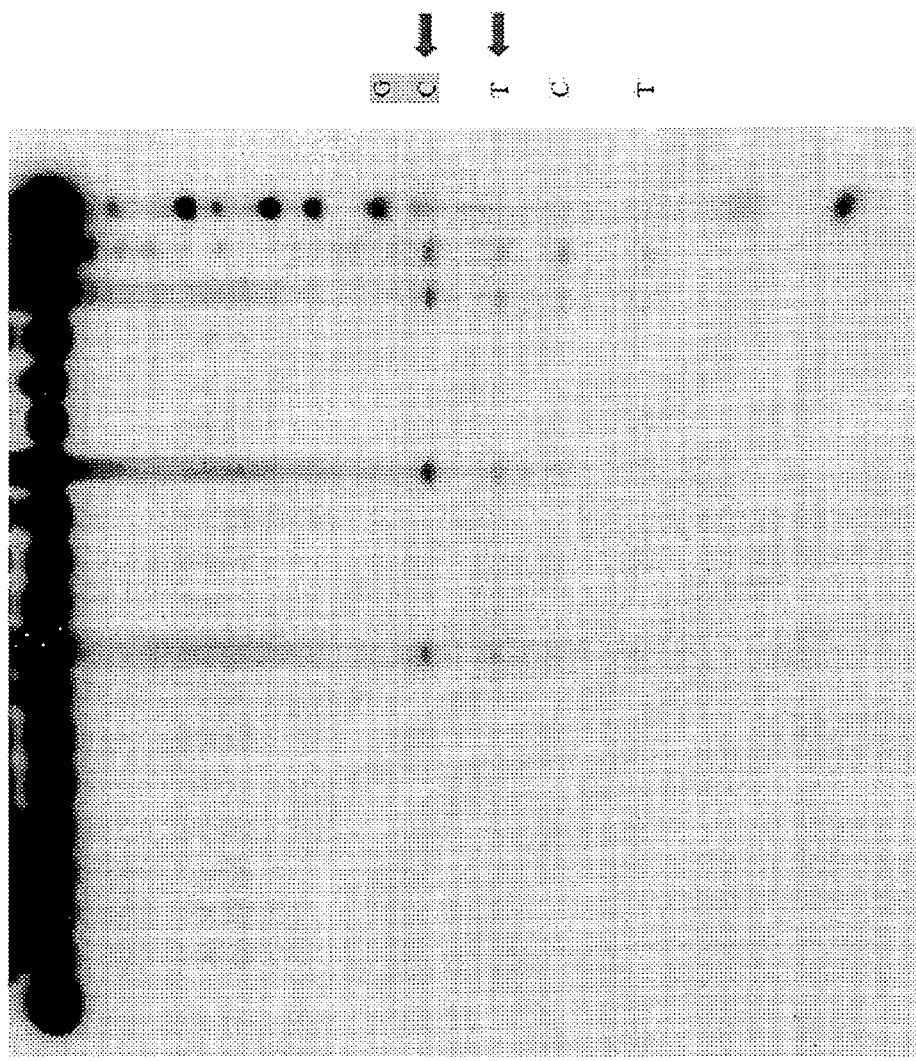
FIG. 21 shows the sequence selective DNA strand scission via Cu(I)-mediated Haber-Weiss chemistry. Strand scission reactions were carried out on duplex 11 (16 bp hemimethylated oligonucleotide duplex 9 following modification with 24a by M.SssI). Reactions were performed in 50 mM Tris buffer (pH 8) for 2 hours at 37° C. The methylase recognition site is boxed in blue and major sites of DNA damage are indicated with an arrow. Scission sites were determined by comparison to Maxam-Gilbert sequencing reactions. Lane 1: DNA standard; Lane 2: duplex 11; Lane 3: duplex 11+20 µM $CuSO_4$; Lane 4: duplex 11+5.8 mM MPA; Lane 5: duplex 11+20 µM $CuSO_4$+5.8 mM MPA (no phenanthroline present); Lane 6: duplex 11-72; Lane 7: duplex 11-72+20 µM $CuSO_4$; Lane 8: duplex 11-72+5.8 mM MPA; Lane 9: duplex 11-72+20 µM $CuSO_4$+5.8 mM MPA; Lane 10: duplex 11-73; Lane 11: duplex 11-73+20 µM $CuSO_4$; Lane 12: duplex 11-73+5.8 mM MPA; Lane 13: duplex 11-73+20 µM $CuSO_4$+ 5.8 mM MPA; Lane 14: duplex 11-74; Lane 15: duplex 11-74+20 µM $CuSO_4$; Lane 16: duplex 11-74+5.8 mM MPA; Lane 17: duplex 11-74+20 µM $CuSO_4$+5.8 mM MPA.

FIG. 21 shows the results of Haber-Weiss mediated strand scission on duplex 11 (hemimethylated duplex 9 modified with 24a by M.SssI) corresponding to lane 6 in FIG. 20. As with previous experiments the specificity of the cleavage is indicated by the lack of faster moving species in control lanes lacking reactant components while each lane containing duplex 11 modified with either 72, 73 or 74 (lanes 9, 13 and 17 respectively) show significant scission products.

D. The Use of Agents 24a, 72, 73 and 74 to Identify Regions of DNA Methylation

DNA damage patterns observed for each MTase convey several interesting features. Because DNA strand scission is directly linked to DNA modification by 24a, it was anticipated that (OP)Cu$^+$-dependent .OH production (following ligation and Cu(II) reduction) would produce damage both to the 5' and 3' side of the MTase-targeted base. The small nature of 24a (and it's ligation products) coupled with the production of highly diffusible .OH was not expected to afford significant protection of specific regions from oxidative damage such as is often the case when using large, high affinity reagents to deliver strand cutting moieties. This appears not to be the case; a marked 5' selectivity is routinely observed. Moreover, damage is much more localized to the MTase recognition sequence than was originally anticipated. Notably, copper oxene or copper-coordinated hydroxyl radical intermediates have been previously implicated by Sigman and others in (OP)$_2$Cu$^+$ mediated DNA damage processes (Sigman et al., Chem. Rev., 93, 2295 (1993)). The impact of such intermediates in lieu of or in addition to .OH production would be expected to be influenced by OP-phen linker length. It is therefore highly interesting that OP-phen conjugates 72, 73 and 74 give rise to almost identical patterns of DNA damage.

For all enzymes evaluated, significant scission is observed in a fashion consistent with damage at the base ordinarily methylated; other damage sites are invariably to the 5' side of the initially formed "azide-linked" base. Although several additional strand scission events of unequal intensity are often observed to the 5' side of the recognition site, little or no cleavage to the 3' side of MTase recognition sites is observed. This biased pattern of strand scission suggests a preferred orientation of the lesion towards the 5' end of the $^{32}$P end-labeled oligonucleotides. Alternatively, it is possible that DNA base modification with 24a (and subsequent ligation partners) predisposes this base and those to its 5' side towards reaction with hydroxyl radical.

VI. Synthesis of Aryl and Alkyl Azide N-Mustards

N-mustards 56 and 67 illustrate the facility provided by click-chemistry intermediates. In order to take advantage of the possibilities offered by the use of a modified Staudinger reaction, cofactor analogs 83 and 87 are modified to include azide residues able to take part in, and provide products of, modified Staudinger reactions as previously described. These azide-bearing N-mustard compounds are significant because they possess the attribute of being easier to synthesize and more stable than the standard 5' aziridine-based agents, bearing the amino acid side chain, thus enhancing resemblance to S-adenosyl-L-methionine, and containing pendant azide groups (both alkyl and aryl) to which other agents can be appended via either a modified Staudinger reaction or Huisgen [2+3] cycloaddition reactions, in addition to methyltransferase-dependent attachment to biological molecules (proteins, peptides, nucleic acids, natural product and natural product-like biosynthetic intermediates, lipids, etc.). A key feature of 83 is that the alkyl azide moiety is well-known to be stable to mild reducing conditions. This enables the continued application of reductive amination chemistry for amino acid-nucleoside convergence. Previous work by the inventors has shown C8 azido adenosine analogs to be remarkably susceptible to any kind of synthetically useful reductants (NaBH$_4$, LiBH$_4$, LiAlH$_4$, Li(OAc)$_3$BH, etc.). Thus, synthesis of compounds 83 and 87 as described below produces compounds with able to take part in, not only methylase catalyzed ligations to biological substrates but also modified Staudinger and cycloaddition reactions.

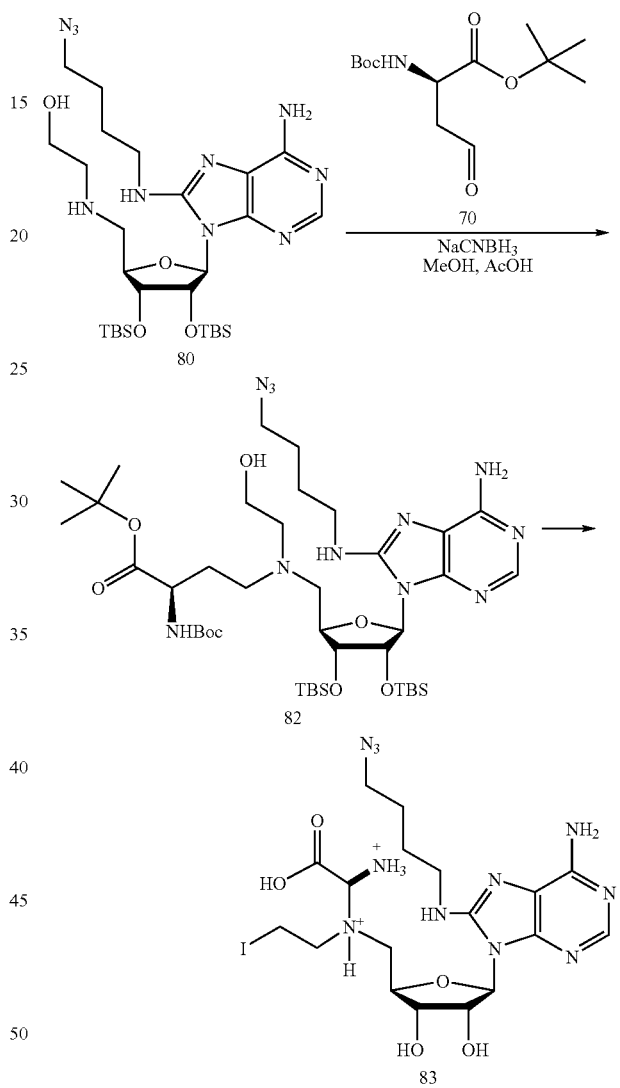

Example 59

Synthesis of 5'-(diaminobutyric acid)-N-iodoethyl-5'-deoxy-8-aminobutylazido adenosine ammonium hydrochloride (83)

As illustrated in SCHEME XVIII, synthesis of N-mustard 83 proceeds from the known 5' ethanolamino adenylate 80 through Boc deprotection of guanidine 39 previously described in EXAMPLES 16 and 21 and illustrated in SCHEME VII. Reductive amination with aldehyde 70 proceeds to tertiary amine 82. Iodination and global deprotection conditions affords the N-mustard (as the ammonium hydrochloride salt) 83. 83 bears the C8 butylazide moiety of 24b used to accomplish sequence selective biotinylation of DNA via a modified Staudinger reaction conditions as illustrated in SCHEMES IX and XVI and described in EXAMPLES 30-32 and 57. DNA modified with the alkylazide nucleoside will take part in [2+3] Huisgen cycloaddition chemistry as described in EXAMPLES 44 and illustrated in SCHEME XIII.

methods illustrated in SCHEME XV and described in EXAMPLE 47 to produce fully deprotected aryl azide species 87. By virtue of the C8 azide, biomolecules modified with 87, in a methyltransferase-dependent way are readily amenable to modified Staudinger reactions as illustrated in SCHEMES IX and XVI and described in EXAMPLES 30-32 and 57.

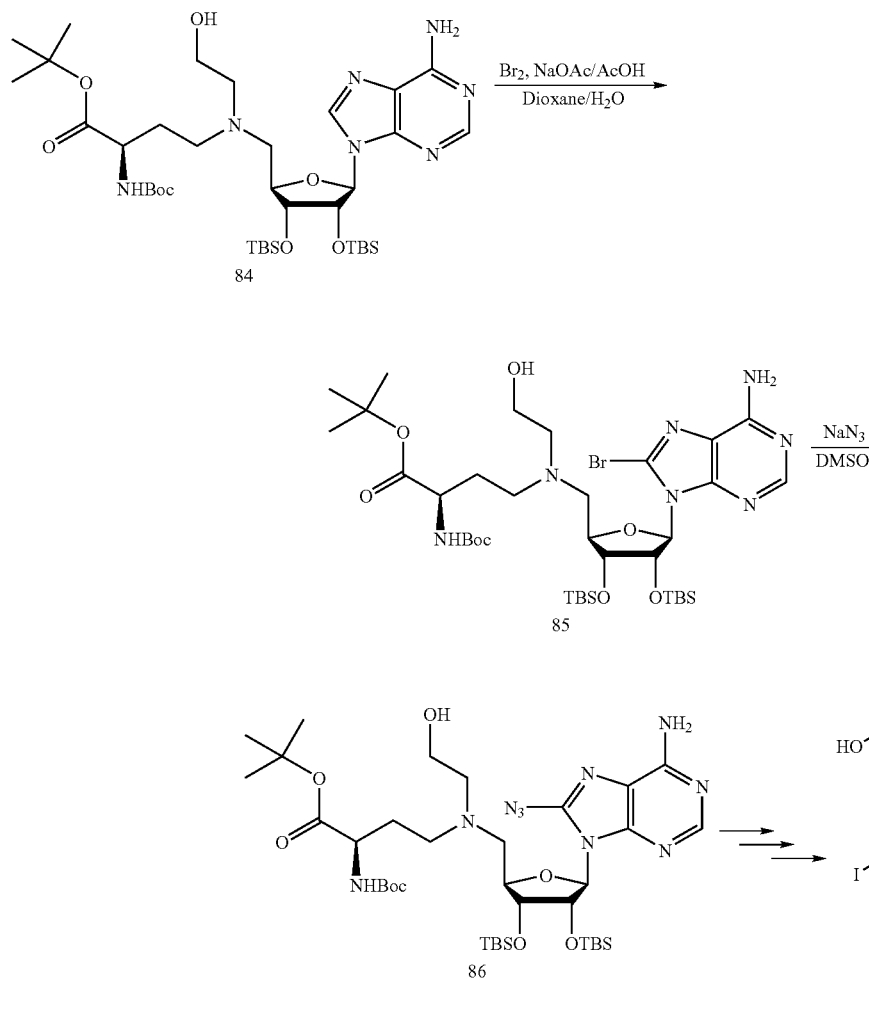

Example 60

Synthesis of 5'-(diaminobutyric acid)-N-iodoethyl-5'-deoxy-8-azido adenosine ammonium hydrochloride (87)

As illustrated in SCHEME XIX, synthesis of 87 begins with the production of amino acid nucleoside conjugate 84, derived from 71 EXAMPLE 45, followed by C8 bromination and subsequent azide installation. Both bromination and azidation is accomplished using methods shown in SCHEME VII and EXAMPLES 19-21. With C8 azide 86 in hand, iodination and global deprotection reactions are performed using While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments.

What is claimed is:

1. A method of derivatizing a methyltransferase substrate comprising:
   providing (i) a methyltransferase substrate selected from the group consisting of a nucleic acid and a polynucleotide, (ii) a methyltransferase, and (iii) a cofactor analog, wherein the cofactor analog is modified at its 5' carbon atom to result in site-specific covalent ligation of the cofactor analog to the methyltransferase substrate by the methyltransferase and wherein the cofactor analog further includes at least one reacting group allowing for ligation of the cofactor analog to a detectable label; and
   reacting the methyltransferase substrate, the methyltransferase, and the cofactor analog under conditions wherein the co-factor analog ligates to the methyltransferase substrate in a reaction catalyzed by the methyltransferase.

2. A cofactor analog of the Formula I:

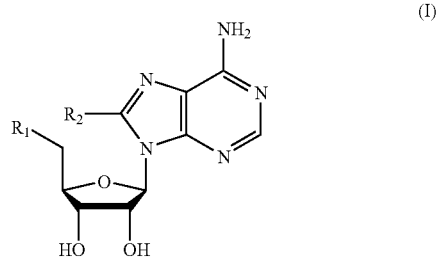

(I)

wherein $R_1$ is attached through a nitrogen atom and is selected from the group consisting of

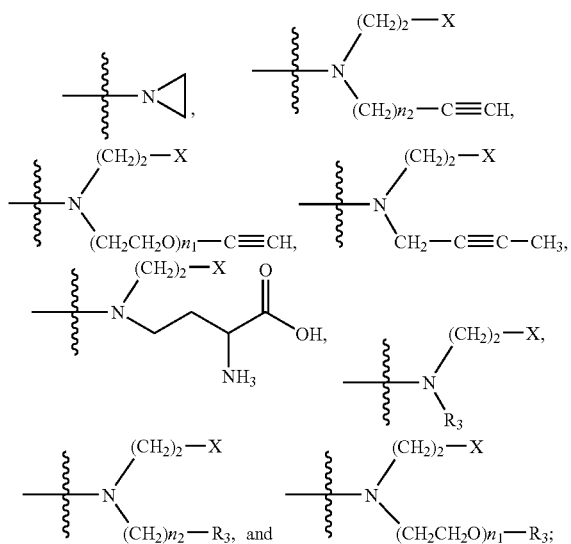

X is a leaving group selected from the group consisting of I, Br, Cl, F, tosylate (OTs), mesylate (OMs) or triflate (OTf);

$R_3$ is selected from the group consisting of:

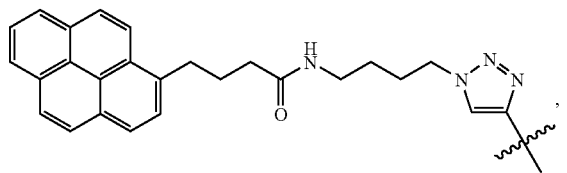

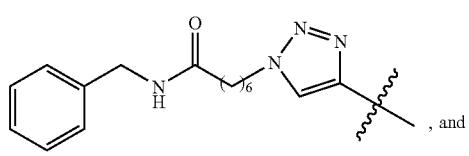, and

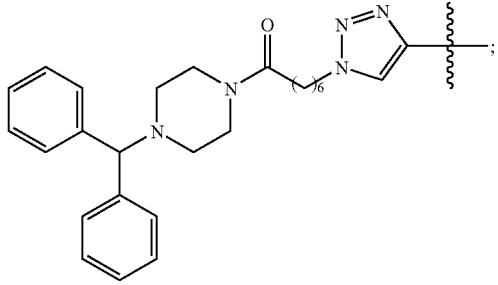;

$R_2$ is independently selected from the group consisting of H, $-N_3$, $-NH(CH_2)_{n2}N_3$, $-NH(CH_2CH_2O)_{n1}N_3$, $-NH(CH_2)_{n2}C\equiv CH$, $-NH(CH_2O)_{n1}C\equiv CH$,

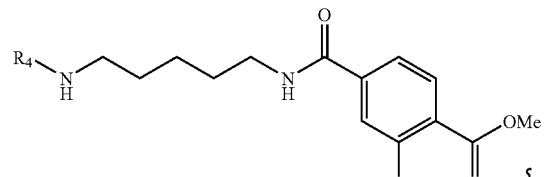

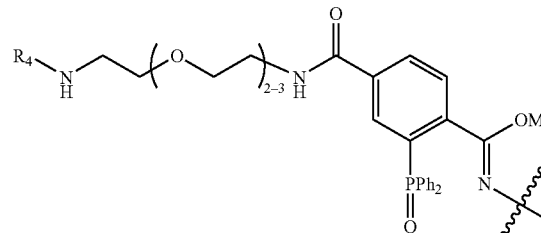

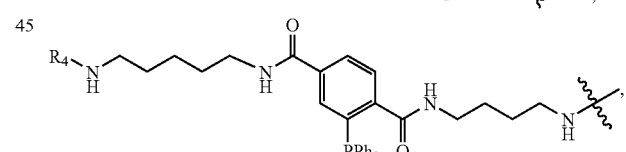

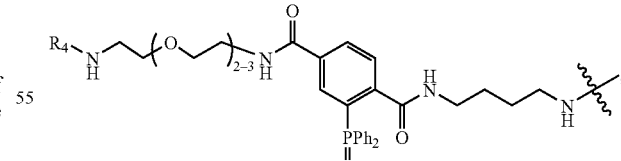

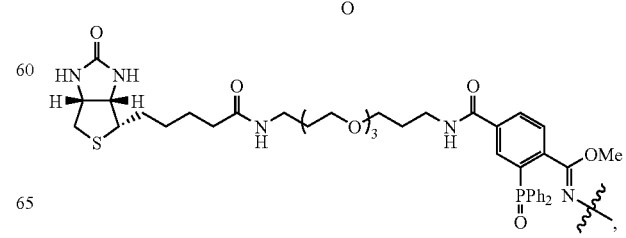

-continued

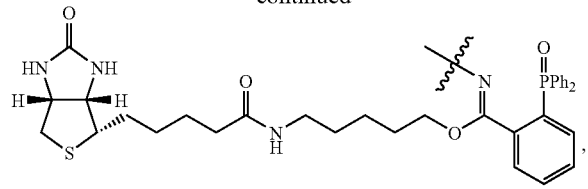

and

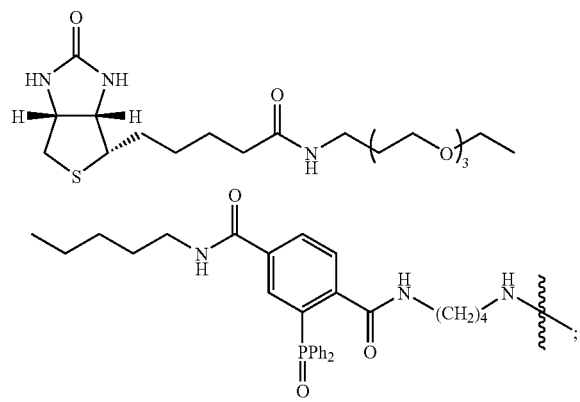

$R_4$ is selected from the group consisting of H, $CH_3$, and triarylphosphine;
n1 is an integer from 1-10 inclusive and n2 is an integer from 2-10 inclusive; and zwitterionic forms and salts thereof;
provided that when $R_1$ is

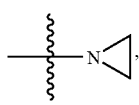

$R_2$ is not $N_3$ or H.

3. A method of determining the methylation state of substrate comprising:
   (a) providing a substrate selected from the group consisting of a nucleic acid and a polynucleotide;
   (b) contacting the substrate with the cofactor analog of claim 2, in the presence of a methyltransferase to form a detectable complex; and then
   (c) detecting the detectable complex, wherein the detected complex identifies an unmethylated methylation site on the substrate, thereby determining the methylation state of the substrate.

4. The method of claim 3, wherein detecting in step (c) is accomplished by gel electrophoresis, phosphorimaging, spectroscopy or photoluminescence.

5. The method of claim 3, further comprising, prior to step (c), contacting the detectable complex with Cu(I) to cleave the substrate.

6. The method of claim 5, further comprising electrophoretically separating the cleaved substrate thereby resulting in a methylation footprint of the substrate.

7. A kit for determining methylation state of a methyltransferase substrate, the kit comprising a cofactor analog according to claim 2 disposed in a first container, and instructions for application of the kit.

8. The kit of claim 7, further comprising a methyltransferase disposed in a second container.

9. The cofactor analog of claim 2, wherein $R_1$ is selected from the group consisting of:

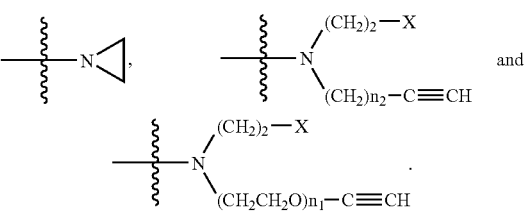

10. The cofactor analog of claim 2, wherein $R_1$ is selected from the group consisting of:

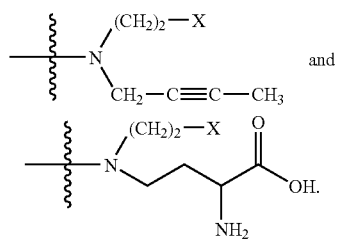

11. The cofactor analog of claim 2, wherein $R_1$ is selected from the group consisting of:

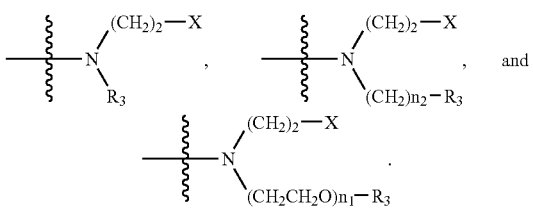

12. The method of claim 1, wherein the cofactor analog is selected from the analogs recited in claim 2.

13. A cofactor analog having the formula:

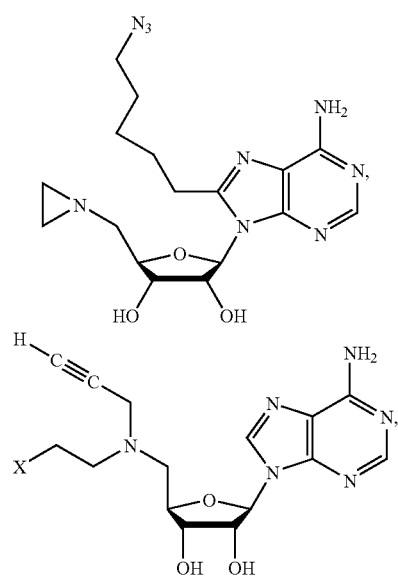

-continued

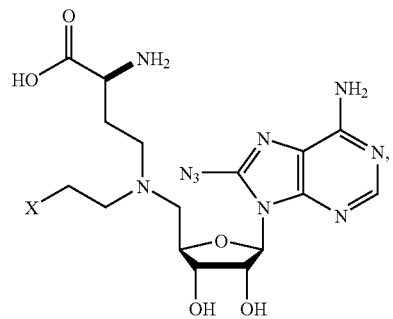

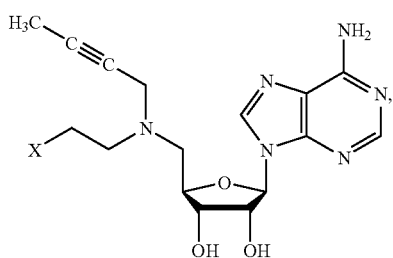

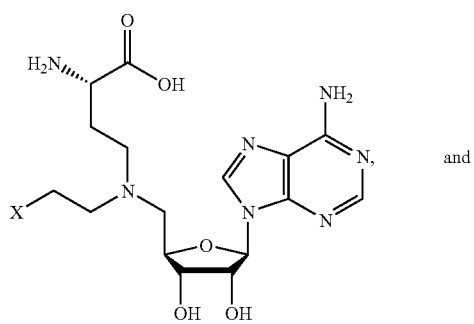

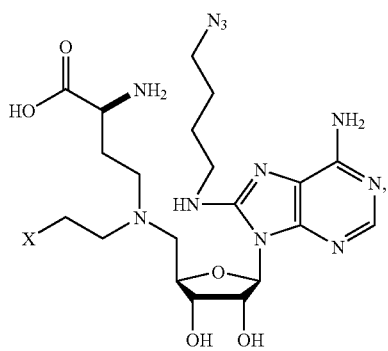

wherein X is a leaving group selected from the group consisting of F, Cl, Br, I, tosylate (OTs), mesylate (OMs) or triflate (OTf), zwitterionic forms and salts thereof.

14. The cofactor analog of claim 13, wherein the cofactor analog is selected from the group consisting of 8-azido-5'-aziridino-5'-deoxy adenosine, 8-(4"-azido-butylamino)-5'-aziridino-5'-deoxy adenosine, 5'-(diaminobutyric acid)-N-iodoethyl-5'deoxyadenosine ammonium hydrochloride, 5'-(Nα-Boc diaminobutyric acid-O-tert-Butyl ester)-N-hydroxyethyl-5'-deoxy-2',3'-bis-(O-triethylsilyl)adenosine, 5'-(diaminobutyric acid)-N-iodoethyl-5'-deoxy-8-aminobutylazido adenosine (bis)hydrochloride and 5'-(diaminobutyric acid)-N-iodoethyl-5'-deoxy-8-azidoadenosine bis(hydrochloride).

15. The method of claim 1, wherein the cofactor analog is selected from the analogs recited in claim 13.

16. A cofactor analog of the Formula I:

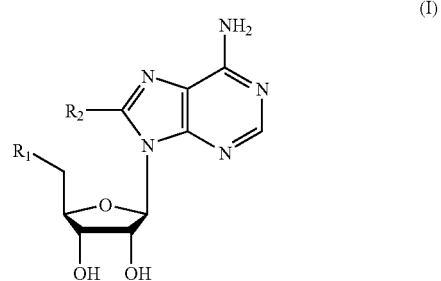

(I)

wherein $R_1$ is selected from the group consisting of

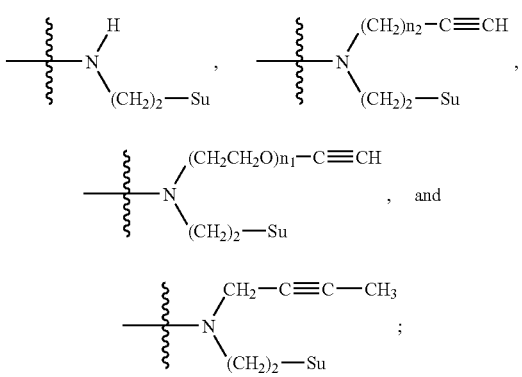

$R_2$ is selected from the group consisting of H, —$N_3$, —NH($CH_2$)$_{n1}N_3$, —NH($CH_2CH_2O$)$_{n1}N_3$, —NH($CH_2$)$_{n2}$C≡CH, —NH($CH_2O$)$_{n1}$C≡CH, Su is a substrate selected from the group consisting of a nucleic acid, a polynucleotide, a phospholipid, a peptide, a polypeptide, a peptide nucleic acid and a protein;

n1 is an integer from 1-10 inclusive and n2 is an integer from 2-10 inclusive, and zwitterionic forms and salts thereof provided that when $R_1$ is

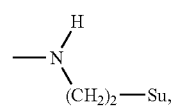

$R_2$ is not $N_3$ or H.

17. The cofactor analog of claim 16, wherein the analog is selected from the group consisting of:

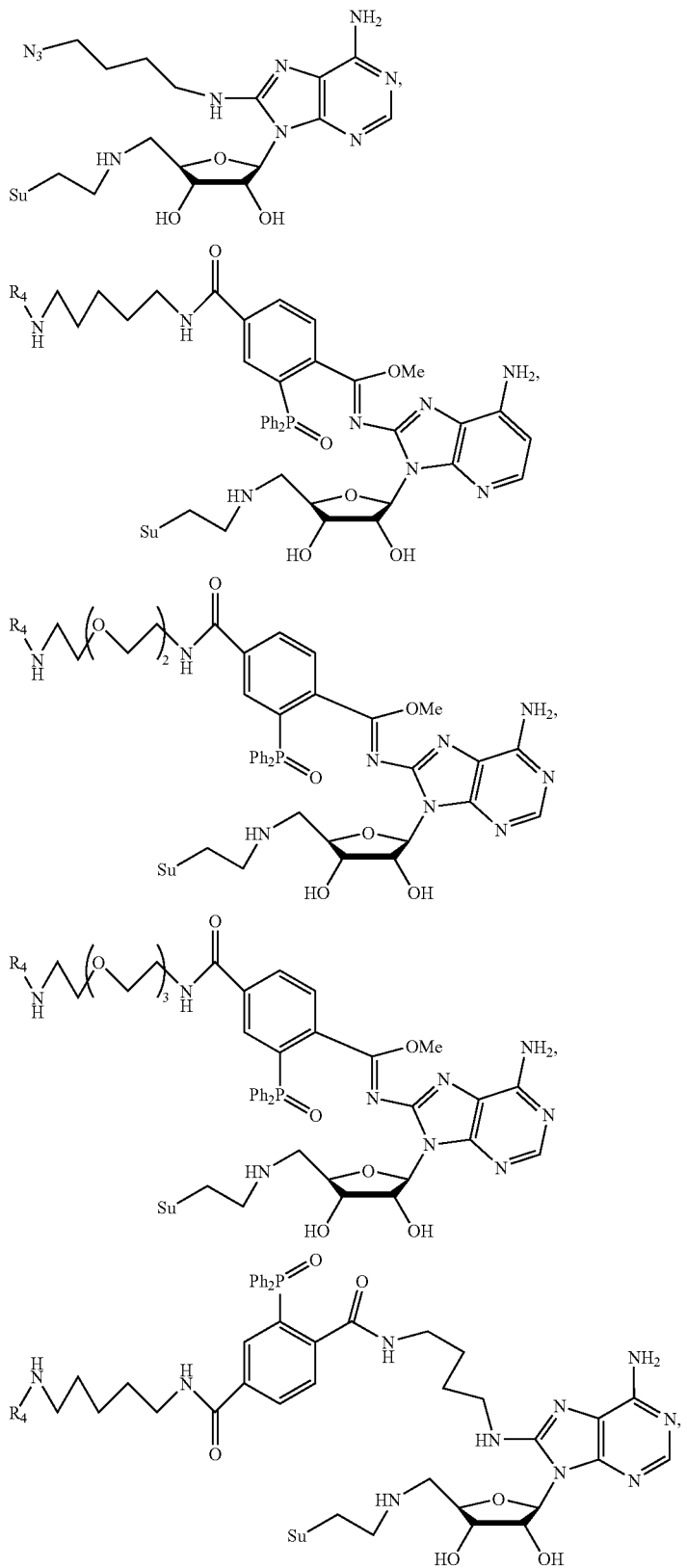

-continued
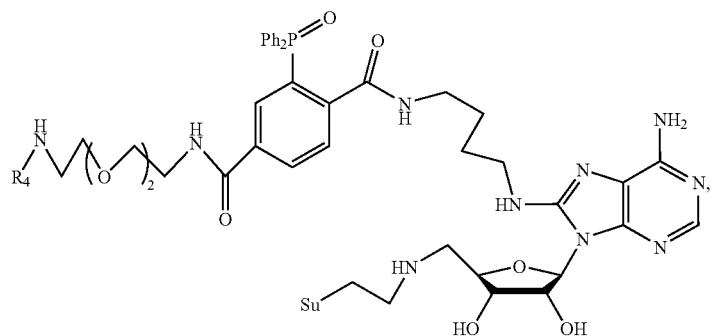
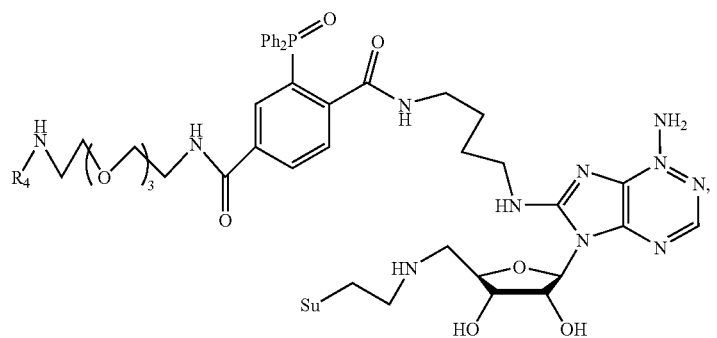
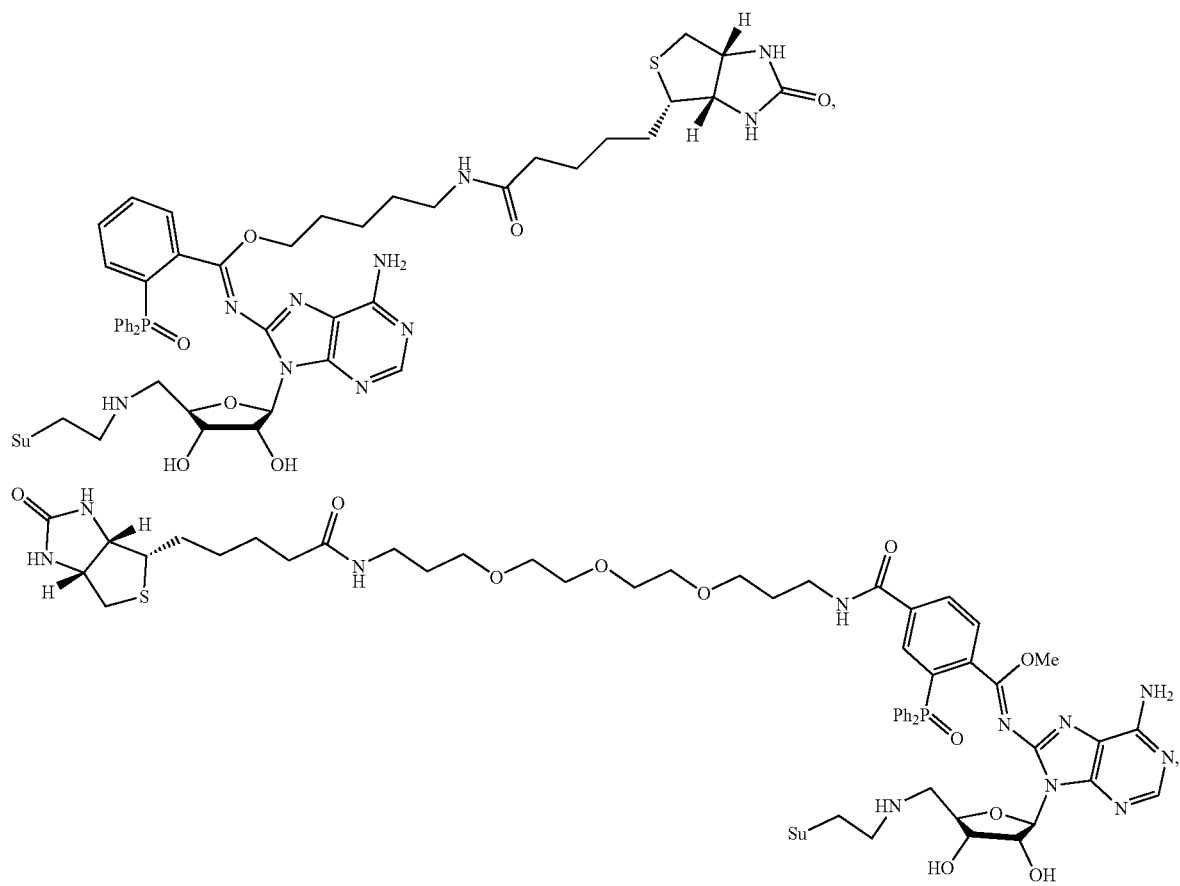

-continued
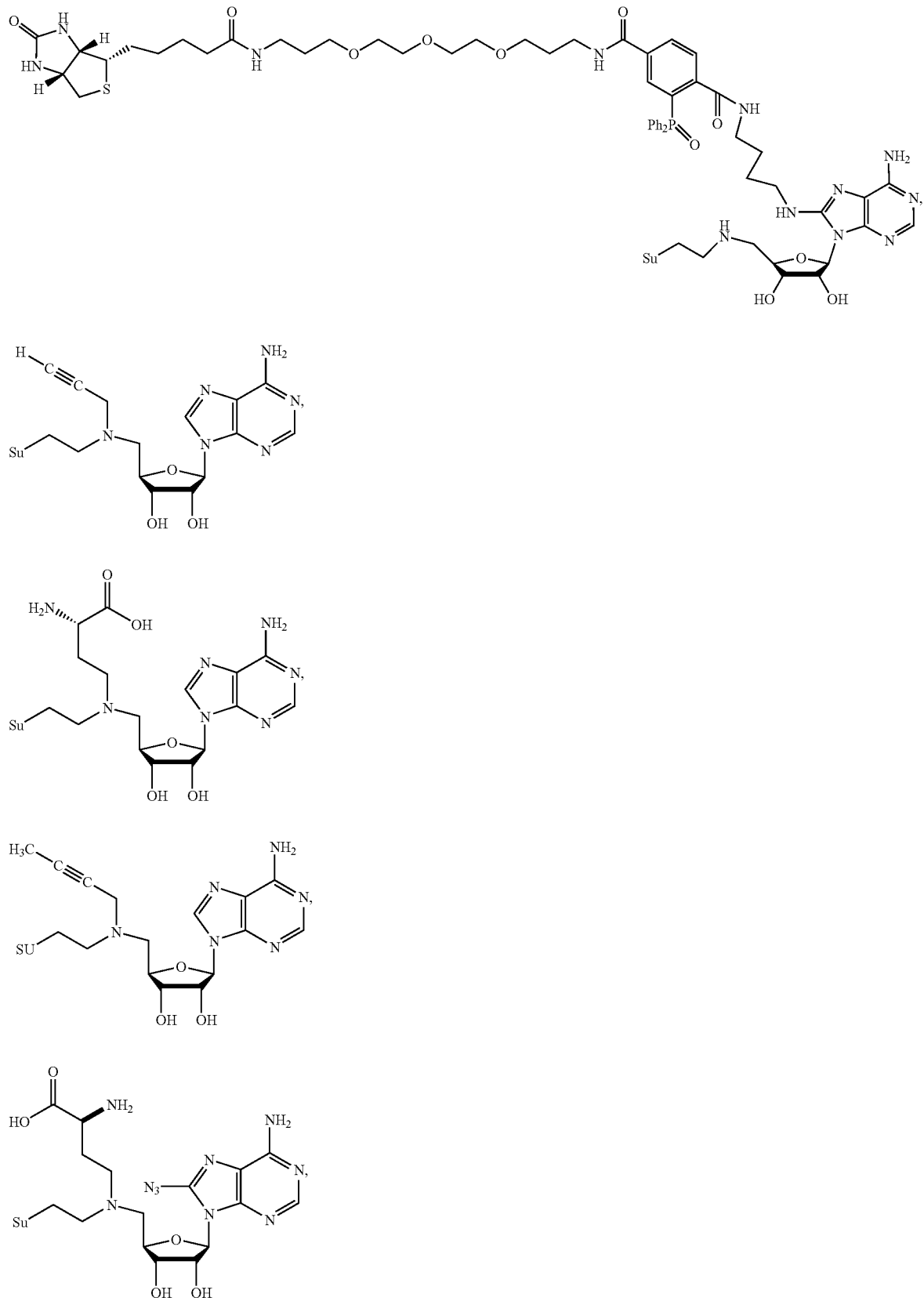

-continued
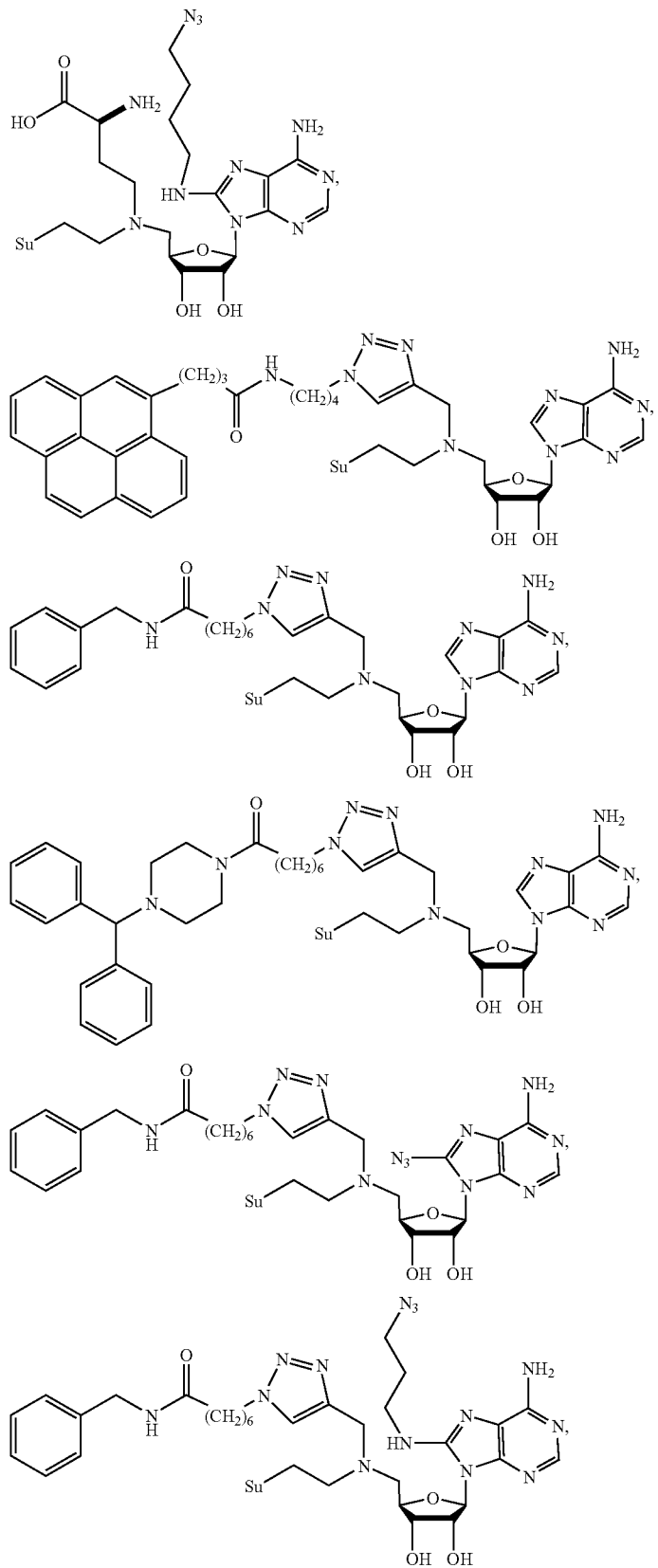

-continued
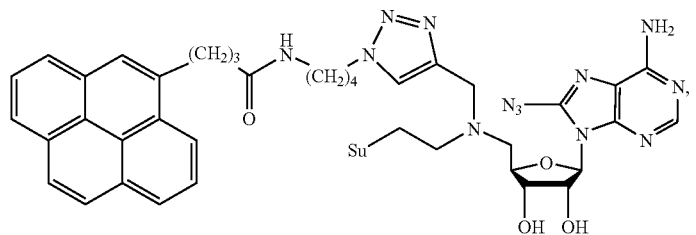
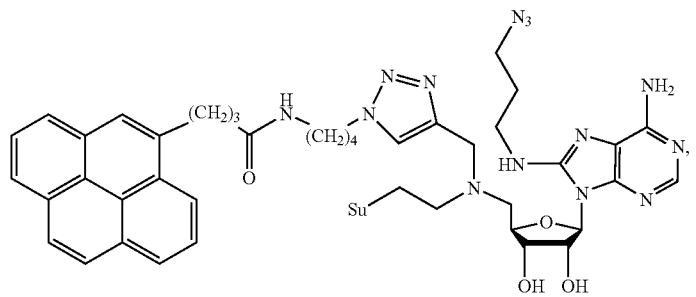
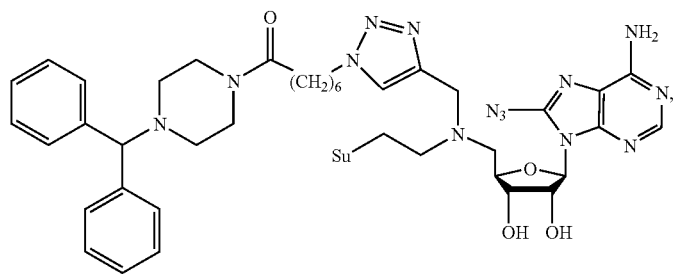
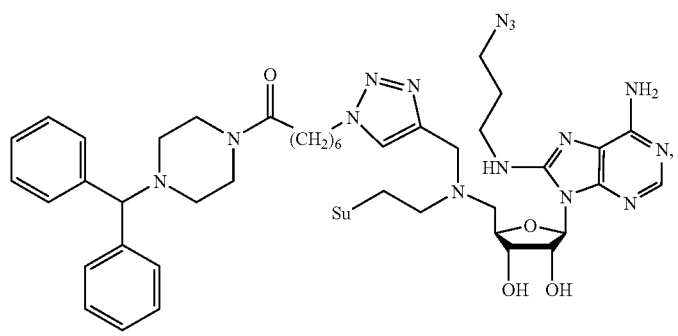
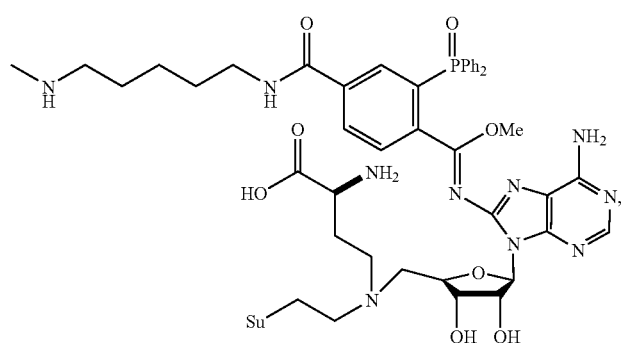

-continued
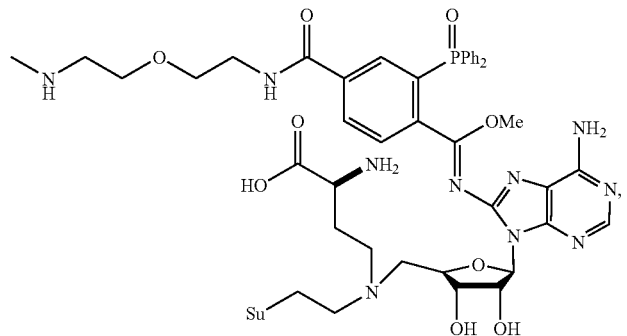
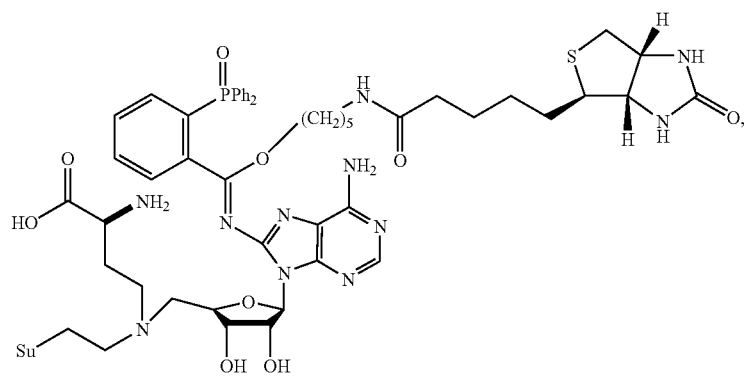
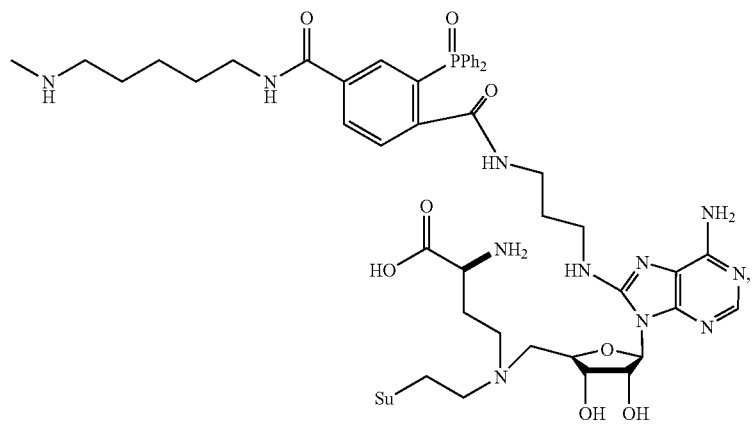
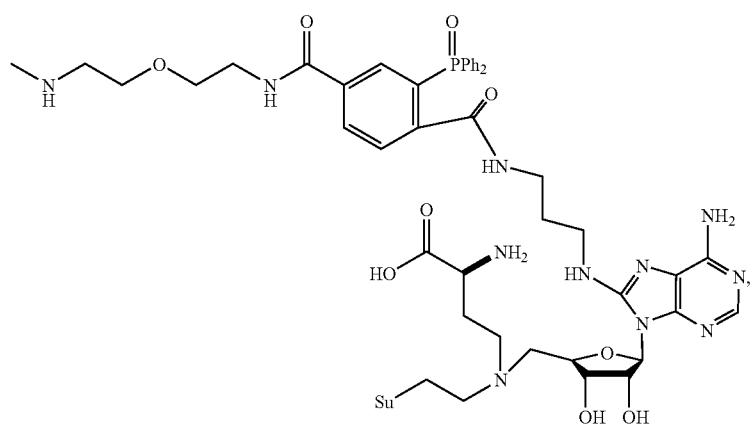

-continued
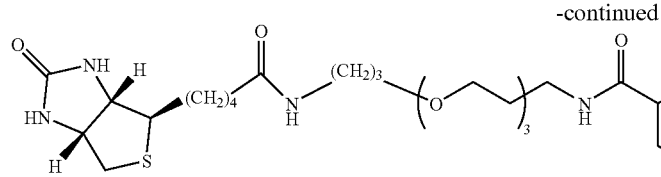
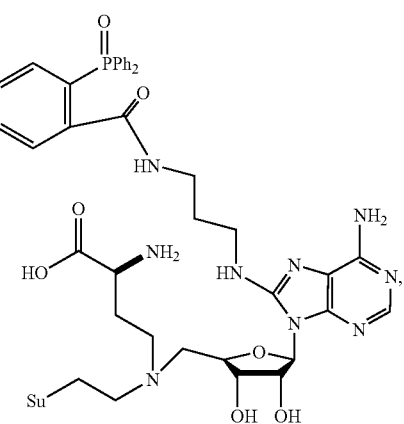
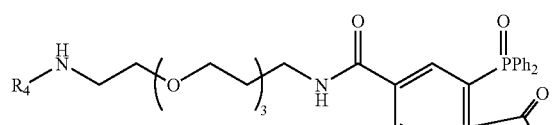
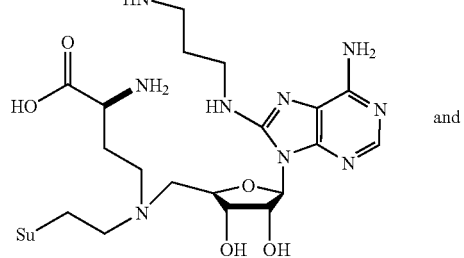
and
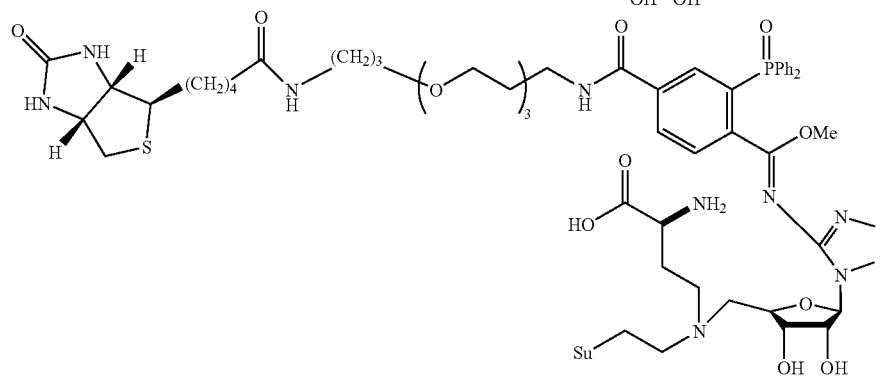
$R_4$ is selected from the group consisting of H, $CH_3$ and
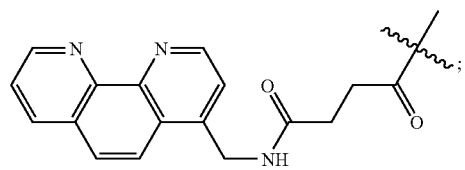
and zwitterionic forms and salts thereof.
* * * * *

SEQUENCE LISTING

<160> NUMBER OF SEQ ID NOS: 25

<210> SEQ ID NO 1
<211> LENGTH: 16
<212> TYPE: DNA
<213> ORGANISM: ARTIFICIAL
<220> FEATURE:
<223> OTHER INFORMATION: SYNTHETIC

<400> SEQUENCE: 1
tgaatctcga gcaccc                                              16

<210> SEQ ID NO 2
<211> LENGTH: 17
<212> TYPE: DNA
<213> ORGANISM: ARTIFICIAL
<220> FEATURE:
<223> OTHER INFORMATION: SYNTHETIC

<400> SEQUENCE: 2
aaacttagag ctctggg                                             17

<210> SEQ ID NO 3
<211> LENGTH: 16
<212> TYPE: DNA
<213> ORGANISM: ARTIFICIAL
<220> FEATURE:
<223> OTHER INFORMATION: SYNTHETIC

<400> SEQUENCE: 3
tgaatgaatt cgaccc                                              16

<210> SEQ ID NO 4
<211> LENGTH: 18
<212> TYPE: DNA
<213> ORGANISM: ARTIFICIAL
<220> FEATURE:
<223> OTHER INFORMATION: SYNTHETIC

<400> SEQUENCE: 4
aaacttactt aagctggg                                            18

<210> SEQ ID NO 5
<211> LENGTH: 6
<212> TYPE: DNA
<213> ORGANISM: ARTIFICIAL
<220> FEATURE:
<223> OTHER INFORMATION: SYNTHETIC

<400> SEQUENCE: 5 gaattc                                                          6

<210> SEQ ID NO 6
<211> LENGTH: 16
<212> TYPE: DNA
<213> ORGANISM: ARTIFICIAL
<220> FEATURE:
<223> OTHER INFORMATION: SYNTHETIC

<400> SEQUENCE: 6
tgaatctcga gcaccc                                              16

<210> SEQ ID NO 7
<211> LENGTH: 18

```
<212> TYPE: DNA
<213> ORGANISM: ARTIFICIAL
<220> FEATURE:
<223> OTHER INFORMATION: SYNTHETIC

<400> SEQUENCE: 7
gggtgctcga gattcaaa                                                 18

<210> SEQ ID NO 8
<211> LENGTH: 16
<212> TYPE: DNA
<213> ORGANISM: ARTIFICIAL
<220> FEATURE:
<223> OTHER INFORMATION: SYNTHETIC

<400> SEQUENCE: 8
tgaatgaatt cgaccc                                                   16

<210> SEQ ID NO 9
<211> LENGTH: 18
<212> TYPE: DNA
<213> ORGANISM: ARTIFICIAL
<220> FEATURE:
<223> OTHER INFORMATION: SYNTHETIC

<400> SEQUENCE: 9
gggtcgaatt cattcaaa                                                 18

<210> SEQ ID NO 10
<211> LENGTH: 16
<212> TYPE: DNA
<213> ORGANISM: ARTIFICIAL
<220> FEATURE:
<223> OTHER INFORMATION: SYNTHETIC

<400> SEQUENCE: 10
tgaatctcga gcaccc                                                   16

<210> SEQ ID NO 11
<211> LENGTH: 18
<212> TYPE: DNA
<213> ORGANISM: ARTIFICIAL
<220> FEATURE:
<223> OTHER INFORMATION: SYNTHETIC

<400> SEQUENCE: 11
gggtgctcga gattcaaa                                                 18

<210> SEQ ID NO 12
<211> LENGTH: 16
<212> TYPE: DNA
<213> ORGANISM: ARTIFICIAL
<220> FEATURE:
<223> OTHER INFORMATION: SYNTHETIC

<400> SEQUENCE: 12
tgaatgaatt cgaccc                                                   16

<210> SEQ ID NO 13
<211> LENGTH: 18
<212> TYPE: DNA
<213> ORGANISM: ARTIFICIAL
<220> FEATURE:
<223> OTHER INFORMATION: SYNTHETIC

<400> SEQUENCE: 13
```
gggtcgaatt cattcaaa                                                  18

<210> SEQ ID NO 14
<211> LENGTH: 16
<212> TYPE: DNA
<213> ORGANISM: ARTIFICIAL
<220> FEATURE:
<223> OTHER INFORMATION: SYNTHETIC

<400> SEQUENCE: 14
tgaatctcga gcaccc                                                    16

<210> SEQ ID NO 15
<211> LENGTH: 18
<212> TYPE: DNA
<213> ORGANISM: ARTIFICIAL
<220> FEATURE:
<223> OTHER INFORMATION: SYNTHETIC

<400> SEQUENCE: 15
gggtgctcga gattcaaa                                                  18

<210> SEQ ID NO 16
<211> LENGTH: 16
<212> TYPE: DNA
<213> ORGANISM: ARTIFICIAL
<220> FEATURE:
<223> OTHER INFORMATION: SYNTHETIC

<400> SEQUENCE: 16
tatatgaatt cttaaa                                                    16

<210> SEQ ID NO 17
<211> LENGTH: 22
<212> TYPE: DNA
<213> ORGANISM: ARTIFICIAL
<220> FEATURE:
<223> OTHER INFORMATION: SYNTHETIC

<400> SEQUENCE: 17
tctttaagaa ttcatatata aa                                             22

<210> SEQ ID NO 18
<211> LENGTH: 13
<212> TYPE: DNA
<213> ORGANISM: ARTIFICIAL
<220> FEATURE:
<223> OTHER INFORMATION: SYNTHETIC

<400> SEQUENCE: 18
tgtcagcgca tga                                                       13

<210> SEQ ID NO 19
<211> LENGTH: 13
<212> TYPE: DNA
<213> ORGANISM: ARTIFICIAL
<220> FEATURE:
<223> OTHER INFORMATION: SYNTHETIC

<400> SEQUENCE: 19
acagtcgcgt act                                                       13

<210> SEQ ID NO 20
<211> LENGTH: 16
<212> TYPE: DNA
<213> ORGANISM: ARTIFICIAL
<220> FEATURE:

```
<223> OTHER INFORMATION: SYNTHETIC

<400> SEQUENCE: 20
tgaatctcga gcaccc                                                    16

<210> SEQ ID NO 21
<211> LENGTH: 18
<212> TYPE: DNA
<213> ORGANISM: ARTIFICIAL
<220> FEATURE:
<223> OTHER INFORMATION: SYNTHETIC, N represents a methylated cytosine
      residue
<220> FEATURE:
<221> NAME/KEY: misc_feature
<222> LOCATION: (8)..(8)
<223> OTHER INFORMATION: n is a, c, g, or t

<400> SEQUENCE: 21
gggtgctnga gattcaaa                                                  18

<210> SEQ ID NO 22
<211> LENGTH: 55
<212> TYPE: DNA
<213> ORGANISM: ARTIFICIAL
<220> FEATURE:
<223> OTHER INFORMATION: SYNTHETIC

<400> SEQUENCE: 22
tgaactgacc gttcagaatt ctacttcgat aaggcgccta acgtacctga atcaa         55

<210> SEQ ID NO 23
<211> LENGTH: 58
<212> TYPE: DNA
<213> ORGANISM: ARTIFICIAL
<220> FEATURE:
<223> OTHER INFORMATION: SYNTHETIC, n represents 5-methyl cytosine
<220> FEATURE:
<221> NAME/KEY: misc_feature
<222> LOCATION: (36)..(36)
<223> OTHER INFORMATION: n is a, c, g, or t

<400> SEQUENCE: 23
acttgactgg caagtcttaa gatgaagcta ttccgnggat tgcatggact tagttttt      58

<210> SEQ ID NO 24
<211> LENGTH: 16
<212> TYPE: DNA
<213> ORGANISM: ARTIFICIAL
<220> FEATURE:
<223> OTHER INFORMATION: SYNTHETIC

<400> SEQUENCE: 24
tgaatctcga gcaccc                                                    16

<210> SEQ ID NO 25
<211> LENGTH: 18
<212> TYPE: DNA
<213> ORGANISM: ARTIFICIAL
<220> FEATURE:
<223> OTHER INFORMATION: SYNTHETIC, n represennts a 5 methyl cytosine
      residue.
<220> FEATURE:
<221> NAME/KEY: misc_feature
<222> LOCATION: (11)..(11)
<223> OTHER INFORMATION: n is a, c, g, or t

<400> SEQUENCE: 25
aaacttagag ntcgtggg                                                  18
```